US011459605B2

(12) United States Patent
Mallet et al.

(10) Patent No.: US 11,459,605 B2
(45) Date of Patent: Oct. 4, 2022

(54) METHOD FOR THE DIAGNOSIS OR PROGNOSIS, IN VITRO, OF PROSTATE CANCER

(71) Applicants: BIOMERIEUX, Marcy-l'Etoile (FR); HOSPICES CIVILS DE LYON, Lyons (FR)

(72) Inventors: François Mallet, Villeurbanne (FR); Nathalie Mugnier, Lyons (FR); Philippe Perot, Lyons (FR)

(73) Assignees: BIOMERIEUX, Marcy l'Etoile (FR); HOSPICES CIVILS DE LYON, Lyons (FR)

( * ) Notice: Subject to any disclaimer, the term of this patent is extended or adjusted under 35 U.S.C. 154(b) by 325 days.

(21) Appl. No.: 14/367,635

(22) PCT Filed: Dec. 18, 2012

(86) PCT No.: PCT/FR2012/052970
§ 371 (c)(1),
(2) Date: Jun. 20, 2014

(87) PCT Pub. No.: WO2013/093324
PCT Pub. Date: Jun. 27, 2013

(65) Prior Publication Data
US 2014/0370503 A1    Dec. 18, 2014

(30) Foreign Application Priority Data

Dec. 20, 2011 (FR) ...................................... 1162027

(51) Int. Cl.
C12Q 1/6869 (2018.01)
C12Q 1/6886 (2018.01)
G01N 33/574 (2006.01)

(52) U.S. Cl.
CPC ......... *C12Q 1/6869* (2013.01); *C12Q 1/6886* (2013.01); *G01N 33/57434* (2013.01); *C12Q 2600/158* (2013.01)

(58) Field of Classification Search
CPC combination set(s) only.
See application file for complete search history.

(56) References Cited

U.S. PATENT DOCUMENTS

| 7,776,523 B2 * | 8/2010 | Garcia | C12Q 1/6886 435/6.14 |
| 2001/0053519 A1 * | 12/2001 | Fodor | B01J 19/0046 435/6.11 |
| 2004/0009481 A1 * | 1/2004 | Schlegel | C12Q 1/6837 435/6.14 |
| 2007/0037147 A1 | 2/2007 | Garcia et al. | |
| 2015/0119265 A1 * | 4/2015 | Perot | C12Q 1/702 506/9 |

FOREIGN PATENT DOCUMENTS

| WO | 02/46477 A2 | 6/2002 | |
| WO | WO 0246477 A2 * | 6/2002 | ........... C07K 14/005 |

OTHER PUBLICATIONS

Perot et al (PLOS One (2012) vol. 7, pp. e40194).*
Benner et al (Trends in Genetics (2001) vol. 17, pp. 414-418).*
Greenbaum et al (Genome Biology 2003, vol. 4, article 117, pp. 1-8).*
Cheung et al (Nature Genetics, 2003, vol. 33, pp. 422-425).*
Saito-Hisaminato et al. (DNA research (2002) vol. 9, pp. 35-45).*
Wu (Journal of Pathology, 2001, vol. 195, pp. 53-65).*
Munroe et al (Molecular and Cellular Biology (1990) vol. 10, pp. 3441-3455).*
Score search (GenCore version 6.4.1, Sep. 29, 2015).*
Subramanian et al (Retrovirology (2011) vol. 8, 90 (pp. 1-23)(e published Nov. 10, 2011).*
GenBank Accession No. AC087436.5 GI:22024601 (http://www.ncbi.nlm.nih.gov/nuccore/22024601, (Jul. 31, 2002)).*
Ncbi blast ( http://blast.ncbi.nlm.nih.gov/Blast.cgi, May 27, 2016).*
Maher (Nature (2009) vol. 458, pp. 97-103).*
Lower ( Proceedings National Academy of Science (1996) vol. 93, pp. 5177-5184).*
Wang-Johanning (Cancer (2003) vol. 98, pp. 187-197), Schlegel et al (US20040009481).*
Caron ( Science (2001) vol. 291, pp. 1289-2992 and supplemental content).*
Wada (Genes & Development (1998) vol. 12, pp. 343-356).*
BLAST » blastn suite » RID-K1T8B4S5015 (https://blast.ncbi.nlm.nih.gov/Blast.cgi, downloaded Jun. 25, 2018).*
Kovalskaya (virology (2006) vol. 346, pp. 373-378).*
Gen Bank Accession AC087436.5 (https://www.ncbi.nlm.nih.gov/nucleotide/AC087436.5?report=genbank&log$=nuclalign&blast_rank=4&RID=V0X1MCER014; Jul. 31, 2002).*
Gen Bank Accession M10976.1 (https://www.ncbi.nlm.nih.gov/nuccore/M10976, Apr. 27, 1993).*
Merriam Webster.com (https://www.merriam-webster.com/dictionary/suspect, downlaoaded May 20, 2020).*
Stauffer (Cancer Immunity (2004) vol. 4, pp. 1-18).*
Gimenez (Nucleic acid research (2010) vol. 38, pp. 2229-2246).*
Yi (Journal of General Virology (2004) vol. 85, pp. 1203-1210).*
Ishida (cancer immunity (2008) vol. 8, pp. 1-10), Pace (nucleic Acid research (2004) vol. 32, D50).*
Yi (Genes Genet Sys (2007) vol. 82, pp. 89-98).*
"Homo sapiens chromosome 8, clone RP11-1082L8, complete sequence." Nov. 23, 2001, pp. 1-62, XP002681866.
"Human DNA sequence from clone RP4-603I14 on chromosome 1p31.3-33," Oct. 15, 1999, pp. 1-38, XP002695969.

(Continued)

*Primary Examiner* — Steven Pohnert
(74) *Attorney, Agent, or Firm* — Oliff PLC

(57) ABSTRACT

The present invention relates to a method for the in vitro diagnosis or prognosis of prostate cancer, which includes a step of detecting at least one expression product of at least one HERV nucleic acid sequence, the use of said nucleic acid sequences, once isolated, as one or more molecular marker(s) and a kit comprising at least one specific binding partner of at least one of the expression products of the HERV nucleic acid sequences.

18 Claims, 3 Drawing Sheets
Specification includes a Sequence Listing.

(56) References Cited

OTHER PUBLICATIONS

"Homo sapiens chromosome 3 clone RP11-296N12, Working Draft Sequence, 30 unordered pieces," Aug. 16, 2000, pp. 1-36, XP002695970.

Seifarth, W., et al., "Comprehensive Analysis of Human Endogenous Retrovirus Transcriptional Activity in Human Tissues with a Retrovirus-Specific Microarray," Journal of Virology, Jan. 2005, pp. 341-352, vol. 79, No. 1.

Paces, J. et al., "HERVd: the Human Endogenous RetroViruses Database: update," Nucleic Acids Research, 2004, vol. 32.

Stauffer, Y. et al., "Digital expression profiles of human endogenous retroviral families in normal and cancerous tissues," Cancer Immunity, Feb. 11, 2004, pp. 1-18, vol. 4, No. 2, XP002695976.

Nickerson, D.A., et al., "DNA sequence diversity in a 9.7-kb region of the human lipoprotein lipase gene," Nature Genetics, Jul. 1998, pp. 233-240, vol. 19.

Navarro, G. et al., Summary of "Flexible Pattern Matching in Strings: Practical On-Line Search Algorithms for Texts and Biological Sequences," ISBN 0-521-81307-7.

Irizarry, R.A., "Exploration, normalization, and summaries of high density oligonucleotide array probe level data," Biostatistics, 2003, pp. 249-264, vol. 4, No. 2.

Johnson, W. E., "Adjusting batch effects in microarray expression data using empirical Bayes methods," Biostatistics, 2007, pp. 118-127, vol. 8, No. 1.

Tusher, V.G et al.,"Significance analysis of microarrays applied to the ionizing radiation response," PNAS, Apr. 24, 2001, pp. 5116-5121, vol. 98, No. 9.

Storey, J.D., "Statistical significance for genomewide studies," PNAS, Aug. 5, 2003, pp. 9440-9445, vol. 100, No. 16.

Sep. 4, 2013 International Search Report issued in International Application No. PCT/FR2012/052970.

* cited by examiner

METHOD FOR THE DIAGNOSIS OR PROGNOSIS, IN VITRO, OF PROSTATE CANCER

Endogenous retroviruses constitute the progeny of infectious retroviruses which have integrated, in their proviral form, into germ line cells and which have been transmitted via this means into the genome of the progeny of the host.

The sequencing of the human genome has made it possible to reveal the extremely high abundance of transposable elements or derivatives thereof. In fact, repeated sequences represent close to half the human genome and endogenous retroviruses and retrotransposons make up 8% of said genome, with the number of elements, at the current time, coming to more than 400,000.

The abundance of endogenous retroviral elements (ERVs) currently present in the human genome is the result of about 100 endogenizations which have successfully taken place during the course of the evolution of the human line. The various waves of endogenization are spread out over a period ranging from 2 to 90 million years before our era and have been followed by the expansion of the number of copies via phenomena of the "copy/paste" type with the possibility of the appearance of errors, resulting, starting from an ancestral provirus, in the formation of a family of HERVs, i.e. a set of elements which exhibit sequence homologies. The oldest elements, those of the HERV-L family, supposedly became integrated before the emergence of mammals. Two families, HERV-F and HERV-H, appeared during the period when the first primates were making their appearance. The HERV-FRD and HERV-K(HML-5) families, integrated 40 to 55 million years ago, are specific for higher primates. On the other hand, the HERV-W and HERV-E families, for example, became integrated 5 to 10 million years later, after the separation with New World monkeys, and are specific for the Catarrhini (Hominoids and Cercopithecidae).

The ERV sequences are represented on all the chromosomes, with a varying density according to the families, and there is no correlation between the physical proximity of ERVs and their phylogenetic proximity.

For a long time, ERVs have been considered to be parasites or to be simple DNA waste. Nevertheless, the impact of ERVs on the organism is not only limited to their past participation in modeling the genome or to deleterious recombinations which may still provide support.

The abundance and the structural complexity of ERVs makes analyses of their expression very complicated and often difficult to interpret. The detection of HERV expression may reflect the transcriptional activation of one or more loci within the same family. The activated locus or loci may in addition vary according to the tissue and/or the context.

The present inventors have now discovered and demonstrated that nucleic acid sequences corresponding to precisely identified loci of endogenous retroviral elements are associated with prostate cancer and that these sequences are molecular markers of the pathological condition. The sequences identified are either proviruses, i.e. sequences containing all or part of the gag, pol and env genes flanked in the 5' and 3' positions by long terminal repeats (LTRs), or all or part of the LTRs or of the genes isolated. The DNA sequences identified are respectively referenced as SEQ ID NO: 1 to 75 in the sequence listing, their chromosomal location is identified in the table below (NCBI 36/hg18), as are their expression, overexpression or underexpression represented by the "expression ratio" between cancer sample and normal sample. When the expression of the nucleic acid or the change in the expression of the nucleic acid is specific for prostate tissue, this information is indicated by the symbol "x" in the target tissue column. This signifies that, if an expression or a change in expression of the nucleic acid concerned is determined in a biological compartment other than prostate tissue, this represents, remotely, a signature of prostate cancer. The DNA sequences identified as being specific for prostate tissue are respectively referenced as SEQ ID NOs: 1, 3, 4, 8, 10, 11, 15, 16, 21 and 32. The DNA sequences identified as being not specific for prostate tissue are respectively referenced as SEQ ID NOs: 2, 5, 6, 7, 9, 12, 13, 14, 17, 18, 19, 20, 22, 23, 24, 25, 26, 27, 28, 29, 30, 31, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74 and 75.

TABLE

| SEQ ID NO: | Chromosomal location | Target tissue | Cancer/normal expression ratio |
|---|---|---|---|
| 1 | (−) chr 8: 125981185-125988649 | x | 6.5 |
| 2 | (−) chr 11: 60237235-60238528 | | 5.1 |
| 3 | (−) chr 19: 20721466-20730278 | x | 3.5 |
| 4 | (−) chr 1: 46569499-46569788 | x | 2.7 |
| 5 | (−) chr 2: 165222667-165224367 | | 2.4 |
| 6 | (−) chr 5: 146727162-146727562 | | 2.4 |
| 7 | (−) chr 7: 79651365-79652053 | | 2.3 |
| 8 | (−) chr 3: 75004674-75009922 | x | 2.2 |
| 9 | (+) chr 19: 60146916-60147844 | | 2.1 |
| 10 | (+) chr 3: 74957891-74960634 | x | 2.1 |
| 11 | (−) chr 19: 58096473-58098768 | x | 2.1 |
| 12 | (+) chr 1: 46568022-46568774 | | 2.1 |
| 13 | (+) chr 6: 142192789-142193227 | | 2.1 |
| 14 | (+) chr 8: 8063655-8067207 | | −2.0 |
| 15 | (+) chr 19: 15807768-15807978 | x | 2.0 |
| 16 | (−) chr 13: 94759022-94759378 | x | 2.0 |
| 17 | (+) chr 12: 31851416-31851846 | | −2.0 |
| 18 | (−) chr 4: 92495874-92498563 | | 2.0 |
| 19 | (+) chr 4: 69952306-69955060 | | 1.9 |
| 20 | (−) chr 2: 157905798-157908183 | | −1.9 |
| 21 | (+) chr 1: 46558555-46559522 | x | 1.9 |
| 22 | (−) chr 10: 20449793-20453869 | | −1.9 |
| 23 | (−) chr X: 135840667-135841473 | | 1.9 |
| 24 | (+) chr 20: 24856581-24861663 | | 1.9 |
| 25 | (+) chr 4: 153982431-153982932 | | 1.9 |
| 26 | (−) chr 1: 144779633-144780605 | | 1.9 |
| 27 | (−) chr X: 153489882-153497212 | | −1.9 |
| 28 | (+) chr 11: 117186039-117190257 | | −1.8 |
| 29 | (−) chr 3: 117306894-117312765 | | 1.8 |
| 30 | (+) chr 8: 8094180-8100651 | | −1.8 |
| 31 | (+) chr 2: 188084458-188084785 | | 1.8 |
| 32 | (−) chr 10: 93051085-93057066 | x | 1.7 |
| 33 | (−) chr 2: 54587807-54590183 | | 1.7 |
| 34 | (−) chr 2: 188741658-188747663 | | 1.7 |
| 35 | (+) chr X: 92571323-92580146 | | 1.7 |
| 36 | (−) chr 4: 92408723-92409131 | | 1.6 |
| 37 | (+) chr 8: 90837193-90837630 | | 1.6 |
| 38 | (+) chr 2: 201711970-201712935 | | −1.6 |
| 39 | (−) chr 1: 154420719-154426128 | | 1.6 |
| 40 | (+) chr 6: 152853219-152859441 | | −1.6 |
| 41 | (−) chr 7: 139899253-139900211 | | −1.6 |
| 42 | (+) chr 1: 146832410-146833382 | | 1.6 |
| 43 | (−) chr 1: 144779633-144780605 | | 1.6 |
| 44 | (+) chr 1: 148879269-148880889 | | −1.6 |
| 45 | (−) chr 5: 34514678-34514916 | | 1.6 |
| 46 | (−) chr 3: 176879333-176879730 | | 1.6 |
| 47 | (+) chr 8: 74896654-74897392 | | 1.5 |
| 48 | (−) chr 20: 15911118-15913833 | | 1.5 |
| 49 | (−) chr 6: 14405150-14411033 | | 1.5 |
| 50 | (−) chr 5: 92818136-92819135 | | −1.5 |
| 51 | (−) chr 8: 54598330-54600779 | | 1.5 |
| 52 | (−) chr X: 78969339-78970117 | | 1.5 |
| 53 | (+) chr 3: 147554294-147559942 | | 1.5 |
| 54 | (−) chr 1: 15334421-15335379 | | 1.5 |
| 55 | (−) chr 8: 12395268-12398823 | | −1.5 |
| 56 | (−) chr 3: 171872658-171878745 | | −1.5 |

TABLE-continued

| SEQ ID NO: | Chromosomal location | Target tissue | Cancer/normal expression ratio |
|---|---|---|---|
| 57 | (−) chr 2: 207379807-207385596 | | 1.5 |
| 58 | (+) chr 6: 131686129-131689771 | | −1.4 |
| 59 | (−) chr 4: 47707230-47708025 | | 1.4 |
| 60 | (−) chr 2: 142963716-142969364 | | 1.4 |
| 61 | (+) chr 5: 130936343-130941430 | | −1.4 |
| 62 | (−) chr 3: 186574589-186580188 | | 1.4 |
| 63 | (+) chr 18: 70111304-70117249 | | −1.4 |
| 64 | (−) chr 8: 56851123-56851350 | | 1.4 |
| 65 | (+) chr 19: 63013510-63014746 | | 1.3 |
| 66 | (+) chr 3: 75269085-75276706 | | 1.3 |
| 67 | (−) chr 19: 58067390-58068685 | | 1.3 |
| 68 | (+) chr 8: 91057690-91058157 | | 1.3 |
| 69 | (+) chr 7: 35702274-35703153 | | 1.3 |
| 70 | (−) chr 13: 90298826-90304533 | | −1.2 |
| 71 | (−) chr 13: 40347160-40352498 | | 1.2 |
| 72 | (−) chr 7: 130691523-130692332 | | 1.2 |
| 73 | (+) chr X: 9597773-9597824 | | −1.2 |
| 74 | (+) chr 10: 92557026-92562997 | | 1.2 |
| 75 | (+) chr 5: 43015565-43018176 | | 1.2 |

The subject of the present invention is therefore a method for the in vitro diagnosis of prostate cancer or for the in vitro prognosis of the seriousness of prostate cancer in a biological sample taken from a patient, which comprises detecting at least one expression product of at least one nucleic acid sequence, said nucleic acid sequence being chosen from the full-length sequences identified in SEQ ID NOs: 1 to 75 or from the sequences which exhibit at least 99% identity, preferably at least 99.5% identity and advantageously at least 99.6% or at least 99.7% identity with one of the full-length sequences identified in SEQ ID NOs: 1 to 75.

The diagnosis makes it possible to establish whether or not an individual is ill. The prognosis makes it possible to establish a degree of seriousness of the disease (grades and/or stages) which has an effect on the survival and/or quality of life of the individual. In the context of the present invention, the diagnosis may be very early.

The percentage identity described above has been determined by taking into consideration the nucleotide diversity in the genome. It is known that nucleotide diversity is higher in regions of the genome that are rich in repeat sequences than in regions which do not contain repeat sequences. By way of example, Nickerson D. A. et al. (1) have shown a diversity of approximately 0.3% (0.32%) in regions containing repeat sequences.

The ability to discriminate a cancerous state of each of the sequences identified above has been demonstrated by means of a statistical analysis using the SAM procedure (5), followed by correction by means of the rate of false positives (6) and by elimination of the values below $2^6$. Consequently, each of the sequences identified above exhibits a significant difference in expression between a tumor state and a normal state. As a result of this, a difference in expression observed for one of the abovementioned sequences constitutes a signature of the pathological condition. Of course, it is possible to combine the differences in expression noted for several of the sequences referenced above for example by one or more combinations of 2, 3, 4, 5, 6, 7, 8, 9, 10 and more even up to 75 of the listed sequences, preferably by one or more combinations of 2, 3, 4, 5, 6, 7, 8, 9, 10 of the sequences respectively identified in SEQ ID NOs: 1, 3, 4, 8, 10, 11, 15, 16, 21 and 32. In particular, the sequences identified in SEQ ID NOs: 1, 4 and 10, taken alone or in combination (in pairs or all three) constitute one or more preferred signatures.

Thus, in the method of the invention, at least two expression products respectively of at least two nucleic acid sequences are detected, said nucleic acid sequences being chosen from the sequences identified in SEQ ID NOs: 1 to 75 or from the sequences which exhibit at least 99% identity, preferably at least 99.5% identity and advantageously at least 99.6% or at least 99.7% identity with one of the sequences identified in SEQ ID NOs: 1 to 75.

In one embodiment of the method according to the invention, the expression product of at least two nucleic acid sequences is detected, said at least two nucleic acid sequences being chosen from the sequences identified as being specific for prostate tissue, i.e. chosen from the group of sequences identified in SEQ ID NOs: 1, 3, 4, 8, 10, 11, 15, 16, 21 and 32 or from the sequences which exhibit at least 99% identity, preferably at least 99.5% identity and advantageously at least 99.6% or at least 99.7% identity with one of the sequences identified in SEQ ID NOs: 1, 3, 4, 8, 10, 11, 15, 16, 21 and 32.

In another embodiment of the method of the invention, the expression product of at least one sequence chosen from the sequences identified as being specific for prostate tissue, i.e. chosen from the group of sequences identified in SEQ ID NOs: 1, 3, 4, 8, 10, 11, 15, 16, 21 and 32 and the expression product of at least one sequence chosen from the sequences identified as being not specific for prostate tissue, i.e. chosen from the group of sequences identified in SEQ ID NOs: 2, 5, 6, 7, 9, 12, 13, 14, 17, 18, 19, 20, 22, 23, 24, 25, 26, 27, 28, 29, 30, 31, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74 and 75 or the expression product of at least one sequence chosen from the sequences which exhibit at least 99% identity, preferably at least 99.5% identity and advantageously at least 99.6% or at least 99.7% identity with one of the sequences identified in SEQ ID NOs: 1, 3, 4, 8, 10, 11, 15, 16, 21 and 32 and the expression product of at least one sequence chosen from the sequences which exhibit at least 99% identity, preferably at least 99.5% identity and advantageously at least 99.6% or at least 99.7% identity with one of the sequences identified in SEQ ID NOs: 2, 5, 6, 7, 9, 12, 13, 14, 17, 18, 19, 20, 22, 23, 24, 25, 26, 27, 28, 29, 30, 31, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74 and 75, are detected.

Preferably, in the method of the invention, the expression product of at least one nucleic acid sequence, preferably of at least two nucleic acid sequences or of three nucleic acid sequences is detected, said nucleic acid sequences being chosen from the group of sequences identified in SEQ ID NOs: 1, 4 and 10, or from the sequences which exhibit at least 99% identity, preferably at least 99.5% identity and advantageously at least 99.6% or at least 99.7% identity with the sequences identified in SEQ ID NOs: 1, 4 and 10.

The expression product detected is at least one RNA transcript, in particular at least one mRNA or at least one polypeptide.

When the expression product is an mRNA transcript, it is detected by any appropriate method, such as hybridization, sequencing or amplification. The mRNA may be detected directly by bringing into contact with at least one probe and/or at least one primer which are designed so as to hybridize to the mRNA transcripts under predetermined experimental conditions, demonstrating the presence or the absence of hybridization to the mRNA and optionally quantifying the mRNA. Among the preferred methods, mention may be made of amplification (for example, RT-PCR, NASBA, etc), hybridization on a chip or else sequencing. The mRNA may also be detected indirectly using nucleic acids derived from said transcripts, such as cDNA copies, etc.

Generally, the method of the invention comprises an initial step of extracting the mRNA from the sample to be analyzed.

Thus, the method may comprise:
(i) a step of extracting the mRNA from the sample to be analyzed,
(ii) a step of detecting and quantifying the mRNA from the sample to be analyzed,
(iii) a step of extracting the mRNA in a reference sample, which may be a healthy sample originating in the same individual, or
(iv) a step of detecting and quantifying the mRNA from the healthy sample,
(v) a step of comparing the amount of mRNA expressed in the sample to be analyzed and in the reference sample; it being possible for the determination of an amount of mRNA expressed in the sample to be analyzed which is different than the amount of mRNA expressed in the healthy reference sample to be correlated with the diagnosis or the prognosis of the seriousness of prostate cancer (the difference in the amount of mRNA in the cancerous prostate tissue relative to the amount of mRNA expressed in the healthy prostate tissue being indifferently an expression, an overexpression or an underexpression); and in particular:
(i) an extraction of the mRNA to be analyzed from the sample,
(ii) a determination, in the RNA to be analyzed, of an expression level of at least one RNA sequence in the sample, preferably of at least two RNA sequences in the sample, the RNA sequence and the RNA sequences respectively being the transcription product of at least one nucleic acid sequence chosen from the sequences identified in SEQ ID NOs: 1 to 75 or from the sequences which exhibit at least 99% identity, preferably at least 99.5% identity and advantageously at least 99.6% or at least 99.7% identity with one of the sequences identified in SEQ ID NOs: 1 to 75, and
(iii) a comparison of the expression level of the RNA sequence(s) defined in (ii) with a reference expression level; it being possible for the determination of an expression level of the RNA to be analyzed which exhibits a difference relative to the reference expression level to be correlated with the diagnosis or the prognosis of prostate cancer (as determined above); or
(i) a step of extracting the mRNA from the sample to be analyzed,
(ii) a step of detecting and quantifying the mRNA from the sample to be analyzed,
(iii) a step of comparing the amount of mRNA expressed in the sample to be analyzed relative to an amount of reference mRNA, it being possible for the determination of an amount of mRNA expressed in the sample to be analyzed which is different than the amount of reference mRNA to be correlated with the diagnosis or the prognosis of prostate cancer (the difference in the amount of mRNA in the sample to be analyzed relative to the amount of reference mRNA being indifferently an expression, an overexpression or an underexpression).

In one embodiment of the method of the invention, DNA copies of the mRNA are prepared, the DNA copies are brought into contact with at least one probe and/or at least one primer under predetermined conditions which allow hybridization, and the presence or absence of hybridization to said DNA copies is detected.

The expression product which is detected may also be a polypeptide which is the translation product of at least one of the transcripts described above. In this case, the polypeptide expressed is detected by bringing into contact with at least one specific binding partner of said polypeptide, in particular an antibody or an antibody analog or an aptamer. The binding partner is preferably an antibody, for example a monoclonal antibody or a polyclonal antibody which is highly purified or an antibody analog, for example an affinity protein with competitive properties (Nanofitin™).

The polyclonal antibodies can be obtained by immunization of an animal with the appropriate immunogen, followed by recovery of the desired antibodies in purified form, by taking the serum of said animal, and separation of said antibodies from the other serum constituents, in particular by affinity chromatography on a column to which an antibody specifically recognized by the antibodies is bound.

The monoclonal antibodies can be obtained by means of the hybridoma technology, the general principle of which is summarized below.

Firstly, an animal, generally a mouse, is immunized with the appropriate immunogen, and the B lymphocytes of said mouse are then capable of producing antibodies against this antigen. These antibody-producing lymphocytes are then fused with "immortal" myeloma cells (murine in the example) so as to give rise to hybridomas. The cells capable of producing a particular antibody and of multiplying indefinitely are then selected from the heterogeneous mixture of cells thus obtained. Each hybridoma is multiplied in the form of a clone, each one resulting in the production of a monoclonal antibody in which the properties of recognition with respect to the protein may be tested, for example, by ELISA, by one-dimensional or two-dimensional Western blotting, by immunofluorescence, or using a biosensor. The monoclonal antibodies thus selected are subsequently purified, in particular according to the affinity chromatography technique described above.

The monoclonal antibodies may also be recombinant antibodies obtained by genetic engineering, using techniques well known to those skilled in the art.

Nanofitins™ are small proteins which, like antibodies, are capable of binding to a biological target, thus making it possible to detect it, to capture it or quite simply to target it within an organism. They are presented, inter alia, as antibody analogs.

Aptamers are synthetic oligonucleotides capable of binding a specific ligand.

The invention also relates to the use of at least one nucleic acid sequence, once isolated, as a molecular marker for the in vitro diagnosis or prognosis of prostate cancer, characterized in that said nucleic acid sequence consists of:
(i) at least one DNA sequence chosen from the sequences SEQ ID NOs: 1 to 75, or
(ii) at least one DNA sequence complementary to a sequence chosen from the sequences SEQ ID NOs: 1 to 75, or
(iii) at least one DNA sequence which exhibits at least 99% identity, preferably at least 99.5% identity and advantageously at least 99.6% or at least 99.7% identity with a sequence as defined in (i) and (ii), or
(iv) at least one RNA sequence which is the transcription product of a sequence chosen from the sequences as defined in (i), or
(v) at least one RNA sequence which is the transcription product of a sequence chosen from the sequences which exhibit at least 99% identity, preferably at least 99.5% identity and advantageously at least 99.6% or at least 99.7% identity with a sequence as defined in (i).

In one embodiment, use is made of at least two nucleic acid sequences which consist of:
(i) at least two DNA sequences chosen from the sequences SEQ ID NOs: 1 to 75, preferably chosen from the sequences identified in SEQ ID NOs: 1, 3, 4, 8, 10, 11, 15, 16, 21 and 32 and in particular the sequences SEQ ID NOs: 1, 4 and 10, or
(ii) at least two DNA sequences respectively complementary to at least two sequences chosen from the sequences SEQ ID NOs: 1 to 75, preferably chosen from the sequences identified in SEQ ID NOs: 1, 3, 4, 8, 10, 11, 15, 16, 21 and 32 and in particular chosen from the sequences SEQ ID NOs: 1, 4 and 10, or
(iii) at least two DNA sequences which exhibit respectively at least 99% identity, preferably at least 99.5% identity and advantageously at least 99.6% or at least 99.7% identity with two sequences as defined in (i) and (ii), or
(iv) at least two RNA sequences which are respectively the transcription product of two sequences chosen from the sequences as defined in (i), or
(v) at least two RNA sequences which are the transcription product of two sequences chosen from the sequences which exhibit at least 99% identity, preferably at least 99.5% identity and advantageously at least 99.6% or at least 99.7% identity with the sequences as defined in (i).

A subject of the invention is also a kit for the in vitro diagnosis or prognosis of prostate cancer in a biological sample taken from a patient, which comprises at least one specific binding partner of at least one expression product of at least one nucleic acid sequence chosen from the sequences identified in SEQ ID NOs: 1 to 75 or from the sequences which exhibit at least 99% identity, preferably at least 99.5% identity, advantageously at least 99.6% or at least 99.7% identity with the nucleic acid sequences identified in SEQ ID NOs: 1 to 75 and no more than 75 specific binding partners of the expression products of the nucleic acid sequences identified in SEQ ID NOs: 1 to 75 or of the nucleic acid sequences which exhibit at least 99% identity with the nucleic acid sequences identified in SEQ ID NOs: 1 to 75, preferably at least 99.5% identity and advantageously at least 99.6% or at least 99.7% identity with one of the sequences identified in SEQ ID NOs: 1 to 75.

In one embodiment, the kit comprises at least two respectively specific binding partners of at least two expression products of at least two nucleic acid sequences chosen from the sequences identified in SEQ ID NOs: 1 to 75 or from the sequences which exhibit at least 99% identity, preferably at least 99.5% identity and advantageously at least 99.6% or at least 99.7% identity with the nucleic acid sequences identified in SEQ ID NOs: 1 to 75 and no more than 75 specific binding partners of the expression products of the nucleic acid sequences identified in SEQ ID NOs: 1 to 75 or of the nucleic acid sequences which exhibit at least 99% identity, preferably at least 99.5% identity and advantageously at least 99.6% or at least 99.7% identity with the nucleic acid sequences identified in SEQ ID NOs: 1 to 75.

For example, the kit comprises at least two respectively specific binding partners of the expression product of at least two nucleic acid sequences chosen from the group of sequences identified in SEQ ID NOs: 1, 3, 4, 8, 10, 11, 15, 16, 21 and 32 or of the sequences which exhibit at least 99% identity, preferably at least 99.5% identity and advantageously at least 99.6% or 99.7% identity with the sequences identified in SEQ ID NOs: 1, 3, 4, 8, 10, 11, 15, 16, 21 and 32.

Preferably, the kit comprises a specific binding partner of the expression product of at least one nucleic acid sequence chosen from the group of sequences identified in SEQ ID NOs: 1, 4 and 10 or of the sequences which exhibit at least 99% identity, preferably at least 99.5% identity and advantageously at least 99.6% or at least 99.7% identity with the sequences identified in SEQ ID NOs: 1, 4 and 10.

In particular, the kit comprises 1, 2 or 3 specific binding partner(s) of the expression product(s) of the nucleic acid sequences identified in SEQ ID NOs: 1, 4 and 10 or of the sequences which exhibit at least 99% identity, preferably at least 99.5% identity and advantageously at least 99.6% or at least 99.7% identity with the sequences identified in SEQ ID NOs: 1, 4 and 10.

The at least specific binding partner of the expression product corresponds to the definitions given above.

The invention also relates to a method for evaluating the efficacy of a treatment and/or a progression in prostate cancer, which comprises a step of obtaining a series of biological samples, and a step of detecting at least one expression product of at least one nucleic acid sequence in said series of biological samples, said nucleic acid sequence being chosen from the sequences identified in SEQ ID NOs: 1 to 75, with one of the sequences identified in SEQ ID NOs: 1 to 75 or of the sequences which exhibit at least 99% identity, preferably at least 99.5% identity and advantageously at least 99.6% or at least 99.7% identity with the sequences identified in SEQ ID NOs: 1 to 75.

In one embodiment, at least two expression products of at least two nucleic acid sequences are detected, said two nucleic acid sequences being chosen from the sequences identified in SEQ ID NOs: 1 to 75 or from the sequences which exhibit respectively at least 99% identity, preferably at least 99.5% identity and advantageously at least 99.6% or at least 99.7% identity with the sequences identified in SEQ ID NOs: 1 to 75.

In another embodiment of the method, the expression product of at least one nucleic acid sequence, preferably of at least two nucleic acid sequences or of three nucleic acid sequences is detected, said nucleic acid sequences being chosen from the group of sequences identified in SEQ ID NOs: 1, 4 and 10 or from the sequences which respectively exhibit at least 99% identity, preferably at least 99.5% identity and advantageously at least 99.6% or at least 99.7% identity with the sequences identified in SEQ ID NOs: 1, 4 and 10.

The term "biological sample" is intended to mean a tissue, a fluid, components of said tissue and fluid, such as cells or apoptotic bodies, and excreted vesicles, comprising in particular exosomes and microvesicles. By way of example, the biological sample may be derived from a biopsy of the prostate carried out beforehand in a patient suspected of suffering from prostate cancer or may be derived from a biopsy carried out on an organ other than the prostate in a patient presenting metastases. In this second case, when the change in expression of the nucleic acid (molecular marker) is specific for the prostate organ, it is possible to work back to the primary cancer, i.e. to the prostate cancer. The biological sample may also be a biological fluid, such as blood or a blood fraction (serum, plasma), urine, saliva, cerebrospinal fluid, lymph, maternal milk, sperm, and also components of said fluids, in particular excreted vesicles as defined above. For example, the detection of a transcript specific for the prostate tissue in an exosome or a microvesicle, originating from an epithelial cell, is a sign of the presence either of a primary cancer or of metastases, without it being necessary to take a sample at the level of the organ.

FIGURES

FIGS. 1 and 2 represent the differential expression observed in prostate cancer for a set of HERV sequences. More specifically, FIG. 1 (clustering) groups together in an exploratory manner the HERV elements which have an expression tropism associated with prostate cancer compared with all the control tissues, and FIG. 2 shows the statistical differences in expression of HERV elements between normal prostate and tumoral prostate.

EXAMPLES

Example 1

Figure 1:
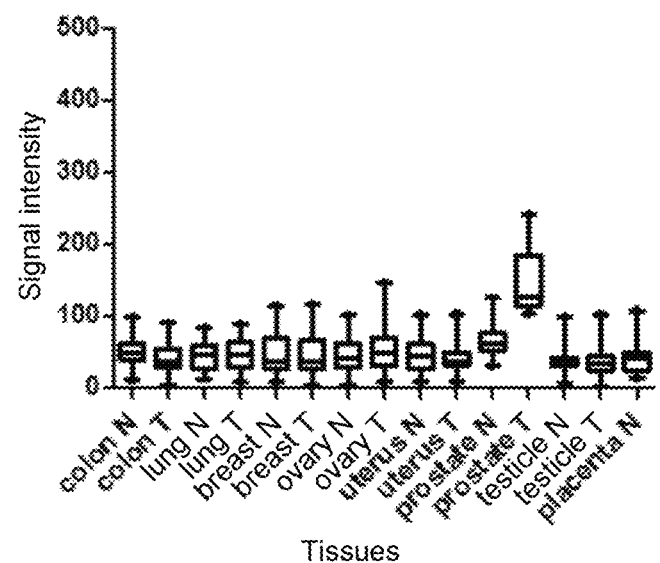
Figure 2:
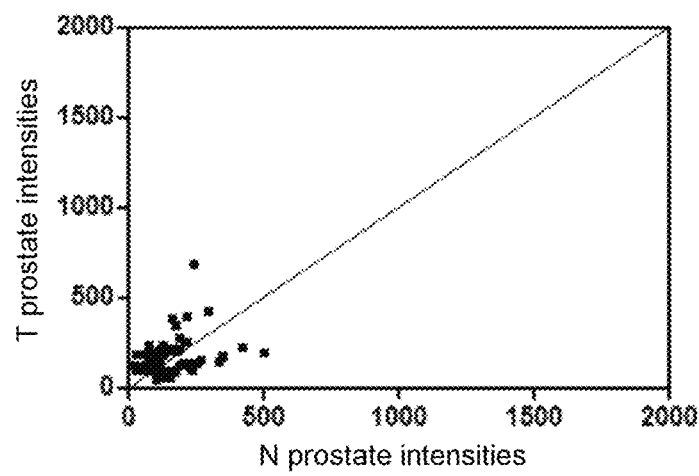

Identification of HERV Sequences Exhibiting Differential Expression in Prostate Cancer Method:

The identification of HERV sequences exhibiting differential expression in prostate cancer is based on the design and the use of a high-density DNA chip in the GeneChip format, called HERV-V2, designed by the inventors and the fabrication of which was subcontracted to the company Affymetrix. This chip contains probes which correspond to HERV sequences that are distinct within the human genome. These sequences were identified using a set of prototypical references cut up into functional regions (LTR, gag, pol and env), and then, by means of a similarity search on the scale of the whole human genome (NCBI 36/hg18), 10 035 distinct HERV loci were identified, annotated and finally grouped together in a databank called HERVgDB3.

The probes which are part of the composition of the chip were defined on the basis of HERVgDB3 and selected by applying a hybridization specificity criterion, the objective of which is to exclude, from the creation process, the probes having a high risk of hybridization with an undesired target. For this, the HERVgDB3 sequences were first segmented in sets of 25 overlapping nucleotides (25-mers), resulting in a set of candidate probes. The risk of nonspecific hybridization was then evaluated for each candidate probe by performing alignments on the whole of the human genome using the KASH algorithm (2). An experimental score marks the result of the hybridization, addition of the impact of the number, of the type and of the position of the errors in the alignment. The value of this score correlates with the target/probe hybridization potential. Knowledge of all the hybridization potentials of a candidate probe on the whole of the human genome makes it possible to evaluate its capture specificity. The candidate probes which exhibit good capture affinity are retained and then grouped together in "probe sets" and, finally, synthesized on the HERV-V2 chip.

The samples analyzed using the HERV-V2 high-density chip correspond to RNAs extracted from tumors and to RNAs extracted from the healthy tissues adjacent to these tumors. The tissues analyzed are the prostate, with breast, ovary, uterus, colon, lung, testicle and placenta as controls. In the case of placenta, only healthy tissues were used. For each sample, 50 ng of RNA were used for the synthesis of cDNA using the amplification protocol known as WTO. The principle of WTO amplification is the following: random primers, and also primers targeting the 3' end of the RNA transcript, are added, before a step of reverse transcription followed by a linear, single-stranded amplification denoted SPIA. The cDNAs are then assayed, characterized and purified, and then 2 µg are fragmented, and labeled with biotin at the 3' end via the action of the terminal transferase enzyme. The target product thus prepared is mixed with control oligonucleotides, then the hybridization is carried out according to the protocol recommended by the company Affymetrix. The chips are then visualized and read in order to acquire the image of their fluorescence. A quality control based on standard controls is carried out, and a set of indicators (MAD, MAD-Med plots, RLE) serve to exclude the chips that are not in accordance with a statistical analysis.

The analysis of the chips first consists of a preprocessing of the data through the application of a correction of the background noise based on the signal intensity of tryptophan probes, followed by RMA normalization (3) based on the quantile method. A double correction of the effects linked to the batches of experiments is then carried out by applying the COMBAT method (4) in order to guarantee that the differences in expression that are observed are of biological and not technical origin. At this stage, an exploratory analysis of the data is conducted using tools for grouping together data by Euclidean partitioning (clustering) and, finally, a statistical analysis using the SAM procedure (5) followed by a correction via the rate of false positives (6) and elimination of the values below $2^6$ is applied in order to search for sequences exhibiting a differential expression between the normal state and the tumor state of a tissue.

Results:

The processing of the data generated by the analysis of the HERV-V2 DNA chips using this method made it possible to identify a set of "probe sets" exhibiting a statistically significant difference in expression between the normal prostate and the tumoral prostate. The results of the clustering and also the search for differential expression within the control samples moreover demonstrated HERV elements of which the differential expression is specifically associated with the tumoral prostate.

The nucleotide sequences of the HERV elements exhibiting a differential expression in the tumoral prostate are identified by SEQ ID NOs: 1 to 75, the chromosomal location of each sequence is given in the NCBI reference 36/hg18, and the "target tissue" information (a cross) indicates the elements in which the differential expression was observed only in the comparison between normal prostate and tumoral prostate (compared with the comparisons within the control tissues). A value which is an indication of the ratio of expression between normal state and tumor state is also provided, and serves to order the sequences in the interests of presentation only.

Example 2

Detection of HERV Sequences in Biological Fluids

Principle:

The inventors have shown that HERV sequences are detected in biological fluids, which makes it possible, inter alia, to characterize a prostate cancer through recourse to remote detection of the primary organ. A study was carried out on 20 urine samples and 38 serum samples originating from different individuals.

The sera and the urines were centrifuged under the following conditions:

Sera: 500 g for 10 minutes at 4° C. The supernatant was recovered and centrifuged again at 16 500 g for 20 minutes at 4° C. The supernatant of this second centrifugation, devoid of cells, but also comprising exosomes, microvesicles, nucleic acids and proteins, was analyzed on chips. The chip is the HERV-V2 chip used according to the modes previously described.

Urines: after collection, centrifugation at 800 g for 4 minutes at 4° C. The pellet was recovered with RNA protect cell reagent™. Then, centrifugation at 5000 g for 5 minutes before addition of the lysis buffer to the pellet. The chip is the HERV-V2 chip used according to the modes previously described.

Figure 3:
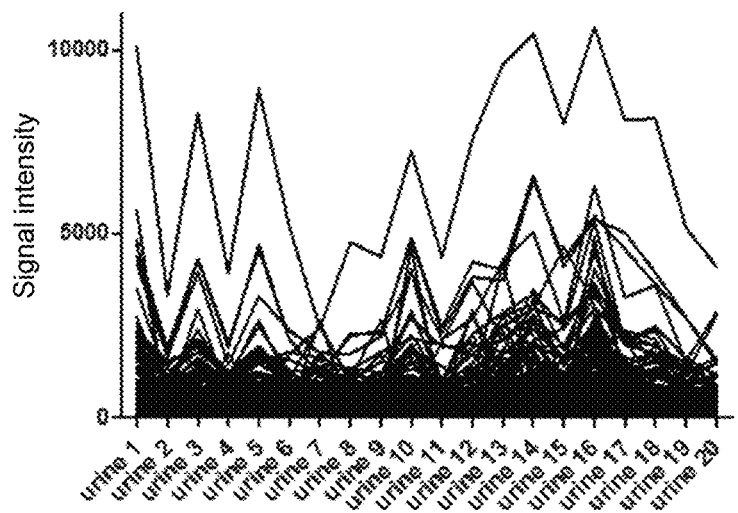
FIGS. 3 and 4 show the detection of HERV sequences in two biological fluids: urines and sera.
Figure 4:
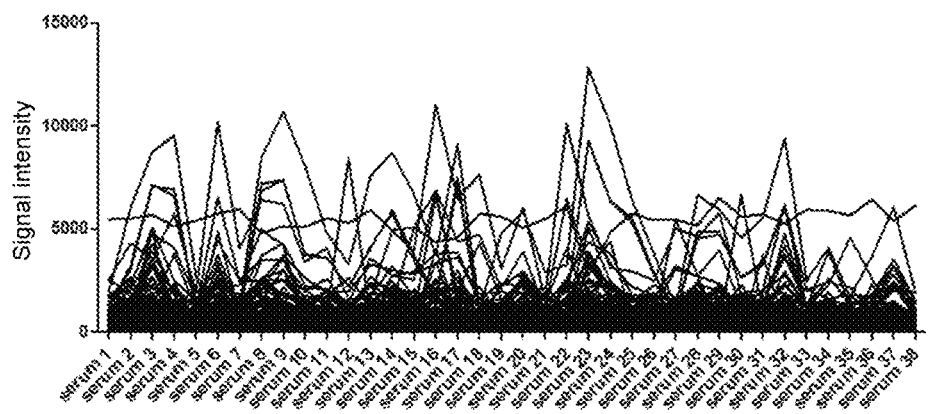

Results:

A large number of positive signals, including the expression signals corresponding to the sequences listed in the table above, was detected both in the serum supernatants and in the cell pellets originating from urines, as illustrated in FIGS. 3 and 4. This confirms that biological fluids, in particular serum and urine, are a usable source of biological material for the detection of HERV sequences. It is commonly accepted that the positivity threshold is about $2^6$, i.e. 64.

Example 3

Demonstration of a Differential Expression of HERV Sequences in Biological Fluids in the Case of Prostate Cancer Principle:

Two clinical classes were identified: (PBPNeg) absence of prostate cancer established by means of biopsy references; (CAPR) prostate cancer established after anatomopathological analysis of pieces of prostatectomies of the patient. The urines of the patients were collected and treated according to the protocol described above. The HERV-V2 chip was used according to the modes previously described in order to demonstrate the HERV sequences exhibiting a differential expression between the two clinical classes in a study including 20 patients.

Figure 5:
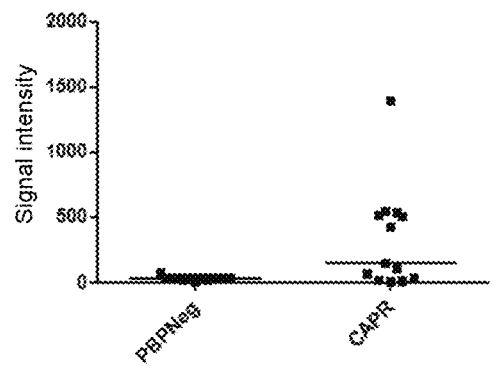
FIGS. 5 to 7 show three examples of HERV sequences which exhibit a differential expression in urines in combination with the clinical cancer status of the patients.
Figure 6:
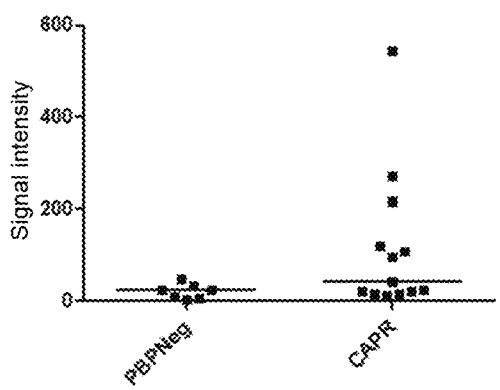
Figure 7:
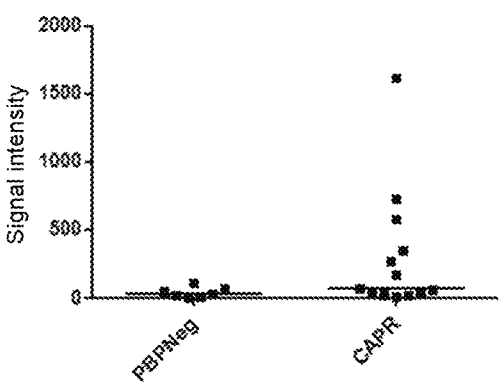

Results:

A set of HERV sequences exhibiting a statistically significant differential expression between the clinical classes was identified. Three examples among these HERV sequences are shown in FIGS. 5 to 7. Each point represents the value of expression of the sequence under consideration in an individual. The horizontal bar indicates the median of the values. The three examples show the discriminating nature of the expression level of the sequences under consideration insofar as the variances of the PEPNeg and CAPR groups are significantly different (Fisher's test, p-value less than 0.05).

LITERATURE REFERENCES

1. Nickerson, D. A., Taylor, S. L., Weiss, K. M., Clark, A. G., Hutchinson, R. G., Stengard, J., Salomaa, V., Vartiainen, E., Boerwinkle, E. and Sing, C. F. (1998) DNA sequence diversity in a 9.7-kb region of the human lipoprotein lipase gene. *Nat. Genet.,* 19, 233-240.
2. Navarro, G. and Raffinot, M. (2002) Flexible Pattern Matching in Strings: Practical On-Line Search Algorithms for Texts and Biological Sequences. Cambridge University Press.
3. Irizarry, R. A., Hobbs, B., Collin, F., Beazer-Barclay, Y. D., Antonellis, K. J., Scherf, U. and Speed, T. P. (2003) Exploration, normalization, and summaries of high density oligonucleotide array probe level data. *Biostatistics (Oxford, England),* 4, 249-264.
4. Johnson, W. E., Li, C. and Rabinovic, A. (2007) Adjusting batch effects in microarray expression data using empirical Bayes methods. *Biostatistics (Oxford, England),* 8, 118-127.
5. Tusher, V. G., Tibshirani, R. and Chu, G. (2001) Significance analysis of microarrays applied to the ionizing radiation response. *Proceedings of the National Academy of Sciences of the United States of America,* 98, 5116-5121.
6. Storey, J. D. and Tibshirani, R. (2003) Statistical significance for genomewide studies. *Proceedings of the National Academy of Sciences of the United States of America,* 100, 9440-9445.

The invention claimed is:

1. A method for detecting at least two RNA transcripts, comprising:
 obtaining a biological sample that is collected from a human patient suspected of having prostate cancer; and
 detecting, in the biological sample, the presence or absence of at least two RNA transcripts comprising a first RNA transcript expressed by a first nucleic acid sequence having at least 99% identity with SEQ ID NO: 1, and a second RNA transcript expressed by a second nucleic acid sequence having at least 99% identity with SEQ ID NO: 3.

2. The method as claimed in claim 1, further comprising detecting, in the biological sample, the presence or absence of a third RNA transcript expressed by a third nucleic acid sequence having at least 99% identity with of SEQ ID NOs: 4, NO: 4, 8, 10, 11, 15, 16, 21, or 32.

3. The method as claimed in claim 2, wherein the third nucleic acid sequence has at least 99% identity with SEQ ID NO: 4 or 10.

4. The method as claimed in claim 1, wherein the at least two RNA transcripts are mRNA transcripts.

5. The method as claimed in claim 1, wherein the at least two RNA transcripts are detected by hybridization, amplification, or sequencing.

6. The method as claimed in claim 4, wherein the mRNA transcripts are detected by bringing the mRNA transcripts into contact with a probe and/or a primer, and detecting the presence or absence of hybridization to the mRNA transcripts.

7. The method as claimed in claim 4, wherein the mRNA transcripts are detected by detecting the presence or absence of cDNAs obtained from the mRNA transcripts.

8. A method for detecting at least two RNA transcripts, comprising
 obtaining a biological sample that is collected from a human patient that has been diagnosed with prostate cancer; and
 detecting, in the biological sample, the presence or absence of at least two RNA transcripts comprising a first RNA transcript expressed by a first nucleic acid sequence having at least 99% identity with SEQ ID NO: 1, and a second RNA transcript expressed by a second nucleic acid sequence having at least 99% identity with SEQ ID NO: 3.

9. The method as claimed in claim 8, further comprising detecting, in the biological sample, the presence or absence of a third RNA transcript expressed by a third nucleic acid sequence having at least 99% identity with SEQ ID NO: 4, 8, 10, 11, 15, 16, 21, or 32.

10. The method as claimed in claim 9, wherein the third nucleic acid sequence has at least 99% identity with SEQ ID NO: 4 or 10.

11. The method according to claim 7, wherein the presence or absence of the cDNAs is detected by bringing the cDNAs into contact with a probe and/or a primer, and detecting the presence or absence of hybridization to the cDNAs.

12. The method according to claim 1, wherein the first nucleic acid sequence is SEQ ID NO: 1, and the second nucleic acid sequence is SEQ ID NO: 3.

13. The method as claimed in claim 12, wherein
 the at least two RNA transcripts are mRNA transcripts, and
 the mRNA transcripts are detected by detecting the presence or absence of cDNAs obtained from the mRNA transcripts.

14. The method as claimed in claim 12, further comprising determining an expression level of the at least two RNA transcripts in the biological sample.

15. The method as claimed in claim 12, wherein
 the at least two RNA transcripts are mRNA transcripts, and
 the mRNA transcripts are detected by bringing the mRNA transcripts into contact with a probe and/or a primer, and detecting the presence or absence of hybridization to the mRNA transcripts.

16. The method as claimed in claim 1, further comprising determining an expression level of the at least two RNA transcripts in the biological sample.

17. A method for detecting at least two RNA transcripts, comprising:

obtaining a biological sample that is collected from a human patient suspected of having prostate cancer;

detecting, in the biological sample, the presence or absence of a first RNA transcript expressed by a first nucleic acid sequence having at least 99% identity with SEQ ID NO: 1 by contacting the first RNA transcript or cDNA obtained therefrom with a first probe or primers to respectively hybridize to or amplify a region within the first RNA transcript or cDNA obtained therefrom that is defined by a distinct region within the first nucleic acid sequence; and detecting, in the biological sample, the presence or absence of a second RNA transcript expressed by a second nucleic acid sequence having at least 99% identity with SEQ ID NO: 3 by contacting the second RNA transcript or cDNA obtained therefrom with a second probe or primers to respectively hybridize to or amplify a region within the second RNA transcript or cDNA obtained therefrom that is defined by a distinct region within the second nucleic acid sequence.

18. The method as claimed in claim 1, wherein no more than 75 specific binding partners are used to detect the at least two RNA transcripts.

\* \* \* \* \*

SEQUENCE LISTING

```
<160> NUMBER OF SEQ ID NOS: 75

<210> SEQ ID NO 1
<211> LENGTH: 7464
<212> TYPE: DNA
<213> ORGANISM: Homo sapiens

<400> SEQUENCE: 1
gagagacagg actaactgga tttcctagac cgactaagaa ttcctaagcc tggctgggga      60
aagtgaccgc acccacctgt aaaacacagg gcttgtaact cagctcacat ctgaccaatc     120
aggtagtaaa gagagctcac taaaccacca attaggctaa aagcaggagg taaagaaata     180
atcaatcacg tattgcctga gagcacaggg ggagggacag tgattgggat ataaatacag     240
gcatttgagc cggcagtggc aacccacttt gggtcccctc ctgttgaatg ggagctctgt     300
tttcactcta ttaaatcttg caactgcaca ctcttctggt ctgtgtttgt tccggcttga     360
gctgagcttt tgcttgccat ccacgcactg ctaaataccg ccatcgcaga cccactgttg     420
actttcaccc ctccagatct ggcagagtct tgctgtgttt ctgatccagc gaggtgcccc     480
```

```
ttgccgctcc cgttcaggct agagactagc cattgttcct gcatggctaa gtgcctgggt    540
tcatcctaat cgagctgaac actagtcgct gggttccaca gttctttcc gtgacccatg     600 gcttctaata gagctataac actcaccgca tgcccaagg ttccattcct cagaattcat     660
gaggccaaga accccaggtc agagaacaaa aggcttgctg ccatcttggg agtggccgcc    720
accatcttgg gagctctaag aacaaagacc cacccgtaac atttggtggc aactgtacgg    780
ggattctcca aagtggtgag taatattgga ccacttttgc ttgctattct gtcctatcct    840
tccttagaat tggaggaaaa taggccaggc gtggtggctc atgcctgtaa tcccagcact    900 tgggaggcc gaggcaggca gatcacaagg tcaggagatc gagaccatcc tggctaacac     960
agtgaaaccc tgtctctact gaaacataca aaaattagc ctggcgtggt ggcacgtgcc    1020
tgtaattcca gctactcagg aggctgaggc aggagaatca cttgaacccg ggaggcagag   1080
cttgcagtga gccgagatcg tgccactgca ccccagcctg ggtgacagag ggagactcca   1140
tctcaaaaaa aaaaaaaaaa aaaagaatt ggatgaaaat accaggcaac tctcagccag    1200
ttaaaaatta ttaccgtggc cagcggactt aagactcagg tgtgaggctt cctgggtaaa   1260
ggttttctaa taacctccag cccttctggg ttgggaggat tggtctgcct ggaaccagct   1320
tctgctttca caatttcctg ggggaagccg agggccgact agaggcagaa agctatcatc   1380
ctgaactcct ggcattggct ggtcaagatc atggtgcagc cagaagtctc tactcaacag   1440
ccgcccatgt gtgcgcccct atctctcctt gtgacccata cctcctgggt ccgaaacacg   1500
actttcttgg aagtgtagcc ccaaaattct ccttacctct gaatctactt cctctgatcc   1560
ctgcctccta gatactaatg attcagactt tcacttcctc tcccaagtat tagagcaagt   1620
tgtacctcca aagggatcta gggaagctct atgctgtgtc cttaggcatc tatgctatga   1680
acccagggag tcttgcccct ggtgcccctc ctaatttagg tatatagctc tccacatggg   1740
cagttatatg ggactcgttc ccaccatcc ttgccagagc cccaagttct attatgagcc    1800
atagccccag gtttgtaaat ggctaggagg attgctctcc cattgtgtaa gatgctctcc   1860 tccccaatt tctacccaga gcttacccca ctgcaataca atgtccaagc cttggctcct    1920
tggccaggac cttagaactg ataacccagt gctttaacaa ctggaactag gtctacaaca   1980
atataataga tcaggatgaa agcgaactga gtaaattaaa gggaggcgca tattcctaca   2040
gtggcaaatg ggggcaacga gcaaacatcc ttccactgtg ttcccaaaat ccatctacaa   2100
aaagagagga aagagagaca gaaaagaagg aaaaagggga aagagagaga ggagagagag   2160
agagagaagg gaaagagaga agagagagac aggtagtcta aagagagaga agagagaaag   2220
tcaaagacag agagagaaac agtaaagaaa aatagtgta ccctattact ttaaaagcaa    2280
ggtaaattta ggaactataa ttaataattg aaggtcttct ccaggactct ataacactcc   2340
aataccaact tgttgtcagt gtaaacaagg gcgtagcccg aaagcactga ccagtgac     2400 aaccgtagcc ttcatatcaa aaatcctcaa ccccatagcc cacggatggc ccaaatgcat   2460
tcaatctgtg gcccaaatgc attcaatctg tagcagcaac tgctttgcta gcagaagaaa   2520
gtagaaaaat aacttttaga gaaaacctca ctgtgagcgc atctcaccag tttagaagta   2580
tcctaagtaa ataaaaggca aaaggtagc ttactaactc aaaaatctta agtataggg     2640 ctattctgtt agaaaaagat ggtttaacat taaccactga aaattcccctt aacccagcac  2700 atttcctaac agggtgttta atcttaatt accatacaaa ggtccaacca aacctaggag    2760 aaactcccctt cagaacagga cgatagatgg ttcctcccgg gtgattgagg aataaaaaga  2820
```

```
cacagtgggt attcagtaat cgatagggaa actcttgtaa aagcagagtt aggaaaattg    2880
cctaataaat ggtctgtcca aacgtgcaag ctgtttgtac tcagccaagc cttaaagtac    2940
ttgcataata aaaaaaacca tctatacaaa ttctaagtta atttggacta acaaggtct    3000 tattaatagc aaaggataat tgaaatccca aacttagaag ttttcaaca aaagtaaagt     3060 ttgctaaaag ttaacagtgt aacctgtatt atcctaactt ctaatcttgt ggccttagcc    3120
agtctagtcc acagacataa aggaagttcg ctttggaaaa aatgtttatc ttaaaaaaaa    3180
aactctatct caatcctgac ttagaaggtt acctacaccc tctctgaaat gaattttcat    3240
aagaactgtt gttattgga atgcatcttg atggggcaac tgggttgtta tcaaatactc     3300
aggaacccag cccagctcta gaactcacct ctgagcgcaa aggcaatgtt gggcatgctg    3360
gtaaaggacc actggaatcc agcagtctgt accccttct ttgtggtcaa gaaaggcggc     3420
aaaacaggtg caggactgct acatcagtga gcataaataa tctgataagc agaggtccat    3480
gggtgcttat gcaccctgga aaagaataag cattaggacc atagagatgc tctagaacta    3540
atgctcatcg gaaaatgact aagggtgctg gcatccctat tttcttttc cagatgggaa     3600 acattcccct caagggaaaa acgcccctaa gatgtattct ggagaattag gaccaatttg    3660
gccctcagat gctgagaaag aatgacttat attcttctgc agtaccgcct ggccacaata    3720
tcctctttaa gggggagaaa cctggcctcc tgagggaagt ataaattata acaccatctt    3780
acagctagaa ctcttttgta gaaagaggg caaatggagt gaagtgccat atgtgcaaac     3840
tttcttttca ttaataaaca actcacaatt atgtaaaaag tgttatttat gccctacagg    3900
aagccctcag agtctacctc cctaccccgg tgtcccccag ctccttcctc aactaataag    3960 gaccccctt caacccaaat ggtacagaaa gagatagaaa aaggggtaaa caatgaacca     4020
aagagtgcca gtattccctg gttatgcccc ttccaagtgg tgggaggagg agaatttggc    4080
ccagtcagag tgcatgtacc tttttccctc tcagatttga aggaaattaa aatagaccta    4140
ggtaaattct cagataatcc tgatggctat attgatgttt tacaagggtt aggacaatcc    4200
tttgatctga catagagaga tatgttactg ctagatcaga caccccaaat gacagaagta    4260
ccgccgtaac tgcagcccga gagtttggcg atctctggta tctcagtcag gtcaatgata    4320
ggatgacaac agaggaaaga gaacaattcc ccactggcca gcaggcagtt gccagtgtag    4380
accctcactg ggacacagaa tcagaacctg gagattggtg ccgcagacat ttgctaactt    4440
gagtgctaaa aggtctaagg aaaactagga agaagcctat aaattattca atgatgtcca    4500
ctataacaca gggaaagaag aaaatcttac tgccattctg gagagactaa gggaggcatt    4560
gaggaagcat acctctctgt cacctaactc tattgaaggc caactaatct taaaggataa    4620
gcttatcact cagtcagttg cagacattag aaaaaacttc aaaagtccac cttagccccg    4680
cagcaaaact tagaaaccct attgaacttg gcaacctcag cttttataa tagagatcag     4740 gaggagcagg tggaatggga caaatgggat ttaaaaaaaa aaaggccacc gctttagtca    4800
tggccctcag gcaagcggac tttggaggct ctggaaaagg gaaaggctgg gcaaatcaaa    4860
tgcctaatag gacttgcttc cagtgcggtc tccaaggaca cttttaaaaaa gattgtctga   4920 atagaaataa gctgccccct cgtccatgcc ccttatgtca agggaatcac tggaaggccc    4980
actgccccag ggaacaaagg tcctcttgag tcagaagcca ctaaccagat gatccagcag    5040
caggactgag ggtgcccagc acaagtgtca gccccatgcca tcaccctcac agagctccgg   5100
gtatgcttga ccattgaggg ccaggaggtt aactatctcc tggacgctgg catgccttc     5160 tgagtcttac tctcctgtcc cagacaactg tcctccagat ctgtcaaaat ccaaggggtc    5220
```

```
ctaggacagc cagtcactag atacttctcg cggtcactaa gttgtgacta gggtacttta    5280
ctcttttcac atggttttct aattttgcct gaaagaccca ctcctgtgtt agggagagac    5340
attctagcaa aagcaggggc cattacacac actaattaag gaaactcaga aagccaatac    5400
ccatttagta gaatgacac ctgaagcaca agctgctttc caggccctaa agaaggccct     5460
aacgcaagcc ccagtgttaa gcttgccgat gggcaagact tttctttata tgtcacagaa    5520
aagacaggag tagctctagg agtccttaca gaggtccgag ggaccagctt gcaacctgtg    5580
gcatacctga gtaaggaaat tgatgtagtg gcaaagggtt ggcctcactg tttatgcgta    5640
gtggcagcag tagcagtatt agtatctgaa gcagttaaaa tgataaaggg aagagatctt    5700
acatgtggac atctcatgat gtgaacggca tactcactgc taaaggagac ttgtggctgt    5760
cagacaacct tctgcttaaa tatcaggttc tattatttga agggccagtg ctgtgactgc    5820
gcacttgtgc aactcttaac ccagccacat tcttacaga caatgaagaa aagatgcata    5880
actgtcaaca attgctcaaa cctacgccac ttgaggggac cttctagaag ttcccttgac    5940
tgatcctgac ctcaacttgt atactgatgg aagttccttt gtagaaaaag acttcaaaa     6000 ggtggggtat gcactggtca gtgataatgg aatacttgaa agtaatcccc tcactccagg    6060
agacaatgct agttattcct gtgaacctct agaggatctg cacctgctct tcaagtgaca    6120
accatgagga aagtaactag aatcgcagat gcccatggcc ctcccttgtc atatatttct    6180
ctttactgtt ctcttactct cttgcactct cactgcacct cttgcatgct gctgtactac    6240
cagtagctcc ccttaccaag agcttctatg gagagcatgg cttccagaa atattgatgc     6300 cccactgtat aggagttttt ctaaaggaaa ccccatttc accacccaca cccatttgcc     6360
cctgcacttc aggccataca tttcaatccc tgtatcttta acctccttgt taagtttgtc    6420
tcttccagaa tcaaaactgt aaaactacaa attgttcttc aaatggagcc ccagatgcag    6480
tctatgacta agatcaacca cagacccttg gactggcctg ctagcccatg ctccgatgtt    6540
gatgacatcg aaggcacccc tcctgaggaa atctgaactg cgagacccct cctatgcccc    6600
aattcagcag gaagcagtta gaacggtcat cggccaactt ccccaacagc acttgggttt    6660
tcctgttgag agggggatt gagagacagg actagctgga tttcctaggc tgactaagaa      6720
ttcctaagcc tagctgggga aggtgaccac acccacctttt aaaatatagg gcttgtaact    6780
cagcttacat ctgaccgatc aggtagtaaa gagagctcac taaactacca attaggctaa    6840
aagcaggagg taagaaaata gtcaatcatc tatcacctga gagcacaggg ggagggacag    6900
tgattgggat ataaacacag gtatttgaga ggcagtggca accccctttg ggtcccctcc    6960
cattgaatgg gaactctgtt ttcactctat taaatcttgc aactgcacac tcttctggtc    7020
tgtgtttgtt ccggctcgag ttgagctttt gcttgctgtc cacccactgc taaacgctgc    7080
cgtcacagac ccactgttga ctttcacccc tctggatctg gcagggtgtc cgctgtgttt    7140
ctgatccagc gaggtgccca ttgccgctcc tgttggggct agaggctaac cattgttcct    7200
gcatggctaa gtgccctggt ttgtcctaat cgagctgaac acaagttgct gggttccacg    7260
gttctcttcc atgacccatg gcttctaata gactataaca ctcaccgcac ggcccaaggt    7320
tccactcctt gtaattcgtg aggtcaagaa ccccaggtca gagaacaaaa agcttgctgc    7380
catcttggga gtggctgccc ccatttcggg gcagcctgcc accatcttgg gagctctaag    7440
aacaatgacc cacccgtaac agtt                                           7464

<210> SEQ ID NO 2
```

```
<211> LENGTH: 1293
<212> TYPE: DNA
<213> ORGANISM: Homo sapiens

<400> SEQUENCE: 2
gtggggaaaa gaaagagaga tcagattgtt actgtgtctg tgtagaagga agtagacata      60
ggagactcca ttttgttctg tactaagaaa aattcttctg cctcgagctg ctgttaatct     120
gtaaccctac ccccaaccct gtgctccctg aaacatgtgc tgtgtcaagt cagggttaga     180
tggattaagg gttgtgcagg gtgtgctttg ttaaacaaat gcttgaaggc agcacgcttg     240
ttaagagtca tcaccggccg ggcgcggtgg ctcacgcctg taatcccagc actttgggag     300
gccgaggcgg gtggatcatg aggtcaggag atcgagacca tcctggctaa caaggtgaaa     360
ccctgtctct actaaaaata caaaaaatta gccgggcgcg gtggcgggtg cctgtagtcc     420
cagctactcg ggaggctgag gcaggagaat ggcatgaacc cgggaagtgg agcttgcagt     480
gagccgagat tgcgccactg cagtccgcag tccggcctgg gcgacagagc gagactccgt     540
ctcaaaaaaa aaaaaaaaa aaaaaaaaag agtcatcacc actccctaat ctcaaaccac     600
tccctaatct caagtaccca gagacacaaa acactgcgga aggccacaga gacctctgcc     660
taggaaagcc aggtattttc caaggtttct ccccatgtga tagtctgaaa tatggcctca     720
tgggatggga aagacctgac cgtcccccag cccaacaccc gtaaagggtc tgtgctgagg     780
aggattagta aagaggaag aacggctct ttgcagttga ggtaagagga aagcttctgt     840
ctcctgctcg tctctgggca atggaatgtc tcggtgtaaa gtccattgta tattccattt     900
actgagatag gggaaaactg ccttagggct ggaggtggga catgctggca gcaatactgc     960
tccttaaggc attgagatgt ttatgtatat gcacatcaaa agcacagcac tttttttctt    1020
accttgttta tgatgcagag acatttgttc acgtgtttac cttctgacct tctctccact    1080
attatcctat tacccatgcc caataatgat caataaatac taagggaact cagaggccag    1140
tgcccacgtg gatcctctgt atgctgaacg ccggtcccct aggccccctt tttcttctc    1200 tgtactttat ctctgtgtct ctttcttttc caagtctctt gttccaccta acgagaaaca    1260
cccacaggtg tgaaggggca acccaccccct tca                                1293

<210> SEQ ID NO 3
<211> LENGTH: 8812
<212> TYPE: DNA
<213> ORGANISM: Homo sapiens

<400> SEQUENCE: 3
atggtatgag gtcaccactt ctcctgttgt ccttctcagt tcctccccaa cctcccctt      60 tccccagttt ataagacagg agaaaaggga gaaagcaaaa agttgaaaag aaacagaagt     120
aagataaata gctagatgac cttggcacca ccacctggcc ctggtggcta aaatataata     180
ttattaaccc ctgaccaaaa ctgttggtgt tatctgtaaa ttccagatat tgtatgagaa     240
agtactgtaa aactttttat tctgttagct gatgtaggta gccccagtc atgtttctca     300 cgcttacttg acctattatg acttttcat gtagacccct tagagttgta agcccttaaa     360
agggctagga atttcttttt tggggagctc ggctcttaag atacgagtct gccaatgctc     420
ccggccaaat aaaaaacctc ttccttcttt aatctggtgt ctgaggagtt ttgtctgtga     480
ctcgtcctgc tacatttctt ggttccctgg ccaggaagca aggtaattga aggacagtcg     540
aggcagcccc ttaggtggct taggcctgcc ctgtggagca tccctgcagg ggactctggc     600
cagcttgagt gacgcggatc ctgagagcgc tcccaggtag gcaattaccc cggtggaaag     660
```

```
cctcgtcaga gcagtgcgtg gcaggcccct gtggaggatc aatgcagtgg ctgaacactg      720
ggaaggaaca ggcacttgga gtccagacat ttgaaacttg gtaagactgg tcttcggaac      780
ttgcccactc catttgagtg gaagcgtggc ctgatcaacc acggcatgcc tgtactggca      840 cttttggtttt tgttttttgac ttgacttgaa ttgcttgata cttttggtttt ggtttgacct   900 ggcttggatt tctggatact ctgattttgg ttttgattct ggtttggtga aaactgaaaa      960
agtgtgtgtg tgcactttt acccattctt tgttttgtgg tgtgcatgtg gtgtgagctt      1020
ggtgttttgt cttgaggaaa catggatcag acacaaaata agcctactcc tctaggaact     1080
atgttgaaaa attttaagaa gggatttaat ggagactatg gggttactat gacaccaggg     1140
aaacttagaa ctttgtgtga aatagattgg ccaacattag aagtggggttg gccatcagaa    1200 ggaagcctgg acaggtccct tgtttctaag gtatggcaca aggtaactag taagtcagga    1260
cactcagacc agtttccata catagacact tggttacagc tggtgctaga ccccccacag     1320
tggctaagag ggcaggcagc agcagtgcta gtagcaaagg gacagatagt caaggaagga    1380
ttctgctcca cccgctgagg gaaatcaact cctgaagttc tgttcgacca aacatcagaa     1440
gatccattgc aggagatggc accagtgatc ccagtgttgc cctcccctta tcagggagag    1500
aggctcccca cttttgagtc cacagtgctt gcgcctctgc cagacaaatg tatccctagg    1560
ccactcagag tagacaagag aggaggtgaa gcctcgggag aaaccctcc cttggcagct     1620 catttaagac ccaaaacagg gatacaaatg cccctgagag agcagcagta tactggaata    1680
gatgaggatg ggcacatggt ggagagtcgt gttttttgtgt accagccctt cacctctgcc   1740
gaccttctca actggaaaaa caataccccg tcctatactg aaaagccgca agctctaatt    1800
gatttgctcc aaactattat ccagacccat aaccccactt gggctgattg ccaccagttg    1860
ctcatgttcc tctttaaaac agatgaaagg tgaagggtgc ttcaagcagc aactaagtgg    1920
ctagaggaac atgcactggc tgattaccaa accccccaag agtatgtaag gacacagtta    1980
ccaggaaccg acccccagtg ggacccaaat taaagagagg atatgcaaag gctaaaccga    2040
tacaggaaag ctctcttaga aggattaaag aggagagccc agaaggccac aaacattaac    2100
aaggtctctg aggtcattca gggaaaagaa gaaagtccag caaaattcta cgagagactg    2160
tgtgaggctt attgtatgta tactcccttt gatcccgata gccctgaaaa tcaacgcatg    2220
attaacatgg ctttagttag tcaaagcaca gaagacatta aagaaaaact gcagaaaaag    2280
gctgggtttg cagggatgaa cacatcacag ttattagaaa tagccaacca ggtgtttgta    2340
aacagggatg cagcaagccg taaggaaaac cacatagaga atgaacgtca ggcccggcga    2400
aacgccgacc tgttagctgc agcaattaga ggggtccccc caaagaggca agggaaaagg    2460
ggggccctgg gaaagaaact cagcctggct gtcagagctt gcagtgtaat cagtgtgctt    2520
atcgtaaaga aataggatat tggaagaaca aatgccctca gctaaaagga aaacaaggtg    2580
actcggagca ggaggctcca gacaaggagg aaggggccct gctcaacctg gcagaagggt    2640
tattggactg aggggggactg ggctcaagga cctccaaaga gcctatggtc aggatgacag    2700 ttggggggtaa agacattgat tttcttgtag ataccagtgc tgaacattcg gtagtaactg    2760
cctcagtcgc ccccttatcc aaaaagacta ttgacatcat cggagccatg ggagtttcag    2820
caaaacaagc tttctgcttg ccccagactt gtactatagg aggacataaa gtgattcatc    2880 agttttttgta catgcctgat tgtcccttgc ccttgtgggg aagagacttg cttagcaaac    2940
tgagagccac tatctctttt acagagcacg gctctttgct gctaaagtta cccggaacag    3000
```

```
gagtcattat gaccettatg ctcccccgag aggaggaatg gagacttttc ttaactgagc    3060
cgggccaaga gataagacca gctctggcta agcggtggcc aagagtgtgg gcggaagaca    3120
accctccagg gttggcagtc aaccaagccc ccgtgcttat agaagttaag cctggggtcc    3180
agccggttag gcaaaaacag tacccggtcc tcagagaagc tcttgaaggt atccaggtcc    3240
atctcaagtg cctaagaacc tttagaatta tagttccttg tcagtctcca tggaacactc    3300
ccctcctgcc tgttcccaag cctgggacca aggactacag gccggtacag gatttgcgct    3360
tggttaatca ggctacagtg actttacatc aacagtacc taacctgtac acattgctgg     3420
ggttgctgcc agctgaggac agctggttca cctgcttgga cctgaaagat gctttcttta    3480
gcatcagatt agccctgag agacagaagc tgtttgcctt tcagtgggaa gatccagagt     3540
caggtgtcac tactcaatac acttggaccc agcttcccca aaggttcaag aactccccca    3600
ccatctttgg ggaggcgttg gctcgagacc tccagaagtt tcccaccaga gacctaggct    3660
gcgtgttgct ccagtacgtt gatgaccttt tgctgggaca ccccacggca gtcgggtgcg    3720
ccaagggaac agatgctcta ctccggcacc tggaggactg tgggtataag gtgtccaaga    3780
aaaaaagctc agatctgccg acagcaggta tgttacttgg gatttactat ccaacagggg    3840
gagcacagcc tgggatcaga agaaagcag gtcatttgta atctaccgga gcctaagacc     3900
agaaggcagg tgagagaatt cttaggggct gtgggttttt gcagactgtg gatcccaaac    3960
tttgcagtat tagctaagcc tttgtatgag gtcacaaagg cggggaccca ggaacctttt    4020
gaatggggat cccagcaaca gcaagccttt catgagttaa aggaaagact tatgtcagtc    4080
ccagccctgg ggctacctga tctgacaaag cctttacat tgtatgtgtc agagagtgaa     4140
aagatggcag ttggagttt aacccaaact gtggggccct ggctgaggcc ggtggcctac     4200
ctctctaaac aactagacgg ggtttctaaa ggatggcccc cgtgtttgag ggccttggca    4260
gcaactgccc tgctagtaca agaagcagat aagctgattc ttgggcaaaa cctgaacata    4320
aaggaccccc atgctgtggt gactttaatg aatactagag gacatcattg gctaacgaat    4380
gctagactta ctaagtacca aagtttgctt tgtgaaaatc cccatataac cattgaagtt    4440
tgtaacaccc tgaaccccgc taccttgctc ccagtattag gatccctgt cgagcatgac     4500 tgtgtagaag tgttggactc agtttactct gggcatcagt agactgggaa ctatacgtgg    4560
atgggagcag ctttgtcaac ccacaagaag agagatgtgc agggtatgcg gtggtaactc    4620
tggacactgt tgctgaagcc agatcgtttc cccagggcac ttcaactcag aaagctgaac    4680
tcattgcttt aattcgggcc ttagaactca gtgaaggtaa gactgtaaac atttacactg    4740
actcttgata tgtcttttta acccttcaag tgcatggagc attatgtaaa gaaaagggcc    4800
tattgaactc tggggaaaaa gacataaaat atcaacaaga aatcttgcaa ttattagaag    4860
cagtatggaa accccacaag gtggctgtta tacattgcgg aggacaccag tgagcttcca    4920
ccttggtggg tttggggaat tcctgcactg acttagaggc tcaaaaagca gcatctgccc    4980
ccttccgggc atcagtgaca gcccccctgc tccctcaagc acctgatctt gtacctactt    5040
attctaaaga agaaaaggac tttctccagg cagagggagg acaagtgatg gaggaaggat    5100
ggatttggtt accagatggg agagtagctg tgccacagct gctaggagct gcagttgtac    5160
tggctgtgca taaaaccacc catctaggtc aggaatcact tgaaaagttg ttaggctggt    5220
atttctacat ctcgcatttg tcagcccttg ccaaaacagt gacgcagcgg tgtgttacct    5280
gccgacagca taatgcgaga caaggtccag ctgttccccc tggcatacaa gcttatggag    5340
cagcccccct tgaagatctc caggtggact tcacagagat gccaaagtgt ggaggtaaca    5400
```

```
agtatttact agttcttgtg tgtacctact ctgggcaggt ggaggcttat ccaacacgaa    5460
ctgagaaagc tcatgaagta actcgtgtgc ttcttcgaga tcttattcct agatttggac    5520
tgcccttacg gattggctca gataatgggc tggtgtttgt ggctgacttg gtacagaaga    5580
cggcaaaggt attggggatc acatggaaac tgcatgctgc ctaccagcct cagagttccg    5640
gaaaggtaga gcggatgaat cggactatca aaatagttt agggaaagta tgtcaagaaa     5700
caggattaaa atggatacag gctcttccta tggtattatt taaaattaga gtacccctt     5760 ctaaaagaac aggatattcc ccttatgaaa tattatatca taggccccct cctatattgc    5820
ggggacttcc aggcactccc cgagagttag gtgaaattga gttacagcga tagctacagg    5880
cttcaggaaa aattacacaa acaatctcgg cctgggtaaa tgagagatgc cctgttaact    5940
tattctcccc agttcaccct ttctccccag gtgatctagt gtggatcaag gactgaaacg    6000
tagcctgttt gtgtccacgg tggaaaggac cccagactgt catcctgagc actcccaccg    6060
ctgtgaaggt agagggaatc ccaacctgga tccaccacag ccgtgtaaaa cctgcagtgc    6120
ctgaaacctg ggaggcaaga ccaagcccag aaaacccctg cagagtgacc ccgaagaaga    6180
caacaagccc tgctccagtc acaccggaa gctgactggt ccacgcacgg ccgaagcatg     6240
cagaagctca tcatgggatt catttttctt aaattttgga cttatacagt aagggcttca    6300
actgatctta ctcaaactgg ggactgttcc cagtgtattc atcaggtcac cgaggtagga    6360
cagcaaatta aaacaatgtt tctgttctat agttattata aatgtatagg aacattaaaa    6420
gaaacttgtt tgtataatgc tactcagtac aatgtatgta gcccaggaaa tgaccgacct    6480
gatgtgtgtt ataacccatc tgagcctcct gcaaccacca ttttgaaat aagaataaga     6540 actggccttt tcctaggtga tacaagtaaa ataataacta gaacagaaga aaaagaaatc    6600
cccaaacaaa taactttaag atttgatgct tgtgcagcca ttaatagtaa aaagctagga    6660
ataggatgtg attctcttaa ctgggaaagg agctacagaa taaaaaataa atatgtttgt    6720
catgagtcag gggtttgtga aaattgtgcc tattggccat gtgttatttg ggctacttgg    6780
aaaaagaaca aaaaggaccc ggtttatctt cagaaggggg aagccaaccc ctcctgtgct    6840
gctggtcact gtaacccact agaactaata attaccaatc ccctagatcc ccattggaaa    6900
aagggagaac gtgtaaccct ggggattgat gggacagggt taaaccccca agttgccatt    6960
ttaattagag gggaggtcca caagtgctct cccaaaccag tatttcaaac cttttataag    7020
gagctgaatc tgccagcacc agaatttcca aaaaagacaa aaaatttgtt tctccaatta    7080
gcagaaaatg tagctcattc ccttaatgtt acttcttgtt atgtatgcgg gggaaccact    7140
atcggagacc gatggccttg ggaagcccga gagttggtgc ctactgatcc agctcctgat    7200
ataattccag ttcagaaaac ccaagctagc aacttctggg tcctaaaaac ctcaattatt    7260
ggacaatact gtatagctag agaagggaaa gactttatca tccctgtagg aaagcttaat    7320
tgtataggac agaagttgta taacagtaca acaaagacaa ttacttggtg gggcataaac    7380
cacactgaaa agaatccatt tagtaaattt tcaaaattaa aaactgcttg gctcatcca     7440 gaatctcatc aggactggat ggctcccgct ggactatact ggatatgtgg gcacagagcc    7500
tacattcggt tacctaataa ataggcaggc agttgtgtta ttggcactat taagtcgtcc    7560
tttttcttat tacccataaa aacaggtgag accctaggtt tccctgtcta tgcctcccga    7620
gaaaagagag gcatagttat aggaaactgg aaagataatg agtggcgccc tgaaaggatc    7680
atacagtatt atgggcctgc cacatgggca caagacggct catggggata ccgaaccccc    7740
```

```
atttacatgc tcaatcggat catacggttg caggccatct tagaaataat tactaatgaa      7800
actggcagag ctttgactgt tttagctcgg caggaaaccc aaacgaggaa tgctatctat      7860
cagaatagac tggccttgga ctacttgcta gcagctgaag gaggagtttg tggaaaattt      7920
aacttaacca attactgcct acaaatagat gatcaaggac aggtggttga aaacatagtc      7980
agggacatga caaggtggc acatgtgcct gtacaggttt ggcacaagtt taatcctgag       8040
tctttatttg gaaaatggtt tccagctata ggaggattta aaaccctcat tgtaggtgta      8100
ttgctagtga taggaacttg cttgctgctc ccctgtgtat tacccttgct ttttcaaatg      8160
ataaaatatt ttgttgttac tttagttcat cagaaaactt cagcacatgt gtattataca      8220
aatcactatc gctctatctc acaaagagac taaaaagtg aggacgagag taagaactcc       8280
cactaaaagt gaaaattctc aaggggggg aaatatggta tgaggtcgcc acttctcctg       8340
ttgtccttct cagtttctcc ccaacctccc cttttcccta gtttataaga caggagaaaa      8400
gggagaaagc aaaagttga aaagaaacag aagtaagata aatagctaga cgaccttggc       8460
accaccacct ggccctggtg gctaaaataa taataatatt attaacccct gaccaaaact      8520
attggtgtta tctgtaaatt ccagacactg tatgagaaaa tactgtaaaa cttttttgttc     8580 tgttagctga tgtatgtagc ccccagtcat gtttctcacg cttacttgat ctattatgac     8640
tttttcatgt agacccctta gagttgtaag cccttaaaag ggctaagaat ttcttttttcg     8700 gggagctcgg ctcttaagac acgagtctgc caatgatccc ggccgaataa aaacctctt      8760 ccttctttaa tctggcgtct gaggagtttt gtctgcgact catcctgcta ca             8812
```

<210> SEQ ID NO 4
<211> LENGTH: 289
<212> TYPE: DNA
<213> ORGANISM: Homo sapiens

<400> SEQUENCE: 4

```
tgggtcaggc aaataagccc acccccactag gaactatgtt aaaaagagaa tttcaagaga      60
gaatttaagg gagattacgg tgttactgtg gcaccaggaa aacttaaaac tttgtgtgaa      120
atagactgga cagcattaga ggtgggttgg cctggacagg tccgttgttt caaaggtatg      180
acagaaggcc acctgtaagc caaggcaccc agaccagttt ctgtacatag acagttacag      240
ctggttttag acccccttcc cccccacagc agtcaagaga atagcagca                 289
```

<210> SEQ ID NO 5
<211> LENGTH: 1700
<212> TYPE: DNA
<213> ORGANISM: Homo sapiens

<400> SEQUENCE: 5

```
gttacaataa tacagggaag agatcttact gtgtggacat ctcatgatgt gaacggcata      60
ctcactgcta aaggagactt gtagctatca gacaaccatt tacttaaaca tcaggctctg     120
ttacttgaag ggccagtgct gcgactgcac acttgtgcaa ctcttaaccc agccacattt     180
cttccagaca atgaagaaaa gatagaacat aactgtcaac aagtaattgc tcaaacctat     240
gccactcgag gggacctttt agtgtttccc ttaactgatc ctgacctcaa cttgtatact     300
gatggaagtt cctttgtaga aaaggacttt caaaaagcgg ggtatgcagt ggtcagtgat     360 aatggaaatac tttaaagtaa tcccctcact ccaggaacta gtgctcagct ggcaaaacta     420
atagccctca ctcgggcact agaattagga gaaggaaaaa gagtaaatat atatacagac     480
tctaggtatg cttacctagt cctccatgcc catgcagcaa tatggagaga aagggaattc     540
```

```
ttaatttcga gggaacacct atcaaacatc aggaagccat taggagatta ttattggctg      600
tacagaaacc taaagaggtg gcagtcttac actgctgggg tcatcagaaa ggaagggaaa      660
gggaaataga agggaactgt caagcagata ttgaagccaa aagagccaca aggcaggacc      720
ctccattaga gatgcttata gaaggacccc tagtatgggg taatcccctc caggaaacca      780
agccccaatg ctcagcagga gaaatagatt ggggaacctc atgaggacac agttttctcc      840
cctcaggatg gctagccacc aaagaaggaa aagtactttt gcctgcagct aaccaatgga      900
aattacttaa aacccttcac caaatctttc acttaggcat tgatagcacc catcagatgg      960
ccaaattatt atttactgga ccaggccttt tcaaaactat caggcagata gtcagggcct     1020
gtgaagtgtg ccaaagaaat aatcccctgc actgcaggcc atacatttca atccctatat     1080
ctttaacctc cttgttaagt ttgtctcttc cagaatcaaa gctgtaaaac tacaaatcgt     1140
tcttcaaatg gagccccaga tgcagtccat gactaagatc taccgtggac ccctggaccg     1200
gcctgctagc ccatgctctg atgttaatga cattgaaggc accctcccca aggaaatctc     1260
aactgcacca cccctactat gccccagttc aacaggaagc agttagagcg gtcttcggcc     1320
aacctcccca aaagcacttg ggttttcctg ttgagagggg ggactgagag acaggactag     1380
ctggatttcc taggccgact aagaatccct aagcctagct gggaaggtga ccgcttccat     1440 cttttaaacac ggggcttaca acttaactca cacatgacca atcagatagt aaggagagct     1500
cactaaaatg ctaattaggc aacaacagga ggtaaagaaa tagccaatca cctgttgcct     1560
gagagcacag cgggagggac aatgatcggg atataaaccc aggcattcaa gccggcaaca     1620 gcaacccccct ttgggtcccc tccctttgta tgggagctct gttttcactc tacttcactc     1680
tatcaaatct tgcaactgca                                                  1700

<210> SEQ ID NO 6
<211> LENGTH: 400
<212> TYPE: DNA
<213> ORGANISM: Homo sapiens

<400> SEQUENCE: 6
gtcaggcctc tgagcccaag ctaagccatc atatcccctg tgacctgcac atacacatcc       60
agatggctgg ttcctgcctt aactgatgat attccaccac aaaagaagtg aaaatggccg      120
gttcctgcct taactgatga cactaccttg tgaaattcct tctcctggct catcctggct      180
caaaacgtcc cccgctgagc accttgtgat cctcaccccct gcccaccaga gaacaacccc      240
cctttttcct ttacctaccc aaatcttata aaacggcccc actcctatct cccttcgctg      300
attctctttt cggactcagc ccacctgaaa cccaggtgaa atagccttgt tgctcacaca      360
aagcctgttt ggtggtctct tcacatggat gtgagtgaaa                            400

<210> SEQ ID NO 7
<211> LENGTH: 688
<212> TYPE: DNA
<213> ORGANISM: Homo sapiens

<400> SEQUENCE: 7
ttatagtagg tagctagtca ggcatgagca gggcaggaga gggttccacc tgaccaggaa       60
tgtcaggtga ccatcaggtg atggacagga ggttgttaaa tgtttctcta aaatagtaat      120
tggtcacagc cagtgaaagg gaaaggcagt ctccatatag atagaaaaaa acctgcaact      180
ggtgatcagc agcttcccaa taagatctga agagatgggt gagtgagctc aagcatgcac      240
```

| | |
|---|---:|
| attaagaggc aaaatggtgg agtttaactg gtatatgacc ttcctctagg aatgctagac | 300 |
| tggtaaggga agaatgcctc aagtgagtat gggcacaact ccagtaagca cactgcacag | 360 |
| gctcctctcc caagcgctag caggccactg cgcatgtgaa cagcccaccc caagggaaga | 420 |
| atcaggggag aagggacaca agaccctgga cgtaccaatg tataaaacct caagtcaaaa | 480 |
| ggccaaactg cacaataacc gttcgagtca ccagcttggc cctcttccag gtgcgcgttc | 540 |
| cttccttctg ttcctgctct aaaactttttt aataaatttt cactcctcta aaacttctcg | 600 |
| gtctccctac cttatgcccc tcggccgaat tctttcttct gaggaggtaa gaattgaggt | 660 |
| tgctgcagat gcatcagatt cgctactg | 688 |

<210> SEQ ID NO 8
<211> LENGTH: 5248
<212> TYPE: DNA
<213> ORGANISM: Homo sapiens

<400> SEQUENCE: 8

| | |
|---|---:|
| cctctttggg tccctcccct ttgtatggga gctctgtttt cactctatta aatcttgcaa | 60 |
| ctgcactctg ttctggtccg tgtttgctat ggctcaagct gagcttttcc tcaccatcca | 120 |
| ccactgctgt ttgctgccct tgcagacccg ctgctgactt ccatccctcc ggatccggca | 180 |
| gggtgtccgc tgtgctcctg atccagcgaa ggcacccatt gccactaccg attgggctac | 240 |
| aggcttgcca ttgttcctgc atggctaagt gcccaggttg gtcccagtcg agccaaacac | 300 |
| tagtcactgg gttccacggt tctcttccat gacccacggc ttctaataga gctgtaacac | 360 |
| tcaccacatt gcccaagatt ccattcattg gaatccgtga ggccaagaac cccaggtcag | 420 |
| agaatacgag gcttgccgcc atcttggaag ctgactgcca ccatcttggg agctctggga | 480 |
| gcaaggaccc cctggtaaca tttggcgacc atgaagggac ctccaaagtg atgggaaatg | 540 |
| ttcccccaa ggcaaaaatg cccctaagat ctattctgga gaattgggtc aaatctgacc | 600 |
| ctcagatgtt acaaaacaaa caacttatat tcttctgcag cactgcctgg tcatgatatc | 660 |
| ctcgtggggg atctccttcc aaggggggaga aacctggcct cctgagggaa gtataaatta | 720 |
| taacaccatc ttacagctag acctctttttg tagaaaagaa ggcaaataga gtgaagtgcc | 780 |
| atatgtacaa attttccttt cattaagaga caactcacag ttatgtaaaa agtgtgatttt | 840 |
| atgccctaca ggaagccctc agagtttacc tccctacccg ggcatccccc cgactccttc | 900 |
| cccaattaat aaggatgccc cttcaaccaa aatggtccaa aaggagatag acaaaggggt | 960 |
| aaacaatgaa ccaaagagtg ccaatattcc ctgattatgc cacctccaag tggtgggagg | 1020 |
| aggagaattc ggcccagcca gagtgcatgt accttttttct ctctcagact tgaagcaaat | 1080 |
| taaaatagac ctaggtaaat tctcatataa ccctgatggc tatattgatg ttttacaagg | 1140 |
| gttagggcaa tcctttgatc tgacatggag agatataatg ttactgctaa atcagacact | 1200 |
| aaccccaaat gagagaagtg ccgccataac tgcagcccga gagtttggtg atctctagta | 1260 |
| tctcagtcag gtcaattata ggataaaaac agaggaaaga gaatgattcc ccacaggcag | 1320 |
| caggcagttc tcagtgtaga ctctccactgg gacacagaat cagaacatgg agactggtgc | 1380 |
| caaagacatt tgctaacttg cgtgctagaa gtactaagga aaactaggaa gaagcctatg | 1440 |
| aattattcaa tgatgtccac tataacacag ggaaaggaag aaaatactac cgcctttctg | 1500 |
| gagagactaa gggaggcatt gagaaagcat acctctctgt cacctgactc tattgaaggc | 1560 |
| caactaaact taaaggataa gtttatcact cagtcagctg cagacattag aaaaaaactt | 1620 |
| caaaagtctg ccttaggccc agagcaaaac ttagaaaccc cattgaactt ggcaacctcg | 1680 |

```
gtttttttaa tagagatagg gaggagcagg cagaacaaga caaatgggat aaaaaaacag   1740
aaggccactg ctttagtcat ggccctcaga caagtggact tcggaggctc tgggaaaggt   1800
aaaagctggg caaatcgaat gcctaatagg tcttgcttcc agtgtggtct aaaaggacac   1860
tttaaaaaag attgtccaag tagaaatgag ccgccccctc gtccatgccc cttatgtcaa   1920
gggaattact ggaaggccca ctgcccaagg ggatgaagtt cctctgagtc agaagccact   1980
aaccagatga tccagcagca ggactgaggg tgcctggggc aagtgccagc ccatgccatc   2040
accctcacag agccccaagt atgcttgacc attgagggcc aggaggttaa ctgtctcctg   2100
gaccctggtg cagccttctc aatcttactc tcctgtcctg gacaactgtc ctcctgatct   2160
gtcactatct aaggggtcct aggacagcca gtcactagtt gcttctcttg tctactaaat   2220
tgtgactggg gaactttact cttttcacat gctttttctaa ttatgcctga aagccccact   2280
cccttgttag ggagagatat tctagcaaaa acaggggcca ttatacacct gaacatagga   2340
gaagaaacac ccgtttgttg tcccctgctt gaggaaggaa ttaatcctga agtctggaca   2400
acagaaggac aatatggaag agcaaagaat gcctgtcttc ttccaattaa actaaaggat   2460
tctgcctcct ttccctacca aaggcagtac ccgcttagac ctgaggccca acaaggactc   2520
caaaagattg ctaaggacct aaatgcccaa ggcctagtaa gaccatgcag tagcccctgc   2580
aatactccaa ttttaggagt acagaaaccc aatgggcagt ggaggttagg caagatctca   2640
agattatcaa tgaggctgtt gttcctctat acccagctgt acctaaccct tatactctga   2700
tttcccaaaa acctgaggaa gcaaagtggt ttatactcct ggaccttaag gatgcctttt   2760
tctgcatccc tgtacatcct aactctcaat tcttgtttgc ctttgaagat ccttcaaacc   2820
caacatctca actcacctgg actgttttac cccaagggtt cagggatagc ccccatctat   2880
ttggccaggc attagcccaa gacttgagcc agttcttgta cctggacact cttgtccttt   2940
ggtacgtgga tgatttactt ttagccaccc attcagaaac cttgtgccat caagccaccc   3000
aagcgctctt aaatttcctt gccacctgtg gctacaaggt ttccaaacca aaagctcagc   3060
tctgctcaca gtaggttaaa tacttagggc taaaattatc caaaggcatc agggccctca   3120
gtgaggaatg tatccagccc atactggctt atcctcatcc caaaaccta aagcaactaa   3180 gagtgttcct tggcataaca ggcttctgcc aaatatggat tcccaggtat ggcgaaatag   3240
ccaagccatt atatacacta attaaggaaa ctcagaaagc caatacccat ttagtaagat   3300
ggacaccaga agcagaagca gctttccagg ccctaaagaa atccctaacc caagccccag   3360
tgttaagctt gccaacgggg caagacttt ctttatatgt cacagaaaaa caggaatagc   3420
tctaggagtc cttacacagg tccaagggac aagcttgcaa cctgtggcat acctgagtaa   3480
ggaaactgat gtagtggcaa agggttggcc tcattgttta caggtagggg cagcagtagc   3540
agtcttagtt tctgaaacag ttaaaataat acagggaaga gatcttactg tgtggacatc   3600
tcatgatgtg aacggcatac tcactgctaa agaagacttg tggctgtcag acaaccattt   3660
acttaaatag caggttctat tacttgaagt gccagtgctg cgactgcaca tttgtgcaac   3720
tcttaaccca gccacatttc ttccagacaa tgaagaaaag atagaacata actgtcaaca   3780
agtaattgct caaacctatg ctgctcgagg ggaccttcta gaggttccct tgactgatcc   3840
cgacctcaac ttgtatactg atggaagttc cttggcagaa aaaggacttt gaaaagcggg   3900
gtatgcagtg atcagtgata atggaatact tgaaagtaat cgcctcactc caggaactag   3960
tgctcacctg gcagaactaa tagccctcac ttgggcacta gaattaggag aaggaaaaag   4020
```

```
ggtaaatata tattcagact ctaagtatgc ttacctagtc ctccatgccc atgcagcaat    4080
atggagagag agggaattcc taacttctga gggaacacct atcaaccatc aggaagccat    4140
taggagatta ttattggctg tacagaaacc taaagaggtg gcagtcttac actgccaggg    4200
tcatcagaaa gaagaggaaa gggaaataga aggcaatcgc caagcggata ttgaagcaaa    4260
aaaagccgca aggcaggact ctccattaga aatgcttata gaaggacccc tagtatgggg    4320
taatcccctc tgggaaacca agccccaata ctcagcagaa gaaatagaat gggaacctca    4380
tgaagacata gtttcctccc ctcaggatgg ctagccacca aagaaggaaa aatacttttg    4440
cttgcagcta accaatggaa attacttaaa acccttcacc aaacctttca cttaggcatt    4500
gacagcaccc atcagatgac caaactatta tttactggac cagacctttt caaaactatc    4560
aagcagatag tcagggcctg tgaagtgtgc caaagaaata atcccctgca ctgtaggcca    4620
tacatttcaa tccctctatt tttaatctcc ttgataactt tgtctcttcc agaatcaaag    4680
ctgtaaaact acaaatcgtt cttcaaatgg agccccagat gcagtccatg actaagatct    4740
accgcagacc cctggaccag cctgctagcc catgctctga tgttaatgac atcgaaggca    4800
cccctcccga ggaaatctga actgcacaac ccctactatg ccccaattca gcaggaagca    4860
gttagtgcag acatcagtcg acttccccaa cagcacttgg gttttcctgt tgagagaggg    4920
tactgagaga caggactagc tggatttcct aggccaacta agaatcccta agcctagctg    4980
ggaaggtgac cgcatccacc tttaaacacg gggcttgcaa cttagagcac gccaacaaat    5040
caggtagtaa agacagctcg ctaaaatgct aattaggcaa aaacaggagg taaagaaata    5100
gccaatcatc tatcacctga cagcacacgc gagggaaaa tgatcagaat ataaacccag    5160
gcatttgaac catcaacggc taccctcttt ggatcccctc cctttgtatg ggagctctgt    5220
tttcacacta ttaaatcttg caactgca                                      5248

<210> SEQ ID NO 9
<211> LENGTH: 928
<212> TYPE: DNA
<213> ORGANISM: Homo sapiens

<400> SEQUENCE: 9
gtggggaaaa ggaggacaga tcagactgtt actgtgtcta tgtagaaaga aatagacata     60
agagactcca ttttgttctg tactaagaaa aattcttctg ccttgagatg ctgttaacct    120
gtaaccctag ccccaaccct gtgctcccag aaacatgtgc tgtgtcacac gtgggtttag    180
ggctatgcag gatgtgcttt gttaaacaga tgcttgaagg cagcatgctt gttaaaagtc    240
atcaccactc tctaatctca agcacccagg gacacaatac actgcggaag gctgcaggga    300
cctctgccta gaaaagccag gtattgtcca aagtttctcc ccatgtgata gcctgagata    360
aggcctcgtg ggaagggaaa gaccagaccg taccccagcc cgacacccgt aaagggtctg    420
tgctgaagag gattagtata agaggaaggc cttttttgcag ttaagaggaa ggtatctgtc    480
tcctgctcgt ccctgggcaa tggaatgtct cggtgtaaaa cccgatggta tgttccatcc    540
accgagatag gggaaaaccg ccttagggct ggaggtgaca catgctggca gcaatactgc    600
tctttaatgc accagatatg tttatgtatg agcacatcaa ggcacagcac atttcctaac    660
cttgtttatg acacagacat tgctcacat gttttcctgc tgaccctctc cccactgtta    720
ccctattgtc ctgccacatc cccgtctccg agatggtaga gataatgacc aataaatact    780
gaaggaactc agagacccgg ccggcgcggg tctcctgagc ccacttttct ttctgtgtac    840
tttgtctctg tgtctcttc ttttctcagt ctctcgtccc acctgacaag aaacacccac    900
```
aggtgtggag gggcaggcca ccccttca       928

<210> SEQ ID NO 10
<211> LENGTH: 2743
<212> TYPE: DNA
<213> ORGANISM: Homo sapiens

<400> SEQUENCE: 10
taggtcagat gcaaagtaag cacaccccaa tgggaactat gttaaagaat ttcaagaaag       60
gatttaatgg agactatgga gtcactatga ctccaggaac acttagaagt ttgtgtgaaa      120
tagactggcc agcattagag gtaggttagc catcagaagg aagcctagat aggtcttttgg     180
tttctaaggt atggcaaaag gtaacctgta agccaaggca cccagaccag gttccataca     240
tagacagtta cagctgggttt tagaccccctt tcccccccacg gtagttaaga gaacagcagc     300
ataagtggct ggcagagaca aggaaagacc agcagagaga agaaaaaaaa aaaaaagcca     360
tctataccaa ttgtaagtta atttagacga aacaagatct tattattagc aaaggataat     420
tgaaatccca aacttacaag gttttcaaca aatgtgaagt ttgctaaaag ttaacagtgt     480
aacatgtatt atgataactt ctaatcttgt ggccttagac agtctagtcc aaagacataa     540
agaatgtttg ctttaaaaaa aaaaaaggtt gggggaggca gaatttacat ataaaaaaag     600
ttatatggta aattccttgtc ccgaaataaa ttaactggtt gtttaaagaa aaaaatgttt     660
ataataagtc aaaaattgag acatgttaaa aaaattgtcc gtgaaagtcg tgaaagaaaa     720
aatgttataa aaaaatttta tgcaaaaaat gttgtataat ttaaaagtga taaggcctcc     780
tgagtactat tgaagaaagt ttatgtgcaa ggtgtataaa aaaaagtaaa atataccttt     840
ggtaaaaaga ttataaggag gcataagaat gtggatttttt acctacatta aaaggttaaa     900
aaaattattg ttttgaaagt ttaagcaagt tttaaaatgt taattgtaaa gaaaattctg     960
tgtataaaca tattagctaa agttaaaaag gtatcaccca gtttttctgt gaactggaca    1020
ttaaagtaaa aatgcaacag gttttttttc ttaaagcatc aacctgctct ttaacaaaaa    1080
ttataaaagg ttaaaagag tctataaaat cttaccttat ggtcaaacat gaaaaattgg    1140
ataaatatgt ctacaaggtt ttcttaaaat taagtttaac attaataaca ctaatataaa    1200
ggtaaaattt agcttatctg gtataaaaat catacaagaa gcattattaa acataaaatg    1260
gtgtttagct ttcttttggtc taaaaactaa taaaaattgg tgctaaagga aacattcatt    1320
ttactgagag atcatagaag ttaaagactt aaaacaaact ttggcaatga agagagcata    1380
ccaagatgca aatgcctggt tgaaatggat caaatattcc atctgcacgt taaacaaaag    1440
caattgttat gcttgtgcac atggcaggcc agaggccctg attgtccccc ttccactaag    1500
gtggtcctcc agtcgaccag gtgtgggctg catggtagct cttttctagg attctacagc    1560
ctggagtaat aagtcatgcc aagctctctc tgctatatcc tgaagtccct gtgggtcagc    1620
ccctgagggc catccagttt ccgtctccca acactaagtt cacttcatgt ctctgatggc    1680
agggaggaga cagcattcct tggagacctg aaaggatgcg gggagcttaa aaattttcaa    1740
gagcttatca atcagtcagc tcttgttcat ccccgagcag atgtgtggta gtattgtggt    1800
ggacctttac tgggcactct gctgaataac tagagtggca attgtgcttt agcccatttg    1860
gctatccctt tcaccctggc atttcatcaa ccagaggtaa atatatatat ataaataaag    1920
acatcataaa gtgagagaag gcccttatag gtctttcaac tctcacatct atttagatgc    1980
aattggaacc ctgcaaggaa taccagatca atttaaagct tgaaatcaaa tagttacaag    2040

-continued

```
atttaagtca atattttagt agacgacagt caataaaaat gtattagata aactacatct    2100
attacaacca acagcaatga gcttttcatg agtttaaaag aaaaactcat gtcggtccca    2160
gccctgaagc tacctgacct gacaaaactc tttacactct atatgtcaga aagagaaaaa    2220
atagcggttg gagttttaac ccagactgta gggccctggc caaggccagt ggcctatctc    2280
tcaaaacaac tagacagggt ttccaaaggc tggcccccat gtccaagggc cctggcagca    2340
actgccctgt tagcacaaga agccataagc taactcttag gcaaaaccta acataaagt     2400 ctccccatgc tgtggtgatt ttaataaata ccaaggaca tcattagcta ataaatgcta     2460
gactaactag ataccaaagc ttgctctgtg aaaatccctg cataaccatt gaagtttgca    2520
acaccctaac cctgccacct tactcctggt atcagagagc ccagttaaac ataactgttt    2580
agaggtgctg gactcagttt attctagtag gcccaacctc cgagaccatc cttaaacatc    2640
agtagactga gagctgtacg tggataggag cagcttcgcc aaccctgca aagtgactct      2700 gaagaagacg acaagccctg ctccagtcac acccggaagc tga                       2743

<210> SEQ ID NO 11
<211> LENGTH: 2295
<212> TYPE: DNA
<213> ORGANISM: Homo sapiens

<400> SEQUENCE: 11
tagttcaggc acaaagtaag cccaccccac taagaaatat gttaaagaat ttcaagaaag      60
aatttaaagg agattatggt gtaactgtga ccccaggaaa acttagaact ttgtgtgaaa     120
tagactggcc agcatttgag gtaggttagc catcagaagg aagcctggat gggtccctag     180
tttcaaagat atggcacaag gtaacctgta agccaaggca cccagaccag tttcagtaca     240
cagacagtta cacctggttt tagacctcct cccccgccc ccacagtag ttaaaagaac       300 agcagcataa gtggctggca gaggcaagaa aagaccagca gagagaaaaa gaggccatct    360
ataccaattc taagttaatt tagactaaac aaggtcttat taatagcaaa ggataattga    420
agtcccaaac ttacaaggtt ttcaacaaaa gtgaagtttg ctaaaagtta acagcgtagc    480
atgtattata gtaacttcta atctggtagc cttagacagt ctagtccaaa gacataaagt   540
ttgctttaaa aaattttttt atgcaaaaaa tgtataattt aaaagtaata aggcctccta    600
ttattgaaga aacagtttat gtacaaggtg tataagaaaa gtaaaatata cctatagtaa    660
aaagattata aggaggcata agaatgtgga ttttaccta tattaaaaag ttaaaaaaat     720
tattgtttga agtttaagc aagttttaaa acattaattg taaagaaaat tctgtgtgta    780
aacatattag ctaaagttaa aaaggtatca tccagttttt ctgtgaaacg gacatcaaag    840
taaaaatgca acaggttttt tcttaaagca tcaacctgct cttaacaaa aattacaaaa     900 agttaaaaag agtctacaaa atctaacctt atggtcaaac atgaaaaatt agataaatat    960
gtctacaaag tttcattaaa attaaatta acattagtaa cacactaata taaagtaaa    1020 atttagctta tctggtataa aaatcataca agaagcatta ttaaatataa aatggtgttc    1080
agctttcttt ggtctaaaaa ctaataaaaa tcggtgctaa aggaagcatt cattttacta    1140
gaggatgata gaagttaaag acttaaaaca aactttggca attgagacag cataccaaga    1200
tgcaaatgcc tggttgaaat agatcaaata ttccatctgc acattaaaca aaagcaattg    1260
ttatgcttgt gcacatggca ggccagaggc cctgattgtc cccttccac taaggtggtc     1320 ctgtagttga ccaggtgtgg gctgcatggt agctcttttc caggattcta cagcctggag    1380
taacatatag ctctctctgc tatatcccga agtccctgcg gatcagcccc cgagggcctt   1440
```

```
ccagcttccg tctcccaata ctaagttcac ttcttgtatc tcacggcaga gaggagattt    1500
agcattcctt ggagacctga aaggatgcag tgagcttaag aatttcaag agcttatcaa    1560
```
<br>
```
ccagcttccg tctcccaata ctaagttcac ttcttgtatc tcacggcaga gaggagattt    1500
agcattcctt ggagacctga aaggatgcag tgagcttaag aattttcaag agcttatcaa    1560
tcggtcagcc cttgttcatc tctgagcaga tgtgtggtgg tattgtagta gacctttagt    1620
aggcactctg ccgaataact agagtggcac ttatggttta gtccatttca ccctggtatt    1680
tcatcaacca gaaaaaaaaa aagaaaaac tcatgtcagc cccagccctg aggctacctg    1740
acctgacaaa actctttgca ctctatgtgt cagaaagaaa aaaaaaatg gcagttgaag    1800
ttttaaccca gactgtaagg ccctggccaa ggccagtagc ctgactctca aaacaactag    1860
acgaggtttc ccaaggctgg cccccatgtc caagggccct ggcagcaatg gccctgttag    1920
cacaagaagc agataagcta actcttaggc aaaacataaa cataaagtcc ctttaataaa    1980
taacaaaaga catcattagc taataaacgc tagactaact agataccaaa gcttgctctg    2040
tgaaaatccc cacataacca ttgaagtttg caacacccta accccgccac cttactccta    2100
gtatcaaaga gccagttaa acataactgt ttagaggtgc tggactcagt ttattctagt    2160
gggcccaacc tctgagacca cccttaaaca tcagtagact aggagctgta cgtagataag    2220
agcagcttcg ccaaccctg caaagtgact ctgaagaaga tgacaagccc tgctgcagtc    2280
acacccggaa gctga                                                   2295

<210> SEQ ID NO 12
<211> LENGTH: 752
<212> TYPE: DNA
<213> ORGANISM: Homo sapiens

<400> SEQUENCE: 12
tgcttgaagg cggcatgctc attaagagtc atcaccactc cctaatctca agtacccagg     60
gacacaaaca ctgcagaagg cctcagggac ctctgcctag gaaagccagg tattgtccaa    120
ggtttctccc catgtgatag tctgaaatat ggcctcgtgg gaagggaaag acctgaccat    180
cccccagccc gacacccgta aaggttctgt gctgaggaga attagtaaaa gaggaaggaa    240
tgcctctttg cagttgagac aagaggaagg catctatctc ctgcgcgtcc ctgggcaatg    300
gaatgtctca gtgtaaaacc caattgtata ttccatctac tgagataggg gaaaaccgcc    360
tcaggggtgg aggtgggaca tgcggtgggc aatactgctc tttaaggcat tgagatgttt    420
atgtgtatgc atatctaaag cacagcactt aattctttac cttgttcatg atgcagagag    480
ctttgttcac gtgtttacct gctgaccttc tctccactat tatcctatga ccctgccaca    540
tccccctctc tgagagagaa acacccaata atgatcaata aatactaagg gaacttagag    600
tccggcggga tcctccgtat gctgaacgct ggtcccctgg gcccccttat ttctttctct    660
atactttgtc tccatgtctt tttcttttcc aagtctctcg ttccacctaa caagaaacac    720
ccaaaggtgt ggaggggcaa cccaccccctt ca                                752

<210> SEQ ID NO 13
<211> LENGTH: 438
<212> TYPE: DNA
<213> ORGANISM: Homo sapiens

<400> SEQUENCE: 13
gtcaggcctc tgagcccaag ttaagccatc atatcccctg tgacctgcat gtatacatcc     60
agatggcctg aagtaactga agaaccacaa aagcagtgac aatagccaat tcctgcctta    120
actgatgaca ttccaccatt gtgatttgtt cctgccccac ccaaactgat caattgacct    180
```

```
tgtgacattc cttctcctgg acaatgaatc tcagagctct ccacagagca ccttgtgacc      240 cccacccect gcttgcaaga gaaaaaccac ctttaactgt aatttteeac tacttaccca      300 aatcctataa cactgcacca ccectatctc cctttgctga ctcetttttc ggactcagga      360 cacttgcacc caggtaatta aaagctttat tgctcacaca aagcctgttt gctggtctct      420
tcaaacggat gcacgtaa                                                     438

<210> SEQ ID NO 14
<211> LENGTH: 3552
<212> TYPE: DNA
<213> ORGANISM: Homo sapiens

<400> SEQUENCE: 14
gtcagtcctc tgagcccaag ctaagccatc attatctcct gtgacctgca tgtacatatc       60
cagatggccg gttcctgcct taactgatga cattaccttg tgaaattcct tctccttgct      120
catcctggct ccaaagctcc cctactgagc accttgtggc cccactcct  gcctgccaga      180 gaacaacccc cctttttcct ttacctaccc aaatcctata aaattgcccc accectatct      240 cccttcactg actctctttt tggactcagc ccacctgtac ccaggtgaaa taaacagctt      300
tactgctcac acaaagcctg tttggtggtc tcttcacatg gatgcatgtg aaatttggtg      360
ccgtgactgg gatcgaggga cttcccttgg gagatcaatc ccctgtcctc ctgctctttg      420
ctctgtgaga aagatccacc tatgacttca ggttctcaga ctgaccagcc caagaaacat      480
ctcaccaatt tcaaatctgg taagcggctt cttttactc tcttctccaa cctccctcac       540
tatccctcca cctctttctc ctcccaatct tggcaccaca cttcaatctc tcccttctct      600
taatttcaat tcctttcatt ttctggtaga gacaaagggg acacgttta tctgtggacc       660 caaaactctg gcaccagtca cggactaggg aaggcagcct ttccttggtg tttaatcatt      720
gcagggacac ctctctgatt attcaccgag gtttcagagg tgtcagacca tgcagggatg      780
cctgccttgt tccttcaccc ttagcagcaa gacctgcttt tctgggggag ggacaagaac      840
ccctcaaccc cttctccttc acccttagca gcatgtccca cttttctggg ggagggacag      900
gaaccccgac ctcttatctc tgcaccccga tcccttattt ccatgccctg acctcatctc      960
tgtgtcccga tcccttattt ccacaacctg acctcttatc tctgcacccc aaccctttat     1020
ttctgtgccc ccaaccettt ccctctattc tggaaggcaa gaaccctcca cccccttctct    1080 ccatgtctct actctctttt tctctaggctt gcctccttca ctatgggcaa gcttccgcct    1140 tccattccc tttcttctcc cttacgctgt gttcttcaaa acctaaaacc tcttcaactc     1200
acacctgacc taaaacctaa atgccttatt ttcttctaca atgctacttg accccaatac    1260
aaactcagca gtggttccaa atagccagag aatggcactt tcaatttttc catcctacaa    1320
gatctagata cttcttgtca taagatgggc aaatgatctg agatgcctga tgtccaggca   1380
ttcttttaca cattggtccc tccctagtct ctgttcccag tgcaactcat ccgaaatctt   1440
cctcctttcc ctcccacctg tccctcagt  cccaaccca  agtgtcgctg agtctttcta   1500
atcttccttt tctacagacc catctgacct ctcccatcct ggccagcctg agctaggtcc    1560
caattcttcc tcagcctcca cttctccacc ctataatcct tttatcacct ccctcctca    1620 cactgggtct ggcttacagt ttaattccgt gactagccct ccccacctg cccagcaatt    1680 tactcttaaa caggtgcctg gagctaaaga catagtcaag gttaatgctc ctttttcttt    1740
atcccaaatc agatagcatt tagcctcttt ttcatcaaat ataaaaatcc accccagttc    1800
atggctcgtt tggcagcaac cctgagatgc tttacagccc tagaccctaa aacgtcaaaa    1860
```

```
ggccgtctta ttctcaatat acattttatt acccaatctg ctcccgacat taaataaaac    1920
tccaaaatta aattccggcc ctcaaacccc acaacaggac ttaattaacc tcaacttcaa    1980
ggtgtacaat aatggagtag aggcagccta gcagcaacat atttctcagt tgcaattcct    2040
tgcctccact gtgagacaaa gcccagccaa atctccagca cacaagaact tccaaacgcc    2100
taaagcgcag tggccaggca ttcctccaga accacctacc ccaggagctt gctacaagtg    2160
ccagaaatct ggccaccaga ccaaggaatg cctgcagccc gggattcctc ctgagccatg    2220
tcccatctgt gcgagaccca actagaaatc ggactgttca actcacctgg cagccactcc    2280
tagagcccct ggaactccag cccaaggctc tctgactgat tccttcccag atcttcttgg    2340
cttagcagct gaagactgac actgcctgat agatcacctc ggaagcctac aggaccatca    2400
cagacgctct aggtaactct cacagtggag gataagtcca tccccttctt aatcaatacg    2460
gaggctaacc actccacatt accttctttt caagggcctg tttcccttcc ctccataatt    2520
gttgtgagta ttgacagcca ggcttctaaa cctcttaaaa ctccccaact ctggtgccaa    2580
cttagacaat actcttttaa gcactccttt ttagttgtcc ccacctgccc agttccctta    2640
ttaggctgag acactttaac taaattatct gcttccctga ctattcctgg actacagcca    2700
catctcattg ccacccacct taacccacaa gtagaagata cctctattcc ctccttggca    2760
acctatcatg caccccttac catctcatta aaacctaatc actcttaccc ctctcaatgc    2820
caatatccca tcccacagca tgctttgaaa ggattaaagc ctgttatcac tcacctgcta    2880
cagcatggcc ttttaaagcc tataaactct ccttacaatt cccccatttt acctgtccta    2940
aaaccagaca agccttacaa gttagttcaa gatctgtgcc ttatcaacca aattgttttg    3000
cctatccacc ccaaggtgcc aaacacatat actctcctat cctcagttcc tccctccaca    3060
acccattatt ctgttctgaa tctcaaacat gctttcttta ctattccttt gcacccttca    3120
tcccagtcac tcттcgcтттт cacttggact gaccctgaca cccatcaagc tcagcaaatt    3180
acctgggctg tactgtcgca aagcttcaca gacagccccc attacttcag tcaagcccaa    3240

atttctccct tatctgttac ctatctcagc ataattctca taaaaacaca cgtgctctct    3300
ctgccgatcg tgtgtgactc atctctcaaa ccccaacccc ttctacaaaa caacaactcc    3360

тттсстттсст gtgcatggtt ggатасттттс acctttagat атстggттттт gccatcctaa    3420 caaaccatt atataaactc acaaaaggaa acctagctga ccccatagat cctaaatcct    3480

ttccccactc ctctttctgt tccttgaaga cagctttaaa gactgccccc accctagtct    3540 tggтттсссtg ac                                                      3552

<210> SEQ ID NO 15
<211> LENGTH: 210
<212> TYPE: DNA
<213> ORGANISM: Homo sapiens

<400> SEQUENCE: 15
caccatgcac cttgtgaccc cctcctctgc tgaggataac cacсттттaac tgtaactttc    60 cacgcctacc caagccctat aaagctgccc ctctcctatc tcccttcact gactctcttt    120

tcggactcag cccacttgca cccaagtgaa ttaacagcct tgttgctcac acaaagcctg    180

attgggtgtc ttctatacgg acacgcgtga                                    210

<210> SEQ ID NO 16
<211> LENGTH: 356
<212> TYPE: DNA
```

<213> ORGANISM: Homo sapiens

<400> SEQUENCE: 16

| gttaggcctc | tgagcccaag | ctaagccatc | atatcccctg | tgacctgcat | gtacacgtcc | 60 |
| agatgcccag | ttcctgtctt | aactgatgac | attaccttgt | gaaattcctt | ctcctggctc | 120 |
| atcctggctc | aaaagctccc | caactgagca | ccttgtgacc | ccaccctg | cctgccagag | 180 |
| aaccccttt | gactgtaatt | ttcgtttacc | tacccaaatc | ttataaaaca | gcctcacccc | 240 |
| tatctccctt | cgcagactct | ttttggactt | agcccgcctg | cacccaggtg | aaataaacag | 300 |
| ccttgttgct | cacacaaagc | ctgtttggtg | gtctctttac | atggacacga | gtgaaa | 356 |

<210> SEQ ID NO 17
<211> LENGTH: 430
<212> TYPE: DNA
<213> ORGANISM: Homo sapiens

<400> SEQUENCE: 17

| gtcaggcctc | tgagcccaag | ctaagccatc | atatcccctg | tgacctgcac | gtatacatcc | 60 |
| agatggcctg | aagtaactga | agaatcacag | aagaagtgaa | aatggcccat | tcctgcctta | 120 |
| acttatgaca | tccaccatt | gtgatttgtt | gctgccccac | cttaactgag | cgattaacct | 180 |
| tgtgaaattc | cttctcctgg | cttagaaact | ccccactga | gcaccttgtg | acccccacct | 240 |
| atgcctgcaa | gagaaaaacc | ccttttgact | gtaattttcc | actacccaca | caaatcctat | 300 |
| aaaacggccc | caccctatc | tcccttcgct | gactctttct | ggactcagcc | cgcctgcacc | 360 |
| cagttgaaat | aaacagcctt | gttgctcaca | caaagcctgt | ttggtggtct | cttcacacgg | 420 |
| atgcgcgtga | | | | | | 430 |

<210> SEQ ID NO 18
<211> LENGTH: 2689
<212> TYPE: DNA
<213> ORGANISM: Homo sapiens

<400> SEQUENCE: 18

| gggtcaggca | caaagtaagc | ccaccccact | gggaactatg | ttaaaaaaaa | aaaaattcaa | 60 |
| gaaagaattg | aggaagcctg | acaggtcccc | ttgtttcaaa | ggtatggcac | aaggtaacct | 120 |
| gtaagccaaa | gcacccagac | cagtttccgt | acacagacag | taacagctgg | ttttagaccc | 180 |
| cctttcctcc | ccacagtagt | taaaagaaca | gcagtataag | cagctggcag | aggcagcaga | 240 |
| gagaaaagga | aagaccagca | gagagaaaaa | aaggccatct | aaaccaattg | taagttaatt | 300 |
| tagactaaac | aaggtcttat | taatagcaaa | ggataattga | aatcccaaac | ttacaaggtt | 360 |
| ttcaacaaaa | gtgaagtttg | ctaaaagtta | acagtgtaac | atgtattatg | gtaacttcta | 420 |
| atcttgtggc | cttagtccca | aagacataaa | gaaagtttgc | tttaaaaaaa | ggaatggtta | 480 |
| tcttcaaaaa | aaaaaaaaaa | aggggggggg | ggcaggcaga | atttaggtaa | aaagagtgtt | 540 |
| atatggtaaa | ttcttgtcct | gaaataaatt | aactggttgt | ttaagaaaaa | aaaaaatgtt | 600 |
| tgtaataagt | cagaaagttg | agacatgttg | aaaaattgtc | ggcgaaagtc | atgaaagaaa | 660 |
| aaatgttata | aaaattgtat | gcaaaaaatg | ttgtataatt | taaagtaat | aaggcctcct | 720 |
| gagtaccatt | aaaaaaaaca | gtttatgtgc | gaagtgtata | agaaaagtaa | aatataccct | 780 |
| tggtaaaaag | attataaagg | ggcataataa | tgtagatttt | tacctacatt | aaaaggttaa | 840 |
| aaaaattatt | gttttaaaag | tttaagcaag | ctttaaaatg | ttaattataa | agaaaattct | 900 |
| gtgtgtaaac | atattagcta | aagttaaaaa | gatatcatcc | agttttctg | tgaactggac | 960 |

```
attaaagtaa aaatgcaaca agttttctt aaagcatcaa cctgctcttt aacaaaaatt    1020
ataaaagatt aaagagtcta taaaatctta ccttatggtc aaacatgaaa aattggataa    1080
atatgtctac aaggctttat taaaattaag tttaacatta ataacacact aatataaagg    1140
taaaatttaa cttatctggc ataaaaatca cacaagaagc attattaaat ataaaatggt    1200
gtttagcttt ctttggtcta aaaactaata aaaataggtg ctaaaggaaa cattcatttt    1260
actagaggat caagaaagtt aaagacttaa aacaaacttc ggcagttaag acagcatacc    1320
aagatacaaa tgcctggatg aaatggatca atattccat ccgcacgtta aacaaagcaa    1380
ctgttatgct tgtgcacatg gcaggttggc aggttagaga ccctgattgt ccccttcca    1440 ctaaggtggt ccttcagtcg accaggcgtg ggctgtatgg tagctgtttt ccaggattct    1500
acagcctgga gtaataagtc atgccaagct ctctctgctg tatcctgaag tccctgcagg    1560
tcatccccga gggccatcca gcttccgtct cccaacacta agttcacttc ttgtctctca    1620
tggcagggga ggagacttag cattccttgg agacctgaag ggatgcagtg atcttaggaa    1680
ttttcaagag cttatcaatc agtcagccct tgttcatccc cgagtggatt tgtggtggta    1740
ttgtggtgga cttttactgg gcactctgcc aaataactag agtggcactt gtgctttagt    1800
ccatttggct atccatttca ccctggcatt tcatcagcca gaggaaaaaa aataataata    1860
agacatcgta aagcaagaga agccccttat aggtctttca actctcacat ctatttagat    1920
gcaattggag ccccacaagg aataccagat caatttaaag cttgaaatca aatagttgta    1980
agatttaagt caatattttg gtagatgaca gtcaataaaa atgtaaatta gataaactac    2040
atctattaca accaacagca acgagctttt cgtaagttaa aaagaaaaac gcatgtcggc    2100
cccagccctg aggctacctg acctgacaaa actctttaca ctctatgtgt cagaaagaga    2160
aaaaatggca gttggagttt taacccagac tgtagggccc tggccaaggc cagtggccta    2220
tctctcaaaa caactagaag gggtttccaa agactggccc ccatgtccaa gggccctggt    2280
agcaacagac ctgttagcac aagaaacaga taagctaact cttgggcaaa acctaaacat    2340
aaagtgtccc catgctgtgg tgattttaat aaataccaaa ggacaccatt agccaatgaa    2400
tgttagacta actagatacc aaagcttgct ctgcaaaaat ccccacataa ccattgaagt    2460
ttgcaacacc ctaaccccac caccttactc ctggtatcag ggagcccagt gaaacattaa    2520
ctgtgtagag gtgttagact ctgtttattc tagtaggccc aacctctgag accacccta    2580 cacatcagta gactgggagc tgtacgtgga tgggagcagc ttcgccagcc cctgcaaagt    2640
gactctaaag aagatgacaa gccctgctcc agtcacaccc ggaagctga              2689
```

<210> SEQ ID NO 19
<211> LENGTH: 2754
<212> TYPE: DNA
<213> ORGANISM: Homo sapiens

<400> SEQUENCE: 19

```
tggatcaggt gcaaagtaag cccacccac tgagaactat gttaaagaat ttcaagaaag     60
gatttaatgg agactatgga gtcactatga ctccaggaaa acttagagct ttgtgtgaaa    120
tagactggcc agcattagag gtaggttgga catcagaagg aagcctggac aggtcccttg    180
tttcaaaggt atgacacaaa gtaacctgta aaccaaggca ccaagaccag tttccataca    240
tagacagtta cagctgtctt tagacccctt ccccccaac agtagttaag agaacagcag    300
cataagcagc tggcagaggc aaggaaagac cagcagagag aaaaaaaagg ccatctatac    360
```

-continued

```
caattctaag ttaatttaga ctaaacaagg tcttattaat agcaaaggat aattgaaatc    420
ccaaacttac aaggttttca acaaaagtga agtttgctaa agttaacag tgtaacacat     480 attatggtaa attctaatct tgtggcctta gacagtctag tccaaagaca tcaaaaaagt    540
ttgcttaaaa aaaagaaat ggttatcttc aaaaaaaaaa aaaaaaaaaa aaagaagggg     600
aggcaaaatt tacgtaaaaa gagtgttata tggtaaattc ttgttctgaa ataaattggt    660
tgtttcaaga aaaaatgtt tgtaataagt caaaagttg agacatgttg aagaattgtc      720
agtggaagtc gtgaaaaaaa gttataaaaa tttatgcaaa aaggttttat aatttaaaag    780
taatttggcc tcttgagtac tattgaagaa acagtttatg tgcaaagtgt ataaaaaagt    840
aaaacatacc tttggtaaaa agattataag gaggcataaa aatgtggatt tttacctaca    900
ttaaaaggtt aaaaaaatta ttgttttaaa agtttaagca agttttaaaa cattaattgt    960
aaagaaaagt ctgtgtgtaa acatattagc taaagttaaa aagatatcat ccagttttc    1020 tgcgaactag acataaaagt aaaaatgcaa caggtttttt ttcttaaagc atcaacctgc   1080
tctttaacaa aaattataaa aggttaaaaa gagtctataa aatcttacct tatggtcaaa   1140
catgaaaaat tagataaata tgtcttcaag gttttattaa aattaagttt aatattaata   1200
gcatactaat ataaaggtaa aatttagctt atctggtata aaaatcatac aagaagcatt   1260
attaaatatg aaatggtgtt tagctttctt tggtctaaaa actaatacaa attggtgcta   1320
aaggaaacat tcattttact agaagatcac agaagttaaa gacttaaaaa aaactttggc   1380
aattaagaca gcataccaag atgcaaatgc ctggttgaaa tagatcaaat attccatctg   1440
cacgttaaac aaaagcaatt gttatgcttg tgcacatggc aggccagagg ccctaattgt   1500
cccctttcca ctacagtggt cctccagttg accaggcgta ggctgcatgg taactctttt   1560
ccaggattct acagcctgga gtaataagtc atgccaagct ctctctgcta tatcctgaag   1620
tccctgtggg tcagcctccg agggccatcc agcttccatc tcccaacact aagttcactt   1680
cgtgtctctc acagcaggga ggagacagca ttccttagag acctgaaagg atgcagtgag   1740
cttaagaatt ttcgaaaggt tatcaatcag tcagccgttg ttcatccccg agcagatgtg   1800
tggtggtatt gtggtggacc tttactaggt actctgctga ataagtagag tggcacttgt   1860
gctttagtcc atttggctat ccctttcatc ctggcatttc atcaaccaga ggaagaaaag   1920
aaaataataa gatatcataa agcgagagaa gccccttata ggtcttccaa ctctcatatc   1980
tatttagatg caattagagc cccgcaagga ataccagatc aatttaaagc ttgaaatcaa   2040
atagctacag gatttaagtc aatattttgg tagatgacag tgaataaaaa tgtagattag   2100
ataaactaca tctattacaa ccaacagcaa agagcttttc atgagttaaa aaaaaaaaa    2160 ctcatgtcgg ccccagccct gaggttacct gacctgactc tgtgaagtct gtgtgtcaga   2220
aaagaaaaaa atggcagttg gagttttaac tcagactgtg gggcactggc caaggccagt   2280
ggcctatctc tcaaaacaaa aagacagggt ttccaaaggc tggcccccat gtccaagggc   2340
cctggcagca atggccctgt taccacaaga agcagataag ctaactctta gacaaaacct   2400
aaacataaag tctccccatg ctgtggtgat tttaataaat actaaaggac accattagct   2460
aataaatgtt acactaagta gataccaaag cttgctctgt gaaatccccc acataaccat   2520
tgaagtttgc aacaccctaa ccctgccacc ttactcctgg tatcagagag cctagttaaa   2580
cataactgtt tagaggtgct ggactcagtt tattctagta ggcccaacct ccgagacaat   2640
ccttaaccat cagtagacta ggagttgtat gtagatagga gcagcgtcac caaccccctgc  2700 aaagtgactc tgaagaagac tacaagccct gctccagtca cacccagaag ctga         2754
```

<210> SEQ ID NO 20
<211> LENGTH: 2385
<212> TYPE: DNA
<213> ORGANISM: Homo sapiens

<400> SEQUENCE: 20

| | | | | | |
|---|---|---|---|---|---|
| ctataaaaga | agtgaaaata | gtcagttcct | gccttaactg | atgacattcc | accattgtga | 60 |
| tttgttactg | ccccacctga | actgatcaat | tggcctttgtc | acattccttc | tcctggacag | 120 |
| tgaatctcag | gagctcccca | ctgagcacct | tgtgaccccc | gcccctgtcc | acaagagaac | 180 |
| aaccccttt | aagtctaatt | ttccactacc | tacccaaatc | ctataaaact | gtcccacccc | 240 |
| tatctcccctt | tgctgactcc | ttttttttgg | attcagcttg | cctgcaccca | ggtgattaaa | 300 |
| aagtttattg | ctcacacaaa | gcctgtttgg | tggtctcttc | acatggacat | gcataacatt | 360 |
| tggtgccaaa | gacctgggac | aggggactcc | ttcaggagac | tcatcccggg | tcctcaccct | 420 |
| cactccgtga | ggagatcacc | tatgaccttg | ggtcctcaga | ccagccaaag | gaacatctca | 480 |
| ccaatttaa | atcaggtaag | tggcctcttt | ttgttctctt | ctccagcctg | tcttgttagc | 540 |
| cctccaccct | tcaatctctc | ccttccttaa | tttggttcc | tttccttttc | tggtagagac | 600 |
| agaggagaca | cgttttatcc | atgaactcaa | aactccggca | acagtcatgg | acttgggaag | 660 |
| acagtcttcc | cttggtgttt | aatcactgtg | gggatgcctg | ccttgatcct | tcaccttggt | 720 |
| ggcaagtacc | accttccctg | ggtggcaaga | ccacctcccc | ccacactgtg | tctctatcct | 780 |
| ctcttttctc | taaactcacc | ttttaactat | gggcaaactt | ccaccctcca | ttcctccttc | 840 |
| ttctccctta | ccctgtgttc | tcaagaactt | acacctcttc | aactcacacc | tgacctaaaa | 900 |
| cctaaatgcc | ttattttctt | ctgcaatact | gcttggcccc | aatacaaact | tgacaatggt | 960 |
| tctaaatgac | cagaaaatgg | cacttttgat | ttctccatcc | tacaagatct | agataatttt | 1020 |
| tgtcgaaaaa | tgggcaaatg | gtctgaggtg | cttgacatcc | gggcattctt | ttacacattg | 1080 |
| gtccctccct | agtctctgct | cccaatgcaa | cttgtcccaa | atctttcttc | cttctctcct | 1140 |
| gtctgttcct | tcagttttcca | ccccaagctc | tgagtccttt | gaatcctcct | ttctacaaa | 1200 |
| cccatctgac | ctctcccagc | ctccccaggc | tgctcttcac | caggccgagc | aaggtcccaa | 1260 |
| ttcttcctca | gcctctgctc | cctcacccta | taatccttct | atcacttccc | ctcctcacac | 1320 |
| ctgttccagc | ttacagtttc | gttctgtgac | tagctctccc | caacctgccc | aacaatttcc | 1380 |
| tcttagagag | gtggctggag | ctaaaggcat | agtcaaggtt | aatgctcctt | tttctttatc | 1440 |
| cagcctctcc | caaatcagtt | agcatttagt | ctctttttca | tcaaatataa | aaacctagtc | 1500 |
| cagttaatgg | cctgtttggc | aagaaccctt | agatgcttta | ccgctctaga | cccagagggg | 1560 |
| ccagaaggcc | gtcttattct | caatatgcat | tttattaccc | aatctgctcc | caacgttaga | 1620 |
| aaaaactcca | aaattatat | tccgggcctc | aagccccaca | ataggactta | attaacctct | 1680 |
| ccttcaaggt | gtacaataat | agagaagagg | cagccaagca | gcaatgtatt | tctgagttac | 1740 |
| aattacttgc | ctctgctgtg | tgagagagaa | accccagcca | catctccagc | acaaaagaac | 1800 |
| ttcaaaacat | ctaaaccaca | gtggccaggc | attcctccag | gacctcctcc | cccaggatct | 1860 |
| tgcttcaaat | gctggaaatc | tggccactgg | gctaaagaat | gccagcctg | ggattcctcc | 1920 |
| taagccatgt | cccatctgtg | tgggaaccca | ctggaaccag | ctcacccggc | agccactccc | 1980 |
| agagcccctg | gaactctggc | ccaaggctct | ctgactgact | ccttcccaga | tcttctcggc | 2040 |
| ttagcggctg | aagactgacg | ctgcctgatc | acctcagaag | cctcctggac | catcacagat | 2100 |

| | |
|---|---|
| gctttgggta actcttacag tggagggtaa gtccacctcc ttcttaatca atatggaggc | 2160 |
| tacccactcc acattacctt cttttcaagg gcctgtttcc cttgcctcca taactgttgt | 2220 |
| aggtattgat gaccaggctt ctaagcctct taaaactccc caactctggt gccaacttgg | 2280 |
| acaacattct tttatgcact cctttttcagt tatccccacc tgcccagctc ccttattagg | 2340 |
| tcgagacatt ttaactaaat tttctgcttc cctgactatt cccgg | 2385 |

<210> SEQ ID NO 21
<211> LENGTH: 967
<212> TYPE: DNA
<213> ORGANISM: Homo sapiens

<400> SEQUENCE: 21

| | |
|---|---|
| gtggggaaaa gaaagaggga tcagattgtt actgtgtctg tgtagaaaga agtagacata | 60 |
| ggagactcca ttttgttctg tactaagaaa aattcttctg ccttgagatg ctgttaatct | 120 |
| gtaaccttac ccccaaccct gtgctctctg aaacatgtgc tgtgtcaact cagggttaaa | 180 |
| tggattaagg gctgtgcaag atgtgctttg ttaaacagat gcttgaaggc agcatgctcc | 240 |
| ttaagagtca tcaccactcc ctaatctcaa gtacccaggc aaacactgcg gaaggcttca | 300 |
| gggacctctg cctaggaaag ccaggtattg tccaaggttt ctccccatgt gatagtctga | 360 |
| aatatggcct cgtgggaagg gagagacctg accatccccc agcccgacac ccgtaaaggg | 420 |
| tctgtgctga ggagaattag taaaagagga gggaatgcct ctttgcagtt gagacaagag | 480 |
| gaaggcatct ctctcctgcg cgtccctggg caatggaatg tctcagtgta aacccaatt | 540 |
| gtatattcca tctactgaga taggggaaaa ccgcctcagg ggtggaggtg ggacatgcgg | 600 |
| tgggcaatac tgctctttaa ggcattgaga tgtttatgtg tatgcatatc taaagcacag | 660 |
| cacttaattc tttaccttgt ctatgatgca gagacctttg ttcacctgtt tatctgctga | 720 |
| ccttctctcc actattatcc tatgaccctg ccacatcccc ctctctgaga gagaaacacc | 780 |
| caagaatgat caataaatac taagggaact cagaggctgg caggatcctc catatgctga | 840 |
| acgctggtcc cctgggcccc cttatttctt tctctatact ttgtctccgt gtctttttct | 900 |
| tttccaagtc tcttgttcca cctaacgaga aacacacaca ggtgtggagg ggcaacccgc | 960 |
| cccttca | 967 |

<210> SEQ ID NO 22
<211> LENGTH: 4076
<212> TYPE: DNA
<213> ORGANISM: Homo sapiens

<400> SEQUENCE: 22

| | |
|---|---|
| gtcaggcctc tgagcccaag ctgagccatg atattccctg tgacctgcac gtacacatcc | 60 |
| agatggccag ttcctgcctt aactgatgac attccaccac aaaagaagtg aaaatggcct | 120 |
| gttcctgcct taactgatga caatgtcttg tgaaattcct tctcctggct catcctggct | 180 |
| caaaagctcc cccactgagt accttgtgac ccccactcct gcccgccaga gaacaacccc | 240 |
| cttttttcctt cacctatcca aatcctataa aacggcccca ccccatctc ccttcgctga | 300 |
| ctctctttttc ggactcagcc cgcctgcacc caggtgaaat aaacagccat gttgctcaca | 360 |
| caaagcctgt ttggtggtct cttcactcag acacgcagga aatttggtgc cgtgacttgg | 420 |
| attgggggac ctcccttgag agatcaaccc ctgtcctcct gtcctttgct ccgtgagaaa | 480 |
| gatccaccta cgacctcagg tcctcagacc taccagccca aggaacatct caccaatttt | 540 |
| aaatcgggtg agcggcctct tcttactctc ttctccaacc tctctcactg tccctcaacc | 600 |

```
actttctcct ttccactctt caatctctcc cttctcttaa tttcaattcc tttcattttc    660
tggtagagac aaaggagaca cgttttatcc gtggacccag aactctggca ccggtcaagg    720
actagggaag gcagccttcc cctggtgttg aatcattgca gggatgcctc tctgattatt    780
tacccatgtt tcagaggtgt cagaccatgc agggacacct gcctttgtcc ttcatcctta    840
gcggcaagtt ccgctttctt gtgggagggg caagtacccc aaccccttct ctccgtgtct    900
ctacaccttc tctgcctttc tgggggggcaa gaaaccccca acccccttctt cttcacccctt   960 agcagcaagt cccgcttttc taggggaggg ataattaccc caaccccctta tatctctgtg   1020 ccctgatccc ttatttccgt gccccaagct cttatatctc tgcacccaa tcccttattt      1080 ccatgcccca acctcttata tctctgcacc ctgatcctt atttcctcgc ccaacctctt      1140
atatctctgt gccccaatcc cttatttccg tgccctgacc tcgtatctct gtgccccatc    1200
ccctttccca cttttctgga gggtaagaac ccccgaaccc cttccctccg tgtctctact    1260
ctctcttttc tctgggcttg cctccttcac tatgggcaac cttccaccct ccattcctcc    1320
ttcttctccc ttagcctgtg ttcttaagaa cttaaaacct cttcaactct cacctgacct     1380
aaaatctaag catcttattt tcttctgcaa tgccacttga ccccaataca aactcgacag     1440
tagttccaaa tagccagaaa acggcacttt cgattttttcc atcttacaag atctaaataa    1500
ttcttgttgt aaaatgggca aatgatctga gatgcctgac gtccaggcat tcttttacac     1560
atcggtccct ctctagtctc tgttcccaat gcaactcatc ccaaatcttc cttctttccc     1620
tcctgtctgt cccctcagtc ccaacccaa gcgtctctga gtctttctaa tgttcctttt      1680
ctacagaccc atctgacctc tcccctcctc cccaggctgc tcctcgccag gccgagctag    1740
gtcccaattc ttcctcagcc tccactcctc caccctataa tccttttatc acacctcccc     1800
tcctcacacc tggtccggct tacagttttg ttccatgact agccctcccc cacctgccca    1860
gcaatttact cttaaaaagg tggctggagc taaaggcata gtcaaggtta atgctccttt     1920
ttctttatcc caaatcagac agcatttagg ctcttttttca tcaaatataa aaatccagcc   1980
cagctcatga ctcgtttggc agcaaccctg agatgcttta cagccctaga ccctaaaagg    2040
tcaaaaggcc gtcttattct caaaatgcat tttattaccc aatctgctcc cgacactaaa    2100
taaaactcca aaaattaaat tccggccctc aaaccccaca acaggattta attaacctcg    2160
ccttcaaggt gtacaatagt agaaaaaagt tgcaattcct tgcctccact gtgagacaaa    2220
ccccagccac atctccagca cacaagaact tccaaatgcc tgaaccgcag cggccagaca    2280
tttctccaga acctccttcc ccaggagctt gctacaagtg ccagaaatct ggccacaagg    2340
ccaaggaatg cctgcagccc aggattcctc ctaagccgcg tcccatctgt gcgggactcc    2400
actgaaaatc ggactgtcca actcacctgg cagccactcc cagagcccct ggaactctgg    2460
ccgaaggctc tctgactcct tcccagatct tcttggctta gtggctgaag actgatgctg    2520
cccaatcgcc tcgaaagccc cctagaccat cacggacgct gagcttcagg taactcacac    2580
agtggagggt aagtccgtcc ccttcttaat caatacggag gctactcact ccgcattacc    2640
ttattttcaa gggcctgttt cccttgcttc cataactgtg gtgcgtattg acagccaggc    2700
ttctaaacct cttaaaactc cccaaatctg gtgccaatta gacaatactc ttttaagcat    2760
tccttttagt tatccccacc tgcccagttc ccttattagg ctgagacact ttaactacat    2820
tatctgcttc cctgactatt cctggattac agttacatct catggctgcc cttcttccca    2880
atccaaagcc tcctttgcgt cctcctcttg tattccccca ccttaaccca caagtataag    2940
```

| | |
|---|---|
| atacctctac tccctccttg gcaaccgatc atgcaccct taccatctca ttaaaaccta | 3000 |
| atcacccta ccccgattga tgccaatatc ccatcccaca gcatgctttg aaaggattaa | 3060 |
| agcctgttat cactcgcctg ctacagcatg gccttttaaa gcctataaac tctccttaca | 3120 |
| attcccccat tttacctgtc ctaaaaccag acaagccttt caagttagtt caggatctat | 3180 |
| gccttatcaa ccaaattgtt ttgcctatct accccatggt gccaaaccca tacactctcc | 3240 |
| tatcctcaat acctccctcc acaatccatt attctgttct ggatctcaaa catgctttct | 3300 |
| tcactactcc tttgcacctg tcatcccagc ctctcttcgc tttcacttag actgaccctg | 3360 |
| acacccatca ggctcagcaa attacctggg ctgtactgcc gcaaggcttc acagacagcc | 3420 |
| cccattactt cagtcaagcc caaatttcat cctcatctgt acctatctc ggcataattc | 3480 |
| tcataaaaac acatgtgctt tccctgctga ttgtgtccga ttaatctccc aaacctcaat | 3540 |
| cccttacaaa acaacaactc ctttccttcc taggcatggt tagtgcggtc agaattctta | 3600 |
| tacaagagcc aggaccacac cctgtagcct ttctgtgcaa acaacttgac ctgttttagc | 3660 |
| ctagccatca tgtctccgtg cagtggctgc tgccgcccta atactttag aggccctcaa | 3720 |
| agtcacaaac tatgctcaac ttactctcta catgtctcat aacttccaaa atctatttc | 3780 |
| ttcctcatac ctgacacata tacttctctgc tccccagctc cttcagctgt actcactctt | 3840 |
| tgttaagttc cacaattacc attgttcctg gcccggactt caatccggcc tcccacatta | 3900 |
| ttcctgatac cacaactgac acccatgact gtatctctct gatccacctg acattcaccc | 3960 |
| catttccccg tatttccttc tttcctgttc ctcatcctga tcatgcttga tttattgatg | 4020 |
| gcggttccat caggcctaat tgccacacac cagcaaaggc aggctatgct atagca | 4076 |

<210> SEQ ID NO 23
<211> LENGTH: 806
<212> TYPE: DNA
<213> ORGANISM: Homo sapiens

<400> SEQUENCE: 23

| | |
|---|---|
| gacatgacaa agttggtaca tttgcctgta caggtttaac acaggtttga tcctaggtct | 60 |
| atatttagaa aatagtttct agctgtaagc gaatttaaaa ccctcattgt aagtgtatta | 120 |
| ctagtaatag aaacttgctt gctgctcccc tgtgtattac gcttgctcct tcaaatgata | 180 |
| aaaggttttg tagctaccat ggtttgtcaa aaaacttcag cacaagtgta ttacataaaa | 240 |
| cactatcact ctgtctcgca aagagactca agtaaaaat aaaagtgaga actccactaa | 300 |
| ttagtgaaat tctcaaagag ggggataagg aaggagacca ctactattcc tgctgccctc | 360 |
| ctcccccac cttgcctagt tcacaaaaca ggagaaaaga gagaaagcaa aaagttggaa | 420 |
| agaaacaaaa gataaacagc cagacaacct tggcaccacc accgcggccc tagaagttaa | 480 |
| aaaagtaata ataataacaa tccctgacct aaactacttg tgttatctgt aaattccaga | 540 |
| cattgtatga aaaagcattg caaaactttc tgttctgtta gctgatgcat gtagccccca | 600 |
| gtcacgttcc ccatgcttgc ccaatttatc atgacctttt cacgtggacc ccttagagtt | 660 |
| gtgtaagcct ttaaaaaggc caagaatttc ttttcaggg agctcagctc ttaagatgca | 720 |
| aatctgccga cactcccagc cgaataaacc tcttccttct ttaatctggt gtctgaggag | 780 |
| ttttgtctgc agctcttcat gctaca | 806 |

<210> SEQ ID NO 24
<211> LENGTH: 5082
<212> TYPE: DNA
<213> ORGANISM: Homo sapiens

```
<400> SEQUENCE: 24
aagaaactca gcctggctat cagagcttgc agtgtaacca gtgtgcttat tgtaaagaaa      60
taggacattg gaagaacaaa tgccctcagc taaaaggaaa acaaggtgac tcagagcagc     120
aggccccaga caaggaggat ggggccctgc tcaacctggc agaagggtta ctggaatgag     180
ggggactggg ctcaagggcc cccaaaaagc ctgtggtcag gatgaaagtt gggggtaaag     240
acattgattt tcttttagat accggtgctg aacattctgt agtaaccacc ccggtcgccc     300
ccttatccaa aaagactcaa cataattgga gccatggggg tttcagcaaa gcaagctttc     360
tgcttgcccc ggacttgtac tgcaggagga cataaagtga ttcatcagtt tttgtacatg     420
cctgactgtc ccttgccctt gtgggaagg acttgctta gcaagctgag agccactgtc      480
tcttttacag agcatggctc tttgctgcta aagttaccca gaacgggagt tattatgacc     540
cttacggtcc cccgagagga ggaatggaga cttttcttaa tgagccaggc caagtggtgg     600
ccaagagtgt gggcagaaga caaccctcca gggttggcag tcaaccaagc ccccgtactt     660
atagaagtta agcctggggc ccagccagtt aggcaaaaac agtacccggt ccccagagaa     720
gctcttgaag gtatccaggt ccatcaagcg cctaagaacc tttggaatta tggctccttg     780
tcaatctcca tggaacactc ccctcctgcc tgttcccaag cctgggacca aggactaaag     840
gccggtacag gatttgcact tggttaatca agctacagtg actttacatc taacagtacc     900
taacccgtac acattgttgg ggttgctgcc agctgaggac agctggctca cctgcttgga     960
cctttcttta gcatcagatt agcccctgag agccagaaac tgtttgcctt tcagtgggaa    1020
gatccagagt caggtgttac tactcagtac acttggaccc agcttccccg agggttcaag    1080
aactccccca ccatcttggg ggaggagacc tccagaagtt tcccaccaga gacctaggct    1140
gcatgttgct ccagtacatt gatgactttc tgctgggaca ccccacggca gtcgggtggg    1200
ccaagggaac agatgcccta ctctggcacc tggaggactg tgggtataaa gtgtccaaga    1260
aaaaagctca gatctgccga cagcaggtac gttacttggg atttactatc tgacaggggg    1320
agcgcagcct gggatcagaa agaaagcagg tcatttgcaa tctaccagag cctaagacca    1380
gaaggcaggt gagagaattc ttaggagctg tggggttttg cagactgtgg atcccaaact    1440
ttgcagtatt agccaagcct ttgtatgagg tcacaaagtg gggggaacag gaacttttttg   1500 aatgggaatc ccgacaacaa caagcctttc ataagttaaa ggaaaaactt atgtcagccc    1560
cagccctggg gctacccgat ctgacaaagc ctttttacatt gtatgtgtca gagagagaaa    1620
agatggcagt tggagtttta acccaaactg tggggccctg gccgaggccg gtggcctacc    1680
tctctaaaca actacatggg gtttctaaag aatggccccc atgtttgagg gccttggcag    1740
caactgccct gctagtacaa gaagcagata agctgactct tgggcaaaac ctgaacataa    1800
aggctcccca tgctgtggtg acattaatga atactaaagg acatcattgg ctaacgaatg    1860
ttagactcac caagtaccaa agtttgctct gtgaaaatcc ctgtataacc attaaagttt    1920
gtaacaccct gaaccctgct accttgatcc cagtatcaga gagccctgtc aagcatgact    1980
gtgtagaagt gttggactca gtctactcta gcagatctga cctctgagac cggccttggg    2040
catcagtaga ctgggaacta tacgtggatg ggagcagctt catcaaccca caaggagaga    2100
gatgtgcagg gtatgctatg gtaaccctgg acactgttat tgaagacaga tcattgcccc    2160
agggcacttc agcctagaga gctgaactca ttgctttaat ttgggcccta gaactcagtg    2220
aaggtaagac tgtaaacatt tacactgact ctcggtatgc cttttttaacc cttcaagtgc    2280
```

```
atggagcgtt atataaagaa aagggcctat tgaactctgg gggaaaggac ataaaatatc    2340
aacaagaaat tttgcaatta ttagaagcag catggaaacc ccacaaggtg gcagttatgc    2400
attgcagagg acaccagcga gcttccatct tggtgggttt ggggaattcc tgcgctgact    2460
cagaggctcg aaaagcagca tctgcccccct tccaggcatc agtcacagac ccctgctcc     2520 ctcaagcact tgatcttgta gctacttatt cgggagaata gctctgccac agctgctagg    2580
agccgcaatt gtactggttt tgcatgaaac cacccatcta ggtcaggagt cacttgaaaa    2640
gttgttaggc cggtatttct acatctcata tttgtcaacc cttgccaaaa cagtgacgca    2700
gcagtgtgtt acctgccgac agcataatgt gaggcaaggt ctagctgttc cccccggca     2760 tacaagctta tagagcagcc tcctttgaag atctccaggt ggacttcaca gagatgccaa    2820
agtgtggagg taacaagtat ttactagttc ttttgtgtac ctactgtggg tgggtggagg    2880
cttatccaac actaactgag aaagctcgtg aagtaacctg tgtgcttctt cgagatctta    2940
ttcctagatt tggactgccc ttacggatca gctcagataa tgggctaacg tttgtggctg    3000
acttggtaca gaagatagca aaggtattgg ggatcatttg gaaactgcat gccgcctacc    3060
ggcctcagag ttccagaaag gcagagcaga tgaatcagac tatcaaaaat agtttaggga    3120
aagtatgtca ggaaacagga ttaaaatgga tacatgctct ctatagtatt atttaaaatt    3180
agatgtaccc cttctaaaag aacaggatat tccccttagg aaatattata tcatgggacc    3240
cttcccatat tgcagggact tccaggcact tcctgagagt taggtgaaat tgagttacag    3300
cgacagctac aggctttagg aaaaattaca caaacaatct cagcctgggt aaatgagaga    3360
ccctgttagc ttattctccc cagttcacct tttctcccca ggtgttcgag tgtggatcaa    3420
ggactggaac gtagcctctt tgtgcccatg gtggaaagga ccccagactg tcgtcctgat    3480
cactcccact gctgtgaacg tagagagaat cctagcctgg atccatcaca accgtgtaaa    3540
acctgcagcg cctgaatcct gggaggcaag accaagtctg dacaaccctt gcagagtgac    3600
cctgaagaag atgacaagcc ctgctccagt cacacccaga agctgactgg tccacgcaca    3660
gccgaagcat gaggaagctc attgtgggct tcattttct taaattttgg acttacagta    3720
agggcttcaa ctgttcttac tcaaactggg gactattccc agtgtattca tcaggtcagt    3780
gaggtaggac agcaaatgaa aacaatcttt ctgttctata gttattatca atgtatggga    3840
acgttaaaag agacttgttt gtataatgcc actcagtaca aggtatgtag cccaggaaat    3900
gactgacctg atgtgtgtta taacccatct gagccccctaa caaccaccag ttttgaaata    3960
agattaagaa ctggccttt cctaggtgat acaagtgaaa taataactag aacagaagaa    4020
aaaggaatcc ccaaacaagt aactttaaga tttgacgctt gtgcagccat taatagtaac    4080
aagctaggaa caggatgtgg ttctcttaac tgggaaagga gctacagagt agaaaataaa    4140
tatgtttgtc atgagtcagg ggtttgtgaa aattgtgcct tttggccatg tgttatttag    4200
gctacttgga aaaagaacaa aaaggacttg gttcatcttc agaaagggga agccaacccc    4260
tcctgtgctg ccagtcactg taacccacta gaactaataa ttaccaatcc cctagatccc    4320
cattggaaaa agggagaatg tgtaaccctg gggatcaaag ggacagggtt aaaccccaa    4380 gttgccattt tagttcaagg ggaggtccac aagcactctc ccaaaccagt gtttcaaacc    4440
ttttatgagg agttaaatct gccagcacca gaacttctga aaaagataaa aaatttgttt    4500
ctccaattag cagaaaatgt agctcattcc cttaatgtta cttcttgtta tatatgcggg    4560
ggaaccacta tcagagaccg atggccttgg gaagcctgag agttggtgcc cactgatcca    4620
gctcctgata taatgggggc ttgtccagga tctcatcagg actggatggc tctcgctgga    4680
```

| | | | |
|---|---|---|---|
| ctatactgga | tatgtgggca | gagagcctac attcagttac ctaatgaatg ggcagacagt | 4740 |
| tgtgttattg | gcactattaa | gccatccttt ttcttattac cgataaaaac tactggtact | 4800 |
| atctgtaaat | tccagacatt | gtatgagaaa gcactgtaaa acttttttgtt ctgttagctg | 4860 |
| atatatgtag | cctccagtca | cattcctcat gcttacttga tctatcatga cccttttcacg | 4920 |
| tggaccccctt | agagttgtaa | gcccttaaaa gggctaggaa tttcttttttg ggggagcttg | 4980 |
| gctcttaaga | catgagtctg | ccaatgctac cggccaaata aaaacctctt ccttctttaa | 5040 |
| tccagtgtct | caagagtttt | gtctgcagct catcctgcta ca | 5082 |

<210> SEQ ID NO 25
<211> LENGTH: 501
<212> TYPE: DNA
<213> ORGANISM: Homo sapiens

<400> SEQUENCE: 25

| | | | |
|---|---|---|---|
| cctctggacc | agcctgctag | cccacatgct ccgatgttaa tgacatcgaa ggcacccgtc | 60 |
| tcgaggaaat | ctcaactgca | caaccccctac tacaccccaa ttcagcagga agcagttaga | 120 |
| gcggtcgtca | gccaacctcc | ccagcagcac ttgggttttc ctgttgagag cggggactga | 180 |
| gagacaggac | tagctggatt | cctaggctg actaagaatc cctaagccta gctgggaagg | 240 |
| tgaccgcgtc | tacctttaaa | cacggggctt gcaacttagc tcacacccaa ccaatcagat | 300 |
| agtaaagaga | gctcactaaa | atgctaatta ggcaaaaaca ggaggtagag aaatagccaa | 360 |
| tcatctatcg | cctgagagca | cagcaggagg acaatgatc cggatataaa cccaagcatt | 420 |
| cgagccagca | atggctaccc | tctttgtgtc ccctccccttt gtatgggagc tctatttttca | 480 |
| ctctattaaa | tcttgcaact | g | 501 |

<210> SEQ ID NO 26
<211> LENGTH: 972
<212> TYPE: DNA
<213> ORGANISM: Homo sapiens

<400> SEQUENCE: 26

| | | | |
|---|---|---|---|
| gtggggaaaa | gaaagagaga | tcagattgtt actgtgtctg tgtaggaaga agtagacata | 60 |
| agagactcca | ttttgttctg | tactaagaaa aattcttttg ccttgagacg ctgttaatct | 120 |
| gtaaccctac | ccccaacccct | gtgctcccta agacatgggc tgtgtcaact cagggttaaa | 180 |
| tggattaagg | gctgttcagg | gtgtgctttg ttaaacaaat gcttgaaggc agcatgcttg | 240 |
| ttaagagtca | tcaccactcc | ctaatctcaa gtacccagag acacactaca ctgcggaaga | 300 |
| ctgcagggac | ctctgcctag | gaaagccagg tattgtccaa ggtttctccc catgtcatag | 360 |
| tctgaaatac | agcctcatgg | gaagggaaag acctgactgt ccccccagccc gacacccgta | 420 |
| aagggtctgt | gctgaggagg | attagtaaaa gaggaaggaa ggcctctttg cagttgagat | 480 |
| aagaggaagg | catctgtctc | ctgctcatcc ctgggcaatg gaatgtctcg gtgtaaagcc | 540 |
| cgattgtata | ttccatctac | tgagatagga gaaaaccgcc ttaggactgg aggtgggaca | 600 |
| tgctggcagc | aatactgctc | tttaaggcat tgagatgttt atgtatatgc acatcaaaag | 660 |
| cacagcactt | ttttctttac | cttgtttatg atgcagagac atttgttcac gtgtttacct | 720 |
| gctgatcttc | tctccactat | tatcctattg tcctgccaca tcccctctc cggaaacgcc | 780 |
| caataatgat | caataaatac | taagggaact cagaggccag tgcaggcatg ggtcctccgt | 840 |
| atgctgaacg | ccagtcccct | gggcccattt ttctttctct gtactttgtc tctgtgtctc | 900 |

-continued

```
tttctttttcc aagtctctcc ttccacctaa cgagaaacgc ccacaggtgt ggaggggcaa      960
cccatccctt ca                                                          972

<210> SEQ ID NO 27
<211> LENGTH: 7330
<212> TYPE: DNA
<213> ORGANISM: Homo sapiens

<400> SEQUENCE: 27
gtagggaaaa gaaagagaga tcagactgtt actgttgtct atgtagaaaa ggaagacata       60
agaaactcca ttttgacctg taccctgaac gattgttttg ccccgagatg ctgttaatct      120
gtaactttgc cccaaccttg agctcacaga acatgtgtt gtatggaatc aaggtttaag       180
ggatctaggg ctgtgcagta tgtgccttgt taacaaaatg tttacaggca gtatgcttcg      240
taaaagtcat caccattctc cattctcgat aagccagggg cacaatgcac tgcggaaagc      300
cgcagggacc tctgccctgg aaagccgggt attgtccaag gtttctcccc atgtgatagc      360
ctgagatatg gcctcgtggg gcgggaaaga cctgaccgtc ccccagccca acaccgtga       420 agggtctgtg ctgaggagga aggcctcttg cagttgagat aagaggaagg cctctgtctc      480
ctgcctgccc ctgggaacta aatgtctcag tataaaactc gattgtacat tgttctctt      540 ctgagataag agaaaacccg ccgtgtggcg ggaggcgaga catgttggtg gcagcaatgc      600
tgctctgtta ctctttactc cactgagatg tttgggtgga gaaaagcata aatctggcct      660
atgtgcacat ccaggcatag taccttccct tgaacttatt tgtgacacag attcctttgc      720
tcacatgttt tcttgttgac cttctccaca ctatcaccct gttctcctgc acattcccc      780 ttactgagat agtaaaaata gtaatcaata aatactgagg gaactcagag accggtgcca      840
gtgcgggtcc tccgtatgct gagcaccagt ctcctgggcc cactgttctt tctctatact      900
ttgtctctgt gtcttatttc ttttctcagt ctctcgtccc acctgacgag aaatacccac      960
aggtgtggat ggggctggcc ctcttcattt ggcgcccaac gtgggccctt tctctagggt     1020
gaaggtgcgc taagaccgtg agcattgagg acagtcgatg agagattccc gagtacgtcc     1080
acggtgagcc ttgcggtaag cttgtgcaca cggaggaacc cagggtaaca atgggacaaa     1140
ctgaaagtaa atatgcctct tatctcagct ttattaaaat tcttttaaga agaaggggag     1200
ttagagcttc tacagaaaat ctaattatgc tatttcaaac aatagaacaa ttctgcccat     1260
agtttccaga acagggaact ttagatctaa aagactggga aaaaattggc aaagaattaa     1320
aacaagcaag tagggaaggc aaaatcatcc cgcttacagt atgcaatgat tgggccatta     1380
ttaaagcagc tttagaaccg tttcaaacag aagaagatag cgttttggtt tctgatgccc     1440
ctgaaagctg tgtaatagat tgtgaagaag aggcggggac agagttcaag aaaggaacgg     1500
aaagttcaca ttgtgaaaat gtagcagagt ctgtaatggc tcggtcaaca caaagtgttg     1560
actacaatca attacaggag gtaatatatc ctgaatcacc aaaactgggg gaaggaggtc     1620
cagaaccatc ggggccgtca gggctaaaac cacgatggcc acctcctcct cagtcgagtg     1680
agtgctgggg gagggagcct gaaaccaggc tggctgcaac tcggctcgcg gtgcccatta     1740
ttgcccaacc ggcagttcac tgcggtgaag agcaattca gactcgccct gtagcatcct      1800
gtctgggtca acagtggcc gctccctaag gaaaagttag gggcgctaca taaaatagtt      1860
aaaaaaacta tttaaaaaag gacatgtttc acccactgtc tctccttaga attcgccagt     1920
gtttgtaatt cagaaaaaat ccggcagatg gcgcatgcta accgacttaa gagccgctaa     1980
tgccgtaatt caacccatgg gggctctcca acgcaggctg ccctctccgg ccgtgatccc     2040
```

```
caaaggttgg cctttaatta taattgatct gaaggattgc tttttttttt tttttttttt   2100
ttaccattcc tctggcaaaa caggattttg aaaaatttgc ttttgctata ccagccataa   2160
ataataaaga accagccacc aggtttcagt ggaaagtgtt gcctcaggga atgcttaata   2220
gtccaactat ttgtcagact tttgtagctc aagctcttca accagttaga gacatgtttt   2280
cagactgtta tatcattcat tatgttgatg atattttgtg tgctgcagaa atgagagaca   2340
aattaattga ctgttacaca tttctgcaga cagaggttgc caacgcagga ctgacaatag   2400
catctgataa aattcaaaca acagctcctt tcattatttt agaaatgcag gtagaggaaa   2460
ggaaggttaa tcctcaaaag atagatagaa atgagaaaag acacattaaa atatgaaatg   2520
actttcaaaa attgctggga gatattaatt ggattcggtc aaccctaggc atccctactt   2580
atgccatgtc aaatttgttc tctatcttaa gagggatcc agaatcaaat agtaaaagaa   2640
cattaactcc agaggcaact aaagaaattg aattagttga agacaaaatt cggtcagcac   2700
aagtaaatag aatagatcac ttagccccac tccaacttttt gatttttgct actgcacatt   2760
ctccaacagg catcattgtt caaaatacag atcttgtgga gtggtccttc cttcctcaca   2820
gtacgattaa gacttttaca ttgtacttgg atcaaatggc tacattaatt ggtcaggcaa   2880
gactacgaat agtaaaattg tgtggaagtg acccagataa aatcattgtt cctttaaaca   2940
aggaacaggt tacacaagcc tttatcaatt ctggtgcatt gcagattggt cttgctgatt   3000
ttgtgggaat tattgacaat cattacccaa aaacaaaaac cttccagtttt ttaaaattga   3060 ctacttggat tttacctaaa attaccagac atacacccttt agaaaatgct ctgacagtgt   3120
ttactgatgg ttccagcaat ggaaaggtgg cttacaccag gccaaaaaaa cgagtcactg   3180
aaactcaata tcactcagct caaagagcag agttggttgc tgtcatttca gtgttacaag   3240
attttaatca gcttattaac cttgtatcag attctgcata tgtagtacag gctacaaagg   3300
atgttgagac agccctagtc aaatacagta tggatgatcg gttacaccag ctgtttaatt   3360
tgttacaaca aactgtaaga aaaagaaatt tcccatttta tattactcat gttcaagcac   3420
atactaattt accagggcct ttaactaagg caaatgaaca agctgacttg ctagtatcat   3480
ctgcattcat agaagcacaa gaacttcatg ccttgactca tgtaaatgca acaggactaa   3540
aaaataaatt tgatatcaca tggaaacagg caaaaaatat tgtacagcat tgcacctagt   3600
gtcaagtctt acactggccc actcaggagg caggagttaa tcccagaggt ttatgtccta   3660
atgcattatg gcaaatggat gtcacacatg taccttcatt tggaaaaatg tcatttgtcc   3720
atgaagacag ttgatactta ttcacatttc atatgggcaa cctgccagac aggagaaagt   3780
acttcccatg ttaaaagaca tttattatct tgttttgctg tcatgggagt tccagaaaaa   3840
attaaaacag ataatgggcc aggatactgt agtaaagcat ttcaaaaatt cctaaatcag   3900
tggaaaatta cacatacaac aggaatcccc tataattccc aaggacaggc cataattgaa   3960
agaactaata aagctcaatt ggttaaacaa aaaaaggaaa aagatagtaa ggagtataac   4020
actcctcaga tgcaactcaa tctagcactc tatactttaa aattttttaaa cgtttataga   4080 aatcagacca ctacttctgc agaacaacat tttactggta aaaagaacag cccacatgaa   4140
ggaaaactga tttggtggaa agacatcaaa aataagacat gggaaatagg gaaggtgata   4200
acctggggga aaggctttgc ttgcgtttca ccaggaaaaa agtcagcttc ctgtttggat   4260
acccactaga catttaaagt tctacaatga acccatcgga aatgcaaaga aaagcgcctc   4320
cgcggagaca gaaaacccgc aatcgagcat catcgactcg ccaggtgaac aaaatggtgg   4380
```

```
tatcagaaga acagatgaag ttgacatcca ccaaggaagt ggagccgccg acctgggccc    4440
aactaaagaa gttgacacag ttagctgaaa aaagcctgaa gaaaacaagg gtaacacaaa    4500
ctccagagaa tatgctgctt gcagttttga tgattgtatc aatggtggta agtgtcccca    4560
tgtctgcagg agcagctgca gctaattata cttactggac ctatgtgcct ttcccgccct    4620
taattcgggc agtcacatgg atagataatc ctattaaagt atgtgttaat aatagtgcat    4680
gagtaccagg ccccacagat gattgttgcc ctgcccaacc tgaaaaagaa ggaatgatga    4740
taaatatttc cattgggtat cattatcctc ctatttgcct agggaaggca ccaggatatt    4800
taattcctac aacccaaaat tggttggtag aagtacctac tgtcattgcc agcaatagat    4860
ttacttatca catggtaagt gaaatgtcac tcgggccaca gataaataat ttacaggatc    4920
cttcttatca aagatcatta aaatttaggc ctaagaggaa gccttgcccc aaggaaattc    4980
ccaaagaatc aaaaggccca gaagtctcag tttgggaaga atgtgtggct gatactgctg    5040
tggtattaca aaacaatgaa tttggaacta ttatagactg ggcccctcaa ggccaattat    5100
attatgattg tacaggccag actcactgat gttcacaggc cccatccatc tggcccacta    5160
atccggccta tgatagtgat ttaactgaaa ggctggacca ggtttacaga aggttagaat    5220 cacccctatcc atggaaatgg ggtgaaaagg gaatttcatc acttcgaaca aagttagtta    5280
gtcctgttgt tggtcctgaa cacccagaat tatggaagct tactgtgcc tcgcaccaca    5340 ttagaatttg gtctggaaat gaagctatag aacaagaga tcgtaagcca tattatacta    5400
ttaacctaaa ttccaatctg acaattcctt tgcaaagttg tgtaaaaccc ccttatatgt    5460
tagttgtagg aaaaatagtt attaaaccag attcccaaac tataacctgt gaaaattgta    5520
gattgtttac ttgcattgat tcgacttctg attggcagca ccatattctg ctggtgaggg    5580
caagagaggg cgtgtggatc cctgtgtcca tggaccgacc gtgggaggct tccccatccg    5640
tccatatttt aatggaagta ttaaaaggag ttctaactag atccaaaaga ttcatttta    5700 ctttaattgc agtcattatg ggtcttgttg cagtcacagc tactgctgtg gctgctggaa    5760
ttgctttaca ctcctctgtt caaatggtaa aatatgtaaa taattggcaa aagaattcct    5820
caaaattgtg gaattctcag acccaaatag atcaaaaatt ggcaaaccaa attaatgacc    5880
ttagacaaac tgtcatttgg atgcgagata ggctcatgag cttgaaatat cttttttcagt    5940 tacagtgtga ctggaatacg tcagatttt gtattacacc ccgagcctac aatgagtctg    6000
agcatcactg ggccatggtt agatgccatc tacaaggaag agaagataat cttactttag    6060
atatttcaaa attaaaagaa caaattttg aggcatcaaa agcccattta atctggtgc    6120 cagaaactga ggcaatcgtg aaagctgctg atggcctcac aaatcttaat gccgtcactt    6180
gggtaaaaac tatcagaagt tccactattg taaatttcat attaatcctt gtatgtctgt    6240
tctgtctgtt gttagtctac aggtgtatcc aacagctccg aagagacagt gaccagcgaa    6300
aacgggccgt gatgatgatg gtggtttgt cagaaagaaa aggggatat gcaggcaaga    6360 gaaagagaga tcagactgtt actgttgtct gtgtagaaaa ggaagacata agaaactcca    6420
ttttgacctg taccctgaac gattgttttg ccccgagatg ctgttaatct gtaactttgc    6480
cccaaccttg agctcacaga acatgtgtt gtacagaatc aaggtttaag ggacctaggg    6540
ctgtgcagga cgtgccttgt taacaaaatg cttacaggca gtatgcttgg taaaagtcat    6600
cgccattctc cattctcgat aaaccagggg cacaatgcac tgcggaaagc gcagggacc    6660 tctgccctgg aaagcgggat attgtccaag gtttctcccc atgtgatagc ctgagatatg    6720
gcctcgtggg atgagaaaga cctgaccgtc ccccagcctg acacccgtga agggtctgtg    6780
```

```
ctgaggagga ttagtaaaag aggaaagcct cttgcagttg agataagagg aaggcctctg    6840
tctcctgcct gccccctggga actaaatgtc tcggtataaa actctattgt acatttgttc    6900
tcttctgaga taggagaaaa cccaccctgt ggcgggaggc gagacatgtt ggtggcagca    6960
atgctgttct gttactcttt actccactga gatgtttggg tggagaaaag cataaatctg    7020
gcctatgtgc acatccaggc atagtacctt cccttgaact tatttgtgac acagattcct    7080
ttgctcacat gttttcttgc tgaccgtctc cgcactatca ccctgttctc ctactacatt    7140
ccccttactg agatagtaaa ataataatca ataaatactg agggaactca cagaccggtg    7200
ctggtgcagg tcctccggat gctgagtgcc gtctcctggg cccactgttc tttctccata    7260
ctttgtgtct tatttctttt ctcagtctct cgtcccacct gacgagaaat acccacaggt    7320
gtggaggggc                                                           7330

<210> SEQ ID NO 28
<211> LENGTH: 4218
<212> TYPE: DNA
<213> ORGANISM: Homo sapiens

<400> SEQUENCE: 28
tcacatttca atcttggcgc cacacttcaa tctctccctt ctcttaattt caattccttt      60
cattttctga tagagacaaa ggagacacgt ggacccaaaa ctccgtggac ccaaactccg     120
tggacccaaa actccgtgga ctcaaaactc cagcgccctc tggggagggg gcaagtaccc     180
ctcaacccct tctccttcac ccttagtggc aagtcccgct tttctagggg gcaagaaccc     240
ccaatccctt atttccgcac cccgacctct tatctctgtg tcccaatccc ttatttccgc     300
accccgacct cttatctctg tgccccaatc ccttatttcc gtgccccaac cctttctctg     360
cttttctgga gggcaagaaa ccccccacccc cttctccgta tctctactct tttctctagg     420
cttgcctcct tcactatggg caagcttcca ccttccattc ctccttcttc tcccttagcc     480
tgtatcctta agaacttaaa acctcttcaa ctctcacctg acctaaaatc aaagtgtctt     540
attttcttct gcaatgccgc ttgaccccaa tacaaactcg acagtagttc caaatagccg     600
gaaaacagct cttttcaattt ttccatccta caagagctaa ataattcttg tcgtaaaatg     660
ggcaaatgat ctgaggtgcc tgacgtccac gcattctttt acacatcagt cccttcctag     720
tctctgtgcc cagtgcaact cgtcccaaat cttccttctt tccctcccgc ctgtcccctc     780
agtcccaacc ccaagcgtcg ctgagtcttt ctaatcttcc ttttctacag acccatctga     840
cctctcccct cctcgccaga ccaagctagg tcccatttct tcctcagcct ccgctcctcc     900
accctgtaat ctttttatcg cctctcctcc tcacacccgg tctgacttac agtttcgttc     960
tgtgactagc cctcccccac ctgcccagca atttactctt aaaaaggtgg ctggagctaa    1020
aggcatagtc aaggttaatg ctcctttttc tttatcccaa atcagatagc gtttaggctc    1080
tttttcatca aatataaaac cccagccgag ttcatggctc gttcggcagc aaccctgaga    1140
agctttacag ccctagaccc taaaaggtca aaaggccatc ttattctcaa tatacatttt    1200
attacccaat ctgctcccga cattaaataa aactccaaaa attagaatct ggccctcaaa    1260
ccccacaaca ggacttaatt aacctcacct tcaaggtgta caataataaa aaaagttgca    1320
attccttacc tccactgtga gacaaacccc agctacatct ccagcacaca agaacttcca    1380
aacgcctgaa ctgcagcggc caggcgttcc tccagaacct cctcccccag gagcttacta    1440
caagtgctag aaatctggac accaggccaa ggaatgcctg cagcccagga ttcctcctaa    1500
```

```
gccgtgtccc atctgcgcgg gacccactg gaaatcggac tgttcaactc acctggcagc    1560
cactcccaga gcccctggaa ctctggccca aggctccctg actgactcct tctcggctta    1620
gcagctgaag actgaggctg cctgattgcc ttggaagccc cgtagaccat cgcggatgcc    1680
gagctttaag taactctcac agtggagtgt aagtccatcc ccttcttaat caatacggag    1740
gctacccact ccacattacc ttcttttcaa aggcctgttt ccttgcctc cataactgct     1800 gtgcgtattg acagccagac ttctaaacct cttaaaactc cccaactctg gtgccaactt    1860
agacaacact cttttatgca ctctttttta gttatctcca cctgcccagt tcccttatta    1920
ggccgagata ttttaaccaa attatctgct tccctgacta ttcctggatt acagctgcat    1980
ctcattgctg cccttcttcc caatccaaag cctcctttgc gtcctcctct tgtattcccc    2040
caccttaacc cacaagagac ctctactccc tccttggcga ccaatcatgc accccttacc    2100
atctcattaa aacctaatca cccttacccc actcaatgcc aatatcccat cccacagcaa    2160
gctttgaaag gattaatgcc tgttatcact cgcctgctac agcatggcct tttaaagcct    2220
ataaactctc cttacaattc ccccatttta cctgtcctaa aaccagacaa gccttacaag    2280
ttagttcagg atctatgcct tatcaaccaa attgttttgc ctatccaccc catggtgcca    2340
aacccatata ctctcctatc cgcaatacct ccctccacaa tccattattc tgttctggat    2400
ctcaaacgtg ctttctttac tattcctttg cacccgtcat cccagcctct cttcgcttca    2460
cttggactga ccctgacacc catcaggctc agcaaattac tgggctgta ctgccacaag     2520 gcttcacaga cagcccccat tacttcagtc aagcccaaat ttcatcctca tctgttacct    2580
atctcggcat aattctcgta aaacacacg tgctcttcct gctgatcgtg tccgactaat     2640
ctcccaaacc tcaatccttt acaaacaac aactcctttc cttcctaggc atggttagtg     2700
cagtcaaaat tcttacacaa gagccaggac cgcacactgt agcctttctg tgcaaacaac    2760
ttgaccttac tgttttagcc tagccctcat gtctgcgtgc agcggctgcc actgctttaa    2820
tacttttaga ggccttttcct acaaggtctg agaaggccac cacagtcatt tcttcccttc   2880
tgtcagacat aattcctcag tttagccttc ccacctctat acagtctgat aacagaccag    2940
cctttattag tcaaatcagc caagcatttt ttcaggctct tagtattcag tgacagacta    3000
atggtctatt aaaaacacac ctcaccaagc tcagccacca acttaaaaag gactggacaa    3060
tacttttacc actttcccctt ctcagaagtc agacatgtcc tcagaatgct acaaggtaca   3120
gcccatttaa cctcctgtat agatgctcct ttttattagg ccccagtctc attccagaca    3180
ccagaccaac ttcgactgtg ccccaaaaaa cttgtcatcc ctactatctt ctgtctagtc    3240
atactcctat tcaccgttct caactactca tacatgccct gctcttgttt acactgccgg    3300
tttatactgt ttctccaagc catcacagct gatatctcct cgtgctatct ccaaattgcc    3360
actcttaact cttgaagtaa ataaataatc tttgctggca ggactatgct gaatctccat    3420
aggcactctc taattaaatg tcctaggtcc tcccaattct tagacctttt atacctgttt    3480
ttctccttct cttattccat ttagtttttc aattcataca aaaccgtatc caggccatca    3540
ccaatcattc tacatgacaa atgttctttc taacaacccc acaatatcac cccttaccac    3600
aagacctccc ttcagcttaa tctctcccac tctaggttcc cacgccaccc ctaatcccgc    3660
ttgaagcagc ccggagaaac atcgtccatt ctgtctccat accactcccc caaaattttc    3720
accgccccaa cacttcaaca ctattttgtt ttatttttct tattaatata tgaaggcagg    3780
aatgtcaggc ctctgagccc aagccaagcc atcgcatccc ctgtgacttg cacctatacg    3840
cccagatggc ttgaagtaac tgaagaatca caaagaagt gaaaaggccc tgccccgcct     3900
```

```
taactgatga cattccacca ttgtgatttg tttctgcccc accttaactg agtgattaac    3960
cctgtgaatt tccttctcct ggctcagaag ctcccccact gagcaccttg tgaccccct     4020 tccctgccca ccagagaaca ccccctttg actgtaattt ccattatct tcccaaatcc      4080 tataaaacgg ccccacccct atctcccttc gctgactctc tttttggact cagcccgcct   4140
gcacccaggt gaaataaaca gccatgttgc tcacacaaag cctgtttggt ggttctcttc   4200
acacggatgc gcatgaaa                                                  4218

<210> SEQ ID NO 29
<211> LENGTH: 5871
<212> TYPE: DNA
<213> ORGANISM: Homo sapiens

<400> SEQUENCE: 29
gtcaggcctc tgagcccaag ccaagccatc gcatcccctg tgacttgcac gtatatgccc     60
agatggcctg aagtaactga agaatcacaa aagaagtgaa aaggccctgc cccgccttaa    120
ctgatgacat tccaccattg tgatttgttc ctgccccacc ttaactgagt gattaaccct    180
gtgaatttcc ttcttctggc tcagaagctc ccccactgag caccttgtga ccccccgccc    240
ctgcccacca gagaacccct tttgactgta attttccatt accttcctaa atcctataaa    300
acggccccac ccctacctcc cttcgctgac tcttttccga ctcagcccac ctgcacccag    360
gtgaaataaa cagccatgtt gcttacacaa agcctgtttg gtggtctctt cacacggacg    420
cgcatgaaat ttggtgccat gactcggatc gggggacctc ccttgggaga tcaatcccct    480
gttctcctgc tctttgctcc gtgagaaaga tccacctatg acctcaggtc tcagaccga    540 ccagcccaag aaatatctca ccaatttcaa atctggtaag cggcctcttt ttacactctt    600
ctccaacctc cctcactatc cctcaacctc tttctccttt caatcttggc gccacacttc   660
aatctctccc ttctcttaat ttcaattcct ttcattttct ggtagagaca aaggagacac    720
gttttatccg tggacccaaa actccggcgc cggtcacaga ctgggaaggc agccttccct    780
tggtgtttaa tcaatgcagg gaagcctctc tgattattca cccatgtttc aagggtgtca   840
gaccacgcag ggatgcctgc cttggtcctt caccttagc ggcaagacct gcttttctgg     900
ggaaggggca agtactccaa cccccttctct ccttgtctct accccttctc tgcttttctg    960
gggaaagggc aagtacccca ccccttctc tccttgtctc taccccttct ctgcttttct   1020
ggggaagggg caagtacccc aacccttct ctccttgtct ctaccccttc tctgcttttc   1080 tggggggagga gcaagtaccc ctcaacccct tctccttcac ccttagcagc aagtcccact   1140
tttctagggg gcaagaaccc ccaattcctt atttccacac ccgacctct atctctgtg    1200 ccccaatccc ttatttcctc acccctacct cttatctctg tgccccaatc ctttatttcc   1260
acaccccgac ctcttatctc tgtgccccaa tccttatttt ccgcaccca tcctcttatc    1320 tctgtgcccc aatccttat ttccatgccc cgaccccct tccgctttt ctggagggta      1380 agaaccccg aacccttcc ctccgtgtct ctatgctctc ttttctctag gtttgcctcc     1440
ttcactatgg gcaaccttcc accctccatt cctcctcctt ctccctcagc ctgtgttctc    1500
aagaacttaa aacctcttca actcacacct gacctaaaac ccaaatgcct tatttcttc     1560 tgcaatgctg cttgaccccca atacaaacta gacagtagtt ccaaatagcc agaaaacggc   1620
actttcaatt tttccatcct acaagatcta aatatttctt gttgtaaaat gagcaaatgg    1680
tctgaggtgc ctgacgtcca ggcattcttt tacacatcag tcccttccta gtctctgtgc   1740
```

-continued

```
ccagtgcaac tcgtcccaaa tcttccttct ttccctcccg cctgtcgcct cagtcccaac    1800
cccaagcgtt gctgagtctt tctaatcttc cttttctaca gacctatctg acctctcccc    1860
tcctcgccag gccaagctag gtcccaattc ttcctcagcc tctgctcctc caccctataa    1920 tcttttatt gcctccctc ctcacacctg gtccggctta cagtttcgtt cggtgactag       1980
ccctccccca cctgcccagc aatttactct aaaaaggtg gctggagcca aaggcatagt     2040
caaggttaat gctccttttt gtttatccca aatcagatag tgtttaggct ctttttcatc    2100
aaatataaaa acccagccca gttcatgact cgtttggcag caaccctgag atgctttaca    2160
gccctagacc ctaaaaggtc aaaaggccgt cttattctca atatacattt tattacccaa    2220
tctgctcccg acattaaata aaactccaaa aattggaatc tggccctcaa accccacaac    2280
aggacttaat taacctcacc ttcaaggtgt acaataacag aaaaaagttg caattccttg    2340
cctccactgt gagacaaacc ccagccacat ctccagcaca caagaacttc caaatgcctg    2400
aaccgcagcg gccaggcgtt cctccagaac ctcctccccc aggagcttgc tacaagtgcc    2460
agaaatctga ccaccaggcc aaggaatgcc tgcagcccag gatttctcct aagccacgtc    2520
ccatctctgc gggaccccac tagaaatcgg actgttcaac tcacctggca gccactccca    2580
tagcttctgg aactctggcc caaggctctc tgactccttc ccagatcttc ttggcttagc    2640
ggctgaagac tgatgctgcc taattgcctc ggaaacaccg tagaccatca cggacgccga    2700
gcttcaggta actctcacag tggaaggtaa gtccttcccc ttcttaatca atatggaggc    2760
tacccactcc acattacctt cttgtcaagg gcctgtttcc cttgcttcca taactgttgt    2820
gggtattgac ggccaggctt ctaaacctct taaaactccc caactgtgga gccaacttag    2880
acagtactct tttaagcact ccttttagt tatccccacc tgcccagttc ccttattagg      2940
ccgagatact ttaactaaat tatctgcttc cctgactatt cctggattac agctgcatct    3000
cattgctgcc cttcttccca atccaaagcc tcctttgcat cctcctcttg tattcccca    3060 ccttaatcca taagtataag atatctctac tccctccttg gcgaccgatc atgcacccct     3120
taccatctca ttaaaaccta atcacccta ccccgctcaa tgccaatatc catcccaca      3180 gcatgctttg aaaggattaa agcctgttat cactcgcctg ctacagcatg gccttttaaa    3240
gcctataaac tctccttaca attccccat tttacctgtc ctaaaaccag acaagccata     3300
caagttagtt caggatctat gccttatcaa ccaaattgtt ttgcctatcc accccatggt    3360
gccaaaccca tatactctcc tatcctcaat acctccctcc acaatccatt attctgttct    3420
gcagctcaaa cgtgctttct ttactattcc tttgcaccct taatcccagc ctctcttcgc    3480
tttcacttgg actgaccctg acacccatca ggctcagcaa attacctggg ctgtactgcc    3540
gcaaggcttc acagacagac cccattactt cagtcaagcc caaatttcat tctcatctgt    3600
tacatatctc ggcataattc tcttaaaaac acacatgctc gccctgctga tcctgtccga    3660
ttaatctccc aaacctcaat cccttacaaa caacaactc ctttccttcc taggcatggt     3720
tagtgcagtc agaattctta cacaagagcc aggaccgcac cctgtagcct ttctgtccaa    3780
acaacttgac cttactgttt tagcctagcc ctcatgtctg cgtgcagcgg ctgccactgc    3840
tttaatactt ttagaggccc tcaaaatcac aaactatgtt caactcactc tacatttttc    3900
ataacttcca aaatctattt tcttcctcat acctgacgca tatactttc tgctccccgg     3960 ctccttcagc tgtactcact cttccttaag tcccacaatt accattgttc ctggcccgga    4020
cttcaatcca gcctcccaca ttattccaga taccacacct gaccttcatg actgtatctc    4080
tctgatccgc ctgatattca ccccatttcc ccatatttcc ttctttcctg ttcctcaccc    4140
```

```
tgatcacact tgatttatca atggcagttc caccaggcct aataaccaca caccagcaaa    4200
ggcaggctat gctatagtat aagccactag cccacctctt agaacctctc atttcctttc    4260
cattgtggaa atctatcctc aaggaaataa cttctcagtg ttctatctgc tattctacta    4320
ctcctcaagg attattcagg cccctccct tccctacaca tcaagctcga ggatttgccc     4380
ccacccagga ctggcaaatt agctttattc aacatgccct gagtaacaaa aactaaaata    4440
cctcttagtc taggtagaca ctttcactag ataggtagag gcctttccta cacggtctga    4500
gaaggccacc gcagtcattt attcccttct gtcagacata attcctcagt ttagccttcc    4560
cacctctata cagtctgata acagaccagc ctttattagt caaatcagcc aagcattttc    4620
tcaggttctt agtattcagt gacagactaa tggtctatta aaaacacacc tcaccaagct    4680
cagccaccaa cttaaaaagg actggacaat acttttacca ctttcccttc tcagaagtca    4740
gacctgtcct cagaatgcta caaggtacag cccatttgag ctgctgtata gacactcctt    4800
tttattaggc cccagtctca ttccagacac cagaccaact tagactgtac ccccaaaaaa    4860
aacttgtcat ccctactatc ttctgtctag tcatactcct attcaccatt ctcaactact    4920
cacacatgcc ctgctcttgt ttacactgcc ggtttacact gtttctccaa gccattacag    4980
ctgatatctc ctggtgctat ccccaaactg ctactctaaa ctcttgaagt aaataaataa    5040
tctttgctgg caggactatg ctgaatctcc ttaggcactc tctaatcaga tatcctgagt    5100
cgtcccaatt cttagacctt ttatacctgt ttttctcttt ctcttattcc atttagtttc    5160
tcaattcatc caaaaccgta tccaggccat caccaatcat cattctatac gacaaatgtt    5220
tcttctaaca tccccacaat atcacccctt accacaagac ctcccttcag cttaatctct    5280
cccactctag gttcccacgc cgcccctaat cccgcttgaa acagccctga gaaacatcgc    5340
ccattctctc tccataccac cccccaaaaa ttttttgccgc cccaacactt caacactatt    5400
ttgttttatt tttcttatta atataagaag gcaggaatgt caggcctctg agcccaagcc    5460
aagccatcgc atcccctgtg acttgcacgt atatgcccag atggcctgaa gtaactgaag    5520
aatcacaaaa gaagtgaaaa ggccctgccc cgccttaact gatgacattc caccattgtg    5580
atttgttcct gccccacttt aactgagtga ttaaccctgt gaatttcctt ctcctggctc    5640
agaagctccc ccactgagca ccttgtgacc cccgcccctg cccaccagag aacaaccccc    5700
tttgactgta attttccatt acctttccaa atcctataaa acggcccac ccctacctcc     5760 cttcgctgac tctgctttcg gactcagccc acctgcaccc aggtgaaata aacagccatg    5820
ttgctcacac aaagcctgtt tggtggtctt ttcacacgga cgcgcatgaa a             5871
```

<210> SEQ ID NO 30
<211> LENGTH: 6471
<212> TYPE: DNA
<213> ORGANISM: Homo sapiens

<400> SEQUENCE: 30

```
agcaggagtt aaacaatatg gacctaactc tccttatacg agaatattat taaattccat    60
tgctcatgga aatagactta tttcttatga ttgggaaatt ctggctatat cttcccttc     120 accctctcag tatctccagt ttaaaacctg gtggattgat gggtacaag aacaggtacg     180 aaaaaatcag gctactaatc ctgttgctta tatagatgaa gaccaattgc taggaagagg    240
tccaaactgg gacactatta accaacaatc agtaatgaaa atgaggctat tgaacaactg    300
taagggctat ttgcctcagg gcctgggaaa acattcagga cccaggaacc tcatgccctt    360
```

```
cttttagttc aatcagacaa ggctctaaag agccatatcc agactttgtg gcaaggttgc      420
aagatgcagc tcaaaaatcc attgcaggta acgcccgaaa agttattgta gaaataatgg      480
cttatcaaaa cgcaaattca gagtgtcaat cagccataaa gccattaaga ggaaatgttt      540
cagcaggagt tgatgtaatt acagaatatg tgaaggcttg tgatgggatt ggaggagcta      600
tgcataaggc aatgccattg gctcaagcaa ttacaggggt tgctatagga ggacaagtta      660
aaacatttgg gggaaaatgt tataattgtg gtcaaatcgg tcatctaaaa aagaattgcc      720
cgagcttaaa taaacagcaa aaaaaaaaaa aaaaaaaaa aaaaaagag ccacctggcc        780 tgtgtccaag atgtgaaaaa ggaaaacatt gggctaaggc atgtcgttct aaatttgata      840
aaaatggaca accattgtcg ggaaacggca agaggggcca gccccaggcc ccgcaacaaa      900
gtggggcatt cccgattcag ccatttgttc ctcagggttt tcaggacaa caaccccac        960 agtaaatacc accatttcag gaaatcagcc aattacaata cgacaattat cctctgtcac     1020
agcaggcagt gctgcagtag atttatgttc tactcaaatg atttctttac tccgtggaga     1080 gccccctgcaa aagattccta cagggtata tggcccgctg ccacaaggga tggtaggcct     1140
tattttagga agatctagtc taaatttgaa aggagttcaa attcatactg gggtaattga     1200
ctcagattat aaaggggaaa ttcagttagt gatcagctgt actgttccct ggagtgccaa     1260
tccaggtgat agaattgctc aattactgct cttgccttat attaaaattg gggatagcaa     1320
aacagaaaga acaggagggt tgcaagtac caacactgct ggaaaagctg tttattgggc     1380
tagtcagctc tcagagaata gatctgtgtg tacagttact attcatggaa aacaatttga     1440
aggattagtg gatactgggt ctgatgtttc tatcattgcc ttaaatcaat ggccaaaaaa     1500
ttggcctaaa caaaagcctg ttacaggact tgttggtgtg ggcactgcct cagaagtgta     1560
tcaaagtgcc aggattttac attgtctagg acctgataat caagagagta cagttcagcc     1620
tatgattact tctattccaa ttaatttatg gggccgagac ttattagaac agtggcatgc     1680
agagattact attccagtct ctctgtacag ccccacgagt caaaaaatca tgactaaaat     1740
gggatagctc cctggcaaag gactagggaa aaatggagaa ggcattaaag ttccaattga     1800
ggctaaggga aatccagaaa gaaaaggact agggtatcct ttttaggggt ggccactgta     1860
gagcctccaa aacccatttc attaacttgg aaaacagaaa agcctgtatg ggtaaatcag     1920
tggccactac caaaacaaaa gctggaggcc ttacacttat tggcaaaata acaattagaa     1980
aagggacata ctgagcattc attttcgcct tggaattctc ctgtgtttgt aattcagaaa     2040
aaatcaggca gatggcgcat gctaactgat ttaagagccg ttaatgcagt aattcaaccc     2100
atggggcctc tccaacctgg gctgccctct ccagccatga tccccgaaga ctggcccttta    2160 attataattg atctgaagta ttgctttttt accattcctc tggcaaaaca ggattttgaa     2220
aaattggctt tcactatacc agccataaat aataaagaac cagccactag atttcagtgg     2280
aaagtgttgc ctcagggaat gcttaatagt ccaactattt gtcagacttt tgtagctcaa     2340
gttcttcaac cagttagaga caagttttca gactgttata tcattcatta tgttgatgat     2400
attttgtgtg ctgcagaaac aagagacaaa ttaattgact gttacacatt tctgcagaca     2460
gaggttgcaa acgcaggcct gacaatagca tctgataaga ttcagatctc cactcctttt     2520
cattatttgg gaatgcaggt agaggagaga aaaattaaac cacaaaaagt agaaataaga     2580
aaagacacat taagaacatt aaatgacttc aaaaattgct aggagatatt aattggattc     2640
ggccaactct aggcatccct acttatgcca tgtcaaattt gttctctatc ttgagagggg     2700
atccagactt aaatagtaaa agaatattaa ctccagaggc aactaaagaa atagaattag     2760
```

```
ttgaagaaaa atttcagtca gcaaaagtaa atagaataga tcacttagcc ccactccaac    2820
ttttaatttt tgctactgca cattctccaa caggcattat tgttcaaaat acagatcttg    2880
tggagtggtc attccttcct cacagtacag ttaagacttt tacattgtac ttagatcaaa    2940
tggctacatt aattggtcag gcaagactat gaatagtaaa attgtgtgga aatgacccag    3000
ataaaatcat tgtttcttta aacaaggaac aggatagaca agtctttatc aattctggtg    3060
cagggcagat tggtcttgct gattttgtgg gaattattga taatcattac ccaaaagcaa    3120
aaatcttcca gttttgtgaaa ttgactactt ggattttacc taaaattacc agacaaaaac    3180
ctctagaaaa tgctctgacg gtgtttactg atggttccag caacggaaaa gtggcttaca    3240
ctgggccaaa agaacaagtc attgaaactc aatatcactc agctcaaaga gcagaattgg    3300
ttgctgtcat ttcagtgtta caagatttta atcagcctat taacattgtt tcagattttg    3360
catatttagt acaggctaca aaagatgttg agacagccct aatcaaatat agtatggatg    3420
atcagttaaa tcagctgttt aaattgttac aacaaactgt aagaaaaaga aatttcccat    3480
tttatattgc tcatatccga gcacatacta atttaccagg gcctttaact aaggcaaatg    3540
aacaagctga cttgctagta tcatctgcct tcatggaagc acaagaactt caggccctca    3600
ctcatgtaaa tgcaacagga ttaaaaaaca aatttgatat cacatggaaa caagcaaaaa    3660
atgttgtaca acattgtgct cagtgtcaag tcttacacct gcccgctcaa gaggcaggag    3720
ttaatcctag aggtttatgt cctgatgcat tatggcaaat ggacgtcaca catgtacctt    3780
catttgcaaa attgtcattt gtccatgtga cagttgatac ttattcacat ttcatatggg    3840
caacctgcca gacaggagaa agtacttccc atgttaaaag acatttatta tcttgttttg    3900
cagtcatggg atttccagaa aaaattgaaa caggtaatgg gccaggatac tgtagtaaag    3960
catttcaaaa atccttaaat cagtggaaaa ttacacatac aacaggaatc cttaatttcc    4020
aaggacaggc cataattgaa agaactaata gaacactcta agctcaattg gttaaacaaa    4080
agaaggaaaa agtaaggagt acaatactcc ccagatgcaa cttaatctag cactctatac    4140
tttaaatttt ttaaatatat atagaaatca gaccactact tctgcagaac aacatttttac    4200 tggtaaaaag aacagcccac atgagggaaa actgatttgg tggaaagaca acaaaaataa    4260
aacatgggaa ataggtaagg tgataacatg ggggtgaggt tttgcttgtg ttccagcagc    4320
agaaaatcag cttcctcttt gggtacccac tagacatttg aagttctaca atgaacccat    4380
cagaggtgca agggaaggca cctccgcaga gacagagaac ccgcaatcga acatcatcga    4440
ctcgcagggt gaacgaaatg gtgatatcag aagaacagat gaagttgcca tccaccaaga    4500
aagtggggcc gccgacctgg gcccagctaa agaagctgac acagttagct gaaaaaagcc    4560
tggaaaacac aagggtaaca caaactccag agaaatatgct acttgcagat ttaatgattg    4620
tatcagcggt ggtaagtctc cctatgtctt caggagccgc tacagctaac tatacttact    4680
gggcctatgt gattttccca cccttaattc gagcagtcac ttggatagat aatcctattg    4740
aagtatatgt taataacagt gcatgggtac caggccccac agatgaccgt ggccctgccc    4800
aacctgaaga aaaaggaatg atgataaaca tttccattgg gtatcattat cctcctattt    4860
gcctgggaaa agcaccagga tgcttaatgc ctacaatcca aacttggttg atagaagtac    4920
ctactgtcag tgccaccagt aaatttactt atcatatgat aagaggaatg tcgctcaggt    4980
cacaaatgaa taatttacag aattcttcct atcaaagatc attaaaattt aggcctaaag    5040
ggaaaccatg ccccaaggaa attccaaaag aatcaaaaga cccagtagtc ttagtttggg    5100
```

```
aagaatgtgt ggctgatact gcagtggtac tacaaaacaa taaatttgaa actattatag    5160
actaggcccc tcaaggccaa ttatattatg actgtatggg ccagacccac tcatgttcac    5220
aggccccatg tgtctggccc actaatccgg cctgtgatag tgatttaact aaaaggctag    5280
accaggttta taaaggcta gaatcaccct atccatggaa atggggtgaa agaggatttt     5340
catcaccccg accaaagtta gttagtcctg tttttggtcc tgaacaccca gaattatgga    5400
agctcactgt ggcctcgtac cacattagaa tttggtctgg aaatcaagtt atgggaacaa    5460
gaaatcataa gccatattaa ctattaacct aaattccaat ctgaaaattc ctttgcaaag    5520
ttgtgtaaaa cccccttata tgctagttgt agaaaacata gctattaaac cagattccca    5580
aactacaacc agtgaaaatt gtagattgtt tacttgcatt gattcaactt tcgattggca    5640
gaatgctatt ctgttagtaa gggcaagaga aggcgtgtgg atccctgtgt ccatggatcg    5700
accatgggag gcttctccat ccgtacatac cttaagtatt aaaaggagtt ctaattagat    5760
ttaaaagatt cattttttact ttgattgcag tgattatggg tcttattgca gtcacagcta    5820
ctgctgcggc tgctggaatt gctttacact cctctgttca aactgcagaa tatgtgaata    5880
attggcaaaa gaattcctca aaattgagga attcttagac tcaaacaggt caaaaattgg    5940
caaatcaaat taatgatctt agacaaactg ttatttggat gggagatagg ctcatgagct    6000
tagaatatct ttttcagtta cagtgtgact ggaatatgtc agattttct attacacctc     6060 gagcctgtaa tgaatctgaa cagcactggg acatggttag aagccatcta caaggaagag    6120
aagataatct taccttagat atttctaaat tgaaagaaca aattttgaa acatcaaaag     6180 cccagttaaa tctggtgtca gaaacggagg caatggtaaa agctgttgat agcctcacaa    6240
atcttaaccc tgtcacttgg gttaaaacca ttggaaattc cactattgca aattttgtat    6300
taattcttgt atgtctgtcc tctctattgt tagtctacag gtgtatccag cagctccgga    6360
gagacagcga ccagggagaa ggggccatga tgaccatggc ggttttgtca aaaagaaaag    6420
cgggaaatgt agggaaaaga gacagatcag actgtcactg tgtctatgta g             6471
```

<210> SEQ ID NO 31
<211> LENGTH: 327
<212> TYPE: DNA
<213> ORGANISM: Homo sapiens

<400> SEQUENCE: 31

```
tgggtcaggc acaaagtaag cccaccccac caggaactat gttgaaaaat ttcaagaaag      60
gatttaaggg agattatggt gttactctga caccaggaaa agttagaact ttatgtgaaa     120
tagactggcc agcattagag gtggatttcc catcagaagt aagccttgac gggtccgttg     180
tttcaaaggt atggcacaag gtaacctgta agccagggca cgcaaaccag ttcctgtaca     240
tagacacttg gttacagctg gttttagatc cgcctcacag tggttgagag aacagcagca     300
taagcagctg acagaggcaa ggaaaga                                         327
```

<210> SEQ ID NO 32
<211> LENGTH: 5981
<212> TYPE: DNA
<213> ORGANISM: Homo sapiens

<400> SEQUENCE: 32

```
gtcaggcctc tgagcccaag ctaagccatc atatcccctg tgacctgcat gtacacatcc      60
agatggccgg ttcctgcctt aactgacgac attccaccac aaaagaagtg aaaatggcct     120
gttcctgcct taactgatga cattatcttg tgaaattcct tctcctggct catcctggct     180
```

```
ccaaagctcc cccactgagc accttgtgac ccccactcct gcccaccaga gaacaacccc    240 cttttgactgt aattttcctt taccttccca aatcttataa aatggcccca ccccatctcc   300
ctttgctgac tttcttttca gactcagccc tcctgcaacc agttgattaa aagctttatt   360
gctcacacaa agcctgtttg gtggtctctt cacacggatg caagtgaaat ttggtgccgt   420
gacttggatt gggggacctc ccttgggaga tcagtcccct gtcctcctgc tctttgctcc   480 gtgaaaaga ttcacctaca acctcgggtc ctcagaccca ccagcccaag gaacatctta    540
ccaattttaa attgggtaag cagcctcttc ttactctctt ctccaaccta tctcactatc   600
cctcagccac tttctccttt caatcttggc gccaccttc aatctctccc ttctcttaat    660
ttcagttcct ttccttttct ggtagagaca ggagacgcac tttatccatg acccaaaac    720 tctggcgccg tcatggact cgggaagaca gtcttccctt ggtgtttaat cacacaggga    780
cacctgcctg attattcacc cacgtttcag aggtgtttga ccacaagggg atgcctgcct   840
tggtccttga cccttagcag caagtacctc ttttctgggg ggcaagaacc tcccagcccc   900
ttctccttca cccttagcgg caagtagtgc ttttctaggg ggcaagaacc ccccaacccc   960
ttctctccat gtctgtaccc cttctctgct tttctggggg caagaacctc ccaatccctt   1020
atttccacac cccaacctct tatctctgca ccccgatccc ttatttccac gccccgaact   1080
cttatctctg caccccgatc ccttttttct gcacccccgac ctcttatctc tgtgccctga  1140
ttccttattt ccacgccccg acctcttatc tctgtgccct gatcctttat ttccacaccc   1200
tgacctctta tctctgcacc ccaacccctt atttccatgc cccaaccct ttcctgcttt    1260 tctgggggt aagaatcccc aaaccccttc tctccatgtc tctactctct cttttctctg    1320
ggcttgcctc cttcactata ggcaaccttc caccctccat tcctccttct tctcccttag   1380
cctgtgttct caagaactta aaacctcaac tcacacctga cctaaaacct aaatgcctta   1440
ttttcttctg caatgctgct tgaccccagt acaaactcga cagtggttcc aaatagccag   1500
aaaatggcac tttcaatttt tccatcctac aagatctaaa taattcttgt cataaaatag   1560
gcaaaaggtc tgaggtgcct gacatccagg cattctttta cacattgttc cctccctagt   1620
ctctgttccc aatgcgactc gtcccaaatc gtccttcttt ccctcccgcc tgtcccctca   1680
gtcccaaccc caagtgtcgc tgagtctttc taatcttcct ttctaaagac ccatctgact   1740
tctcccctcc tcaccaggcc cagccaggtc ccaattcttc ctcagcctct gctccccat    1800 cctataatcc ttttatcacc tcccctcctc agaccctgtc tagcttacag tttccttcct   1860
ggactagcct tcccccacct gtccagcaat ttcctcttaa aaaggtggct ggagctaaag   1920
gcatagtcaa gtttaatgct ccttttctt tatctgacgt ctcccaaaat cagttagtgt    1980
ttaggctgtt tttaatcaaa tatgaaaaac ccagcccagt tcatggctcg tttggcagca   2040
accctgagat gctttaccgc cctagaccct gaaaggtcag aaagccgtct tattctcaat   2100
atgcatttta ttgtattacc caatctgctc ccaacatgaa ataaagctcc aaaaattaaa   2160
tcccagccct caaaccccac acaggactta attaatctca ccttcaaggt gtacaataat   2220
agagtagagg cagccaagta gcaatgttat ttctgagttg caattccttg cctccactgt   2280
gagacaaacc ccagccacat caccagcaca cgagaactcc aaatgcctga actgcagctg   2340
ccaggggttc ctccagaacc tcctccccca ggagcttgct acaagtgcca gaaatctggc   2400
cactgggcca aggaatgccc acagcctggg attcctccta agccatgtcc catctatgcg   2460
ggaccccact gaaaatcgga ctgttcaact cacctggcag ccacttccag agcccctgga   2520
```

```
actctggccc aaggctctct gactgactct ttcccagatc ttctcggctt agcagctgaa    2580
gactgacact gcctgattgc ctcagaagcc tacaggacca tcacagatgc tctaggtaac    2640
tctcacagtg gagggtaagt ctgtcccctt cttaatcaat acagaggcta cccactccac    2700
attacctcct ttttcaagggc ctgtttccct tgcctccata actgttgtgg gtattgacgg    2760
ccaggcttct aaacctctta aaactcccca actctggtgc caacttagac aatactcttt    2820
taagcactcc tttttagtta tctccacctg cccagttccc ttattaggcc gagatacttt    2880
aactaaatta tctgcttccc tgactattcc tggactacag ctgcatctca ttgctgccct    2940
tctcccaacc caaagcctca gttgtgtaca agccttacaa gttagttcag gatctgcgcc    3000
ttatcaacca aattgttttg cctatccacc ccgtggtgcc aacccatata ctctcctatc    3060
ctcaatacct gcctctacaa tccattattc tgttctggat ctcaaacatg ctttctttac    3120
tattcctttg cacccttcat acccagcctc tcttcgcttt cacttggact gaccctgaca    3180
cccatcaggc tcagcaaatt acctgggctg tactgccaca agtcttcaca gacagccccc    3240
attccttcag tcaagcccat atttcatctt catctgttac ctatctcggc ataattctca    3300
taaaaacaca cgtgctctcc ctgctgatcg tgttcgacta atctcccaaa cctgaatccc    3360
ttctacaaaa caacaactcc tttccttcct aggcatggtt agtgcggtca gaattcttac    3420
acaagagcca ggaccgcacc ctgtagcctt tctgtccaaa caacttgacc ttactgtttt    3480
agcctagccc tcacgtctgc atgcagcagc tgctgctgct ttaatacttt tagaggccct    3540
aaaaatcaca aactatgctc agctcactct ctacagttct caaaccttcc aaaatctatt    3600
ttcttcctca tacctgatgc atatactttc tgcttcccgg ctccttcagc tatactcttt    3660
gttgagtctc ccacaattac cattgttcct ggcacggact tcaatctggc ctcccacatt    3720
attctggata ccacacctga ccctcatgac tgtatctctc tgatccacct gacattcacc    3780
ccatttcccc atatttcctt atttcctgtt cctcaccctg atcacattta gtttattgat    3840
ggcagttcca ccaggcctaa tcgtcactca ccagcaaagg caggctatgc tacagtatct    3900
tccacatcta tcattgaggc tactgctctg accccctcca ctacctctca gcaagccgaa    3960
ctcattgcct taagtcaagc cctcactctt gcaaaaggac taaatgtcaa tatttatact    4020
gactctaaat atgccttcca tatcctgcac cactgtgcaa gagatttcct cactacacaa    4080
aggtcctcta tcattaatgc ctctttaata aaaacgcttc tcaaagctgc tttacttcca    4140
gaggaagctg gagtcattca ctgcaaaggt catcaaaggg catcagatcc catcgctcag    4200
gacaatgctt acgctgataa gatagctaaa aaagcagcta gcattccaac ttatatccct    4260
cactttcagt ttttctcctt ctcatctggc cactcccacc tacttcccca ctgaaacttc    4320
cacctatcaa tctcttccca cacaaggcaa atggttctta gatcaaggaa atatttcct    4380 tccagcctca caggcccatc ctattctgtc gtcatttcat aacctcttcc atgtaggtta    4440
caagccacta gcccgtctct tagaacctct catttctttt ccatcatgga aatctatcct    4500
caaggaaatc acttctcagt gttccatctg ctattctact acccctcagg gattgttcag    4560
gcctcctccc tttcccacac atcaagctca gggatttgtc cctgcccagg actggcaaat    4620
tggctttatt caacatgccc tgagtcagga aactaaaata cctcttggtc tgggtagaca    4680 cttttcactgg atggcctttc ctacagggtc tgagaaggcc actgcggtca tttcttcccg    4740
tctgtcagac ataattattc ggtttggcct tcccacctct acggtccgat agtggaccgg    4800
cctttattag tcaaatcagc caagcagttt ttcaggctgt tggtattcag tgaaaccttt    4860
atatccctta cagtcctcag tcttcaggca gccaccaact taaaaaggac tggacaatac    4920
```

```
ttttacctct ttcttttctc agaattcagg cctgtcctcg aaatgctaca ggtatagccc    4980
atttgagctc ctgtatggat gctccgtttt attaggcccc agtctcattc cagacaccag    5040
accaacttgg actgtgcccc aaaaaacttg tcatccctac tatcttctgt ctagtcatac    5100
tcctattcac cgttctcaac tactcataca tgccctgctc ttgtttacac tgccggttta    5160
cactgtttct ccaagtcatc acagctgata tctcctggtg ctatcccaa  actgccactc    5220 ttaactctta aagtaaataa ataatctttg ctggcaggac tatgctgacc ctccttaggc    5280
actctctaat cagatgtcct gagtcctccc aattcttaga cctttaatac ctgttttctc    5340
cttctctttt tccgtttagt ttttcaattc atacaaaacc atattcaggc catcaccaag    5400
aattctaaat gacaaatgtt tcttctaaca gtcccacaat atcacccctt accacaaaat    5460
cttccttcag cttaatctct cccactctag gttcccacac cgcccctaat cccactcaaa    5520
gcagccctga gaaatatctc tccataccat ccccccaaat ttttgccatc caacacttt    5580 accactattt cattttattt ttcttattaa tataacaaga caggaatgtc aggcctctga    5640
gcccaagcta agccatcata tcccctgtga cctgcacgta cacatccaga tggcctgttc    5700
ttgccttaac tgatgacatt atcttgtgaa attccttctc ctggctcatc ctggctcaaa    5760
agctccccta ctgagcaccc tgtgaccccc acacctgcct gccagagaac aaccccttt     5820 gtaattttcc tttacctacc caaatcttat aaaacagccc cacccatct  cccttctg      5880 actctctttt cggactcagc ccgcctgcac ccagctgatt aaaagcttta ttgctcacac    5940
aaagcctgtt tggtggtctc ttcacatgga cacgagtgaa a                        5981
```

<210> SEQ ID NO 33
<211> LENGTH: 2376
<212> TYPE: DNA
<213> ORGANISM: Homo sapiens

<400> SEQUENCE: 33

```
acaacttgac cttactgttt taggctggcc atcatgtccc cgtgcagcag ctgccgctgc      60
cctaacactt ttagaggccc tcaaaatcac aaactatgct caactcactc tctatagttc     120
tcataacttc caaaatctat tttcttcctc acacctgatg catatacttt ctgctccccg     180
gctccttcag ctgtactcac tctttgttga gtctcccaca gttaccattg ttcctggccc     240
ggacttcaat ccagcctccc acactattcc ggatacatct gactcccatg actgtatctc     300
tctgatccac atgacattca ctcccttct  ccatgtttcc ttctttcctg ttcctcaccc     360
tgatcacact tggtttattg atggcagttc caccaggcct aatcgccact caccagcaaa     420
ggcaggctat gctatagtat cttccacatc tatcactgag ctaccgctc  tgccccctc      480 cattacctct cagcaagctg aactcactgc cttaacttga ccctcactc  ttgcaaaggg     540 actacccatc aatatttata ctgactctaa atatgccttc catatcctgc accaccatgc     600
tgttatatag gcagaaagaa gtttcctcac tatgcaagag tcctccatca ataatgcctc     660
tttaataaga actcttctca aggctgcttt acttccaaag aaagccggag tcattcactg     720
caaaggccat caaaaggctt cagatcccat tgctctggac aacgcctatg ctgataagat     780
agctaaaaaa gcagctagcg ttccaacttc tatccctcag ggcagttttc ctccttctca     840
tctggccact cccacctact ccctcgctga aacttccacc catctcttcc cacacaaagc     900
aaatggttct tggaccaaag aaaaatctcc ttccagtctc acaggccat  tctattcgtc     960 atttcataac ctcttccatg taggttgcaa gccgctagcc cgcctcttag aacccgctag   1020
```

| | |
|---|---|
| cccacctctt agaacctctc atttcctttc catcgcaaaa atctatcctc aaggaaatca | 1080 |
| cttttcagtg ttccatctgc tattctacta ctcctcaaga atttctcagg cccctccct | 1140 |
| tccccacaca tcaagctcgg ggatttgccc cgcccaggac tggcaaattg actttactca | 1200 |
| catgcctcga gtcaggaaac taaaatacct cttggtctgg gtagacactt tcactggatg | 1260 |
| ggtagaggcc tttcccacag ggtctaagaa ggccaccgtg gtcatttatt cccttctgtc | 1320 |
| agacatagtt cctcggtttg gccttctcac ctctatacag tccgataacg gaccggcctt | 1380 |
| tactagtcaa atcacccaag cagtttctca ggctgttggt attcagtggc acctggtttt | 1440 |
| tcctcaaact gccacccta agtctctctt taagtggata gaagatcttc agtggcaagg | 1500 |
| taccctccaa tactttcacc ctgatgaagt cctattcttt acttttatac ttactcttat | 1560 |
| tctcattccc gttcttatgc caccctctac ctctccccag ctatctctat cacactatca | 1620 |
| atctcagtta ctctctccta gccgtttcta atccttcttt aacaaacaat tgctggcttt | 1680 |
| gcatttctct ttcttccaaa atcacaaagg tctcgactta ctgctaaaaa aaaaaaaaag | 1740 |
| gggactctat attttaaat gaagagtgct attttacct aaatcaatct ggcctggtat | 1800 |
| atgacaacat taaaaaaaac tcaaagatag agcctaaaag cttgccaacc aagcaagtaa | 1860 |
| ttacactaac cccccttgga cactctaatt agatgtcctg ggtcctccca attcttagtc | 1920 |
| cttttatacc tgttttctc cttctcttat tcagaccttg tgtcttccat ttagtttctc | 1980 |
| aattcatcca aaaccatatc caggccatca ccaatcattc tatacgacaa atgtttcttc | 2040 |
| taacaacccg acaattatca ccccttacca caaaatcttc cttcagcttc atctctccca | 2100 |
| cactaggttt ccatgttgcc ccagtcctgc tcaaagcagc cctgagaaac attgcccatt | 2160 |
| atctctccat accaccccc aaaattttcc ccaccccaac actttaccac tattttattt | 2220 |
| ttcttattaa tataagaaga caggaatgtc aggcctctga gcccaagcta agccatcata | 2280 |
| tccccagtga cctgcacgta tacatccaga tggcctgaag caactgaaga tacacaaaag | 2340 |
| aagtgaaaat agccttaact gataacattc caccat | 2376 |

<210> SEQ ID NO 34
<211> LENGTH: 6005
<212> TYPE: DNA
<213> ORGANISM: Homo sapiens

<400> SEQUENCE: 34

| | |
|---|---|
| gtcagtcctc tgagcccaag ctaagccatc atatcccctg tgacctgcac atacacatcc | 60 |
| agatggccgg ttccttcctt aactgatgac attccaccac aaaagaagtg aaaatggcct | 120 |
| gccttaactg atggcattgt cttgtgaaat tccttttcct ggttcatcct ggctcaaaag | 180 |
| ctcccctact gagcaccttg tgaccccac tcctgcccac cagagaacaa cccccctttg | 240 |
| actgtaattt tcctttatct acccaaattt tataaaacag ccctacccctt atctcccttg | 300 |
| gctgattctc ttttcggagt catcccgcct gcacccaggt gaaataaaca gccttgttgc | 360 |
| tcacacaaag cctgttggt ggtctcttca cacggacgcg agtgaaattt ggtgccgtga | 420 |
| ctcggatcgg gggacctccc ttgggagatc aatcccctgt cctcctgctc tttgttccgt | 480 |
| gagaaagatc cacctacgat ctctggtcct tagaccaacc agcccaagga acatctcacc | 540 |
| aattttaaat ccagtaagcg gcctcttttt actctcttct ccaacctctc tcacgatccc | 600 |
| tcaacctctt tctcctttca attttggcgc cacacttcaa tctctccctt ctcttaattt | 660 |
| cagttccttt ccttttctgg tagagatgaa ggagacgtgt tttatctgtg acccaaaac | 720 |
| tccggcgctg gtcacggact tgggaagaca gtcttccctt ggtgtttaat cacgcaggga | 780 |

```
cgcctgcctg attattcacc cacgtttcag aggtgtctga ccatgtgggg atgcctgcct     840
tggtccttca cccttagcgg caagtaccgc ttttctgagg ggcatgaacc ccccaaccct     900
tctctctgtg tctctacccc ttctctgctt ttctggggg  caagaagccc cacccctta     960
tctccgtgtc tctactctct cttttctctg ggcttgcctc cttcactatg ggcaagcttc    1020
cgccctccat tccccttag  cctgtgttct taaaaaccca aaacctcttc agctcacacc    1080
tgacctaaaa cctaaatgcc ttattttctt ctgcaatgcc gcttgacccc aatacaaact    1140
cgagagttgt tccaaatagc cagaaaatgg cactttcaat ttttccatct tacaagatct    1200
aaataattct tgttgtaaaa tgggcaaatg gtctgaggtg cctgacatcc aggcattctt    1260
ttacacatcg gtcccaccct agtctctgtg cccagtgcaa ctcatgccaa atcttccttc    1320
tttcctcccc accggtcccc tcagtcccaa cccaagcgt  cactgagtct ttctaatctt    1380
catttctac  agacccatct gacctctccc ctcctcccca gggcgagcta ggtcccaatt    1440
cttcctcagc ctctgctcct ccaccctata atccttttat cacctcccct cctcacagct    1500
ggtccggctt acagtttcat tctgtgacta gccctcccg  acctgcccag caatttcctc    1560
ttaaaaaggt ggctggacct aaaggcatag tcaagattaa tgctccttt  tctttatccc    1620
aaatcagata gtgttttggc tctttttcat caaatataaa aacccagccc agttcatggc    1680
tcgtttggca gcaaccctga gatgctttat agccctagac cctaaaaggt caaaaggccg    1740
tcttattctc aatatacatt ttattaccaa atctgctccc gacattaaat aaaactccaa    1800
aaattaaatt ctggccctca aaccccacaa caggacttaa ttaaccttgc cttcaaggtg    1860
tgcaataata gagtagaggc agccaagtag caacatattt ctgagttgca attctttgcc    1920
tccactgtga gacaaacccc agccacatct ccacacacaa gaacttccaa acgcctaaac    1980
ctcagtggcc aagtgttcct ccaggcccgc ctcccccagg agcttgctac aagtgccaga    2040
aatctggcta ccaggccaag gaatgcccac agcccagaat tcctcttaag ccacgtccca    2100
tctgtgcggg accccactga aaatcagact gttcaactca cctggcagtc attcccagag    2160
cctctggaac tctggcccaa ggctctctga ctccttccca gatcttctcg gcttagcagc    2220
tgaagactga cactgcccga tcgcctcgga agcccttag  accatcacgg atgccgagct    2280
tcgggtaact cttacagtgg aaggtaagtc tgtccccttc ttaatcaata cagaggctac    2340
ccactccaca ttaccttctt ttcaagggcc tgtttccctt accttcataa ctgttgtggg    2400
tattgacggc caggcttcta aacctcttaa aactccccaa ctctggagcc aacttagaca    2460
atactctttt aagcactctt ttttagttat cccagctgc  ccagttccct tattagaccg    2520
agacacttta actaaattat ctgtttccct gactattcct gggctacagc aacacctcat    2580
tgccgccttt tccccagtt  caaagcctcc ttcacatcct cctttgtat  ctccccacct    2640
taacccacaa gtataagaca cctctactcc ctccttagca accgatcatg cacccttac    2700
catcccatta aaacctaatc actcttaccc cgctcaatgc caatatccca tcccacggca    2760
tgctttaaaa ggattaaagc ctattatcac tcacctgcta cagcatggcc ttttaaagcc    2820
tgtcaactcc ccttacaatt cccccatttt acctgtccta aaaccagacg aggcttacag    2880
gttagttcag gatctgcgcc ttatcaacca aattgttttg cctatccacc ccatggtgcc    2940
aaacccatat actctcctat cctcaatacc tccttccaca acccattatt ctgttctaga    3000
tctcaaacat gctttcttta ctattccctt gcacccttca tcccagcctc tcttcgcttt    3060
cacttggact gaccctgaca cccatcaggc tcagcaaatt acctgggctg tactgcccaa    3120
```

```
ggctttacag acggccccca ttacttcaat caagcccaaa tttcttcgtc atctgttacc    3180
tatctcggca taattctcat aaaaacacat gtgctctccc tgctgatcgt gtccagctaa    3240
tctcccaaac cccaatccct tctacaaaac aacaactcct ttccttccta ggcatggtta    3300
gtaaggtcag aattcttaca caagagctgg gaccatgccc tgtagccttt ctgtccaaac    3360
aactggacct tactgtttta gcctagccct tatgtctgca tgcagcagct gccgctgctt    3420
taatactttt aaaggcccta aaaatcacaa agtatgctcc actcactctc tacagttctc    3480
ataactttga aaatctattt tcctcatacc tgacgcatat actttctgat ccccagctgc    3540
ttcagctata ctcactcttt gttgagtctc ccacaattac cattttttcc tggcacggac    3600
ttcaatccgg cctcccacgt tattctagat accacacctg accctcatga ctgtatctct    3660
ctgatccacc tgacattcac cccatttccc catatttcct tctttcgtgt tcctcaccct    3720
tatcacattt ggtttattga tggcagttcc accaggccta accgccactc accagcaaag    3780
gcaggctatg ctatagtatc ttccacatct atcattgagg ctactgctct gccccccctcc   3840
actacctctc agcaagccga actagttgcc ttaactcaag ccctcactct tgcaaaagga    3900
ctatgcgtca atatttatac tgactctaaa tatgcctttc atatcctgca ccaccatgca    3960
agaggtttcc tcactacaca agggtcctct atcattaatc cctctttaat gaaaatactt    4020
ctcaaagctg ctttacttcc agaggaagct ggagtcattc accacaaggg ccatcgaaag    4080
gcatcagatt ccattgctct aggcaacact tacgctgata aggtggctag acaagaagct    4140
agcattccaa cttctgtccc tcaccgccag ttttttctcct tcatatcagt cactcccacc    4200
tactcccccg ctgaaacttc cacctatcaa tctcttccca cacaaggcaa atggttctta    4260
gaccaaggaa agtatctcct agccttagag gcccattgta ttctgttgtc atatcataac    4320
ctcttccatg taggttacaa gccactagcc cctctcttag aacctctcat ttcctttcca    4380
ttatggaaat ctatccttaa ggaaaccact tcttagtgtt ccatctgcta ttctactacc    4440
cctcagggat tgttcgggcc tcctcccttt cctacacatc aagctcaggg atttgcccct    4500
gcccaggact ggcaaattga ctttactcac atgccccgag tcagaaaact aaaatacttc    4560
ttagtctggg tagacacttt cactggatgg gtagaggcct tccccacagg gtctgagaag    4620
gccaccgcgg tcatttcttc ccttctgtca gacataattc cttagtttgg acttcccacc    4680
tctatacagt ccgatagcag actggacttt attagtcaaa tcagccaagc attttttcag    4740
gctcttggta ttcagtgaaa cctttatatc ccttacggtc ctcagtcttc aggaaaggta    4800
gaatggacta ctggtctttt aaaaacacac ctcaccaagc tcagccacca acttaaaaag    4860
gactgtacaa tacttttacc acttgccctt ctcagaattc aggcctgtcc tcggaatgct    4920
acagggtaca gcccatttga gctcctgtat ggacactcct ttttattagg ccccagtctc    4980
attccagaca ccagactaac ttggactgtg ccccaaaaaa cttgtcatcc ctactatctt    5040
ctgtctagtc atactcctat tcaccgttct caactactca tacatgccct gctcttgttt    5100
acactgccag tttacactgt ttctccaagc cagcacagct gatatctcct ggtgctatcc    5160
ccaaactgcc actcttaact cttaaagtaa ataaataatc tttgctggca ggactatgct    5220
gaatctcctt aggcactctc taattagatg tcctgggtcc tcccaattct tacacattta    5280
atacctgttt ttctccttct cttattctgt ttagtttttc aattcataca aaactgtatc    5340
caggccatca tcaataattc taaatgacag atgtttcttc taacaacccc acaatatcac    5400
cccttaccac aaaatcttcc ttcagcttaa tctctcccac tctaggttcc catgccaccc    5460
ctaatcctgc tcaaagcagc cctgagaaac atcgcccatt atctctccat accaccccca    5520
```

```
aacattttca ccgtcccaac actttaccac ttttttcattt tattttttctt attaatataa    5580
gaagacagga atgtcaggcc tctgagccca acctaagcca tcatatcccc tgtgacctgc    5640
acgtacacat ccagatggcc ggttcctgcc ttaactgatg acattccacc acaaaacaag    5700
tgaaaagggc ctgttcttac cttaactgat gacattgtct tgtgaaattc cttctcctgg    5760
ctcatcctgg ctcaaaagct cccctactga gcaccttgtg accccactc ctgcccgcca    5820
gagaacaacc cccttttgac tgtaattttc ctttacctac ccaaatctta taaaacggcc    5880
ctacccttat ctcccttggc tgactctctt ttcggactca gcccgcctgc acccaggtga    5940
aataaacagc cttgttgctc acacaaaggc tgtttggtgg tctcttcaca cggacgcgag    6000
tgaaa                                                                6005

<210> SEQ ID NO 35
<211> LENGTH: 8823
<212> TYPE: DNA
<213> ORGANISM: Homo sapiens

<400> SEQUENCE: 35
atggtatgag accaccactt ctcctgttgt ctttttagt ttctccccaa cctcccttt       60
tccctagttt ataagacagg agaaaaggga gaaagcaaaa agttggaaag aaacagaagt    120
aagataaata gctagacgac cttggtgcca ccacctggcc ctggtggttg aaataataat    180
aatattaacc cctgaccaaa actactggtg ctatctgtaa attccagaca ttgtatgaga    240
aagcactgta aaacttttgtg ttctgttagc tgatgtatgt agcccccagt cacgttcctc    300
atgcttgctt gatccattat gactctttca cgtagacccc ttagagttgt aagcccttaa    360
aagggccagg aatttctttt tggggagct gggctcttaa gacacgagtc tgccgatgct    420
cccagctgaa taaagaaacc tcttccttct ttaattcggt gtctgaggag ttttgtctgc    480
gactcgtcct gctacatttc ttggttccct gactgggaag cgaggtaatt gatagacagt    540
cgaggcagcc ccttaggcgg cttaggcctg ccctgtggag catccctgca ggggactcta    600
gccagcttga gcgacgcgga tcctgagagc gctcccaggt aggcaattgc ctcggtggaa    660
tgcctcgtca gagcagtgtg tggcaggccc cgtggagga tcaacgcagt ggctgaacac    720
cgggaaggaa ctggcacttg gagtctggac atttgaaact tggtaagact ggtctttgga    780
acttgcccac tccatttgag tggaagcgtg gcctgagcac ccatggtgtg cctgtactgg    840
cactttggtt tttgttttg acttgactta aattgcttga tactttggtt ttggtttgac    900
ctggcttgga tttctggata ctctgatttt ggttttgatt ctggtttggt gaaaactgaa    960
aaagtgtgtg tgtgccctt ttacctattc tttgttctgt ggtgtgcgtg tggtgtgagc   1020
tcggtgtttt gtcttaagga acatgggtc agacacaaag taagcttact ccgctaggaa   1080
ctatgttgaa aaattttaag aagggattta atggagacta ggggttact atgacaccag    1140
gaaaacttag aactttgtgt gaaatagatt ggccaacatt agaagtggat tggccatcag   1200
aaggaagcct ggacaggtcc cttgtttcta aggtatggca caaggtaact ggtaagtcag   1260
gacactcaga ccagttttcca tacatagaca cttggttaca tctggtagac ccccgcagt   1320
ggctaagagg gcaggcagca gcagtgctag tagcaaaggg acagatagcc aaggaaggat   1380
cccgctccac ccgccgaggg aaatcaactc ctgaagttct gttcgaccca acatcagaag   1440
atccattgca ggagatggca ccagtgatcc cagtggtgcc ctcccgttac cagggagaga   1500
ggctcaccac ttttgagtcc acggggcttg cacctccaca agacaaacat ccctaggcca   1560
```

```
cccagagtag gcaagagagg aggtgaagcc tcgggagaaa cccctcccct ggcagctggt    1620
ttaagaccca aaacggggat acaaatgccc ctgagagagc agtggtatac tggaatagat    1680
gaggatgggc acatggtgga gaggcgtgtt tttgtgtacc agcccttctt ctctgccgac    1740
ctcctcaact ggaaaaacaa taccccatcc tatactgaaa agccgcaagc tctaattgat    1800
ttgctccaaa ctattatcca gacccataac cccacttggg ctgattgcca ccagttgctc    1860
atgttcctct ttaacacaga tgaaaggcgg agagtgctcc aagcagcaac taagtggcta    1920
gaggaacatg caccggctga ttaccaaaac ccccaagagt atgtaaggac ccagttaccg    1980
ggaaccgacc cccagtggga cccaaatgaa agagaggata tgcaaaggct aaaccgatac    2040
agggaagctc tcttggaagg attaaagagg ggagcccaga aggccacaaa cgtggccatt    2100
cagggaaaag aagaaagtcc agcacaattc tacgagaggc tgtgtgaggc ctattgtatg    2160
tatactccct ttgatcccaa tagtcctgaa aatcagcgca tgattaacat ggctttagtt    2220
agtcaaagtg cagaagacat tagaagaaaa ctgcagaaac aggctgggtt tgcagggatg    2280
aacacatcac agttattaga aatagctaac caggtgtttg taaacaggga tgcagtaagc    2340
cctaaggaaa accgcagaga gaatgaacat caggtccggc gaaatgccga cctgttagct    2400
gcagcaatca caggggtccc cccaaagagg caagggaagg ggggcccccgg aaagaaattt    2460
cagcctggtt gtcagagctt gcagcgtaat cagtgtgctt attgtaaaga aataggacat    2520
tggaagaaca aatgccctca gctaaaagga aaacaaggtg actcggagca ggaggatcca    2580
gacaaggagg aaggggcccct gctcaacctg gcagaaaggt tattggactg aggggggaccg    2640
ggctcaagga cccccaaaga gcctatggtc aggatgacag ttgggggtaa agacattgat    2700
tttcttgtag ataccggtgc tgaacattcg gtagtaacca ccccggtcag cccctttatcc    2760
aaaaagacta ttgacataat tggagccaca ggagtttcag caaacaagc tttctgcttg    2820
ccccggactt gtactgtagg aggacataaa gtgattcatc agttttgta catgcctgat    2880
tgtcccttgc cctgttggg aagggacttg cttagcaaac tgagagccac tatctatttt    2940
acagagcatg gctctttgct gctaaagtta cccggaacgg gagtcattat gacccttatg    3000
gtaccccgag aggaggaatg gaaacttttc ttaactgagt cgggccaaga gataagacca    3060
gctctggcta agtggtggcc aagagtgtgg gcagaagaca accctccagg gttggcagtc    3120
aaccaagccc ccgtacttat agaagttaag cctagggccc agccggttag gcaaaaacag    3180
taccccggtcc ccagagaagc tcttcaaggt atccaggtcc atctcaagtg cctaagaacc    3240
tttggaatta tagttccttg tcagtctcca tggaacactc ccctcctgcc tgttcccaag    3300
cctgggacca aggactacag gccggtacag gatttgcgct tggttaatca ggctacagtg    3360
actttcacacc caacagtacc taactggtac acattgctgg ggttgctgcc agctgaggac    3420
agctggttca cctgcttgga cctgaaagat gctttcttta gcatcagatt agcccctgag    3480
agccagaagc tgtttgcctt tcagtgggaa gatccggagt caggtgtcac tactcagtac    3540
acttggatcc ggcttcccaa agggttcaag aactcccccca ccatcttcgg ggaggcattg    3600
gctcaagacc tccagaagtt tccaccagac acctaggct gcatgttgct ccagtacgtt    3660
gatgaccttt ttctgggaca ccctacggca gtcaggtgcg ccaagggaac agatgctcta    3720
ctccggcacc tggaggactg tgggtataag gtgttcaaga aaaagttca gatctgccga    3780
cagcaggtac gttacttggg atttactatc cggcaggggg agtgcagcct gggatcaaaa    3840
agaaagcaag tcatttgtaa tctaccggag cctaagacca aaggcaggt gagagaattc    3900
ttaggggcag tggggttttg cagactgtgg gtcccaaact ttgcagtatt agctaagcct    3960
```

-continued

```
ttgtatgagg tcacaaaggt gggggactgg gaacattttg aatggggatc ccagtaacag    4020
caagcctttc atgagttaaa ggaaagactt atgtcagccc cagccctggg gctacccgat    4080
ctgacaaagc cttttatatt atatgtgtca gagaaagaaa agatggcagt tggagtttta    4140
acccatactg tggggccctg ccgaggcca gtggcctacc tctctaaaca actagatggg    4200
gtttctaaag gatgacccc atgtttgagg gccttggcag caactgccct gctagtacaa    4260
gaagcagata agctgactct tgggcaaaac ctgaacataa aggcccccca tactgtggtg    4320
actttaatga atactaaagg acatcattgg ctaatgaatg ctagactcac taagtaccaa    4380
agtttgctct gtgaaaatcc ccatataacc attgaagttt gtaacaccct gaaccccgct    4440
accttgctcc tggtatcaga gagccctgtc aagcatgact gtgtagaagt gttggactca    4500
gtttactcta gcagacctga cctccgggac cagccttggg catcagtaga ctgggtacta    4560
tacgtggatg ggagcagctt catcaaccca aaggagaga gatgtgcagg gtatgcggtg    4620
gtaactctgg acactgttgt tgaagcccga tcgttgcccc agggcacttc agctcagaaa    4680
actgaactca ttgcttttaat ttgggcctta gaactcagtg aaggtaagac tgtaaacatt    4740
tacactgact gtcgatatgc cttttttaacc cttcaagtgc atggagcatt atataaagaa    4800
aagggtctat tgaactctgg gggaaaggac ataaaatatc aacaagaaat cttgcaatta    4860
ttagaagcag tatagaaacc acacaaggtg gcagttatgc attgcagagg acaccagtgg    4920
gcttccacct tggtgggttt ggggaattcc cacgctgact tagaggctcg aaaagcagca    4980 tctgcccct tccgggcatc agtcacagcc cccctgctcc ctcaagcacc tgatcttgta    5040
cctacttatt ctaaagaaga aaatgacttt ctccaggcag agggaggaca agtgatggag    5100
gaaggattga ttcggttacc agatgggaga gtagctgtgc cacagctgct aggagctgca    5160
gttgtactgg ctgtccatga aaccacccat ctaggtcagg aatcacttga aaagttgtta    5220
ggctggtatt tctacatctc gcatttgtca gcccttgcca aaacggtgac ccagcggtgt    5280
gttacctgcc gacagcataa tgcgaggcaa ggtctagctg ttccacctgg catacaagct    5340
tatggagaag ccccctttga agatctggat ccaggtggac ttcacagaga tgccaaagtg    5400
tggaggtaac aagtatttac tagttcttgt gtgtacctac tctgggtggg tggaggctta    5460
tccaacacga actgagaaag ctcgtgaagt aactcgtgtg cttctttgag atcttattcc    5520
tagatttgga ctgcctttat ggatcggctc agataacggg ccggcatttg tggctgactt    5580
ggtacagaag atggcaaagg tattggggat cacatggaaa ctgcatgctg cctaccggcc    5640
tcagagttcc ggaaaggtgg agcagatgaa tcggactatc aaaaatagtt tagggaaagt    5700
atgtcaggaa acaggattaa aatggataca ggctctccct atggtattat ttaaaattag    5760 atataccect tctaaaagaa caggatattc cccttatgaa atattatatc ataggccccc    5820
tcctatattg cggggacttc caggcactcc ctgagagtta ggtgaaattg agttacagtg    5880
acagctacag gctttaggaa aaattacaca aacaatctca gcctgggtaa atgagaaatg    5940
ccctgttagc ttattctccc cagttcaccc tttctcccca ggtgatcgag tgtggatcaa    6000
ggactggaac gtagcctttt tgtgtccacg gtggaaagga ccccagactg tcgtcctgac    6060
cactcccacc actgtgaagg tagagggaat cccagcctgg atccaccaca gccatggaaa    6120
acctacagca cctgaaacct gggaggcaag accaagccca gacaacccctt gcagagtgac    6180 cctgaagaag acgacaagcc ctgctccagt cacacctgga agctgactgg tccacacatg    6240
gctgaagcat gaggaagctc atcatgggat tcattttttct taaattttgg acttatacag    6300
```

```
taagggcttc aactgacctt actcaaactg gggactgttc ccagtgtatt catcaggtca      6360
ccgaggtagg acagcaaact aaaacaatct ttctgttcta tagttattat gaatgtatgg      6420
gaacattaaa agaaacttgt ttgtataatg ccactcagta caaggtatgt agcctgggaa      6480
atgactgacc tgatgtgtgt tataacccat ctgagcccct tgcaaccatc gttttttaaaa     6540 taagattaag aaatggcctt ttcctaggtg atacaaggaa aataataact agaacagaag      6600
aaaaaaggaa tccccaaaca aataacttta agatgtgatg cttgtgcagc cattaatagt      6660
aaaaagctag gaataggatg tggttctctt aactgggaaa ggagctacag agtagaaaat     6720
aaatatgttt gtcatgagtc aggggtttat gaaaattgtg cctgttggcc atgtgttatt      6780
tgagctactt ggaaaaagaa caaaaaggac ccagtttatc ttcagaaggg ggaagccaac      6840
ccctcctgtg ctgccggtca ctgtaaccca ctagaactaa taattaccaa tcccctagat      6900
ccccgttgga aaacggaga acgtgtaacc ctggggattg atgggacagg gttaaacccc       6960
caagttgcca ttttaattag aggggaggtc cccaagcgct ctcccaaacc agtatttcaa     7020 acctttatg aggagctgaa tctgccagca ccagaacttc caaaaaagac aaaaaatttg      7080
tttctccaat tagcagaaaa tgtagctcat tcccttaatg ttacttcttg ttatgtatgc     7140
gggggaacca ctatcggaga ccgatggcct tgggaagccc gagagttggt gcctactgat     7200
ccagctcctg acataattcc agttcagaag gcccaagcta gcaacttctg ggtcttaaaa     7260
acctcaatta ttgacaata ctgtatagct agagaaggga aagactttat catccctgta      7320
ggaaagctta attgtatagg tcagaagttg tataacagca caacaaagac aattacttgt      7380
tggggcctaa accacactga aaagaagcca tttagtaaat tttctaagtt aaaaactgct      7440
tgggctcatc cagaatctca tcaggactgg atggctcccg ctggactata ctggatatgt     7500
gggcacagag cctatattcg gttacctgat aaatgggcag gcagttgtgt tattggcact     7560
attaagctgt gcttttctt attacccata aaaacgggtg agctcctagg tttccccatc      7620
tatgcctccc aagaaaagag aggcatagtt ataggaaact ggaaagataa tgagtggccc     7680
cctgaaagga tcatacagta ttatgggcct gccacatggg cacaagacgg ctcatgggga    7740
taccgaaccc ccatctacat gctcaatcgg atcatacggt tgcaggccat cttaaaaata    7800
attactaatg aaactggcag agctttgact gttttggctt ggcaagaaac ccaaatgagg    7860
aatgctatct atcagaatag actggccttg gactacttgc tagcagctga aggaggagtt    7920
tgtggaaact ttaacttaac caattgctgc ctacaaatag atgatcaagg acaggtggtt    7980
gaaaacatag tcagggacat gacaaggtg gcacatgtgc ctgtacagat taaactgtac    8040
acgagtttaa tcctgagtct ttatttggaa aatggttttcc agctatggga ggatttaaaa    8100
ccctcattgt aggtgtattg ctagtaatag gaacttgctt gctgctcccc tgtgtattac     8160
ccttgctttt tcaaataata aaaggttttg ttgctatttt ggttcatcag aaaacttcag     8220
cacaggtgta ttatatgaat cactatcgct ctatctcgca aagagactca aaaagtgagg    8280
atgagagtga gaactcccac taaaaagtga aaattctcaa agggggggaaa tgtggtatga    8340 gaccaccact tctcctgttg tccttcccag tttctcccct acctccccttt ttccctaatt    8400 tataagacag gagaaaaggg agaaagcaaa aagttggaaa gaaacagaag ataaatagct    8460
agatgacctt ggcgccacca cctggccctg gtggttaaaa taataataat attaacccct    8520
gaccaaaact actggtgtta tctgtaaatt ccagacattg tatgagaaag cactgtaaaa    8580 cttttttattc tgttagctaa tgtatgtagc ccccagtcat gttcctcacg cttacttaat    8640
ctattataac tctttcacgt aaaccccctta gagttataag cccttaaaag ggctaggaat    8700
```

```
ttcttttttcg gggagctcgg ctcttaagac atgagtctgc tgacgctccc agctgaataa    8760
aaaaacctct tccttcttta attcagtgtc tgaggagttt tgtctgcgac tcgtcctgct    8820
aca                                                                  8823
```

<210> SEQ ID NO 36
<211> LENGTH: 408
<212> TYPE: DNA
<213> ORGANISM: Homo sapiens

<400> SEQUENCE: 36

```
gtcaggcctc tgagcccaag cctgcacgta tacgtccaga tggcctgaag caagtgaaga     60
atcacaaaag aagtgaaaat ggctggttcc tgccttaact gatgacattc caccattgtg    120
atttgttcct gccccacctt aactgattga ttaaccttgt gaaattcctt ctcctggctc    180
agaacctccc ctgctgagca ccttgtgacc ccgcccctgc ctgtaagaga aaacccccct    240
ttgactgtaa ttttccacta cccacccaaa tcctataaaa cagcccccacc cctatctccc    300 tttgctgact gtctttacgg actcagccag cctgcaccca ggtgaaataa acagccttgt    360
tgctcacaca aagcctgttt ggtggtgtct tcactgggaa gcgcgtga                 408
```

<210> SEQ ID NO 37
<211> LENGTH: 437
<212> TYPE: DNA
<213> ORGANISM: Homo sapiens

<400> SEQUENCE: 37

```
gtcaggcctc tgagcccaag ctaagccatc atataccctg tgacctgcac gtatacatcc     60
agatggcctg aagccactga agaaccacaa aagtgaaaat agccagttcc taccttaact    120
gatgacattc cacgattgcg atttgttcct gcccttccct aactgatcaa tggaccttgt    180
gacactcctt ctcctggaca atgagtctca ggagctcccc actgagcacc ttgtgacccc    240 caccccctgcc cgcaagagaa aaaccccctt taactgtaat tttccactac ctacccaaat    300
cctataaaga ctgcctcacc cctatctccc tttgctgact ccttttttcga actaagtcgg    360 cctacaccca catgattaaa agctttattg ctcacccaaa gcctgtttgg tggtctcttc    420
acactgacgc gcgttaa                                                   437
```

<210> SEQ ID NO 38
<211> LENGTH: 965
<212> TYPE: DNA
<213> ORGANISM: Homo sapiens

<400> SEQUENCE: 38

```
gtggggaaaa gaaagagaga tcagattgtt actgtgtctg tgtagaaaga agtagacata     60
ggagactcca ttttgttctg tactaagaaa aattcttctg cctcgagatg ctgttaatct    120
gtaaccttac ccccaaccct gtgctccctg aaacatgtgc tatgtcaact cagggttaag    180
tggattaagg gctgtgcaag atgtgctttg ttaaacagat gcttgaaggc agcgtgctcg    240
ttaagagtca tcaccactcc ctaatctcaa gtacccaggg acacaaacac tgcggaaggc    300
cgcagggacc tctgcctagg aaagccaggt attgtccaag gtttctcccc atgtgatagt    360
ctgaaatatg gcctcatggg aagggaaaga cctgaccgtc ccccagcccg acacccataa    420
agggtctgtg ctgaggagga ttagtaaaag aggaaggaac gcctgtttgc agttgagaga    480
agaggaaggc atctgtctcc tgccagtccc tgggcaatgg aatgtctcgg tgtaaaacct    540
```

```
gattgtatgt tccatctgct gagataggggg aaaaccgcct tagggctgga ggtgggacat      600
gcgggcagca ctactgctct ttaagtcatt gagatgttta tgtgtatgca tatctgaagc      660
acagcactta attctttacc ttgttcttga tgcagagacc tttgttcacg tgtttatctg      720
ctgaccttct ctccactatt attctatgac cctgccacac ccccctctcc gagaaacacc      780
taaaaatgat caataaatac taagggaact aagaggccgg cgggatcctc cgtatgctga      840
acgccggtcc cctgggcccc ctttttcctt tctctatact ttgcgtctgt gtctttcttt      900
tccaagtctc tcgttccacc taacgagaaa aacccacagg tgtggagggg caacccaccc      960
cttca                                                                  965
```

<210> SEQ ID NO 39
<211> LENGTH: 5409
<212> TYPE: DNA
<213> ORGANISM: Homo sapiens

<400> SEQUENCE: 39

```
gtaggagagc ggtcagggtg atgggagaaa ttacagggaa agacacaaac gttcttggaa       60
ggctgggagg ttttgcaaag cttcgaaaga aaatttggct gaaggcagcc aaattctctt      120
attcggagcc tgagagcaaa gggtagataa caagggaata taaggaact aacctagata       180 aatttgttta ctcctgtctc cagaaacaaa cctttgatca ttcacacaca ggactggtct      240
ctacttgggg gggtgacaat gtttattacc cacaaattgt gtttgcccca agcctttgtc      300
attaaatctg tactaaataa atgtgagtgt caccagctta gtggggctgc gaactctctt      360
cggcccctag tgctggtagt tccctatccc gctctttcac tggataccta tgtctgagta      420
ctcctttcat tcatcgctgg gctagagtct gagggacaga cttagcaggt ggtgccccat      480
gtgagaagtg ctgcaatgga ttgcaatgga accctcgaaa acgaaggtga agagactgtg      540
cggtcagtaa gtcagtaagt cattggtgcc cacttgggat ttccaaattc aagggaattg      600
ttcatgctag ggtttcatca tggacaacag ttatcagctc aacagcaaca gtatataaaa      660
gtattgaaac agctgcttaa agctagcaga acctcggttt cacaggctca attaagggac      720
ctaatgcaaa ctgttgtttc ccctaaccca ttttttcccag aagaaggcat gctagacata     780
gagctctggg aacaagtggg gagaaatctt aaacaacatt atgcacaagg caacaggtc      840 ccagtaacat ctctaacgtt atgggcctta gtcagggctg cttkggctct gctctacaca      900
gaagagcctc aaaagggaag ggaggagaaa cagtcacctt cctatctgcc tccctctacc      960
tcagccccgc tatcactggg aaaaaatacc tgagcccccc ctccaataaa ttgttttttt     1020 ttttttgag atggagtttt cgctcttgtc gcccaggctg gagtgcaacg gcgcgatctc      1080
ggctcaccgc aacctctgcc tcccgggttc aagcgattct tctgcctcag cctcccaagt     1140
aacggattac aggcatgcgc ctccacgcct ggctagtttt gtatttttag tagagatggg      1200
gtttctccat gttggtcagg ctggtctcaa actcctgacc tcaggtgatc cgtccgcctc     1260
ggcctcccaa agtgctagga ttacagatgt gagccactcc gcccagcctc ctataaattg     1320
ttaaaaagac aagggatatg ctacagttat gggaccctat cttaggcaag cggcattaga     1380 agggagctc ttagcctgcc tgtaatgca agatcgacaa gcaatcagg tacatgaacc       1440 cctttctttt gatgcttgta aagagataag aaaaagcatt agagaaaacg gagccgctat     1500
cccatttaca aaaggattaa ttgagtccat agcagacaac ttccgtatga ctccatggga     1560
ctggtcaatg ctagcaaaaa caactttaaa caccagtcaa tacccctct ggagggcaga      1620 atttgatgaa taatgtaaac aaccaaccct tttctagtaa tggccactgt tattcctccc     1680
```

```
ctaccccctaa catggctctc tcaaaatcct atttgggtag aacagtagcc tttaaaggga   1740
gagaaattat aaggagtcca ttaattagtt gaggaacaat aaaagccgg ccatatagaa     1800 ccatcaaaca gcccttggaa ttcacccatt tttgtcattc ccaaaaggtc tggcaaacgg    1860
agacttttgc atgacttacg ggctatcaat gctaatttgc aacctatggg gccccttcaa    1920
cagggcctcc cccatggtaa ttcctcaaga ttggcctata gtcgttattg acttaaaaga    1980
ctgcttttat ttttattttt tttattttt tttattttt gagacggagt ctcgctctgt     2040
tgcccaggct ggagtgcagt ggcgggatct cggctcactg caagctccgc ctcccgggtt   2100
cacgccattc tcctgcctca gcctcccaag tagctgggac tacaggcgcc cgccactacg   2160
cccggctaat tttttgtat tttagtaga cggggttt caccgtttta gccgggatgg       2220
tctcgatctc ctgacctcgt gatccgcccg cctcggcctc ccaaagtgct gggattacag   2280
gcatgagcca ccgcgccgg ccaagactgc ttttatacta ttccccttgc agaacaggac    2340
agagaaaaat ttgtatttac aataccagct atcaataatg aaaggccagc tcacaaatct   2400
cattggaaag ttcctcctca aggaatgctg aacagtccta gcccactctt tcactggata   2460
cctgtgtctg gatatgtctg tatcatataa atcaggcttt gctccccaat agaaaagaat   2520
ttcctaattg caagattatt cattttatgg atcatatttt actagcagcc ccaatggagc   2580
caatgctttt cagtttctat gcctctgtca taaagaatac acagttaaga ggtttaatca   2640
tagcacctga aaaagtacag ttgtcctctc cttggaagta tcttggatac atactaactt   2700
ctcggtcagt aagatgtcaa aaggttaaat taaatattag caacttacac accttaaatg   2760
attatcaaaa aatactgggt ggtattaatt tgcttcaccc catcttgggc ataactactg    2820
ataagttaca aaacctgttt tctatcctaa agggcaatac agccctagac tctcccaggt   2880
atttaactcc tgcagcaaaa agggaaattg aggaaataga gcaagctatt tctcagaggc   2940
agctagatca catagaccca tgatattcag ttctattgtt tgttttttcct actaagcatt   3000 ccccaacaga attaatagga cagatggccc cagggctatg ctttctagaa tgggttttt    3060 gctcacatac cgggactaaa acactatctc cctatatcca gctagttatt gaagtcacct    3120
acacaagctg cagatgatgc aatcagttgc taggttatga ccctgatgtc ataagaattc    3180
ctttgagtaa aaagcaattt gaagcagcat tgccccatct ctaaatcttc agataacact   3240
ttctaattat gtaggccata tagagcatgc ctttactgct gacaaactca ttcagttctt   3300
atcttgtact cctgtaattg tgcctacaaa agtaggcaca tacctaacac tttaatgctt   3360
tttactgacg gctctggtaa aaatggaaaa gtggctattt ggtggagacc acataattcc    3420
ctcacttgtt ctggatttac tagcactcag agagctgggg ttgaagcctt aatattggcc   3480
tggagaactt ttccactcag cctatcaata ttgttggtga ctttgcttac tctgtttatt   3540
gcagaacctt gaaacaggcc tcattaagtc tactgtcgag cccaccgtgt gcacgttttc   3600
ttcaacttca gcaattgctg gatcaacgta cacaccctat ttttatcata cactattcaa   3660
gcccacagct cactgcctgg cccactggct tatggcaata atcaagcaga cctgcaagtt   3720
atgatgtcac tgcttgacca aaccacataa tcacatcaat ttttccacca aaattggagg   3780
aacttaacaa tttcaactta accaaagact agataaacaa attatcctgc agtgcccaga   3840
ttgccagctc acaggcacgt cccctccttt aacaggtatt aaccctaggg actagaacct   3900
aatcagttat agcaaagaga tgttactcaa gtccctgaat ttggaaaact aagatatgta   3960
catgcatccg ttgataccag ttctcactta attagtgctc atgctcttcc tggagagtcc   4020
```

| | |
|---|---:|
| acctggtatg tcattaaaca tcttcttta acctttgcac ttatggggtg acccacaaaa | 4080 |
| attaaaactg ataatggtct ggcttatgct agttcacaat ttcaacaatt ttgttataca | 4140 |
| tggaatatcc agcattccac aggcatccgt ataacccca aggataggcc atagtagaat | 4200 |
| gtgtccattc ctctcttaaa aatatgctca gaaaaccaaa aagggaatt atgagtaagg | 4260 |
| accctgcaac actactagca caagccttat ttacccttaa tttcttaaat ttaaatgata | 4320 |
| aatttcaatc agctatagaa aagcactttg ctaaaacctc tcgagacata aaacccacag | 4380 |
| ttttatggaa agatgtaaat agtaatgtat ggtgtggtcc aaatgatttg ctaacgtgag | 4440 |
| gaagaggata tgcttgtgtt cacacccccc tcaggtcctc tttggattcc agcacaatgc | 4500 |
| atcaaacctt accagagtgt gggtagaacc taacccggta ataaagaaaa taatcctgca | 4560 |
| ggactcagcc ctggacaatg tggcttcctc agacaacaca ggcccagac tgaatgctaa | 4620 |
| agaagacaac tcaggaggct aagcgaatcc tgctccaaac acaaacatgt tcactccaaa | 4680 |
| taatttgttc ctttttatt ctctcacttt gcctactacc tgtacctgct acactctatt | 4740 |
| aggcccatct tctaattctg cctttcttcc accctgttac ttagacaaac accccttcc | 4800 |
| cagcttctaa taaagcaact gctaggctag aagggattga cttaccccaa gtggggttcc | 4860 |
| tcagtaatgg cacacattag actgaggtgc taggtaacac tacatgtcac tccttgattg | 4920 |
| gaaaggaatg ttactgatta tactcaggtt tgtcttacgt tatttactaa ttctaggatg | 4980 |
| caaagccaaa atacaagcag tgaccgctac gcctgacaaa cctgttgctg cacacatctg | 5040 |
| tactcttcaa tcaacaaaac ctgatgcaaa aaacagaaaa gggggagatg taggaaattg | 5100 |
| gtcagggtgg tggaagaaat tatagggaaa gacacaaacc ttcttggaag gccgggaggt | 5160 |
| tttgcaaaag cttcgaaata aaatttggct gaaggcagcc aaattctctt atccagagcc | 5220 |
| tgagagcaaa gggtagataa caagggaatg taaaggaact tatctagata aatttgttta | 5280 |
| ctcctgtctg cagaaaccaa cctttgatca ttcgcctgca ggactgctct ctacttgggg | 5340 |
| ggtcgacaat gttttattac cacaaattgt gtttgctcca agcccttgtc gttaaatctg | 5400 |
| tactaaata | 5409 |

```
<210> SEQ ID NO 40
<211> LENGTH: 6222
<212> TYPE: DNA
<213> ORGANISM: Homo sapiens

<400> SEQUENCE: 40
```

| | |
|---|---:|
| actgaagaac cacaaaataa gtgaaaatgg ctggttcctg ccttaaccga tgacattcca | 60 |
| ccattgtgat ttgttcctgc cccatcctaa ctgatcaatt gatcttgtga aattctttct | 120 |
| ctggacaatg aatctcggaa gctccccatt cagcaccttg taaccctgc ctctgtctgc | 180 |
| aagagaaaaa cccccttga ctgtaatttt ccactaccct cccaaatcct ataaaactgc | 240 |
| cccacccta tctaccttt tcggactcag tctgcctgca cttgggtgat taaaaagctt | 300 |
| tattgctcac acaaagcctg tttgttgggc tcttcacacg gacacacgtg acatttggtg | 360 |
| ctgaagatct gggacagggg gattccttca ggagaccagt cccctgtcct caccctcact | 420 |
| ccatgagaag atccacctat gaccttgggt cctcaggcca gcccaaggaa catcttacca | 480 |
| atttcaaatc gggcaagcgg tctttcact ctcttctcca gcttctctcg ctacctttca | 540 |
| atctccctgt ccttccaatt ccagttcttt ttcctctcta atagagacaa aggagacaca | 600 |
| ttttatctgt ggacacaaaa ctccagcgtg ggtcacggac ttgggaagac agtcttccct | 660 |
| tggtgtttaa tcaccgtgtg gatgcctgcc ctgatcattc acccacattc cactggtgtc | 720 |

```
tgatcactgt ggggatgcct gcctgattat tcacccacat tccactagtg tctgatcact      780
gtggggatgc ctgcctgatt attcacccac attccactag tgtctgatca ctgtggggat      840
gcctgcctga ttattcaccc acattccact agtgtctgat cactgtgggg acgcctgcct      900
tggtcattca cccacattcc cttggtggca aatcaattgt ggagacgcct gctttggctg      960
ctcacccaca ttacagccca gggctgctca ccacccctt ctctgtgtct ctacctttct     1020
ctttaaactt acctccttca ctatgggcaa gcttccaccc tccattcccc cttcttctcc     1080
cttagcctgt gttctcaaga acttaaaacc tcttcatctc acgcctgacc taaaacctta     1140
ctgccttatt ttcttctgca acactgcttg gccccaatac aaactcaaca atggttctaa     1200
atggccagaa aacagcactt ttgatttctc catcttacaa gacctggatg attttcttg      1260 aaaaatgtgc aaatggtctg agatgcctga catccaggca ttcttttaca catcagtccc     1320
tccctagtct ctgctcccag tgcgactcat cacaaatctt cttctctcc tgtctgttcc      1380 ttcagtctcc accccaagct ctgagtcctt gaatcctcc ttttctatgg acccatctga      1440
cctctcccct cctcaccagg ctgctcctca ccaggctgag ccaggtccta attcttcctc     1500
agcctccact ccccagccct ataatccttc tatcacctcc ccctcctccc accctgtctg     1560
gcttatagtt ttgttccacg actagccctc cccaacctgc caacgatttt cctcttacag     1620
aggtggctgc agctcaaggc agagtcaagg ttaaccctcc ttttttctta tctgacctct     1680
ctcaaatcag ttagtgttca ggctcttttt cgtcaagtat aaaagcccag cccagttcat     1740
ggcctgtttg gcaacaaccc ttagatgctt tgccgcccta gacccagagg ggccagaagg     1800
ccgtcctatt ctcaatatgc attttactac tcaacccact cccaacatta gaaaaagctc     1860
caaaaattag attctggccc tcaaaccca caacaagact taatcaatct cgccttcaag      1920
gtgtacaata atagagaaga gtcagccaag cggcaactta tttctgagtt gcaattactt     1980
gcctccactg tgagagaaac cccagccaca tctccagcac acaagaactt caaaatacct     2040
aaaccacagt ggccaggcat tcctccagga ccttctcccc caggatcttg cttcaagtgc     2100
tggaaatctg gccactgggc caaggaatga ccacagcctg ggattcctcc taagccatgt     2160
cccacttgtg caggaaccca ctggaaatag gactgtccaa cttgcctgga agccactccc     2220 agagccctg gaactctggc ccaaggctct ctgactgact ccttcccaga tcttctcagc      2280
ttagcggctg aagactgaca cagcccaatc acctcggaag cctcctggac catcacagat     2340
gctttaggta actcttagag tggagtgtaa gtccataccc ttcttaatca atacggaggc     2400
tacccactcc acattacctt cttttcaagg gcctgtttac cttgccccca taactgttgt     2460
ggatattgat ggccaggctg ctgggcccct taaaactccc ccactctggt gtcaacttgg     2520
aaaacagtct tttatgcctc ttttttagtt atccccatct gcccagttcc cttattagat     2580
caagacattt taagtgaatt atctgcttct ctgactattc ctgggctaca gccacatctc     2640
attgctaccc tttcccctgt tcaaaacctc cttcatgtct tcctcttgta tcccctgcac     2700
ctgaacccac aagtatgaga caactctact ccctccctag caattgacca catgcccatt     2760
actatcccat taaatctaa tcatccttac cctgctcaac accagtatcc catcccacaa      2820
caggctttga gaggactaaa gcctgtccag gatcttcacc ttatcaaaaa aattgtcttg     2880
cctatccacc ccgtggtgcc aaacccatat actctcctat cctcaatacc tccctccaca     2940
accccttatt ctgttctgga tttcaaagat gctttctttg ctattccttt acacccttca     3000
tcccagcctc tcttcgcttt catttggact gaccctgata cccatcagtc tcagcaactt     3060
```

```
acctgggctg tactgctgca aggcttcagg gacagcgccc attacttcag tcaagccctt    3120
tctcatactt tactttcttt ctgtccatct gcttctcacc gtattcaata ttttgacaac    3180
cttctacttt atagcccctc ctacagatct tcccaacagg acatcctcct gctcctccaa    3240
catctattct caaaaggata atgcaactcc cccgtcaaag gccaaatttc ttcctcatcc    3300
attacctatc tcagcataac tcttcataaa agcacatatg ctctccctgt tgatcgtgtc    3360
cggctaatct cccaaacccc aacccctcct acaaagcaac aactcctttc ttcctaggc    3420 atagttaggt actttcgcct ttggatatct gttttgcca tcctgactaa accatcatac    3480
aaaaggaaac ctagctgacc ccatagatcc taaatccttt ccccactcgt ctttccgttc    3540
cttaaaaact gtcctaaaag ctgctcacac actagctctc cctaactcat cccaacccttt   3600 ttcattacac gcagccaaag tacaggactg tgcagtcaga attcttacac aagagccggg    3660
actgcactct gtagcctttc tatccgaaca acctgaccgc acagttctga gctggccttc    3720
atgtctgtat gcagtgacag ccaccgcttt aatacttta gaggccatca aaatcacaag    3780
ctatgctcca tttactctac agttcccata actttcaaaa tccattttcc tcctcacact    3840
tgatgcgtat actttctgct ccctagctcc ttcaactgta ctcactattt gttgaatctc    3900
ccacaattac cattgttcct ggcctggact tcaatctggc ctcccacatt attcctgcta    3960
ccacacctga cccccatgat tgtatctctc tgatccacct ggcattcact ccatttcccc    4020
atatttcctt ctttcctgtt cctcaccctg atcacacttg gtttattgat ggcagttcca    4080
ccaggcctaa ttgccactca ccagcaaagg caggctatgc tatagtatct tccacatcta    4140
tcattcaggc tactgctccg ccctcctcca ctacctctca gcaagccaaa ctcattgcct    4200
taactcaggc cctcactctt gcaaagggac tacacgtcaa tatttatact gaccctaaat    4260
atgccttcca tatcctgcac caccatgctg ttacatgggc tgaaagagtt ttcctcacca    4320
tgcaagggtc ctccatcgtt aatgactctt taataaaaac tcttctcaag gctgctttac    4380
ttccaaagga agctggagtc cttcactgca aaggccatca aaaagcctca gaccccattg    4440
ctcaaggcaa caattatgct gataagacag ctaaagaagc agccagtatt cctacttatg    4500
tccctcatgg ccagtttttc tccttctcat cagtcactcc tactcactct cccactgaag    4560
tttccaccta tcaatccctc cctactcaag gcaaatagtt ctttgaccaa ggaaaattcc    4620
tccttccagc cttacagctc attccattct atcgtttttc ataacctctt ccatgtaggt    4680
tacaagccac tagccctcct cttagaacct ctcatttcct ttccatcatg gaaatctatc    4740
ctcaaggaaa tcacttctca gtgttccatt tgctattctc ccactcctca gggagttcgc    4800
ccctgcccag gattggcaga ttgactttac ccacatgccc cgagtcagga aactaaaata    4860
cctcttggtc tgtgcagaca ctttcactgg atgggtagag gcctttccct cagggtctga    4920
gaaggccacc gcggtcatct cctcccttct gttgacataa ttcctcaatt tagcctcccg    4980
ctctacccag ttgtcccatc aatcccatt acaacttcta atggctgctg ccctagctgg    5040
atccctagtg ttagatatga gttctaaatt tcttttcaaa gaatcaatat gtcagtaggt    5100
tcaattcttt gccttctact tttaaactta acttcctcgt aaagcaaact ttttcaatta    5160
cctgctccac cctgactcat ttcaatcacc tgctccaccc tgactcattc cgattacctg    5220
ctccaccctg actcattctg attacctgtt ccaccctgac tcattccaat gacctgctgt    5280
cataaccatt ttcctgcca aaccactcac cctgtcactc tctttaaatt agccaattga    5340
aattagttta gcctgtgcgg tctaacccta gccaataggg gaaggacgca gcagcagggg    5400
ccacgtgcat cagggataag aaccccttcc cgtcccttgt ccaagtgtgt gctcaccatt    5460
```

-continued

```
gctccatctg taagggtgca accttctata gaagtaactt gccttgctga gaattaaaaa    5520
gaaaatttta tattcgagtg ctatttcttt tgtggcacag aaacttcata tataatacta    5580
ggagtctggg tacaagacac ctctttagt gctctttctc attttttcac tttgcatttc     5640
cagtgttgca caaggtctct tcttctgtga ctcctctacc tacatgtgtc tacctgctaa    5700
taggacaggc acgtgcacac tagttttcct tactcccaaa attcaatttg caaataggac    5760
tgaacagctt cctcttcccc tcatgacacc aacacttcac cactattttg ttttattttt    5820
cttattaata tagaagacag gataggcct cgacttactg ctgaaaaagg agaactctgt     5880
atatttttaa atgaagagtg ttgttttac ccaaatcaat ctggcctggt gtatgacaac     5940
ataaaaaaac tcaaggatag agtccaaaaa cttgccaacc aagcaaataa ttacgctgaa    6000
ccgccttggg cactctctaa ctggatgtcc tggttcctcc caattcttag tcctttatta    6060 cctcttttc tccttctctt attcagacct tgtgtcttct gtttagtttc tcaattcaca     6120
caaaaccaca tccaggccat caccaatcat tctatatgac aaatgctcct tctaacaacc    6180
ccacgatatc accccttacc ccaaaatctt tcttcagttt aa                       6222
```

<210> SEQ ID NO 41
<211> LENGTH: 958
<212> TYPE: DNA
<213> ORGANISM: Homo sapiens

<400> SEQUENCE: 41

```
gtggggaaaa gaaagagaga tcagactgtt actgtgtctg tgtagaaaga agtagacata     60
ggagactcca ttttgttctg tactaagaaa aattcttctg ccttgagatg ctgttaatct    120
ataaccttac ccccaacgcc gtgctctctg aaacgtgctg tgtccactca gggttaaatg    180
gattaagggc ggtgcaagat gtgctttgtt aaacagatgc ttgaaggcag catgctcgtt    240
aagagtcatc accaatccct aatctcaagt acccagggac acaaacactg cggaaggccg    300
cagggacctc tgcctaggaa agccaggtat tgtccaagat ttctcctcat gggatagtct    360
gaaatatggc ctcctgggaa tggaaagacc tgaccgtccc ccagcccgac acccataaag    420
ggtctgtgct gaggagcatt agtataagag gaaggaatgc ctctttgcag ttgagacaag    480
aggaatgcat ctgtctcctg ccgtgcctgc gcaatggaat gtctcggtat aaaacccgat    540
tgtacgttcg atctactgag ataggggaaaa accgccttag ggctggaggt ggaacatgca    600
atactgcttt gtaaagcatt gagatgttta tgtgtatgca tatctaaaag cacagcactt    660
tattctttac cttgtctatg atgcaaagac ctttgttcac gtgtttgtct gctgaccctc    720
tccccactat tgtcttgtga ccctgacaca tcccctctc ggagaaacgc cacgaatga     780 tcaataaata ctaagggaac tcagaggctg gcgggatcct ccatatgctg aacgctggtt    840
ccctgggtcc ccttatttct ttctctatac tttgtctctg tgtcttttc ttttccaagt    900 ctctcattcc acctaacgag aaacaccaac aggtgtggag gggcaaccca ccccttca     958
```

<210> SEQ ID NO 42
<211> LENGTH: 972
<212> TYPE: DNA
<213> ORGANISM: Homo sapiens

<400> SEQUENCE: 42

```
gtggggaaaa gaaagagata tcagattgtt actgtgtctg tgtaggaaga agtagacata     60
agagactcca ttttgttctg tactaagaaa aattctttg ccttgagacg ctgttaatct     120
```

| | |
|---|---|
| gtaaccctac ccccaacccct gtgctcccta agacatgggc tgtgtcaact cagggttaaa | 180 |
| tggattaagg gctgttcagg gtgtgctttg ttaaacaaat gcttgaaggc agcatgcttg | 240 |
| ttaagagtca tcaccactcc ctaatctcaa gtgcccagag acacactaca ctgcggaaga | 300 |
| ctgcagggac ctctgcctag gaaagccagg tattgtccaa ggtttctccc catgtgatag | 360 |
| tctgaaatac agcctcgtgg gaagggaaag acctgactgt cccccagccc gacacccgta | 420 |
| aagggtctgt gctgaggagg attagtaaaa gaggaaggaa ggcctctttg cagttgagat | 480 |
| aagaggaagg catctgtctc ctgctcatcc ctgggcaatg gaatgtctcg gtgtaaagcc | 540 |
| cgattgtata tccatctac tgagatagga gaaaactgcc ttaggactgg aggtgggaca | 600 |
| tgctggcagc aatactgctc tttaaggcat tgagatgttt ctgtatatgc acatcaaaag | 660 |
| cacagcactt ttttctttac cttgtttatg atgcagagac atttgttcac gtgtttacct | 720 |
| gctgatcttc tctccactat tatcctattg tcctgccaca tcccctctc cggaaatgcc | 780 |
| cgataatgat caataaatac taagggaact cagaggccag tgctggcatg ggtcctccat | 840 |
| atgctgaacg ccggtcccct gggcccattt ttctttctct gtactttgtc tctgtgtctc | 900 |
| tttcttttcc aagtctctcc ttccacctaa cgagaaacgc ccacaggtgt ggaggggcaa | 960 |
| cccatcccctt ca | 972 |

<210> SEQ ID NO 43
<211> LENGTH: 972
<212> TYPE: DNA
<213> ORGANISM: Homo sapiens

<400> SEQUENCE: 43

| | |
|---|---|
| gtggggaaaa gaaagagaga tcagattgtt actgtgtctg tgtaggaaga agtagacata | 60 |
| agagactcca ttttgttctg tactaagaaa aattcttttg ccttgagacg ctgttaatct | 120 |
| gtaaccctac ccccaacccct gtgctcccta agacatgggc tgtgtcaact cagggttaaa | 180 |
| tggattaagg gctgttcagg gtgtgctttg ttaaacaaat gcttgaaggc agcatgcttg | 240 |
| ttaagagtca tcaccactcc ctaatctcaa gtacccagag acacactaca ctgcggaaga | 300 |
| ctgcagggac ctctgcctag gaaagccagg tattgtccaa ggtttctccc catgtcatag | 360 |
| tctgaaatac agcctcatgg gaagggaaag acctgactgt cccccagccc gacacccgta | 420 |
| aagggtctgt gctgaggagg attagtaaaa gaggaaggaa ggcctctttg cagttgagat | 480 |
| aagaggaagg catctgtctc ctgctcatcc ctgggcaatg gaatgtctcg gtgtaaagcc | 540 |
| cgattgtata ttccatctac tgagatagga gaaaaccgcc ttaggactgg aggtgggaca | 600 |
| tgctggcagc aatactgctc tttaaggcat tgagatgttt atgtatatgc acatcaaaag | 660 |
| cacagcactt ttttctttac cttgtttatg atgcagagac atttgttcac gtgtttacct | 720 |
| gctgatcttc tctccactat tatcctattg tcctgccaca tcccctctc cggaaacgcc | 780 |
| caataatgat caataaatac taagggaact cagaggccag tgcaggcatg gtcctccgt | 840 |
| atgctgaacg ccagtcccct gggcccattt ttctttctct gtactttgtc tctgtgtctc | 900 |
| tttcttttcc aagtctctcc ttccacctaa cgagaaacgc ccacaggtgt ggaggggcaa | 960 |
| cccatcccctt ca | 972 |

<210> SEQ ID NO 44
<211> LENGTH: 1620
<212> TYPE: DNA
<213> ORGANISM: Homo sapiens

<400> SEQUENCE: 44

```
gtcaggcctc tgagcccaaa ccaagccatc gcatccctg tgacttgcac gtatacaccc      60
agatggcctg aagtaactga agatccacaa aagaagtaaa aatagcctta actgatgaca     120
ttccaccatt gatttgttcc tgtcccaccc taactgatca atgtactttg taatctcccc     180
cacccttaag aaagttcttt gtaattctcc ccacccttga aatgtactt tgtgagatcc      240 accctgccc gcaaaacatt gctctcaact tcaccgccta tcccaaaacc tataagaatt     300
aatgataatc catctcccc tcgctgactct cttttcggca cccaggtgaa ataataccc      360 atgttgctca cacaaagcct gtttggtggc ctcttcacac ggacgcacat gaaaccagct     420
acttgggagg ctgaggcagg agaattgctt gaacccggga ggcggaggtt gcggtgaccc     480
gagatcacgc cattgcactc ctgcctgggc aacaagagca aaattccgtc tcagggaaaa    540
aaaaaaaatt agctgggtgt ggtgggcag gcctgtaatc ccagctactc aggaggctga     600
ggcaggagaa tcacttgaac ctgggaggcg gaggttgcag agtcgagatc atgccattgc    660
cctccagcct gggcgactga gtgagactcc atcttaaaaa aaaaaaaaaa aaaagtcttt    720
tattactttt tgagcattta aagagtattt tttggccaga cggtgtggct cacgcctgta    780
atcccagtat tttgggaggc ccaggcgggt ggatcacttg aagcctccag cctggccaac    840
atggcaggag aatgactgga acccgggagg tggatgttgc agtgagccaa gatggtgtca    900
ctgcactcca gcctgggtga cagagagaga ctctgtctca aagacaaaaa gaaaatttgt    960
tcagtatttt cttcaatcag ctttctcaga ctgaatgttc acccttttaa atattcataa   1020
tgttcctgag aatccattg gctattctgt tttcttcacc cttctccagc cttccctcc     1080 tcaattcgac ccatttcttc cctacttccc aaaagaaaaa atatctactt tggattaata   1140
taaatcagtt taatctaact tattcaagac ttttttggcc tctacttgga ggttcaagaa   1200
aaggtgtgtc aggcctctga gcccaagcta agccatcata tcccctgtga cctgcacata   1260
cacatccaga tggccggttc ctgccttaac tgatgacatt ccaccacaaa agaagtgaaa   1320
atggcctgtt cctgccttaa ctgatgacat tgtcttgtga aattcctttt cctggctcat   1380
cctgtctcaa aaagctcccc tactgagcac cctgtgaccc ccactctgtc cgccagagaa   1440
caacacccct ttgactgtaa tttccttta tctacccaaa tcctataaaa cagccgcacc    1500
cttatcttcc ttcgctgact ctcttttttgg actcagcccg cctgcaccca ggtgaaataa   1560
acagccatgt tgctcacaca aagcctgttt ggtggtctct tcacacgcac gagcatgaaa   1620
```

<210> SEQ ID NO 45
<211> LENGTH: 238
<212> TYPE: DNA
<213> ORGANISM: Homo sapiens

<400> SEQUENCE: 45

```
tacagttgat agctagtcag acacgagcag gataggagag ggctccctgc cctcaccacc      60
aggaatgttg atggtggtga cggtcaggtg gttgttaact gtctctgtaa agtaataatt     120
ggttgcagcc agtgccaggg aagggcagtc ttccagtaga tagaaaacac ctaaaactgg     180
tgatcagcag cttcctgata agacctcagg agttgggcaa gtgggctcag gtgagcac        238
```

<210> SEQ ID NO 46
<211> LENGTH: 397
<212> TYPE: DNA
<213> ORGANISM: Homo sapiens

<400> SEQUENCE: 46

```
gtcaggcctc tgagcccaag ctaagccatc atatcccgtg acctgcaggt atacatccag    60
atggcctgaa gtaactgaag aatcacaaaa gaagtgaaaa tggcctattc ctgccttaac   120
tgatgacatt atcttgtgaa attccttctc ctggctcatc ctggctcaaa agctccccca   180
ctgagcacct tgtgaccccc acccctacca gctagagaac aaccccettt gactgaattt   240 tcctttacct acccaaatcc tataaagggg ccccatccct gtctcccttt gctgactctc   300
tttttggact cagcccgcct gcacccaggt gaaatgaaca gccttgttgc tcacacaaag   360
cctgtttggt ggtctcttca catggatgca agtgaaa                            397

<210> SEQ ID NO 47
<211> LENGTH: 738
<212> TYPE: DNA
<213> ORGANISM: Homo sapiens

<400> SEQUENCE: 47
catcagatgg ccaaatcatt atttactgga ccagaccttt tcaaaactat caagcagata    60
gtcaaggcct gtaaagtgtg ccaaagaaat aatcccctgc actgcaggcc atacatttca   120
atccctctat cttttaacctc cttgttaagt ttgtctcttc cagaattgaa gctgtaaaac   180
tacaaatcgt tcttcaaatg gagccccaga cagtccatga ctaaaatcta ccacagaccc   240
ctggaccggc tgctagccc atgctccaat gttaatgaca ttgaaggcac ccctcctgag    300
gaaatctcaa ctgcacaacc cctactacgt cccaattcag cgggaagcag ttagagtggt   360
tgtcggccaa cctccccaac agcacttggg ttttcctgtt gagaggggc actgagagac    420 aggactagct ggatttccta ggccgacaaa gaatccctaa gcctagctgg aaggtgacc    480 gcttccacct ttaaacacag ggcttgcaac ttagctcaca cctgaccaat cagatagtaa   540
agagagctca ctaaaatgct aattaggcaa aaacaggagg taagaaaata gccaatcatc   600
tgttgcctga gagcacagag ggagggacaa cgatcaggaa ataaacccag acattcgagc   660
tggcaacagc aaccccettt gggtcccctc cctttgtatg ggagctctgt tttcactcta   720
ttaaatcttg caactgca                                                  738

<210> SEQ ID NO 48
<211> LENGTH: 2715
<212> TYPE: DNA
<213> ORGANISM: Homo sapiens

<400> SEQUENCE: 48
agtaagccca ccctactagg aactatgtta aaaaatttca agaaagaatt taaaggagat    60
tacggtgtta ctgtgacacc aggaaaactt agaactttgt gtgaaataga ctggccagca   120
ttagaggtag gttggccatc agaaggaagc ctggacaggt cccttgtttc aaaagtatgg   180
cacaaggtaa cctgtaagcc aaggcaccca ggccagtttc cgtacataga cagttacagc   240 tagtttttaga cccccttccc cccaacagca gttaagagaa cagcagcata agtggctggc   300
agaggcaagg aaagaccagc agagagaaaa agaggccatc tataccaatt ctaagttaat   360
tcagactaaa caagatctta ttaatagcaa aggataattg aaatcccaaa cttacaaggt   420
tttcaacaaa agtgaagttt gctaaaagtt aacagtgtaa catgtattat agtaacttct   480
aatcttgtgg ccttagacag tctagtccaa agacataaag aaagttcgct ttaaaaaga    540 gaagggcggg ggggggaggc aaaatttatg taaaaagagt gttatatagt aaattcttgt   600
cctgaaataa attaactagt tgtttaaaga aaaaatgta ataagtcaaa aagttaagac    660
atgttgaaaa attgtctgca aaagtcgtga aagaaaaaat gttataaaaa aatttatgca   720
```

| aaaaatgttg tataatttaa aagtaataag gcctcctgag taccattaaa gaaacagttt | 780 |
| atgtgcaagg tgtataagaa aagtaaaata tacctttagt aaaaaaatta taaagggaca | 840 |
| taaaaatgtg gattttacc tacattaaaa gttaaaaaaa ttattgtttt aaaaatttaa | 900 |
| gcaagtttta aaacgttaat tgtaaagaaa attctgtgtg taaacatatt agctaaagtt | 960 |
| aaaaagatat cacccagttt ttctgtgaac tggacattaa agtaaaaatg caacaggttt | 1020 |
| ttcttaaagc atcaacctgc tctttaacaa aaattataaa aagttaaaaa aagtctataa | 1080 |
| aatcttacct tatggtcaaa cataaaaaat tagataaata tgtctacaag gttttattaa | 1140 |
| aattaagttt aacattaata acacactaat ataaagtaa aatttaactt atctactata | 1200 |
| aaaatcatac aagaaacatt attaaatata aaatagtatt tagctttctt tagtctaaaa | 1260 |
| actaataaaa ataggtgtta aaggaaacat tcattttact aaaggatcat agaagttaaa | 1320 |
| gacttaaaac aaactttggc aattaagaca gcataccaag aatgcaaatg cctggttgaa | 1380 |
| atggatcaaa tattccatct gcacattaaa caaaagcaat tgttatgatt gtgcacatgg | 1440 |
| caggccagag gccctaattg tccccttcc actaaggtgg tcctccagtc gaccaggcgt | 1500 |
| aggctgcgtg gtagctcttt tctgagattc tacagcctgg agtaataaat catgccaagc | 1560 |
| tctctctgct atatcccaaa gtccctgcag atcagcacct gaggtccatc cagcttctgt | 1620 |
| ctcccaacac taagttcact ttgtgtctct cacagcaagg aggagactta gcattccttg | 1680 |
| gagacctgaa gggatgcagt aagcttaaga atttcaaga gcttatcaat cagtcagccg | 1740 |
| ttgttcatcc ccaagcagat gtgtggtggt attgtggtgg acctttactg ggcactctgc | 1800 |
| tgaataacta gagtggcact tgtgctttag tccatttggc tatccctttc accctggcat | 1860 |
| ttcatcaacc agaggaaaaa caaaaaataa gacatcgtaa agccagagaa gccccttata | 1920 |
| ggtctttcaa ctctcacatc tatttagatg caattggagc cccacaagga ataccagatc | 1980 |
| aatttaaagc ttgaaatcaa atagttacag gatttaagtc aatattttag tagatgacag | 2040 |
| tcaataaaaa tgtagattag ataaactaca tctattacaa ccaacagcaa cgagcttttc | 2100 |
| atgagttaaa aagaaaaact catgttggcc ccagccctga ggctacctga cctgacaaaa | 2160 |
| ctctttacac tctatatgtc agaaagagaa aaaatggcag ttgaagtttt aacccagact | 2220 |
| gtaaggccct ggccaaggcc agtggcctat ctctcaaaac aactagacga ggtttccaaa | 2280 |
| tggcccccac gtccaagcgc cctggtagca acggccctgt tagcacaaga agcagataag | 2340 |
| ctaactctta ggcaaaacct aaacataaag tcctgccatg ctgtggtgat tttaataaat | 2400 |
| accaaaggac accattagct aatgaatgct agactaacta gataccaaat cttgctctgt | 2460 |
| aaaaatccct acataaccat tgaagtttgc aacaccctaa ccccgccacc ttactcctgg | 2520 |
| tatcagagag cccagtttaa cataaactgt gtagaggtgt tagactcagt ttactctagt | 2580 |
| aggcccaacc tccaagacca cccttaaaca tcagtagact aggagctgta cgtggatagg | 2640 |
| agcagcttca cccaccctg caaagtgact ctgaaaaga cgacaagccc cgctccagtc | 2700 |
| acactcagaa gctga | 2715 |

<210> SEQ ID NO 49
<211> LENGTH: 5883
<212> TYPE: DNA
<213> ORGANISM: Homo sapiens

<400> SEQUENCE: 49

| gtcaggcctc tgagcccaag ccaagccatc gcatcccctg tgacttgcac atatacgccc | 60 |

```
agatggcctg aagtaactga agaatcacaa aagaagtgat atgccttgcc ccaccttaac    120
tgatgacatt ccaccacaaa agaagtgtaa atggctggtc cttgccttaa gtgatgacat    180
taccttgtga aagtcctttt cctgcctcat cctggctcaa aaagctcccc cactgagcac    240
cttgtgaccc ccactcttgc ccgccagaga acaacccccc tttgactgta attttccttt    300
acctacccaa atcctataaa acggccccac ccctatctcc cttcactgac tcttttcgga    360
ctcagcccac ctgcacccag gtgattaaaa gctttattgc tcacacaaag cctgtttggt    420
ggtctcttca catggacgcg catgatattt ggtgctgtga cttggattgg gggacctccc    480
ttgggagatc aatcccctgt cctcctgttc tttgctccgt gagaaagatc cacctacgac    540
ctcaggtcct cagaccgacc agcccaagga acatctcacc aattttaaat caggtaagca    600
gcctcttctt actctcttct ccaacctctc tcactgtccc tcaaccactt tctccttttcc   660 actcttcaat ctctcccttc tcttaatttc aattcctttc attttgtggg agagacaaag    720
gagacacgtt ttatccgtgg acccaaaact ccggcgctag tcacggacag ggaaggcagc    780
cttcccttgg tgtttagtca ttgcagggac gcctgattat tcacacgttt caaaggtgtc    840
agaccatgca gggacgcctg ccttggtcct tcacccttag cggcaagtcc tgcttttctg    900 ggaaggggc aagtacccca acctcttctc tccttgtctc taccccttct ctgcctttct     960
gggggagggg caagtacccc tcaaccccctt ctccttcacc cttagcggca agtcccgctt   1020
ttctatgggg caagaacccc caatccctta tttccacgcc ccaacctctt atctctgtgc    1080
cccaatccct tatttccgtg ccccaacctc ttatctctgc gccccaatcc cttatttcca    1140
caccccgacc tcttatctct gtgccccaat cccttattcc cgtgcccaa ccttgtatct     1200 ctgtgcccca gtcccttatt tccacacccc aacctcttat atctctgcac cccaatccct    1260
tatttccatg ccccaacctc ttatctctac gccccaaccc cttttcccac ttttctggaa    1320
ggtaagaacc cccgaaccc ttccctccat ttctctactc tctcttttcc ctaggcttgc     1380
ttccttcact atgggcaacc ttccaccctc cattcctcct tctactccct ggcctgtgt     1440 tctcaaaaac ttaaaacctc ttcaactcac acctgaccta aaacctaaat gccttatttt    1500
cttctacaat gccgcttgac cccaatacaa actcgacagt agttccaaat agccagaaaa    1560
tggcactttg aatttttcca tcctgcaaaa tctaataat tcttgtcata aaataggcaa      1620
acggtctgag gtgcctgaca tccaggcatt cttttacaca tcagtccctt cctagtctct    1680
gtgcccagtg caactcgtcc caaatcttcc ttctttccct cccgcctgtc ccctcagtac    1740
caaccccaag cgtcgctgag tcttttctaat cttccttttc tacagaccca tctgacctct    1800
cccctcctcc ccaggctgct cctcgccagg ccgagctagg tcccaattct tcctcagcct    1860
ctgctcctcc accctataat ccttttatca cctcccctcc tcacacacag tctggcttgc    1920
agtttcgttc cgtgactagc cctcccccac ctgcccagca atttactctt aaaaaggtgg    1980
ctggagctaa aggcatagtc aaggttaatg ctccttttc tttatcccag atcagatagc      2040
gtttaggctc ttttttcatca aatataaaaa tccagcccag ttcatggctc gtttggcagc   2100
aaccctgaga cgctttacag ccctagaccc taaaaggtca aaaggccgtg ttattctcaa    2160
tattcatttt attacccaat ctgctcccga cattaaataa aactccaaaa attggaatct    2220
ggccctgaaa ccccacaaca ggacttaatt aacctcacct tcaaggtgta caataacaga    2280
aaaaagttgc aattccttgc ctccactgtg agacaaaccc cagccacatc tccagcacac    2340
aagaactcca aacgctcaa ccgcagcagc cagacgttcc tccagaacct cctccccgag     2400
gagcttgcta catatcccgg aaatctggcc accgggccaa agaatgcccg cagcccggga    2460
```

```
ttcctcctaa gccgcgtccc atctgtgtgg gaacccactg aaaaccggac tgttcaactc    2520
acctggcagc cacttccaga gccctggaa ctctggccca aggctctctg actgcttccc      2580
agatcttctc ggcttagcgg ctgaagactg acgctgccca atcgcctcgg aagccccta     2640 gaccatcatg gacgccgagc ttcaggtaac tctcacagtg gaaggtaagc ccgtcccctt    2700
cttaatcaat acggaggcta ccctctccac attaccttct tttcaagggc gtttcccttg    2760
cctccataac tgttgtgggt attgacggcc aggcttctaa acctcttaaa actccccaac   2820
tctggtgcca acttagacaa tactcttttta accactcctt tttagttatc cccacctgac   2880 cagttcccctt attaggctga gacactttaa ctaaattatc tgcttccctg actattcctg    2940
gattacagct gtatctcatt gctgcccttc ttcccaatcc aaagcctcct ttgcgtcctc     3000
ctcttgtatt cccccacctt aacccacaag tataagatac ctctactccc tccttggtga    3060
ccgatcatgc accccttacc atctcattaa aacctaatca cccttaccct gctcaatgcc     3120
aatatcccat cccacagcat gctttgaaag gattaaagcc tgttatcact cgcctgctac    3180
agcatggcct tttaaagcct ataaactctc cttacaattc ccccatttta cctgtcctaa    3240
aaccagacaa gctttacaag ttagttcagg atctgcccctt atcaaccaaa ttgttttgcc   3300
tatccacccc atggtgccaa acccatatac tctcctatcc tcaatacctg cctctacaac    3360
ccattattct gttctggatc tcaaacatgc cttctttact attcctttgc acccttcatc    3420
ccagcctctc tttgctttca cttggactga ccctgacacc catgaagctc agcaaattac    3480
ctaggctgta ctgccgcaag gcttcacaga cagcccccat tacttcaatc aagcccgaat    3540
ttcttcctca tctgttacct atctcggcat aattctcata aaaacacacg tgctctccct     3600
gccaatcgtg tccgactgat ctctcaaacc aaagcacctt ctacaaaaca caactcctt    3660 tccttcctag gcatggttag tgcagtcaga attcttacac aagagccagg accgcaccct    3720
gcagcctttc tgtccaaaca acttgacctt actgttttag cctagccctc atgtctgcgt    3780
gcagcggctg ccactgcttt aatacttttta gaggccctca aaatcacaaa ctatgctcaa    3840
ctcactctct acagttctca taacttccaa aatctatttt cttcctcata cctgacgcat     3900
atactttctg ttccccgct ccttcagctg tactcactct ttgttgagtc tcccacaatt     3960
atcgttcctg gcccagactt caatccggcc tcccacatca ttcctgatac cacacctgac   4020
ccccatgact gtatctctct gatccacctg atattcaccc catttcccca aatttccttc    4080
tttcctgttc ctcaccctga tcacgcttga tttattgatg gcggttccac caggcctaat    4140
cgccacacac cagcaaagac aagttatact atagtacaag ccactagccc gcctcttaga    4200
acctctcatt tccttttccat cgtggaaatc tatcctcaag gaaataactt ctcagtgttc    4260
catctgctat tctactactc ctcagggatt attcaggccc cctcccttcc ctacacatca   4320
agctcaagga tttgccccac ccaggactgg caaattagct ttactcaaca tgccccgagt    4380
caggtaacta aaatacctct tagtctaggt agacactttc actggataag tacaggcctt    4440
tcctacaggg tctgagaagg ccaccacagt catttcctcc cttctgtcag acataattcc     4500
tcagtttagc cttcccacct ctatacagtc taataacaga ccagccttta ttagtcaaat    4560
cagccaagca gttttttcagg ctcttagtat tcagtgaaac ctttatatcc cttacggtcc    4620
tccgtcttca agaaaagtag aacggaccaa aggtctttta aaaacacacc tcaccaagct    4680
cagccaccaa cttaaaaagg actggacaat acttttacca ctttcccttc tcagaagtca    4740
ggcctgtcct cggaatgcta cagggtacag cccatttaag ctcctatata gatgctcctt    4800
```

```
tttattaggc cccagtctca ttccagacac cagaccaact tagactgtgc ccccaaaaaa    4860
cttgtcatcc ctactatctt ctgtctagtc atacgcctat tcaccgtttt caactactca    4920
tacatgccct gctcttgttt acactgccgg tttacactgt ttctccaagc catcacagct    4980
gatatctcct ggtgctatcc ccaaactgcc actcttaact cttgaagtaa ataaataatc    5040
tttgctggca ggactatgct gaatctcctc aggcactctc taatcagata tcctgagtcg    5100
tcccaattct tagaccttt  atacctgttt ttctccttct gttattccat ttagtttctc    5160
aattcatcca aaaccgtatc taggccatca ccaatcattc tatacgacaa atgtttcttc    5220
taacatcccc acaatatcac cccttaccac aagacctccc ttcagcttaa tctctcccac    5280
tctaggttcc cacgccaccc ctaatcccgc ttgaagcagc cctgagaaac atcgcccttt    5340
ctctctccat accacccca aaaaatgttc gccgccccaa cacttcaaca ctattttgtt     5400
ttatttttct tattaatata agaaggcagg aatgtcaggc ctctgagccc aagccaagac    5460
atagcatccc ctgtgacttc cacgtatacg cccagatggc ctgaagtaac tgaagaatca    5520
caaaagaagt gaatatgcct tgccccacct taattgatga cattccacca caaagaagt     5580 gtaaatggcc ggtccttgcc ttaagtgatg acattacctt gtgaaagtcc ttttcctgcc    5640
tcatcctggc tcaaaaagct cccccactga gcaccttgtg accccactc  ctgcccacca    5700 gagaacaacc cccctttgac tgtaattttc ctttacctac ccaatcgta  taaaatggcc    5760 ccaccctat  ctcccttcgc tgactctctt ttcggactca gcccacctgc acccaggtga    5820
ttaaaagctt tattgctcac acaaagcctg tttggtggtc tcttcacatg gacgcacatg    5880
aaa                                                                  5883

<210> SEQ ID NO 50
<211> LENGTH: 999
<212> TYPE: DNA
<213> ORGANISM: Homo sapiens

<400> SEQUENCE: 50
tgtgcaggtg tacctagcag ctccaaagag acagcgacca tcgaggacaa gccatgatga      60
caatggtggt tttgtcaaaa agaaaagggg gaaatgtggg gaagagaaag agagatcaga     120
ctgttactgt gtctatgtag aaagaagtag acataagaga ctccattttg ttctgtacta     180
agaaaaatta ttttgcctcg agatgctgtt aatctgtaac cctacccctta accctgtgct    240 ggcagaaaca cgtgctgtga cgactcaagg tttagtggat ttagggctat gcaggatgtg     300 cttttgttaaa caaatgcttg aaggcagcat gcttgttaaa agtcatcacc actccctaat    360
ctcaagtacc cggggacaca aaacactgtg gaaggctgca gggacctctg cctaggaaag    420
ccaggtattg tccaaggttt ctccccatgt ggtaatctga atatggcct  cgtgggaagg    480 gaaagacctg accgttcccc agcccgacac ccgtaaaggg tctgtgctga ggaggattag    540
taaaagagga aggcctcttt gcagttgaga taagaggaag gcatctgtct cctgctcgtc    600
cctgggcaat agaatgtctg ggtgtaaaac ccgattgtat attccatcta ctggagatag    660
gagaaaaccg ccttagggct ggaggtgaga catgctggcg gcaataggca atagtgctct    720
ttaaagcatt gagatgttta tgtatgtgca cattaaaagc acagcacctt ttctcttacc    780
ttgtttatga tgtagagatg tttgttcacg ttttcctgct gaccctctcc ccactattac    840
cctgttgtcc tgccactctc cattgtctcc ctgttgtccc cctctccgat atggtagaga    900
tactaatgaa taaatactga gggaactcag agaccggtgc cggcgtgggt cctccatatg    960
ctgaacgccg gttccctggg cccactttc  tttctctat                           999
```

<210> SEQ ID NO 51
<211> LENGTH: 2449
<212> TYPE: DNA
<213> ORGANISM: Homo sapiens

<400> SEQUENCE: 51

```
agaccaccag ttctcctgct gctctccgcc ttgcctagtt tataaaacaa gagaaaaagg      60
agaaagcaaa aagttaaaaa gaaaaaaagt aagataaata gccagatgac cttggggcca     120
ccaccctgcc ctgatggtta aataataata ataataataa aaataataat aatatcaacc     180
cctgacctca actatttgtg ttatctgtaa attccagaca ttgtatgagg aagcattgta     240
aaactttctg ttctgttagc tgatgcatgt agccccccagt cacattcccc atgcttgtga     300
cccctttcacg tagaccccctt aaagttgtga gcccttaaaa aggccaagaa ttttttttg     360
gggagctcag ctcttaagat gcaagtctgc tgaagctccc ggccgaataa agccgcttcc     420
ttctttaacc cggtgtctga ggagttttgt ctgtagcacg tcctgctaca tttcttggtt     480
ccctgaccag gaagcaaggt gaggcagccc cttaggcagc ttttgcctgc cctgtggagc     540
atccctttgg gtgaccctag ctggcttgag tgacacagat cctgagaaca ctcccaggta     600
ggcatttgcc ctggtggaat gtctcatcag agcagtgtgc cgcaggcccc cgtggaggat     660
caacacagtg gctgaacact gggaaggaac tgatgcttgg agttggacat ctggaatatg     720
gtaagactgg tcttaggaac ttgcctactc catttgagtg gaagcgtggc ctgatcaccc     780
acagtgtgcc tttatttgca cttttggtttt ggttttgatt ttgacttggc ttgaattgct     840
tgatgaacag gtatgcattt atcggcactt tggttttggt tttgattctg atttggtgtg     900
aatttcttga tgagtgagtg acctttttacc ctttgcccctt tttcccttct tgtggcaaga     960
gtggctcacc accccaatta tgaacatagg aactgaaagt gtgtgaaagt gtgtgaatgg    1020
aggggcctaa ttaggctcat cagctgagaa gtggggagtc acagatctct tagtgtgaac    1080
tgtgtgctcc gtgaaagtgt ggggctgact aagactagtg gcaatctaca taccgctaat    1140
aggagctgcc ctacagctca gagttgtagt gggaataagg acctctccaa aggcaagcag    1200
catctaaaaa ctcccataat aggagatggt gtagtcggcc aaaacgagag aaagagtgag    1260
tgtgcaagag tgaatgtgct gcgtcataaa aggaggaata gaagaaaagt caccaaaaca    1320
tcaaaactta ctctattgga gtgcatgtta cagaacctta agaaaggttt tggagggggat    1380
tatagagtta agttaacccc ccagaggttg agaactctct gtgaattaaa attgccttct    1440
tttggtgtta gatggctgac tgaaggaact ttaaacaagg aacaattggc catgtattta    1500
aggtggtgac aagggttgga ggacagccag tgtacccaga tcaaattcct ttatattgac    1560
tcatggctaa atataatata gacaaaacca gcatagatcc agccctgttt aatggcttat    1620
tgcaaaaaag ccaaaagtga agtaagagc agctttgcca gcagacacag agttaaaagg    1680
ggagtcccag agacagcaag agaagccagt tgtacaggaa ctgccaaagg caacagaaat    1740
tctttctccc tatgtcccag cctacccccca ctttaccgag gccaacagcc gcctcagaaa    1800
ccagattcag gagctaacat gccccaggtc tcacgaggat cagagactcc agaggccagg    1860
gaaggagatc aaggtagtca agcgggggtc gtctcagatc tggttgtgct cgagctatgc    1920
aaatgcctct cacggagatg cgaggaccta tctattatga tgaccagggc cacatccgga    1980
gggggcaaca gactttcatc tatcagcccct tttcaaccac tgatctacta aactggaaac    2040
actctgaacc ctgccatctt gctcctggta tcagagagcc ctgtcgtgca taactgtgta    2100
```

| | |
|---|---|
| gaagtgttgg actcggttta ctccagcaga cctgatctcc gggaccagcc ttgggcatca | 2160 |
| gtagactgga agctatatgt ggacaggagc agcttcatca acccacaagg agagagatgt | 2220 |
| gcgggatatg tggtggaacc ctggacactg tcgttgaagc cagatcgttg ctccaaggca | 2280 |
| cttcagccca gaaagatgag ctcattgctt taatttgggc cttagaactc agttaaggta | 2340 |
| agactataaa catttacact gactctcggt atgccttttt aaccctccaa gtgcatggag | 2400 |
| cattatataa agaaaaaggg cctgttgaac tctgggggaa ggacaaaaa | 2449 |

<210> SEQ ID NO 52
<211> LENGTH: 778
<212> TYPE: DNA
<213> ORGANISM: Homo sapiens

<400> SEQUENCE: 52

| | |
|---|---|
| gagagacagg actagctgga tttcctaggc cgactaagaa tccctaagcc tagctgggaa | 60 |
| ggtgaccaca tccaccttta aacatggggc ttgcaactta gctcacaccc gaccaatcag | 120 |
| gtaggaaaga gagatcacta aaatgctgat taggcaaaaa caggaggtaa agaaatagcc | 180 |
| aatcatctat tgcctgagag cacaaccgga gggacaatga tcgggatata aacccaggca | 240 |
| ttcaagccgg caatggctac cctctttggg tcccctccct ttgtatggga gctctgtttt | 300 |
| cactctatta aatcttgcaa ctgcactctt ctggtccgtg tttgttaggg ctcaagctga | 360 |
| gcttctactt gccttccacc actgctgttt gcagtcatcg cagacccgcc gctgacttcc | 420 |
| atccctccgg atatggcagg gtgtccgctg tgctcctgat ccagggaggc gcccattgcc | 480 |
| gctcctgatc aggctagagg cttgctgttg ttcctgcatg gctaagtgcc tgggtttgtc | 540 |
| ctaatcaagc tgaacaccag tcactgggtt ccatggttct cttccatgac ccacggcatc | 600 |
| taatagagcg ataacactca tcgcatggcc caagattcca ttccttggaa tccgtgaggc | 660 |
| caagaaccc agatcagaga acatgaggct tgccaccatc ttggaagcag cccgccacct | 720 |
| ttttggaagc ggcccgccac catcttggga gctctgggag caagaacccc cggtaaca | 778 |

<210> SEQ ID NO 53
<211> LENGTH: 5648
<212> TYPE: DNA
<213> ORGANISM: Homo sapiens

<400> SEQUENCE: 53

| | |
|---|---|
| caggcctctg agcccaagct aagccatcat atccctgtg acctgcacat acacatccag | 60 |
| atggctggtt cctgccttag ctgatgacat tccaccacag aagaagtgaa atggcctgt | 120 |
| tcctgcctta actgatgaca ttatcttgtg aaattccttc tcctggctca tcctggctca | 180 |
| aaagctcccc tactgagcac cttgtgaccc ccactcctgc ccatcagaga caaccccctt | 240 |
| tgactgtaat tttcctttac ctatccaaat cctataaaac ggccccaccc ctatatctcc | 300 |
| cttttctgac tctcttttca gactcagtcc gcctgcaccc aggtgaaata aacagccttg | 360 |
| ttgctcaaac aaagcctgtt tggtggtctc ttcacatgga tgcacatgaa atttggtgcc | 420 |
| gtgtctcgga tcggggaca tcccttggga gatcaatccc ctgtcctcct gcttttttgct | 480 |
| ccgtgagaaa gatccaccta caacctcagg tcctcagacc gaccagtcca aggaacatct | 540 |
| caccaacttc aaatccagta agtggcctct ttttactctc ttttccaacc tctctcacta | 600 |
| tccctcaacc tctttctcct ttcaactgcc acacttcaat ctctcccttc tcttaatttc | 660 |
| aattcctttc attttctcgt agagacaaag gagacacatt ttatccgtgg acccaaaact | 720 |
| ccggcaccag tcatgtactc agaagacagc cttcccttag tgtttaatca ttgtggggat | 780 |

```
gcctctctga ttattcaccc acattccatt ggtgtctgat ctccgcaggg atgcctgact    840
tgatctttca cccatgttcc cttggtggca agtcaattgc ggggacacct gctttggctg    900
ctcacccacg ttgcagccca gggctgctcc ccacccctt  tccatgtct ctaccctctt    960 ctttaaactt gcctccttca ctatgggcaa ccttccaccc tccattcctc cttcttctcc   1020
cttaacctgt gttcttaaaa acctaaaacc tcttcaactc acacctgacc taaaacctaa   1080
atgccttatt ttcttttgca atcctgcctg accccagtac aaactcaaca gtggttccaa   1140
atagccataa aatggcactt tcaattttc  catcctacaa gatctaaata attcttgtcg   1200
taaaatgggc aaacggtctg aggtgcctga tgtccaggca ttctttacac attggtccct   1260
ccttagtctc tgtgcccagt gcaactcctc ccaaatcttc cttctttccc tcccacctgt   1320
cccctcagcc ccaaccccaa gcgttgctga gtctttctaa tcttcctttt ctacagaccc   1380
atctgacctc tccctcctc  accaggccaa gctaggtgcc aattcttcct cagcctcccc   1440
tcttccaccc tataattctt ttatcacctc ccttcctcac acccagtcca ccttacagtt   1500
ttgttctgtg actagccctc ccccacctgc ccagcaattt actcttaaaa aggtggctgg   1560
agctaaaggc atagtcaagg ttaatgctcc tttttctta  tcccaaaaca gcgtttagac   1620 tcttttcat  caaatgtaaa aacccagccc agttcatggc tcatttggca gcaaccctga   1680
gatgctttac agccctagac cctaaaaggt caaaaggcca tcttattctc aatatacatt   1740
acccaatctg ctctcgacat taaataaaac tccaaaaatt aaattctggc cctcaaaccc   1800
cacaacagga cttaattaac ctcaccttca aggtgtacaa aatagagta  gaggcagcca   1860 agtagcagcg tattttgag  ttgcaattcc ttgcctccac tatgagacaa accccagcca   1920
catctccggc acacaagaac ttccaaacgc ctaaaccgca gtggccaggc attcctccag   1980
gcctgcctcc cctaggagct tgctacaagt gctagaaatc tggccatcag gccaaggaat   2040
gcccgcagcc tgggattcct cctaagccat gtcccatctg tacgggacca cactgaaaat   2100
cagactgttc aactcacctg gcagccactc ccagagcccc tggaactctg gcctaaggct   2160
ttctgactga ctccttccca gatcttctca gcttagcagc tgaagactga cactgcccga   2220
tagccttgga agcccctag  accatcacgg atgccgagct ttaagtaact ctcacagtgg   2280
aaggtaagtc catcccttc  ttaatcaata cgaaggctac ccacaccaca tctccacatt   2340
accttctttt caaaggactg tttcccttgc ctccataact gttgtgggta ttgatggcca   2400
ggcttctaaa cctcttaaag ctccctaact ctggtgccaa gttagaaaat actctttaa   2460 gcactccttt ttagttatcc cagttccttt attaggccaa gacactttaa ctaaattatc   2520
cacttccctg agtattcctg gactacagcc acatctcatt gccacccttc ttcccaatcc   2580
aaagcctccc ttgtgtcctc ccttttttat ccccccacct taaccccacaa ggataagata   2640 cctctactcc ctccttggcg actgatcacg catcccttac catctcatta aaacctaatc   2700
acccttaccc tgctcaatgc caatctccca tcccacagca tgcttcaaa  ggattaaagc   2760 ctgttatcac tggcctgtta cagcatgacc ttttaaagcc tataaattct tcttacaatt   2820
cccccatttt acccgtccta gaaccagaca agccttacag gttagttcag gatctgcacc   2880
ttatcaacac aattgttttg cctattcacc ccatggtgca aaaccatat  actctcctat   2940 cctcaatacc tccctccaca acccattatt ctgttctgga tctcaaacat gctttcttta   3000
ctattccttt gcacccttca tcccagcctc tctttgcttt cacttggact gaccctgaca   3060
cccatcagtc tcagcaaatt acctgggctg tactgccaca aagcttcaca gacagccccc   3120
```

-continued

| | |
|---|---|
| attacttcag tcaagccaaa atttcatcct catctgttac ctatctcagc ataattctca | 3180 |
| gaaaaacaca cgtgctctcc ctgccgatca tgtccagctg atccctcaaa ccacaacacc | 3240 |
| ttctgcaaaa caacaactcc tttccttcct aggcatggtt ggatactttt gacttcagat | 3300 |
| acctggtttt gccatcctaa caaaaccatt atataaactc acaaaaagaa acctagctga | 3360 |
| cccaatagat cctaaatcct ttccccactc ctctttccat tccttgaaga cagttttaga | 3420 |
| gactgccccc accctagctc tccctgactc atcccaactc ttttcattat ccacagccga | 3480 |
| agtgcagggc tgtgcagtcg gaattcttac acaagaactg ggaccgcacc ccgtagcctt | 3540 |
| tttatccaaa caacttgacc ttactgtctt gcttagccct caagtctgtg tgcagcaggt | 3600 |
| gccaccacaa ccccaatact tttagaggcc cttaaaatca caaactatgc tcaacttact | 3660 |
| ctctgcagtt ctcataactt ccaaaatcta ttttcttcct cactcctgac acatatactt | 3720 |
| tctgctccct ggctccttca gctgttctca ctctttggtg agtctcccac aattaccatt | 3780 |
| gttcctggcc cagacttcag tctggtctcc cacattattc ctgataccac aactgacccc | 3840 |
| catgactgta tctctctgat ccacctgaca ttcaccccat ttccccatat ttccttcttt | 3900 |
| cctgttcctc accctgatca cactttgttt attgatggca attccagcag gcctaatggc | 3960 |
| cacacaccag caaaagcagg ctatgctatg gtacaagcca ctagcccgcc tcttagaacc | 4020 |
| tctcatttcc tttccatcgt ggaaatctat ccgcaaggaa ataacttctc agtgttccat | 4080 |
| ctgctattct actactcctc agggattatt caggcccccct cccttcccta cacatcaagc | 4140 |
| ttggagattt gccccacccc agcactggta aattggcttt actcagcatg ccccaagtca | 4200 |
| gataactaaa atacctctta gtctaagcag acactttcgc tggataagta gaggcctttc | 4260 |
| ctacagggtc tgagaaggcc accacagtca tttcttccct tctgtcagac ataattcctc | 4320 |
| ggtttgggct tccatctctc atacagtctg ataacggacc agcctttatt agtcaaatca | 4380 |
| gccaagcagt ttttcaggct cttggtgttc attgaaacct ttatatccct tacggtcctc | 4440 |
| cgtcttcaga aaaagtagaa cagactgagg tctttttaaa aacacacctc acgaagctca | 4500 |
| gccaccaact taaaaaggac tggacagtac ttttaccact ttcccttctc acaagtcagg | 4560 |
| cctgtcctca gagtgctaca aggtacagcc cattcgagct cctgtataga tgctccttt | 4620 |
| tattaggccc cagtctcatc ccagacacca gaccaactta gactgcaccc caaaaaactt | 4680 |
| gtaatccta ctatttccta tctagtcata ctcctattca ctgttctcaa ctactcataa | 4740 |
| atgccctgct cttgtttaca ctgctggttt acactgtttc tccaagctat cacagctgat | 4800 |
| atctcctggt gctatcccca aaccaccact cttaactctt agagtaaata ataatctttt | 4860 |
| gctggcaagg ctatgctgaa cctccttagg cactctctaa ttagatgtcc taggtcctcc | 4920 |
| caattcttag tccttaata cctgtttttc tccttctctt attccgtta gttttcaat | 4980 |
| tcatacaaaa ccgtatccag gccatcacta ataattctac atgacaaatg tttcttttaa | 5040 |
| caacccgca atattgccct ttaccacaaa atcttcctc agcttaatct ctcccactct | 5100 |
| aggttccat gccgcccta atcctgctca aagcagccct gagaaacatc acccattatc | 5160 |
| tctccatacc acccgcaaaa attttcactg tcccaacact ttaccactat ttcattttat | 5220 |
| ttttcttatt aatataagac aggaatgtca ggactctgag tccaagctaa gcctgtgacc | 5280 |
| tgcacgtaca catccagatg gctggttcct gccttaactg atgacattcc accacaaaag | 5340 |
| aagtgaaaat ggcctgttcc tgccttaact gatgacattc tcttgtgaaa ttccttctcc | 5400 |
| tggctcattc tggctcaaaa gctccctgc tgagcacctt gtgaccccca ctcctgcccg | 5460 |
| ccagagaata acccccttt gactgtaatt ttccttacc tacccaaatc ctataaaatg | 5520 |

```
gccccacctc tatctccctt ctctgactct cttttcggac tcagcccgcc tgcacccagg    5580
tgaaataaac agccttgttg ctcacagaag gcctgtttgg tggtctcttc acacagacgt    5640
gcacgaaa                                                             5648
```

<210> SEQ ID NO 54
<211> LENGTH: 958
<212> TYPE: DNA
<213> ORGANISM: Homo sapiens

<400> SEQUENCE: 54

```
gtggggaaaa gaaagagaga tcagattgtt actgggtctg tgtagaaaga agtagacata      60
ggagactcca ttttgttctg tactaagaga aattcttctg ccttcagatg ctgttaatct     120
gtaaccttac ccccaaccct gtgctccctg aaacatgtgc tgtgtccact cagggttaaa     180
tggattaagg gctgtgcaag gtgtgctttg ttaaacagat gcttgaaggc agcatgcttg     240
ttaagagtca tcaccactcc ctaatctcag gtacccaggg acacaaaaca ctgcggaagg     300
ccgcagggac ctctgcctag gaaagccagg tattgtccaa ggtttctccc catgtgatag     360
tctgaaatat ggccttgtgg gaagggaaag acctgaccgt cccccagccc gacacccata     420
aagggtctgt gctgaggcgg attagtaaaa gaggaaggaa cgcttctttg cagttgagac     480
aagaggaagg catctgtccc tgggcgatgg aatgtctcag tataaaaccc gattgtatgt     540
tccatctact gagataggga aaaccgcct tagggctgga ggtgggacag gcgggcagca      600
atactgctct tcaaggcatt gagatgttta tgtgtatgca tatctaaagc acagcactta     660
attctttacc ttgtctatga tgcagagaac tttgttcacg tgtttacctg ctgaccttct     720
ctccgctatt atcctatgac cctgccacat ccccctctct gagaaacacc caagaatgat     780
gaataaatac taagggaact cagaggccgg cggggatcct ctgtctgctg aacgccggtc     840
ccctgggccc ccttttctct ttctctatac tttgtctctg tgtctctttc ttttccaagt     900
ctctcgttcc acctaacgag aaacacccac aggtgtggag gggcaaccca cccccttca     958
```

<210> SEQ ID NO 55
<211> LENGTH: 3555
<212> TYPE: DNA
<213> ORGANISM: Homo sapiens

<400> SEQUENCE: 55

```
gtcagtcctc tgagcccaag ctaagccatc attatctcct gtgacctgca tgtacatatc      60
cagatggccg gttcctgcct taactgatga cattatcttg tgaaattcct tctccttgct     120
catcctggct ccaaagctcc cctactgagc accttgtggc ccccactcct gcctgccaga     180
gaacaacccc ccttttcct ttacctaccc aaatcctata aaattgcccc acccctatct      240
cccttcactg actctctttt tggactcagc ccacctgtac ccaggtgaaa taaacagctt     300
tactgctcac acaaagcctg tttggtggtc tcttcacatg gatgcatgtg aaatttggtg     360
ccgtgactgg gatcgaggga cttcccttgg gagatcaatc ccctgtcctc ctgctctttg     420
ctctgtgaga aagatccacc tatgacttca ggttctcaga ctgaccagcc caagaaacat     480 ctctgaccaatt tcaaatctgg taagcggctt cttttttactc tcttctccaa cctccctcac     540
tatccctcca cctctttctc ctcccaatct tggcaccaca cttcaatctc tcccttctct     600
taatttcaat tcctttcatt ttctggtaga gacaaagggg acacgtttta tctgtggacc     660
caaaactctg gcaccagtca cggactagtg aaggcagcct ttccttggtg tttaatcact     720
```

```
tgcagggaca cctctctgat tattcaccga ggtttcagag gtgtcagacc atgcagggat    780
gcctgccttg ttccttcacc cttagcagca agacctgctt ttctggggga gggacaagaa    840
cccctcaacc ccttctcctt caccctttagc agcatgtccc acttttctgg gggagggaca   900
ggaaccccga cctcttatct ctgcaccccg atcccttatt ccatgccct gacctcatct     960 ctgtgtcccg atcccttatt ccacaacct gacctcttat ctctgcaccc caacccttta    1020
tttctgtgcc cccaacccctt tccctctatt ctggaaggca agaaccccccc acccttctc   1080 tccatgtctc tactctctct tttctctagg cttgcctcct tcactatggg caagcttccg   1140
ccttccattc cccttcttc tcccttaccc tgtgttcttc aaaacctaaa acctcttcaa    1200
ctcacacctg acctaaaacc taaatgcctt attttcttct acaatgctac ttgacccca    1260 tacaaactca gcagtggttc caaatagcca gagaatggca ctttcaattt ttccatccta   1320
caagatctag atacttcttg tcataagatg ggcaaatgat ctgagatgcc tgatgtccag   1380
gcattctttt acacattggt ccctccctag tctctgttcc cagtgcaact catccgaaat   1440
cttcctcctt tccctcccac ctgtcccctc agtcccaacc ccaagtgtcg ctgagtcttt   1500
ctaatcttcc ttttctacag acccatctga cctctcccat cctggccagc ctgagctagg   1560
tcccaattct tcctcagcct ccacttctcc acctctataat cctttttatca cctcccctcc  1620 tcacactggg tctggcttac agtttaattc cgtgactagc cctcccccac ctgcccagca   1680
atttactctt aaacaggtgc ctggagctaa agacatagtc aaggttaatg ctccttttc    1740 tttatcccaa atcagatagc atttagcctc ttttttcatca aatataaaaa tccacccag    1800 ttcatggctc gtttggcagc aaccctgaga tgctttacag ccctagacct taaaacgtca    1860
aaaggccgtc ttattctcaa tatacatttt attacccaat ctgctcccga cattaaataa    1920
aactccaaaa ttaaattccg gccctcaaac cccacaacag gacttaatta acctcaactt   1980
caaggtgtac aataatggag tagaggcagc ctagcagcaa catatttctc agttgcaatt   2040
ccttgcctcc actgtgagac aaagcccagc caaatctcca gcacacaaga acttccaaac   2100
gcctaaagcg cagtggccag gcattcctcc agaaccacct accccaggag cttgctacaa   2160
gtgccagaaa tctggccacc agaccaagga atgcctgcag cccgggattc ctcctgagcc   2220
atgtcccatc tgtgcgagac ccaactagaa atcggactgt tcaactcacc tggcagccac   2280
tcctagagcc cctggaactc cagcccaagg ctctctgact cattccttcc cagatcttct   2340
tggcttagca gctgaagact gacactgcct gatagatcac ctcggaagcc tacaggacca   2400
tcacagacgc tctaggtaac tctcacagtg gaggagaagt ccatcccctt cttaatcaat   2460
acggaggcta accactccac attaccttct tttcaagggc ctgtttccct tgtctccata   2520
actgttgtga gtattgacag ccaggcttct aaacctctta aaactcccca actctggtgc   2580
caacttagac aatactcttt taagcactcc ttttttagttg tccccacctg cccagttccc   2640
ttattaggct gagacacttt aactaaatta tctgcttccc tgactattcc tggactacag   2700
ccactcctca ttgccaccca ccttaaccca caagtagaag atacctctat tccctccttg   2760
gcaacctatc acgcacccct taccatctca ttaaaaccta atcactctta cccctctcaa   2820
tgccaatatc ccatcccaca gcatgctttg aaaggattaa agcctgttat cactcacctg   2880
ctacagcatg gccttttaaa gcctataaac tctccttaca attccccat tttacctgtc    2940 ctaaaaccag acaagcctta caagttagtt caagatctgt gccttatcaa ccaaattgtt   3000
ttgcctatcc accccaaggt gccaaacaca tatactctcc tatcctcagt tcctccctcc   3060
acaacccatt attctgttct gaatctcaaa catgctttct ttactattcc tttgcaccct   3120
```

```
tcatcccagt cactcttcgc tttcacttgg actgaccctg acacccatca agctcagcaa    3180
attacctggg ctgtactgtc gcaaagcttc acagacagcc cccattactt cagtcaagcc    3240
caaatttctc ccttatctgt tacctatctc agcataattc tcataaaaac acacgtgctc    3300
tctctgccga tcgtgtgtga ctcatctctc aaacccaac cccttctaca aaacaacaac     3360
tcctttcctt cctgtgcatg gttggatact ttcaccttta gatatctggt tttgccatcc    3420
taacaaaacc attatataaa ctcacaaaag gaaacctagc tgaccccata gatcctaaat    3480 ccttttcccca ctcctctttc tgttccttga agacagcttt aaagactgcc cccaccctag   3540
tcttggttcc ctgac                                                     3555

<210> SEQ ID NO 56
<211> LENGTH: 6087
<212> TYPE: DNA
<213> ORGANISM: Homo sapiens

<400> SEQUENCE: 56
gtcagggctc tgagcccaag ctaagccatc atatcctctg tgacctgcac gtatacatcc      60
agatggccgg ttcctgcctt aactgatgac attccaccac aaaagaagtg aaaatggcct     120
gttcctgcgt taactgatga cattgtcttg tgaaattcct tctcctggct catcctggct     180
caaaagctcc cctactgaac accttgtgac cccccactcc tgcccaccag agaacaactc     240
cctttgactg taattttcct ttacctaccc aaatcttata aaacggcccc acccctgtct     300
cctttcactg actctctttt tggactcagc ccgcctgcac ccaggtgaaa taaacagcca     360
tgttgctcac acaaagcctg tttggtggtc tcttcacacg gacacgcatg aaatttggtg     420
ctgtgactca gatcagggga cctcctttgg gagatcaatc ctctgtcctc ttgctctttg     480
ctctgtgtaa aagatccacc tacgacctca ggtcctcaga cccaccagcc caaggaacat     540
ctcaccaatt ttaaatcggg taagcggcct cttcttactc tcttctccaa cctctctcac     600
taaccgtcag ccactttctc ctttccactc ttctgtctct cccttctctt aatttcaatt     660
cctttcattt tctggtagag acaaaggaga cacattttat ctgcgaaccc aaaactccgg     720
cgccggtcat gggctgggaa ggcagccttc ccttggtgtt taatcattgc agggatgcct     780
ctctgattat tcacccatgt ttcagaggtg tcagaccatg cagggatgcc tgccttggtc     840 cttcacccctt agcggcaagt cccattttt ggggggagag gcaagtaccc caaccccttc     900
tctccatgtc tctaccccctt ctccaccttt ctgggggca agaaaccccc aacccttct    960 ccttcaccct tagtggcaag tcctgctttt ctggggagg ggcaagtacc ccaacctcgt    1020
atctctgcac cccatccctt atttccatgc cctgacctct tatatgtctg cacctgatc    1080 ccttatttcc atgccccaac ctcttatatc tctgtgccct gatcccttat ttccatgccc    1140
cgacctcata tctctgtgcc ccaacccctt tcccgctttt ctggagggta agaacccccg    1200
aaccccttcc ctccgtgtct ctactcttac ttttctttaa acttgcctcc ttcactatag    1260
gcaaccttcc atcctccatt cctccttctt ctcccttagc ctgtgttctt aagaacataa    1320
aacctcttca actctcaccg gacctaaaac ctaaatgcct tattttcttc tacaatgcca    1380
catgacccca atacaaactc aacagtggtt ctaaatggca agaaaatggc actttcgatt    1440
tctccatcct acaagatcta aataatttt gtcaaaaaat aggcaaatgg tctgaggtgc     1500
ctgatgccca ggaactcttt tacacatagt ccctctctag tctctgttcc caatgcaact    1560
agtcccaaat cttccttctt tcctccctc ctgtccccctc agtccaaacc ccaagtgtcg    1620
```

```
ctgagtctttt gtaatcttcc ttttctacag acccatctga cctctcccct cctccccagg   1680
ccaagctagg tcccaattct tcctcagcct ctgctcctcc accctataat cttttttatca   1740
cctcccctcc tcacacctgg tctggcttac agtttcattc catgactagc cctcccccac   1800
ctgcccagca atttactctt aaaaggtgg ctggagctaa aggcatagtc aaggttaatg    1860
ctccttttc tttatcccaa attagttaga tttaggctct ttttcatcaa atataaaaat    1920
ccagcccagt tcatggctca tttggcagcc accctgaaac gctttacagc cctagaccct   1980
aaaaagtcaa aaggctgtct tattctcaat atacatttta ttacccaatc tgctcctgac   2040
attaaataaa actccaaaaa ttaaattcca gccctgaaac cccacaacag gatttaatta   2100
acctcacctt caaggtgtac aataatagag gcagccaagt agcaacatat ttctgagttg   2160
caattccttg cctccactgt gagacaaacc ccagccacat ctccagcaca caagaacttc   2220
caaacgccta aaccacagtg gccaggtgtt cctccagaac caccttcccc aggagcttgc   2280
tataagtgcc agaaatctgg acaccaggcc aaggaatgcc cacagcccag gattcctcct   2340
aagccatgtc ccatctgtgc gggaccccac tggaaatcag actgttcaac tcacatggca   2400
gccactccca gagcccctgg aactctggcc caaggctctc tgactgactc cttcccagat   2460
cttcttggct tagcagctga agactgacag tgcccgatcg cctcagaagc ctacagaacc   2520
atcacggaca atctaggtaa ctctcacagt ggaaggtaag tccgtcccct tctcaatcaa   2580
tatgggaggct acccactcca cattaccttc ttttcaaggg cctgtttccc ttgcctccat   2640
aactgctgta ggtattgatg gccaggcttc taaacctctt aaaactcccc aactctggtg   2700
ccaacttaga caacactctt ttaagcactc cttttaagtt atcccccacct gcccagttcc   2760
gttattaggc cgagacactt taactaaatt atctgcttcc ctgactattc ctggactaca   2820
gctacatctc attgccgccc ttcttcccaa tccaaagcca catttgtgtc ctcctcttgt   2880
atccccccaa cttaacccac aagtataaga tacctctact ccctccttgg caaccgatca   2940
tccaccccctt accgtctcat taaaacctaa tcacccttac cccgctcaat accaatatcc   3000
tatcccatac catgctttga aaggataaag gcctgttatc actcacctgc tacagcatgg   3060
ccttttaaag cctataaact ctccttacaa ttccccccatt ttacctgtcc taaaaccaga   3120
caagccttac aagttagttt aggatctatg ccttatcaac caaattgttt tgcttatcca   3180
ccctgtagtg cccaacccgt acactctttt gtcctcaata ccttcctcca caactcacta   3240
ttccgttctt gatcttaaag atggtttttt cactattccc ctgaacctct cgtcccagcc   3300
tctctttgct ttcatctgga ctgaccctga cacccatcag ccccagcagc ttacctgggc   3360
tgtgctgcca caaggtttca gggacagtcc ttattacttc agccaagctc tttctcatga   3420
tttattttct ttccaccct ctgcttctca cctattcag tatattgatg accttctttg    3480
tagcccctcc tttgaatctt ctcaacaaga cacacttctg ctccttcagc atttattctc   3540
caaaggatat cgggtatccc cctccaaagc tcaaatttct tctgcatccg ttacctcggc   3600
ataattcttc acaaaaacac acgtgctctc cctgccgatc atgtctgact gatctctcaa   3660
accccaaccc cttctacaaa acaactactc ctttccttcc tgggcgtgat tggatacttc   3720
cgcctttgga tacctggttt tgccatccta acaaaaccat tatataaact cacaaaagga   3780
aacctagctg accccataga tcctaaatcc tttccccact cctctttccg ttccttgaag   3840
acagctttag agactgcccc cactctagct ctccctgact catcccaacc cttttcatta   3900
cacacagcca aagtgcaggg ctgtgcagtc agaattctta cacaaggact gggatcgtgt   3960
cctgtaggct ttttgtccaa acaacttgac cttactgttt taggctggcc atcatgtctc   4020
```

```
tgtgcagcgg ctgatgccac cctaataatt ttagaggccc ttaaaatcac aaactatgct    4080
caactcactc tctacagctc tcataatttc caaaatctat tttcttcctc acacctgacg    4140
cacatacttt ctgctccctg gctccttcag ctatactcac tctttgttga gtctcccaca    4200
attaccattg ttcctggccc agacttcaat ccagcctccc acattattcc ggataccaca    4260
cctgaccctc ataactgcaa ctctctgatc cacctgacgt tcaccacatt tccccacatt    4320
tctttcttcc ctgtttctca ccctgatcac agttggttta ttgatggcag ttccaccagg    4380
cctaatcacc acacaacagc aaaggcaggc tatgctatag tacaagccac tagcccacct    4440
cttaaaacct ctcatttcct ttccattgtg gaaatctatc ctcaaggaaa taacttctca    4500
atgttccatc tgctattcta ctacttctca gggattattc aggcccctc ccttccctac     4560 acatcaagct tgaggatttg ccccacccca ggactggcaa attagcttta ctcaacatgc    4620
cccgagtcag ataactaaaa tacctcttag tctaggtaga caatttcact ggataagtag    4680 aggccttttcc tgcaggtctg agaaggccac cacagtcatt tcttcccttc tgtcagacat    4740
cctcagttta gccttcccac ctctatacag tctgataacg gaccagcctt tattagtcaa    4800
atcagccaag cattttttca ggctctcagt attcagtgaa acctttatat cccttatggt    4860
cctccgtctt caagaaaagt agaatggact aaaggtcttt taaaaacaca cctcaccaag    4920
ctcagccgcc aacttaaaaa ggactggaca atacttttac cactttccct tctcagaatt    4980
caggcctgtc ctcagaatgc tacaaggtac agcccattta agctcctgta tagacactcc    5040 ttttttattag gtaccagtct cattccagac accagaccaa cttaaactgt gacccaaaaa    5100
acttgtcatc cctattattt tctgtgtagt catactctta ttcacctgtt ctcaactact    5160
cgtacatgcc ctgctcttgt ttacactgcc agtttacact gtttctccaa gccatcacag    5220
ctgatatctc ctggtgctat ccccaaacca ccactcttaa ctcttaaagt aaataaacaa    5280
tctttactgg caaggctatg ctgagtctcc ttaggcactc tctaattaca tgtcctaggt    5340
cctcccaatt cttggtcctt taatacctgt ttttctcctt ctcttattcc atttagtttt    5400
tcaattcaaa caaaactgta tccaggccat caccaataat tctaaatgac aaatgtttct    5460
tctaacaacc ccacgacatc accacttacc acaaaatctt ccttcagctt aatctctccc    5520
actctaggtt cccacgccgc ccctaatcct gctcaaagca gccctgagaa acatcgccca    5580
ttatctctcc ataccacccc aaaaaaattt tcaccatccc aaccctttac cactatttca    5640
ttttattttt cttattaata taagaagaca ggaatgtcag gcctctgagc ccaagctaag    5700
ccatcatatc ccctgtgacc tgcaggtaca cacccagatg gctggttcct gccttaactg    5760
atgacattcc accacaaaag aagtgaaaat ggcctgtttc tgccttaact gatgacattg    5820
tcttgtgaaa ttccttctcc tggctcatcc tggctcaaaa tctcccccac tgagtacctt    5880
gtgaccccca ctcctgcccg ccagagaaca actccctttg actgtaattt tcctttacct    5940
acccaaatct tataaaatgg ccccacctct atctcccttc tctgactctc ttttcgaact    6000
cagcccgcct gcacccaggt gaaataaaca gccatgttgc tcacacaaag cctgtttggt    6060
ggtctcttca cacagacgtg catgaaa                                        6087
```

<210> SEQ ID NO 57
<211> LENGTH: 5789
<212> TYPE: DNA
<213> ORGANISM: Homo sapiens

<400> SEQUENCE: 57

```
gtcaggcctc tgagcccaag ccaagccatc gcatccctg tgacttgcat gtatatgccc     60
agatggcctg aagtaactga agaatcacaa aagaagtgaa tatgccctgg cccgccttaa    120
ctgatgacat tccaccacaa aagaagtgta atggccggt cattgcctta actgatgaca    180
ttaccttgtg aaagtccttt tcctggctca tcctgactca aaaatcaccc ccactgagca    240
ccttgcgacc cccactcctg cccgccagag aacaaacccc ctttgactgt aattttcctt    300
tacctaccca atcctataa aacgccca cccttatctc ccttctctga ctctcttttc      360
ggactcagcc cgcctgcacc caggtgaaat aaacagccat gttgctcaca caaagcctgt    420
ttggtggtct cttcacacgg acgcgcatga aatttggtgc cgtgactcag atcggggtac    480
ctcccttggg agatcaatcc cctgtcctcc tgttctttgc tccatgagaa agatccacct    540
acgatctcag gtcctcagac cgaccagccc agggaacatc tcaccaattt taaatcaggt    600
aaacggcgtc ttactctctt ctccaacctc tctcactgtc cctcaaccac tttctccttt    660
ccactcttca atctctccct tttcttaatt tcaattcctt tcattttctg ggagagacaa    720
aggagacacg ttttatccgt gggcccaaaa ctccggcgcc ggtcacggac tgggaaggca    780
gccctccatt ggtgtttaat cattgcaggg acgcctgatt atacacccac gtttcaaggg    840
tgtcagacca cgtagggatg cctgccttgg tcctttaccc ttagcggcaa gtcccgcttt    900
tctggggaag gggcaagtac ctcaaccct tctctccttg tctctacccc ttctctgctt    960
ttctgggaga ggggcaagta ccctcaacc ccttctcctt cacccttagc ggcaagtccc    1020
gcttttctac agggcaagaa cccccaatcc cttatttcca caccccaacc tcttacctct    1080 gtgcccaat cccttatttc catacccaa cctcttatct ctgcacccca atcccttatt    1140
tccacacccc aacctcttat ctctgtgccc caatcccta tttctgtgcc ccaacctctt    1200
atctctgcac cccaaccct tttcccactt ttctggaagg taagaactcc tgaaccct     1260 ccctccgttt ctctactctc tcttttctct aggcttgctt ccttcactat gggcaacctt    1320
ccaccctcca ttcctcttc tactcccttg gcctgtgttc tcaaaaactt aaaacctctt    1380
caactcacac ctgacctaaa acctaaatgc cttattttct tctgcaatgc cgcttgaccc    1440
caatacaaac tcaacagtag ttccaaatag ccagaaaatg cactttgaa tttttccatc    1500 ctgcacaatc taaataattc ttgtcgtaaa ataggcaaac ggtctgaggt gcctgacgtc    1560
caggcattct tttacacatc agtcccttcc tagtctctgt gcccagtgca acttgtccca    1620
aatcttcctt cttttccctcc cgcctgtccc ctcagtccca accccaagcg tcgctgagtc    1680
tttctaatct tccttttcta cagacccatc tgacctctcc cctcctcgct agcccaagct    1740
aggtccccat tcttcctcag cctccgctcc tccaccctgt aatctttta tcgcctcccc    1800 tcctcacacc tggtccggct tacagtttcg ttctgtgact agccctcccc cacctgccca    1860
gcaatttact cttaaaaagg tggctggagc taaaggcata gtcaaggtta atgctccttt    1920
ttctttatcc caaatcagaa gcgtttaggc ccttttcat caaatataaa acccagccc    1980 agttcatggc tcgtttggca gcaaccctga gacactttac agccctagac cctaaaaggt    2040
caaaaggccg tcttattctc aatatacatt ctattaccca atctgcttcc aacattaaat    2100
aaaactccaa aaattggaat ctggccctca accccacaa caagacttaa ttaacctcac    2160
cttcaaggtg tacaataaca gaaaaagtt gcaattcctt gcctccactg tgagacaaac    2220
cccagacaca tctccagcac acaagacttc caaacgcctg aaccgcagca gccaggcgtt    2280
cctccagaac ctcctccccc aggagcttgc taaatgtgct ggaaatctgg ccactgggcc    2340
aaggaatgcc cgcagcccgg gattcctcct aagccgcgtc ccaactgtgt gggaccccac    2400
```

```
tgaaaatcgg actgttcaac tcacctggca gccactccca gagtccctgg aactctggcc    2460
caaggctctc tgactgactc cttcccagaa cttctcggct tagcggctga agactgacac    2520
tgcccgatcg ccttggaagc ccctagacc atcacggatg ctgagcttcc ggtaactctc     2580
acagtggaag gtaagccagt ccccttctta atcaatacgg aggctaccca ctccacatta   2640
ccttcttttc aagggcctgt ttccttgcc tccataactg ttgtgggtat tgatggccag    2700
gcttctaaac ctcttaaaac tccccaactc tggtgccaac ttagacaata ctcttttaag   2760
cgctcctttt tagttatccc cacctgccca gttcccttat taggctgaga cactttaact   2820
aaattatctg cttccctgac tattcctgga ctacagctaa atctcattgc cacccttctt   2880
cccagtccaa agcctccttt gcgtcctcct cttgtatccc ccaccttaa cccacaagta    2940 taagatacct ctactccctc cttggtgacc gatcatgcac cccttaccat ctcattaaaa   3000
cctaatcacc cttaccccac tcaatgacaa tatcccatcc cgcagcatgc tttaaaaga    3060 ttaaagcctg ttatcactcg cctgctacag catggccttt taaagcctat aaactctcct   3120
tacaattccc ccatttacc tgtcctaaaa ccagacaagc cttacaagtt agttcaggat    3180
ctgcgcctta gcaaccaaat tgttttgcct atccaccccg tggtgccaaa cccatatact   3240
ctcctatcct caataccctcc ctctacaacc cattattctg ttctggatct caaacatgct  3300
ttctttacta ttcctttgca tcccagcctc tcttcgcttt cacttggact gaccctgaca   3360
cccatcaagc tcagcaaatt acctaggctg tactgccgca aagctcacag acagccccat   3420
tacttcaatc aagcccaaat ttcttcctca tctgttacct atctcggcat aattctcata   3480
aaaacacacg tgctctccct gccaatcgtg tccgactaat ctctcaaacc ccagcacctt   3540
ctacaaaaca caactccctt tccttcctag gcatggttag cgcggtcaga attcttacac   3600
aagagccagg accacaccct gtagcctttc tgtccaaaca acttgacctt actgttttag   3660
cctagccctc atgtctgcaa gcagcggctg ccactgcttt aatacttta gaggcccta   3720 aaatcacaaa ctatgctcaa ctcactctct acagttctca taacttccaa aatctatttt   3780
cttcctcata cctgacgcat atactttctg cttcccggct ccttcagcta tactcactct   3840
tcgttgagtc tcccacaatt accgttgttc ctgcccaga cttcaatccg gcctcccaca    3900
ttattcctga taccacacct gaccccatga ctgtatctct ctgatccacc tgacattcac   3960
cccatttccc cagattttct tctttcctgt tcctcaccct aatcatgctt gatttattga   4020
tggcggttcc accagaccta atcgccacac accagcaaag gcaggttata ctatagtaca   4080
agccactagc ccgcctctta gaacctctca tttccttcc atcgtggaaa tctatcctca   4140
aggaaataac ttctcagtgt tccatctgct attctactac tcctcaggga ttattctggc   4200
cccctccctt ccctacacat caagctcgag gatttgcccc acccaggact ggcaaattag   4260
ctttactcaa catgccctga gtcaggaaac taaaataccct cttagtctaa atagacactt   4320
tcactgaata agtaaaggcc tttcctacag ggtctgagaa ggccactgca gtcatttctt   4380
cccttctgtc agacataatt cctcagttta gccttccac ctcaatacag tctgataaca    4440
gatgagcctt tattagtcaa atcagccaag cagttttca ggctcttagt attcagtgaa    4500
acctttatat cccttacggt cctccgtctt caagaaaagt agaatggact gaaggtcttt   4560
taaaaacaca cctcaccaag ctcagccacc aaaaaggact ggacaatact tttaccactt   4620
tcccttctca gaattcaggc ctgtcctcgg aatgctacag ggtacagccc atttaagctc   4680
ctgtatagac gctccttttt attaggcccc agtctcattc cagacaccag accaacttag   4740
```

| | |
|---|---|
| actgtgccta cctccccaaa aaaaaacttg tcatactcct attttctgtc tagtcatact | 4800 |
| cctattcacc gttctcaact actcatacat gacctgctct tgtttacact gccagtttac | 4860 |
| actgtttctc caagccatca cagctgatat ctcctggtgc tgtccccaaa ctgccactct | 4920 |
| taactcttga agtaaataaa taatctttgc tggcaggact atgctgaatc tccttaagca | 4980 |
| ctctccaatc agatatcctg agtcgtccca attcttagac cttttatacc tgttttctc | 5040 |
| cttctgttat tccatttagt ttttcaattc atacaaaacc gtatccaggc catcaccaat | 5100 |
| cattctatac gacaaatgtt tcttctaaca accccacaat atcacccctt accacaagac | 5160 |
| ctcccttcag cttaatctct cccactctag gttcccacgc cgcccctaat cccgcttgaa | 5220 |
| gcagccctga gaaacatcgc ccattctctc tccataccac cccccaaaa ttttcaccgc | 5280 |
| cccaaaactt caacactatt ttgttttatt tttttatta atataagaag gcaggaatgt | 5340 |
| caggcctctg agcccaagcc aagccatcgc atcccctgtg acttgcaggt atacgcccag | 5400 |
| atggcctgaa gtaactgaag aatcacaaaa gaagtgaata tgccctgccc cgccttaact | 5460 |
| gatgacattc caccacaaaa gaagtgtaaa tggccggtcc ttgccttaac tgatgacatt | 5520 |
| accttgtgaa agtcctttc ctggctcatc ctgactcaaa atcacccc actgagcacc | 5580 |
| ttgcgacccc ccactcctgc ctgtcagaga acaaaccccc tttgactgta attttccttt | 5640 |
| acctacccaa atcctataaa acggccccac ccttatctcc cttctctgac tcttttctga | 5700 |
| ctcagcccgc ctgcacccag gtgaaataaa cagccatgtt gctcacacaa agcctgtttg | 5760 |
| gtggtctctt cacacggacg cgtgtgaaa | 5789 |

<210> SEQ ID NO 58
<211> LENGTH: 3642
<212> TYPE: DNA
<213> ORGANISM: Homo sapiens

<400> SEQUENCE: 58

| | |
|---|---|
| gtcaggcctc tgagcccaag ccaagccatc gcatcccctg tgacttgcac gtataagccc | 60 |
| agatggcctg aagtaactga agaatcacaa aagaagtgaa tatgccctgc cccaccttaa | 120 |
| ctgatgacat tccactacaa aagaagtgaa aatggccggt ccttgcctta agtgatgaca | 180 |
| ttaccttgtg aaagtccttt tcctggctca tcctggctca aaaacctccc ccactgagca | 240 |
| cctttcgacc ccgactcctg cccgccagag aacaaacccc ctttgactgt aattttcctt | 300 |
| tacctaccca atcctataa aacagcccca cccttatctc ccttcactga ctctcttttc | 360 |
| cgactcagcc tacctgcacc caggtgaaat aaacagccat gttgctcacg caaagcctgt | 420 |
| ttggtggtct cttcacacgg acgcgcatga atttggtgc cgtgacttgg atcggggac | 480 |
| ctcccttcgg agatcaatcc cctgtcctcc tgttctttgc tccatgagaa agatccacct | 540 |
| acgacctcag gtcctcagac tgaccagccc aagaaacatc tcaccaattt caaatccggt | 600 |
| aagcggcctc ttttactct cttctccaac ctccctcact atccctcaac ctctttctcc | 660 |
| tttcaatctt ggcgccacac ttcaatctct gccttctgtt aatttcaatt cctttcattt | 720 |
| tctggtagag acaaaggaga cacttttat ccgtggaccc aaaactccgg cgccagtcac | 780 |
| ggactaggaa ggcagccttc ccttggtgtt taatcattgc agggacacct ctctgattat | 840 |
| tcacccatgt ttcaaggtg tcagaccact cagggacacc tgccttggtc cttcacccctt | 900 |
| agcggcaagt cctgcttttc tggggaaggg gcaagtaccc caactctttc tctccttgtc | 960 |
| tctacccctt ctctgctttt ctggggagg ggcaagtacc cctcaacccc ttctccttca | 1020 |
| cccttagcag caagtcccgc ttttccagag gaggggcaag taccccaacc tcgtatctct | 1080 |

```
gtgccccaat cccttatttc cacgccacaa cctcttatat ctctgcaccc cagtcccttta  1140
tttccacacc ctgacttctt atctctgcac cccaatccct tatttccatg ccccgacccc  1200
ttatttctgt gccccgaccc cttatttcca tgccccgacc ccttatttct gcaccccatc  1260
ccttatttct gtgccgcaac ctcttatctc tgtgccccaa cccctttttcc cacttttcta  1320
gaaggtaaga accccgaac cccttccctc catttctcta ctctctcttt tctctaggct  1380
tgcttccttc actataggca actttccacc ctccattcct ccttctactc ccttaacctg  1440
tgttctcaaa aacttaaaac ctcttcaact cacacctgac ctaaaaccta aatgtcttat  1500
tttcttctgc aatgctgctt gaccccaata caaactcgac agtagttcca aatagccaga  1560
aaacggcact ttcaattttt ccattctaca agatctaaat acttcttatc gtaaaatagg  1620
caaatggtct gaggtgactg acgtccaggc atttttaca catcagtccc ttcctagtct  1680
ctgtgcccag tgcaactcgt cccaaatctt ctttcccttc cgcctgtccc ctcagtccca  1740
accccatgca tcactgagtc tttctaatct tcttttcta cagacccatc tgacctctac  1800
cctcctcgcc aggccaagct aggtcccaat tcttccaccc tataatcttt ttattgcctc  1860
ccctcctcat acctggtccg gcttacagtt ccttccgtg actagccctc ccccacctgc  1920
ccagcaattt cctcttaaaa aggtggctgg agccaaaggc atagtcaagg ttaatgctcc  1980
tttctcttta tcccaaatca gatagcgttt aggctctttt tcatcaaata taaaaaccca  2040
gcccagttca tgtctcattc ggcagcaacc ctgcgacgct ttacagccct agaccctaaa  2100
aggtcaaaag gccatcttat tctcaatata cattttatta cccaatctgc tcctgacatt  2160
aaataaaact ccaaaaatta gaatctggcc ctcaaacctc acaacaggat ttaattaacc  2220
tcaccttcaa ggtgtacaat aatagaaaaa agttgcaatt ccttgcctcc actgtgagac  2280
aaacccagc cacatctcca gcacacaaga aattccaaac acctgaacca cagcggccag  2340
gcattcctcc agaacctcct cccccaggag cttgctacaa gtgccagaaa tctgaccacc  2400
aggccaagga atgcctgcag cccaggattc ctcctaagcc gtgtcccatt tgtgcaggac  2460
cccactggaa atcggactgt tcaactcacc tggcagccac tcccggagcc cctggaactc  2520
tggcccaaga ctctctgact gactccttct cggcttagcg gctgaagact gacgctgccc  2580
ggtcgcctcg gaagcccgt agaccatcag ggacgccgag cttttgggtaa ctctcacagt  2640
ggaaggtaag cccgtcccct tcttaatcaa tacagaggct acccactcca cattaccttc  2700
ttttcaaggg tctgtttccc ttgcctccat aactgttcta ggtattgacg gccaggcttc  2760
taaacctctt aaaactcccc aaatctagtg ccaacttaga caatactctt ttaagcactc  2820
cttttttagtt atccccacct gcccagttcc cttattaggc tgagacactt taactaaatt  2880
atctgcttcc ctgactgttc ctggactaca gctgtatctc attgccgcct ttcttcccaa  2940
tccaaagctt cctttgcgtc ctcctcttgt atcccccac cttaacccac aagtataaga  3000
tacctctact ccctccttgg tgaccgatca tgcaccccctt accgtgtcat aaaaacctaa  3060
tcacccttac cccactaaat gccaatatcc catcccgcag cacgctttaa aaagattaaa  3120
gcctgttatc actggcctgc tacagcatgg ccttttaaag cctataaact ctccttataa  3180
ttcccccatt ttacccatcc taaaactgca caagtcttac agattagttc aggatctgca  3240
tcttatcaac caaactgttt tgcctatcca ccctgtggtg cccaagctgt acactctttt  3300
gtcctcaata ccttcctcca caactcacta ttccgtgctt gatcttaaag atgcttttt  3360
cactattccc ctgcacccct cgtcccagcc tctcttcgct ttcacttaga ctgaccctga  3420
```

| | |
|---|---|
| cacccattag gctctgcaaa ttacctaggc tgtactgccg caaggcttca tagacagccc | 3480 |
| ccattacttc agtcaagccc aaatttcatc ctcatctgtt acctatctcg ccataattct | 3540 |
| cataaaaaca cacgtgctct ccctgctgat catgtccgat taatctccca aacctcaatc | 3600 |
| ccttacaaaa caacaactcc tttccttcct aggcatagtt ag | 3642 |

```
<210> SEQ ID NO 59
<211> LENGTH: 795
<212> TYPE: DNA
<213> ORGANISM: Homo sapiens

<400> SEQUENCE: 59
```

| | |
|---|---|
| gagagacacg actagctgga tttcctaggc cgactaagga atccccaagc ctagctggga | 60 |
| aagtgaccgc ttccaccttt aaacatggga cttgcaactt agctcacacc cgaccaatca | 120 |
| gatagtaagg agagctcact aaaatgctaa ttaggcaaaa acaggaggta agaaatagc | 180 |
| catctgctgc ctgagagcac agcaggaggg acaatgatca ggatataaac ccaggcattc | 240 |
| gagccagcaa tggcaacccc cttttgggtcc cctcccttttg tacgggagct ctgttttcac | 300 |
| tgtgtttcac tctattaaat cttgcaactg cactcttctg gtccatgttt gttacagctc | 360 |
| gagctgagct ttcgcttgcc gtccaccact gcccaccact gtcgtttgct gccatcgcag | 420 |
| acctgctgct gacttccatc cctctggatc cggcaaggtg tgtgctgtgc tcctgatcca | 480 |
| gcaaggtgcc cattgccagt cccgattggg ctaaaggctt gccattgttc ctgcacggct | 540 |
| aagtgcctgg gttcatccta atcgagctga acactagtca ctgggttcta cggttctctt | 600 |
| ccatgaccca cggcttctaa tagagctata acactcacca catggcctaa gattccattc | 660 |
| cttggaatcc gtgaggccaa gaaccccagg tcagagaaca cgaggcttgc caccatcttg | 720 |
| gaagcgaccc accaccatct tggaagtggc tcgccaccat cttgggagct ctgtgagcaa | 780 |
| ggaccctgg taaca | 795 |

```
<210> SEQ ID NO 60
<211> LENGTH: 5648
<212> TYPE: DNA
<213> ORGANISM: Homo sapiens

<400> SEQUENCE: 60
```

| | |
|---|---|
| gtcaggcctc tgagctaagc catcatatct cctgtgacct gcacgtatac atccagatgg | 60 |
| cctgaagtaa ctgaaaaatg acaaagaag tgaaaatggc ccgttcctac cttaacagat | 120 |
| gacattacct tgtgaaattc tcctggctca tcctggctca aaagctcccc cactgagcac | 180 |
| ctggtgacct ccaccctgc cagccagaga caaccccct ttgactgtaa ttttccacta | 240 |
| cctacccaaa tgttataaaa tggcccacc ccatctccct ttgctgactc tcttttcgga | 300 |
| ctcagcccgc ctgcacccag gtgattaaaa agctttattg ctcaccaggt ttggtggtct | 360 |
| tttcacatgg acaggagtga aatttggtgc tgtgacttgg atcggggggac cttccttggg | 420 |
| agatcaatcc cctgtcctcc tgctcttttgc tctgtgagaa agatccacct acgacctctg | 480 |
| gtcctcagac taaccagccc aaggaacatc tcaccaattt taaatccagt aagcagcctc | 540 |
| tccttactct cttctccagc ctctctcact atccctcaac ctctttctcc tttcaatctt | 600 |
| ggtgccacac ttcaatctct cccttctctt aatttcagtt cctttccttt tctggtagag | 660 |
| acaaaggaaa tgtgttttat ccatggaccc aaaactccgg cgccggtcac ggactccaga | 720 |
| agacagtctt ctgttggtgt taatcacgt ggggatgcct gcctgattat tcacccacgt | 780 |
| ttcagaggtg tctgaccacg cagggacgcc tgccttggtc cttcactctt agcggcaagc | 840 |

```
accactttc tgggggcaa gcaccctctg accccttctc tctgtgtctc taccccttcg    900
ccactttcca gggggcaag tacccccac cccttctctc catgtctcta ctcttctctt    960
taaacttgcc tccttcactg tgggcaacct tccaccctcc attcctcctt cttctccctt  1020
agcttgtgtt ctcaagaact taaaacctct tcaactcttg cctgacctaa aatctaagca  1080
tcttattttc ttctgcaaca ctgcttgacc ccagtacaaa ctcaacagtg gttccaaata  1140
gccagaaaat ggaactttcg attttctat cctacaagat ctagataatt cttgtcataa   1200
aatgggcaaa caatctgaga tgcctgacat ccaggcattt tttacacatt tttccctccc  1260
tagtctctgt tcccaatgag acttgtccca aatcctcctt ctttccctcc tgcctgtccc  1320
ctcagtccca accccaagtg tcactgagtc tttctaatct tccttttcta cagacccatc  1380
tgacctctcc cctcctcccc aggctgctcc ttgccaggcc gagctaggtc ccaattcttc  1440
ctcagcctcc actcctccac cctgtaatcc ttttgtcacc tcccctcctc acaccggtc   1500
cagcttacag tttcattctg caaatagccc tcccccacct gcccagcaat ttcctcttaa  1560
aaaggtagct gtagctaaag gcatagtcaa ggttaatgct ccttttgtt tatctgacct   1620
ttcccaaatc agttagcatc taggctcttt ttcacaaaat atgaaaacct agcccagttc  1680
atggcttgtt tgttagcaac cctgagatgc tttacagccc cagaccctta aaggtcaaaa  1740
ggccatctta ttctcaatat acattttatt acccaatctg ctcctgacat aaataaaac   1800
tccaaaaatt aaattccggc cctcaaaccc cacaacagga cttaattaac cttgccttca  1860
aggtgtataa taatagagta gaggcagcca agtagcaatg tgtttctgag ttgcaattcc  1920
ttgcctccac tgtgagacaa atcccagcca catctccagc acgcaagaac ttccaaacgc  1980
ctgaactgct gcaaccagac gttcttccag ggcctcctcc cccaggaact tgcttcaagt  2040
gctgaaaata ctgggccaag gaatgctcac agcctgggat tcctcctaag ccatgtccca  2100
tctgtatggg tccccactgg aaatcagact gtccaacctg gcagccactc ccagaacccc  2160
tggaactctg ccccaaggct gtctgactga ctccttccca gatctactcg gcttagcggc  2220
taaagactga tgctgcccaa tcacctcgga agtctacagg accatcacag acgctttggg  2280
taactcttac attggagggt aagtccatcc ccttcttaat caataggag ctactcaca    2340
tcacattacc ttctttcaa gggcctgttt cctttgcctc cataactgtt gtgggtattg    2400
atggccaggc ttctaaacct cttaaaactc cgcaactctg gtgccaactt aaacaatact  2460
cttttaagca ctccttttta gttgttgcca cctgcccagc tcccttatta agttgagaca  2520
ttttaactaa attgtctgct tccctgacta ttcctgggct acagccacac ctcatggctg  2580
ccttttcctc caattcaaag cctcctttgc atcctcccct tgtatctccc aaccttaaac  2640
cacaagtata ggatgcctct actccccct tggcgacaaa tcatgcaccc cttaccatcc    2700
cattaaaacc taatcaccct tgcctgctca atgccaatat cccatcccac agcacgcttt  2760
aaaaggatta aagcctgtta tcacttgcct gttacagcat ggccttttaa agcctataaa  2820
ctctccttat gactccccca ttttacctgt ccaaaaacca gacaagcctt acaggttagt  2880
tcaggatctg caccttataa tccaaattgt ttttgcctat ccaccccatg gtgccaaagc  2940
catatactct cctatcctca atacctccct ccacaaccca ttattctgtt ctggatctca  3000
aatatgcttt cttttactatt cctttgcacc cttcatccca gcctctcttc aatttcactt  3060
ggactgaccc tgacacccat caggctcagc aaaattcctg ggcagtactg caacaaggct  3120
tcacagacag ccccccattac ttcagttaag cccaaatttc ttcctcatct gttacttatc  3180
```

```
tcagcataat tctcataaaa acacacatgc tctccctgct gatcgtgtcc gactaatctc    3240
ccaaacccca atctcttcta taaaacaaca actccttcc ttcctaggca tggttagtgc    3300
ggtcagaatt cttacacaag agccgggacc acaccctgta gcttttctgt ccaaacaact    3360
tgaccttact cttttagcct agccctcatg tctacatgca gtggctgccg atgctttaat    3420
acttttagag gccctaaaaa tcacaaacta tgctcaactc actctctaca tttctcataa    3480
cttccaaaat ctattttctt tctcccacct gatgcatata ctttctgctc ccagctcct     3540 tcagctatac tcactctttg ttgagtctcc cgcaattacc attgttcctg gcctggactt    3600
caatctggcc ttccacgtta ttcctgatac cacacctggt ccccatgact gtatctctct    3660
aatccacctg acactcactc catttcccta tattctttcc tgttactcac catgaacaca    3720
cttggtttat tgatggcagt tccaccaggc ctaattgcca ctcaccagca aaggcaggct    3780
gtgctatagt atcttccaca tgtatcattg aggctaccac tctgccccat ccactacctc    3840
tcagcaagct gaactcattg ccttaactcg ggccctcact cttgcaatgg gactacatgt    3900
caatatttat actgactcta aatatgcctt ccatatcctg caccaccatg ctgttatatg    3960
ggctgaaaga ggtttcctca ctacgcaagc ttcgtccatt attaatgtct cattaataaa    4020
aatgcttctc aaagccactt tacgtccaaa ggaagctgaa gtcattcact gcaaaagcca    4080
tcaaaaggca tcagatccca tcgctcagga caacgcttat gctgataagg tagctaaaac    4140
ttccgcctat caatctcttc ccacacaagg caaatggttc ttggaccagt gaaaatacct    4200
ccttccagcc tcacaggcca attctattct gttgtcattt cagaacctct tccgtgtagg    4260
ttacaagcca ctagcctgcc tcttagaacc tctcatttcc tttccattgt ggaaatctat    4320
ccacaaggaa atcacttctc agtgttccat ctgctcttct actactcctc agggattgtt    4380
caggccccct cccttctctt tacatcccct cccttctctg cacatcaagc tcagggattt    4440
gccccgaccc aggactggca aattgacttt actcatatgc ctcgagtcag gaaactaaaa    4500
tacctcttga tctgggtaga ccctttcact ggatgaatag aggcctttcc cacagggtct    4560
gggaaggcca ccatggtcat ttcttccctt ctgtcagaca caattcctca gtttggcctt    4620
cccgcctcta tatagtctga taacggactg gtctttacta gtcaaatcac ccaagcagtt    4680
tctcaggctc ttggtattca gtagaacctt cctatccctt acggtcctca atcttcagga    4740
aaggtaaaac ggactaatgg tcttttaaaa acacacgtca ccaagctcag cctccaactt    4800
aaaaaaagga ctctgtcaag aatagagcta aaaaaactca ccaagcaagc aagtaattac    4860
actgaacccc cttggacact ctctaattgg atgtcctgga tcctcccaat tcttagtcct    4920
ttaatacctg ttttctcct tctcttattc tgaccttgtg tattccattt agtttttcaa    4980
ttcatacaaa accgtatcca ggccatcatc agtaattcta tacgataaat gtttcttcta    5040 acaacccgc aatatcaccc cttactacag aatcttcctt cagcttaatc tctcccactc    5100
taagttccca tgccaccca atcccgctcg aagcagccct aagaaacatt gctcattatc    5160
tctccatacc actccccaaa attttgcca ccccaactgt ttaccactat tttgttttat    5220
tttttcttat taatataaga agacaggaat gtcaggcctc tgagcccaag ctaagccatc    5280
atatcccctg tgacctgcac gtatacatcc agatggcctg aagtaactga agaatgacaa    5340
aagaagtgaa aatggcctgt tcctgccgta actgatgaca ttaccttgtg aaattccttc    5400
tcctggctta tcctggctca aaagctcccc tactgagcac cttgtgactc ctaccctgc    5460 cagtcagaga acaaccccct ttgactgtaa tctcccacta cctacccaaa tcttataaaa    5520
cggctccacc ccatctccct ttgctgactc tgttttcaga ctcagcccac ctgcacccag    5580
```

-continued

```
gtgattaaaa agctttattg cccacacaaa gcctgtttgg tgttgtcttc acatggatag    5640
gagtgaaa                                                              5648

<210> SEQ ID NO 61
<211> LENGTH: 5087
<212> TYPE: DNA
<213> ORGANISM: Homo sapiens

<400> SEQUENCE: 61
cttccccctt agcctgtgtt cttaaaaacc taaaacccct tcaactaaca cctgacctaa      60
aacctaaatg tcttattttc ttctgtaata ccacttggcc ccaatacaaa ctcgacaata     120
gttccaagtg gccagagaaa tggcactttc gatttgtctt cttacaaaac ctagataatt     180
tttgtcaaaa attgcgcaaa tggtctgagg tgccttacat ccatgcattt tttacacttc     240
gctccctccc tagtctctgc tcccagtgcg actcatccca gactttcctt cttttctctcc    300 catctgctcc tttcagtctc tgctccaagc tcagagtcct ctgaatcctc cttttccact     360
gaccactctg acctctctcc ttctccctg gccgcacctt gccaggctga atcaggtccc      420
aattcttcgg cagcctctgc tcccccactc tataaccctt ccattacctc cctcctcac      480 acctggtctg gcttacagtt tcgtttagca attagctctc ccctacctgc ccaacaattt     540
cctcttacag aggtggctgg agctgaaggc atagtcaggg tacgtgtccc cttttctcta     600
tcagaccttt cccaaatcag ccagcgttta gggtctttct catcagactc cactaaacat     660
atacaggaat tccaatatct aactcagtcc tacaatctaa cctggagtga cttaaatgga     720
gtcactccat ttaaatggag aggtcgtcct gacctctacc ctctcctcag atgaacaaga     780
aagagtttac tttctagccc agtcctacgc agatacccac cggcttcatg agccaggctt     840
ccaagagggc accagggcag ttccccgaga ggattcccat tggcaatacc agacggactc     900
cccaggtata gctaggcaag attacacagt ctcctgccta gtcaagtggc tcaaaaaggc     960
agcatacaaa gttgttaatt atgacaggct aaaggaaact acccacggta aagatgaaaa    1020
cccagcccag ttcatggccc acttagcagc taccccttaga cactttacag ccctagaccc    1080
agaggggcca gaaggccacc ttatccttaa tatgcatttt atcacccaat ccactcctga    1140
cattaggaaa aaattccaaa agttggattc tggcccttaa accccacaac aggatttaaa    1200
caatctcacc ttcaaggtgt tcaataacag agaagaagcc accaagcagc agcgtatctc    1260
taaattacag ctacttgcct tcactgtgag acaacccaca accatgtctc cagcatacaa    1320
aaccttcaga acatccaagc cacagctccc atgggctcca tcaaaacctc ctcatggacc    1380
ttgcttcaaa tgccaaaagc ctggccactg ggcctcagaa tgcctgcagc ccgggattcc    1440
ttctaagctg tgccctatct gtgcgggacc ccactggaag tcagattgtc caattccaat   1500
cgccgctgct cctaaagctc ctggagctca aacccaatgt tccttggcca actccttccc    1560
agatcttggc ttagcggctg aagactgaca ctgcccgatc gccttggaag acccctggac    1620
catcatggat gccgagcttc gggtaactct tacagtggag ggtaagtcca ttccctgttt    1680
aatcaatacg ggggctaccc actccacatt accttctttt caagggcctg ttttccttgc    1740
ctccataact gttgtgggta ttgacagcca ggcttcaaga cccccttaaaa ctccccaact    1800 ctggtgccaa cttggacaac attcttttat gcactctttt ttagttctcc ccacctgccc    1860 agttcccctta ttaggccgag acattttaac taaattatct gtttccctga ctattcctgg   1920
actacagcca cacctcattg ctgccctttt acccgattca aggcctcctt tgaatcctcc    1980
```

```
tctcgtgtct ccctccctac cttaatccaa aagtatggga tacctctact ccctccttgg    2040
cgaccaatca ggcaccccct accatcccat taaaacctaa tcaccttac cccgctcaac     2100 gccagtaccc catcccacaa caggctttaa gaggactaaa gcctgttatc actcacctgt    2160
tacagcatgg ccttttaaag ctcacaaatt ctccttacaa ttctcctatc ctacctgtcc    2220
agaaaccaga caaatcttac aggttggttc aggatcttcg ctttattaac caaattgtct    2280
tacctatcca gcctgtggtg ccaaacccat acactctcct atcctccata cctccctcca    2340
caactcatta ttctgtcctc gacctcaaag atgctttctt cactattcct ttgcacccct    2400
cattccaacc tcttttcact ttcacatgga ttgaccctga cagccaccaa tctcagcaac    2460
ccacctggac tgtactgcca aggcttcaga gacagccccc attactttag tcaagctctt    2520
tctcatgatc tactttcttt ccatccgttt ctcaccttat tcaatatatg gacgaccttc    2580
tcctctgcag cccctcttac gaatcttccc aacaggacat cctcctgctc cttcaacatc    2640
tgttctcaaa gaagtatcgc gtatcccct ctaaagccca gatttcttcc ccatccgtta     2700
ccgatcttgg catagtcctt catcaaaaca caagtgctct ccctgctgtg tccagctaat    2760
ctccgaaacc caacccctt ctacaaagca caactccttt ccttcctag gcgtggttgc      2820 acactttcgc ctttggatac caggttttgc catcctaact aaaccactat ataaactcac    2880
aaagggaaac ctgactgacc ccacagaccc taagtccttt ccccattctt cttttttgttc   2940 cttaaagaca gccctagaaa cagctcccac attagcactc cctaattcat cccaatcctt    3000
cttcttacat atggctgaaa acaaggctg tgcggtcgga gttctcttac acaggaatca     3060
ggcccatgac ctgtagtctt cctatccaaa taacttaacc tcacagttct aggctggccc    3120
tcatgtctac gtgcagtggc agccaccact tcaatacttc tagaggccct caagatcaca    3180
aaccattccc cacttactct ctacaactct cataactttc aaaatctatt tttctcctca    3240
cacttgaagc atatactttc tgcccgactc cttcaaccgt actcactatt cattgaaact    3300
cctacaatta ccattattcc tggcacagac ttcaaccccgg cctctcacct tatacctagc   3360
accaaacctg aacctcgtga ctgtatctct ctaatccata tggcattctc cccatttccc    3420
catatttccc tcttttcctgt tcctaatcca gactgcgctt ggtttactga tggtagttct   3480
tcaaggccca atcgttagtc atcggcaagg gcaggctatg ctgtagtgtc ttccacatct    3540
gtcactgaag cttcctgccc tgcccgcttc cactacctct caacgtgcca aacttattgc    3600
tttaacccgg gctctcaccc ttgcaaaggg actacatgtc aatatctaca ctaattccaa    3660
gtatgctttc cacatcctac atcaccatgc tgttatatgg gcagaaagag gtttttctcac   3720 cacacaaggg tcctccatca tcaacgcttc cttaataaga atcctcctta aggctgctct    3780
actgcccaag gaagccggag tcattcaccg caagggggcat caaaggtcac cagatcccac   3840
tgcttgaggc aacgcttatg ctgacaatgc agcaaaagta gcagctagta ttctcacatc    3900
tgtccctcac gaccagtttt tttccttctc atttatcact cccacctatt ctcccactga    3960
aactattact tatcaatccc ttcctactca aggcaaatgg ttcttggatc aaggaaaatt    4020
cctccttcct gcctcacagg ctcattctat cttatcattc tttcatgacc ttttctcatgt   4080 gggttacaag ccaatggccc atctcttaga acctctcatt tcttttccat catggaaatc    4140
catcctcaag gaaattattt tcagggttc catctgctac tctaccaccc ctcagggata    4200
tctcaggccc cctccctttc cgacacatca agctcgagga tctgcccca cacaagactg     4260 gcagattgac tttacccata tgccccgact caaaaaacta agataccttt tggtctgggt    4320
agatacattc actggatggg tagaggccca cagggtctga gaaggccacc gcagtcattt    4380
```

-continued

| | |
|---|---|
| cttcctgtca gacataattc ctcagtttga ccttcccacc tctatacagt ccgataacgg | 4440 |
| accggccttc attagtcagg tccctcaagc agtctcccag gccttcggca tccagtggaa | 4500 |
| ccttcattcc ccctaccatc ctaaatcttc aggaatggta gaaagaacta atggtctttt | 4560 |
| aaaaacacct caccaaactc agcctccaaa ttaaaaaaga ctggactgta cttttaccat | 4620 |
| ttgccctcct tagaattaga gcctgtcctc aagaagctac agggtatagt ccatttgaac | 4680 |
| ttttatatgg atgtaccttc ttgttgggcc tcaatctcgt gccagacacc agccctctag | 4740 |
| gcgactatct tccagtcctc cagcaggcta gacaggaaat tcgccaggct gctaatcttc | 4800 |
| tcttgtctac tccagattcc cagccatatg aagacaccct agctggatga tcagttcttg | 4860 |
| ttaagaatct gatccctcaa actctataat cttgatggac cagaccctac ttagtcatct | 4920 |
| acagtaccct aactgccgtc cgcctgcagg accctcccca ttgggttcac cattctggaa | 4980 |
| taaagctgtg tccattggac agccagcctg atccctcctc ttcctcttgg aagtcacaag | 5040 |
| tactctcccc tacttccctt aaactcactc gcatttctga agaacag | 5087 |

<210> SEQ ID NO 62
<211> LENGTH: 5599
<212> TYPE: DNA
<213> ORGANISM: Homo sapiens

<400> SEQUENCE: 62

| | |
|---|---|
| tgactccttt ttcagactca gcccgcctgc accaggtgaa ataaacagcc ttgtggctca | 60 |
| cacaaagcct gtttagtggt ctcttcacac agacacgtga gacacttggt gccaaagacc | 120 |
| cgggtcagtg ggactccttc gggagaccag tcccctgtcc tcaccctcac tccatgaaga | 180 |
| gatccaccta caacctcggg tcctcagacc aaccagccca aggaacatct cactgatttt | 240 |
| aaattgggta agtggcctct ttttactctc ttctccaacc tctctcacta tccctcaacc | 300 |
| tcttctctcct ttcaatcttg gagccatcct tcaatctctc ccttctctta atttcaattc | 360 |
| cttttcatttt ctggtagaga caaggagac accttttatc cgtggaccca aaactccggc | 420 |
| gtctgtcacg gactcgggaa gacagccttt ccttggtgtt taatcactgc ggggatgcct | 480 |
| ctctgattat tcgcccacgt tccattggtg tctgatctcc gcaggacgc ctgccttggt | 540 |
| cattcaccca cattcccttg gtggcaagtc aattgcaggg acacctgctt tggctgctca | 600 |
| cccacgctgc agcctggggc tgctgcccgc cccctttctc cgtgtctcta cccttctctt | 660 |
| taaacttgcc tccttcacca tgggcaacct tccaccccttc attcctcctt ttcccttagc | 720 |
| ctatgttctc aagaacttaa aacctcttca actcttgcct gacctaaaat ctaagcgtct | 780 |
| tatttcttc tgcaacactg cttggcccca atacaaacac gacaatggtt ctaaatggcc | 840 |
| agaaaatggc acttttgatt tctccatcct acaagaccta gataattttt gtcaaaaaat | 900 |
| gggcaaatgg tctgaggtgc ctgacatcca ggcattcttt tacacgtcgg tccctcccta | 960 |
| gtctctgctc ccaatgcgac tcatcccaaa tctttcttct ttctctcctg tctgttcctt | 1020 |
| cagtctccac cccaagctct gagtcctttg aatccttctt ttctatggac tcatgtgacc | 1080 |
| tctccccttc tccccaggct gctcctcgcc aggccaagcc aggtcccaat tcttcctcag | 1140 |
| cctctgctcc ccgaccctat aatccttcta tcacctcccc cctcacacc ggtctggctt | 1200 |
| acagtttcat tccgtgacta gccctcccca acctgcccag caatttcctc tttaaagggt | 1260 |
| ggctggagct aaaggcatag tcaaggttag tgctctttt tctttatccc aaatcagata | 1320 |
| gcgtttaggc tctttttcat caaatataaa aacccagccc agttcatggc ccgtttggca | 1380 |

-continued

```
gcaaccctga gatgctttat agccctagac cctgtaaggt cagaaggccg tcttattctc    1440
aatatgcatt ttatttatt acccaatctg ctcccgatat taaataaagc tccaaaaatt    1500
atgaaacccc acaacaggac ttaattaacc tcgccttcaa ggtgtacaat aatagagtag   1560
aggcagccaa gtagcaatgt atttctaagt tgtaattcct tgcctccact gtgagacaaa   1620
ccccagccac atctccagca cacaagaact ccaaacacct gaaccgcagc tgccaggggt   1680
tcctccagaa cctccccca ccccaggagc ttgctacaag tgccgaaat ctggccactg     1740
ggccaaggaa tgcccgcagc ccgggattcc tcccaagcca tgtcccatct gtgcgggacc   1800
ccactgaaaa tcggactgtc caactcgccc ggcagccact cccagagccc ctggaactct   1860
ggcccaaggc cccttcccag atcttctcgg cttagcggct gaagactgac actgcccgat   1920
cgcctcggaa gcctcctgga ccatcacaga tgctttaggt aattcttaca gtggagggta   1980
agtccatccc cttcttaatc aatacggagg ctacctactc cacattacct tcttttgaag   2040
ggcctgtttc ccttgcctcc ataactgttg tgggtattga cggccaggct tctaaatctc   2100
ttaaaactcc ccaactctgg tgccaacttg acaacattc ttttatgcac tccttttag     2160
ttatccccac ctgcccagct cccttattag gtcaagacat tttaactaaa ttatctgctt   2220
ccctgactat tcctgggcta cagccacacc tcattgccgc ccttttctcc agttcaaagc   2280
ctccttcaca tcctctcctt gtatctcccc accttaaacc acaagtatag gacacctcta   2340
ctccctcctt ggtgaccgat catgcacccc ttaccatccc attaaaacct aatcacccctt  2400
accctgctca atgccaatat cccatcccac agcatgcttt aaaaggatta aagcctgtta   2460
tcactcgcct gttacagcat ggccttttaa agcctataaa ctcttcttac agttccccca   2520
ttttacctgt ccaaaaaccg gacacgactt gcaggttagt tcaggatctg tgccttatca   2580
accaaattgt cttgcctatg cacccccatga tgccaaagcc atatactctc ctatcctcaa  2640
tacctccctc cacaacctct ccacaaccca gtattctatt ctggatttca aacatgtctt   2700
ctttactatt ccttgcaccc ttcatcccag cctctctttg ctttcacttg gactgaccct   2760
gacacccatc aggctcagca aattacctgg gctgtactcc acaaggcttc acagacagcc   2820
cccattactt tagtcaaacc caaatttctt catcatccat tacctatctc gacataattc   2880
tgcatgaaaa cacacgtgct ctccctgctg atcacgtccg gttaatctcc caaacccaa    2940
ccccttctac aaaacaacaa ctcctttcct tcctgggcat ggttaggtac ttctgccttt   3000
ggatatctag ttttgccatc ctgactaaac cattatataa actcacaaaa gcaaacctag   3060
ttgaccccac agatcctaaa tccttttccct actcccctttt ccattcctta aaaacagcc   3120
ctaaaagctg ctcccacact ggctctccct aactcatcac tcccttttca ttacatacag   3180
ccgaagtgca gggctgtgtg gtcggagttc tcacacaaga gccgggactg cgccctgtag   3240
cctttctgtc caaacaactt gaccttactg ttttagccta gccctcacgt ctgcgtgcag   3300
tggctgccgc tgccttaata cttttagagg ccctcaaaat cacaaactat gctcaactca   3360
ctctctacag ttctcataac ttccaaaatc tattttcttc ctcacacctg acacatatac   3420
tttctgctcc ccggcttctt cagctgtact cactctttgt tgagtctccc acagttatcg   3480
tcgttcctgg cccggacttc attccagcct cacacattat tctggatacc acacctgacc   3540
cccatgactg tatctctctg atccacctga catccactcc atttccccat gtttccttca   3600
ttcctgttta tcaccctgat cacacttggt ttattgatgg cagttctacc aggcctaatc   3660
accactcacc agcaaaggca agctatgcta tagtatcatt caggctaccg ctctgccccc   3720
ctccactacc tctcagcaag ccaaactgac tgccttaact tgagctctca ctcttgcaaa   3780
```

-continued

```
gcgactatgc gtcaatattt atactgactc taaatatgcc tttcacatcc tgcaccacca    3840
tgctgttata tgggcagaaa gaaatttcct cactaggcaa gggtcctcca tcattaatgc    3900
ctccttaata aaaactcttc tcaaggcccc tttacttcca agaaagatg gagtcattca     3960 ctgcaaaggc catcaaaagg catcagatcc cattgctcag acaatgctt atgctgataa     4020 gatagctaaa aaagcagcta gcgttccaac ttgtatccct cacggcagtt tttctccttc    4080
tcatcgggcc actcccacct actccctcgc tgaaacttcc acctatctct cccgcacaa     4140 ggcaaatggt tcctggacca agaaaatat ctccttccaa cctcacaggc ccattctatt     4200
ctgttgtcat ttcataacct cttccatgta ggttacaagc cgctagcctg cctcttagaa    4260
cctctcattt cctttcatt gtgggaatct atcctcaagg aaatcacttc tcagtgttcc     4320
atctgctatt ctactactcc tcaagaattt ctcaggcccc ctcccttccc tacacatcaa    4380
gttcggggat ttgcccaccc aggactggca aattgacctt actcagatgc ctcgtgtcag    4440
gaaactaaaa taactcttgg cctgggtaga cactttcact ggatgggtag aggcctttcc    4500
cacagggtct aagaagccac tgcagtcatt tcttcccttc tgtcagacat aattcctcgg    4560
tttgggcttc ccacctttat acagtccaat aatggaccag cctttactag tcaaatcacc    4620
caagcagttt ctcaggctct tggtattcag tggtgcctgg ttttacctca aactgccacc    4680
cttaagtctc taagtggata gaagatcttc agtgacaaag taccctccaa cagtttcacc    4740
ctgatgaagt cctgttcttt acttttatgc ttactcttat tctcattccc attcttatgc    4800
caccctctac ctctctccag ctatctccac cacactatca atctcagtca ctctctccta    4860
gccatttcta atccttttg ctggctttgt atttctcttt cctccaaaat caccaaggta     4920
ttgacttact cactgctaaa aaaaaagggg gactctatgt ttttaaatga agagtgctgt    4980
ttttacctaa atcaatctgg cctggtatat gacgacatta aaaaaaactc aaagatagag    5040
cctaaaagct tgccaaccaa gtaagtaatt acgctaaccc cgcttggacc cccttggaca    5100
ctctaattgg atgtcctggg tcctcccgat tcttagtcct ttaatacctg tttttctcct    5160
tctcttattc ggacctcgta tcttccgttt agtttctcaa ttcatccaaa actgtatcca    5220
ggccatcagc aatcattcta tatgacaaat gtttcttcta acaacccac aatatcaccc     5280 cttaccacaa aatcttcctt cagcttaatc tctcccactc taggttccca cgccgccct    5340 aatcccgctc gaagcagcac tgagaaacat cgcccattat ctctccatac aaccccaaa    5400 aatttttcgcc acccccaacac tttaccacta ttttgtttta ttttctttat taatataaga   5460
agacaggaat gtcaggcctc tgagcctaag ccaagccatc atatcccag tgacctgcag     5520 tatacatcta gatggcctga agtaactgaa gatccacaaa aaggagtgaa aatagcctta    5580
actgatgaca ttccaccat                                                 5599
```

<210> SEQ ID NO 63
<211> LENGTH: 5945
<212> TYPE: DNA
<213> ORGANISM: Homo sapiens

<400> SEQUENCE: 63

```
gtcaggcctc tgagcccaag cctgcacata tacatccaga tggcctgaag caactgaaga     60
atcacaaaag aagtgaaaat gctgaagcaa ctgaagaatc acaaaagaag tgaaaatggc    120
cggttcctgc cttaactgat aagacagtca cctgtcctcc tgctctttgc tctgtgagaa    180
agatccacct acaacctcgg gtcctcagac caaccagctc caggaacatc tcaccaattt    240
```

```
taaattgggt aagcagcttc tttttactct cttctccaac ctctctcact atctctcaac    300
ctctttctcc tttcaatttt ggcaccaccc ttcaatctat cccttccctt aatttcagtt    360
cctttccttt tctgatagag acagaggaga tgtgttttat ccgtgaaccc aaaactccgg    420
cactggtcac ggactcgaga agacagtctt cccttggtgt ttaatcactg cagggatgcc    480
tgcctgatta ttcacccaca tttcagaggt gtctgatcac cacagggaca cctgccttga    540
tccttcacct tggtgtcaag taccgacccc ccctgtgtct ctgccctctc ttttctctgg    600
gcttgcctcc ttcactatgg gcaaccttcc accctccatt cctccttctt ctcccttagc    660
ctgtgttctc aagaacttaa aacctcttca actctcgcct gacctaaaac ctaaacacct    720
tattttcttc tgcaatacca cctgacccca atacaaactt gacagtggtt ccaaatagcc    780
agaaaatggc actttcaatt tctccaccct acaagatcta gataattctt gtcgtaaaat    840
gggcaaatgg tctgaggttc ctgacatcca ggcattcttc tacacatcag tcccgcccta    900
gtctctgctc ccaatgcgac tcatcccaaa tctttcttct ttctctcctg tgtgttcctt    960
cggtctccac cccaagctct gagtactttg aatcctcctt ttctgtggag ccatctgacc   1020
tctcccctgc tcgccgggct gagccaggtc ccaattcttc cgcagcctct gttccccac    1080 tctataatcc ttctatcact tcccctcctc acacctagtc cggcttatgg ttttgttcct   1140
tgactagccc taccccacct gcccaacaat ttcctcttaa agaggtggct ggagctaaag   1200
gcatagtcaa ggttgttgct cctgtttct ttatccgacc tctcccaaaa cagttaggct    1260 cttttcatc aaatataaaa ccccagccca gttcatggcc cgtttggcaa caacccttaa    1320
acgccttacc gccctagacc cagagaggcc agaaggccgt cttattctca gtatgcattt    1380
tattacccaa cccactcctg acgttagaaa aagctccaaa aattggattc cagccctcaa   1440
accccacaac aggacttaac cttgccttca aggtgtacaa aatagagaa gagtggcaat    1500 tacttgcctc tgctgtgaga gaaacttcag ccacatctcc agcatacaag aatttcaaaa   1560
cgcctaaacc gcagtggcca ggcgttcttc caagacctcc taccccagga tcttgcttca   1620
agtactgaaa atgtggccac tgggccaagg aatgtctgca gcccggattc ctcctaagca   1680
atgtcccatc tgtgcaggac cccactggaa attggactgt ccaactcacc tggcagccat   1740
tcctagagtt cctggaactc tggcgcaagg ctcactgact gactccttcc cagatcttct   1800
cggcttagtg gctgaagact gacactgccc gatcgcttg gaagcctcct ggaccatgat    1860
agatgcttta ggtaactctt acagtggagg atgagtccat cccttctta atacggaggc    1920 tatccactgc acattacctt cttttcaagg gcctctttcc cttgcctcca taacagttgt   1980
gggtattgac ggccaggctt ctaaacctct taaaactccc caattctggt gccaactggg   2040
acagtattct tttatgcgct ccttttagt tattccgcc tgcccagttc ccttattagg     2100
tcgaggcatt ttaactaaat tatctgcttc cctgactatt cctaggctac agccacacct   2160
cattgtcacc cttttccca gttcaaagcc tccttcacat attttccttg tatctcctca    2220
ccttaatcca caagtatgag acatctctac tccctccttg gcaactgatc atgcacccct   2280
taccatccca ttaaaaccta atcacccta ccctgctcaa caccaatatc ccatcccaca    2340
gcacgcttta aaagaattaa agcctgttat cactcacttg ttacagcatg gcctataaa    2400 gcctataaac tctccttaca attccccat tttaccctc ataacccat tctgttctgg     2460 atctcaaaca tgctttcttt actattcctt tgcacctttc atcccagcct ctcttcgctt   2520
tcacttagac tgaccctgac acccatcagc ctcagcaact tacctgggct gtactggcgc   2580
aaggcttcag ggacagcccc cattacttca gtcaagccca aatttcttcc tcatccgtta   2640
```

```
cctatctcgg cataattctt cataaaaata catgtgctct ccctgctaat catgtccagc    2700
taatctccca aaccccaacc ccttctacaa aacaactcct ttccttccta ggcatggtta    2760
ggtacttttg cctttagata cctggttttg ccatcctaac gaaaccattc attctcccca    2820 tttcccccata ttacctcttt cctgttcccc acccagacca cgcttggttt attgatgata   2880
gttcttccag gcccaatcgc caatcactgg caaaggcagg ctatgctata gtgtcttcca    2940
catctatcac tgaggctacc actctgcccc cctccactac ctctcagcaa gccaaactca    3000
ttgtcttaac ctgggccctc actcttgcaa agggactgca tgtcaatatt tatactgact    3060
ctaaatatgc cttccatatc ccgtaccacc atgctgttat atgggctgaa agaggtttcc    3120
tcactacaca agggtcctcc atcattaatg cctctttaat aaaaactctt ctcaaggcca    3180
ctttacttcc aaaggaagct ggagtcattc actgcaaggg ccatcaaaag gcatcagatc    3240
gcgtcgctca gggcaatgct tatgctgata aggtagctaa agaagcagct agcattccta    3300
cttctgtccc tcacggccag ttttttctcct tctcatcagt cactcctact tactctccca    3360
ctgaagtttc tacctatcaa tccctcccca ctcaaggtaa atggttctta gaccaaggaa    3420
aatatctcct tccagcctca caggcccatt ctattctgtc gtcacttcat aacctcttcc    3480
atgtatgtta taagctgcta acccgcctct tagaacctct catttccttt ccatcgtgga    3540
aatctattct caaggaaatc gcttctctgt gttctatctg ctattctact cctcagggat    3600
tgttgaggcc ccctcccttc cctacacatc aagctcggag atttgcccct gcccaggact    3660
ggcaaattga ctttactcgt atgccccgag tcaggaaact aacatacctc ttggtctggg    3720
aagacacttt caccagatag gtagaggcct ttcccacagg gtctgagaag gccaccgtgg    3780
tcatttcttc ccttctgtca gacataattc cttggtttgg acttcccact tctgtgcagt    3840
ccaatagcgg acgggccttt attagtcaaa tcacccaagc agtttctcag gctcttggta    3900
ttcagtggaa acttcatacc ccttatcgtc ctcaatcttc aggaaaggta gaacggacta    3960
atggtctttt aaagacacac ctcactaagc tcagcctcca atttaaaaag gaccggatag    4020
tacttttacc acttttccctt ctcagaatta gagcctgtcc tcgagatgct acagagtaca    4080
gcccatttga acttttatat ggatgccctt tcttgctcgg ccccaacctc gtcccagaca    4140
ccagccctct aggtgactat cttccagtcc tccagcaggc tagacaggaa atttgccagg    4200
ctgctaatct tctcttgcct attccagatt cccagcctta tgaagacacc ctatctggac    4260
gatcagttct tgttaagaat ctgacccctc aaactctaca acctcgacgg accggaccct    4320
acttagtcat ctataatacc ctaactgccg tcctcctgca ggaccctccc cattgggttc    4380
accgttccag aataaagccg tgtccattgg acagccagcc tgatctctcc tcttccttct    4440
ggaagtcgcg agtactcacc cctacttccc ttaaactcac ccacatttct gaagaacagt    4500
agtaaccctt atgagcctaa tacatccctt cattttgtta ggtctatcct tccttaccag    4560
agtctttgca acagggcctt atgcagtcac ccccactact tagactgcat cccaaaaact    4620
tttcatccct gctctcttct gtctagtcat actcctattc ttcgttttca cctctccata    4680
catgccctgc ccttgtctac actgccagct tatacttttc ctccaaacca tcatagctgg    4740
tcctggtctt atccctaac tgccactctt aactccctct tggaatggat aaatggcctt    4800
tgctggaaaa gcacactcca cttcttcac ccattttaca tttccagttt cgccttacgc    4860
aaggtctctt cttcctctgt ggctcctcca cctgcatgtg tccacctgtt aatgagacag    4920
gaacatgtac actagttttc cttaccccaa aaatcaattt gcaaataaga ccgagcagct    4980
```

```
tcctgttccc ctcatgacac caacacttca ctattatttt attttttctt attattaata    5040
taagaagaca ggaataggcc ttgacttact cactgctgaa aaaggaagac tctgtatatt    5100
tttaaatgaa gactgttgtt tttacctaaa tcagtctggc ctggtatatg caacataaa     5160 aaaattcaag gatagaggcc aaaaactcac cagccaagca ataatcatg ctgaaccccc     5220 ttaggcactc tctaatttga agtcctgggt cctcccaatt cttagtcctt taatacttgt    5280
ttttctcctt ttcttattcg gaccttatgt cttctgttta gtttctcagt tcatacaaaa    5340
ccatatccag gccatcacca atcatcctat atgacaaatg ctccttctaa caaccccaga    5400 atatcaccccc ttaccacaaa atcttccttc ctcttaatct ctcccactct aggttcccat   5460
gccaccccta atcctgctcg aagcagccct gagaaacatc acccattatc tctccatacc    5520 acccccccaaa attttcccca ccccaacact tcaccactgt ttgttttttct tattaatata  5580 agaagacaag aatgtcagga ctctgagccc aagcctgcac atatacatcc agatggcacg    5640
aagctactga agaatcacaa agaagtgaa atggtcggt tcctgcctta actgatgaca      5700
ttaccttgtg aaattccttc tggctcagaa gctcccccac tgagcaccttt gtgacccccg   5760 cccctgccct caagagaaca accccctttg actgtaattt tccactacct acccaaatcc    5820
tataaaactg ccccagccct aacttccttt gctgactctc ttttttggact tagcccacct   5880 gcaattaaaa agctttattg ctcacacaaa gcctgttggt ggtcccttca cacggacaca    5940
cgtga                                                                5945

<210> SEQ ID NO 64
<211> LENGTH: 227
<212> TYPE: DNA
<213> ORGANISM: Homo sapiens

<400> SEQUENCE: 64
tagtggtgta cgcagccccc agtcacgtac cccttgcttg ctcaatcaat cacgatcctc       60
tcatgcagac cccccttagag ttgtgagccc ttaaaaggga caggaattgc tcgctcgggt    120
tgctcggctc ttgagacagg agtcttgccg atgctcctgg ccgaataaac cccttccttc     180
tttaacctgg tgtctgaggg gttttgtctg cggttcttcc tgctaca                   227

<210> SEQ ID NO 65
<211> LENGTH: 1236
<212> TYPE: DNA
<213> ORGANISM: Homo sapiens

<400> SEQUENCE: 65
ggggaaaaga aagagagatc agactgttac tgtgtcgatg tagaaagaag cagacataag       60
agactccatt tgttcagta ctaagaaaaa ttattctgcc ttgagatgct gttaatctgt      120
aaccctactc ccaaccctgt gctccagaaa catgtgctgt gtcaactcaa ggttaaatgg     180
attttgggct atgcaggacg tgcttttgtta aacaagtgct tcaaggcagc atgcttgtta   240
aaagtcatca ctactcccta ctctcaagga cccagggaca caaaacactg cctaggaaag    300
ccaggtattg cccaaggttt ctccccatgt gatagcctga gatatggcct catgggaagg    360
gaaagacctg acagcccgac gccagtaaag gggctgtgct gaggattagt aaaagaggaa    420
ggcctctttg cagttgagat aagaggaggg catctgtctc ccgctcatcc ctgggcaatg    480
gaatgtctgg gtgttaaaac ccaattgtat attccatata ctgagatagg agaaaaccgc    540
cttagggctg gaggtgagac atgctggagg caatactgct ctttaaggca ttgagatgtt    600
tatgtatatg cacatcaaaa gcacagcact tttttctttta ccttgtttat gatgcagaga   660
```

```
catttgttca catgtttttcc tgctgaacct ctccccacta ttaccctatt gacctgccac    720
atggtagaga taatgatcag taaatactga aggaactcgg agactggtgg cggcaggggg    780
aaggcagggt tcctccgtat gctgagcgcc agtcccctgg gcccactttt cttttttttt    840
tttatttttt attctttatt gagacggagt ctcgctctgt tgctcaggct ggagtgcggt    900
ggcacaatcg cggctcactg caagctccgc ctgccgggtt cacgccattc tcctgcctca    960
gcctctccga gtagctggga ctacaggcgc ccgccaccac gcctggctaa ttttttttgta   1020 ttttttagtag agacagggtt tcaccgtggt ctcaatctcc tgacctcgtg atccgcctgc   1080
ctcggcctcc caaagttctg ggattacaag catgagccac cgcacccagc ccacttttct   1140
ttctctatat tttggatctg tgtctctttc ttttctcaag tctctcattc cacctgacga   1200
gaaacaccca caggtgtgga gaggcaggcc acccttt                             1236
```

<210> SEQ ID NO 66
<211> LENGTH: 7621
<212> TYPE: DNA
<213> ORGANISM: Homo sapiens

<400> SEQUENCE: 66

```
tggatgagat gcaaagtaag cccactccat tatggactgt gttaaagaat ttccaaaaac     60
attttaatgg agattatggg gttactatga ccccaggaag acttaggacc ttgtgtgaga    120
tagattggcc acattagaag tgggttggcc atcagaagga agcctacaca gtccctagtc    180
tcaaagttat ggcagaaggt aactggtaag ccaggactcc caggccagtt tccgtagaca    240
cttggctaca gctggtttta gactcgccac agtggttaag aggacaggca gcagcagtac    300
tagtggcaaa aggacagaga gccaaggaag aatcccgctc cacccgccga gagaagtcgg    360
ctcctaaagt cctgtccgac ccaacattag aggattcatg gcaacaaaca gcaccagtgc    420
ccacccgccc cttcaccaag aaggaaggcc tcccacccga gcttcacaa ggcctacata    480 cccctagacc acccagagta gaaaagaaag gatgcaagac cttggaagaa acctcgccct    540
tggcagcccg tttgaggcct agaactggga tacaaaagcc cctgaaagag caacagtata    600
ctggggtaga cgaggatggc catatggtgg aaatgtgtgc ctttgtgtac caacccttca    660
cctctgccag tctcctcaat tggaaaaaca atacgtcatc ctatactgaa aagcctcaag    720
ctataattga tttgctccaa actattaccc agacccacaa ccctacttgg ttgattgcc    780 accagttgct catgtaccta tttaactcag atgaaaggtg aagggtgctc caggcagcaa    840
ctaagtggct agaggaacat gttctggctg attacccaaa cccccaagag tatgtgagga    900
tccaattacc aggaacagac ccccagtggg acccaaatga agacagggt atgcaaaggc    960 taaaccggta cagggaagcc cttctggaag gcttaaaaaa gagacctcaa aggccacaaa   1020
tgttaacaaa gtcattcaag gaaagatag agtctggcac aattctatga gagactatgt   1080
gaggcctatc gtacatatac tccctctgat cccgatagcc ctgaaaatca gcgcatgatt   1140
aacatgactt tggttagtca aagtgcagaa cacattagaa gaaaactaca gaaacaggct   1200
gggtttgcag gtatgaatac ttcacagtta ttggagatag ccaaccaggt gtttgtgaat   1260
agagatgcgg taagccacag agagaaccac agagagagca aatgccaagc ccagtgaaac   1320
gccgacctgc tagctgcagc tattagaggg gttcccccga aggagcaaga aaggggggc   1380 ctggggaaaa atacccagtc tggccatcca tgcttgcagc gtaaccagtg tgcttactgt   1440
aaggaaatag gacattggaa ggacaagtgc ccacagttga aagggaaaca aggtggctct   1500
```

```
gagcaggagg cctcagacaa ggacgaaggg gccttgttca atctggcaga agggttactg    1560
gactgagggg gaccgagctc atgtgacccc aaagagccca tggtcaggat gacagtcggg    1620
ggcaaggaca ttgagtttct tgtcaatact gttgctgaac attcagtatt aaccatcccg    1680
gtcacccact tatccaaaaa aactattgat ataatcggag ccccaggggt ttcggcaaag    1740
caaactttct gtttgcccca gacctgcact gtgtgggca tgaagcgatt caccagttcc     1800
tgtacatggc tgactgcccc ttgcctttac tgggcaaggg acctacttag caagcggaga    1860
gccactatct cttttacaaa gcatggctct ttacagctaa agttacctgg aatgggagtc    1920
attgtgtttc ttacggttcc ttgggaggag aatggagac tcttcttaac tgagccaggc     1980
caagagatag gaccagctct ggctaagcgg tggccaaggg tgtgggtgga agacaaccct    2040
ccaggtttgg caatcaacca gcccctgta cttagaagct aagcctgggg cccagccatt     2100
caggcaaaag cagtaccagg tccccagaga accattgag ggcatccagg tccatctcaa     2160
gcacctgagg gcctttggaa ttatagtccc atgtcagtcc cctcctacct gttcccaagc    2220
cagggaccag ggactacagg ccagtacagg atttgtgctt ggtcaaccaa gctacagtga    2280 cttgcaccc aacggtacct aaccatcata cattgttggg gttgctgcca gctgaggaca      2340
gctggttcac ctgctttgac ctaaaagact cttttctttag tatcaaacta gcccctgaga    2400
gccaaaaact gtttgccttt cagtgggagg atctggggtc aggtgtcacc actcagtaca    2460 cttgaccca gctcccccaa gggttcaaga actcccccac catctttggg gaggtgctgg     2520
cttgagacct ccagaagttt cccaccagag acctaggctg cgtgctgctc cattaggtca    2580
acgacctctg ctgggacacc ccacggcagt cgggtgtgcc aagggaatga ataccctgct    2640
ccagcaccta gaagactgtg ggtataaggt gtccaagaag aaagctcaga ttgcagacag    2700
caggtacgtt atctgggatt tactatccga caggagagc gcagcctggg atcagaaaga     2760
aagcaagtca tctgcaacct gtcagagcct aagaccagaa ggcaggtaag agaattctta    2820
ggagctccag ggttctgcaa gttgcagatc tcaaagtttg cagtattggc taagcccctg    2880
tacagagaca caaagcgggg agacaaggaa ccttttgaat gggagtccca acagcaatga    2940
gcttttcatg agttaaaaga gaagctcttg ttggcctcag ccctgggget acctgaccta    3000 acaaaacctt ttacactgta tgtgtcagaa agagaaaaaa tggcagttgg agttttaacc    3060
cagatgatgg ggctctggcc aagaccgata gcctacctct ccaaacagct agatggagtt    3120
tctaaggttg ccccccatgc ttaagagcct tggcagcaac tgccctgtta gtacaagagg    3180
cagataagct aactgttggg caaaacctaa acataaaggc cccccatgct gtggtaacac    3240
taatgaacat caaaggacat cattggttaa cgaatgctag actaactagg aaccaaagct    3300
tgctctgtga caattcccgc ataaccattg aagtttgcaa caccctgaac cctgtcacct    3360
tgctcctgat atcagagagc ccagttgaac ataactgtgt agaggtattg gactcagttt    3420
attctagcag gcccaacctc cgagaccatc cttggacatc actagactgg gagctataca    3480
tggaagggag cagcttcgtc aacccaagga gagaggtgtg ctggatatgc agaggtaacc    3540
ctggacggtg tcattgaagc caaattgttg ccccagggta ctttagccca gaaggcagaa    3600
ctcattgctt taattcaggc cttagagcta agtgaaggta agactaaaca tttacactga    3660
ctctaggtgt gccttttaa ctcttcaagt gcatgggca ttatacaagg aaaaaggcct      3720
attgaactct gggggacaag atgtaaagta tcagcaagag atcctgcaac tattagaggc    3780
agtgtggaag ccccaaaagg tggcagtcat gcactgcagt agacaccagt gagattctac    3840
cttgattgcc ttggggaact cccaagctga ctcagaggct caaaaagcaa catccacacc    3900
```

```
ctaccgggca tcagtcacag catcccctgc tccctcagga acctgacctt gtacatactt    3960
attctaaaga agagaagtac tttctccagg cagagggagg gcagatgata gaagagggat    4020
ggatccagta attggacaga agaatagctg tgccacaact gctaggagcc accgtcgtac    4080
tggctgtgca tgagaccacc ctcctaggcc aagagtcact tgaaaagttg ttaggccagt    4140
atttctaaat ctcgcatctg tcagcccttg ccaaaacagt ggcgcagcca tatgttacct    4200
gctggcagca cgatgctagg caaggtccaa ccattctgcc catcatacaa gcttatggag    4260
cagccccctt ggaagatctc cgagtagact tcaccaagat gcccaaatgt ggaggtaaaa    4320
agtatttgct agttctagtg tgtacgtact ctgggtgggt ggaggcctat ccaacatgaa    4380
ctgagaaaac tcgtgaagta acccatgtgc ttctccaaga tctcatgcct aggtttggac    4440
tgcacttacg aatcagcttg acaatgggc cggcgtttgt ggctgacttg gtacagaaga    4500
cagctaaggt attggggatc acatggaaac tacataccgc ctaccaacca caaagttccg    4560
gaaagggagc agatgaatca gactaccaaa acataattta gtgaaagtgt gtcaagaaac    4620
agggttaagg tgggtacaag ctctccctgt ggtattgttt aagattagat gtaccccttc    4680
taaaagaaca ggctattctc cttatgaaat attatatcat aggcccccctc ccatactatg    4740
gggactccca ggtactcctc gagacctagg tgaaattgag ttacagagac agctacaggc    4800
ttcagggaaa attacacaaa caatttcagc ctgagtaaat gagagatgcc ccatcagctt    4860
attctcccca gttcacccct tctcccagg gtgtggatca aggattagaa cgtaaccccc    4920
ttgtggccat ggtggaaagg accccagact gtcgtcttga ccacagccat aaaggtagag    4980
ggaatcccag cctggatcca ccacagccac gttaaacctg cagcacctga gacctgggag    5040
gtaagaccaa gcccggacaa cgcctgcaaa gtgactctga agaagacgac aagccctgct    5100
gcagtcacac ccggaagctg actggtccac acacggccga agcatgagga aactcatctt    5160
gggactcctt ttccttaaac tttggactta tagagtaagg acttcaactg accttcctca    5220
gactgaggac aattcccagc atatatatca agtcactgag ataggacaaa aggttgctgt    5280
agtccattat tttatagtta ttatgagtgt accgggactc taagaggaac ttgtttgtat    5340
aatgctactc tatacaaggt atgtagccca ggaagtgacc agcctgatgt gtgctctaac    5400
ccatctgagc ctcctatgac taccatttt gaaataagat tgaggactgg gagctgggga    5460
aaagctgata tgagtagagt agtaactaga atagaagaga aaggagtccc caaacaaatt    5520
ttcttaaaat ttgatgcctg tgcagcaatc aacagtgacc tgtatggaaa tagaataaga    5580
tgtagctctc tagattggga aaggggctat atagtagaaa ataagtatgt ttgtcatgaa    5640
ttaggactat gtactgatga atgtagttac tggtcctgtg ttatttaggc cacctggaaa    5700
aaaatatgag aaggaccctg tcctccttca aaaaggaaag agtaactctt catgcacttg    5760
tggttactgt aacctattag aactactaat taccaatccc cttgatcccc attggaaaac    5820
aggagagtat gtaaatttag gaatcaatgg aactggactg gatccctgag taaatatttt    5880
agtccaaggg gaggtccaca ggctctctcc caaaccagtg tttcagacat tttatgatga    5940
gctgaatctg ccagcaccag agcttccaca aaaagaaaa gaacttgttt ctccatttag    6000
cagaaaatgt agctcatttc ctcaatgtta cttcctgtta catatgtggg ggaaccacta    6060
tgggagaccg atggccttgg gaagcccgag aattggtgcc tactgatcca gttcctgaca    6120
taattccagt ccagaagact tctgggtctt gaaaacctct attactgaac aatactgcat    6180
agctagggaa tgaaaagact tcaccatccc tgtaggaagg ctcaattgtc taggacagag    6240
```

```
gtctaggaca gaggctgtat aacggcacaa cagggacagt cacctggtgg ggtctaaacc      6300
atactgaaaa gtatgtaaat ttccttcatt acattccttc agtaaatttc ctaaattaca      6360
gattgcttgg cccatccaca atctcatcga gactggacgg ctcctactgg actatactgg      6420
atatgtaggc acagagtcta cactcagtta cctgatcaat ggccaggtag ttgtgtcatt      6480
ggcaccagta agccatccgt tttcctactg cccgttagaa caggtgagct cttaggtttc      6540
cctgtctatg tctcccgaga aaagaggagc atagctatag gaaattggaa aggtgatgag      6600 tggcccccc ccgaaaggat cacacagtac tataggcctg ccacatgggc acaagatggc       6660
ttgtggggat actgagcccc tatctacatg ctcaactgga tcatactgtt acaggccatc      6720
ttagaaataa tcactaaaga aactggcaga gctttgactc ttttagccca gcagaaaccc      6780
caaatgagaa atgccatcta gcagaataga ttggccttag actatttgct ggcagctgaa      6840
ggaggagtct gtggaaaatt caacttgacc aattgctgtc tgcaaataga tggtcaagga      6900
caagtagtcg aaaatatagt tagagacatg acaaagctgg cacatgtacc catgcaggtt      6960
tggcatgggt ttgatccttg atccctgttt ggaaaatagt ttccagctct aggaggattt      7020 aaaacttta ataggaat aataatagtg ttaggaacat gcatgttact cccctgtatg         7080
ttacccatat ttctaccacc ttagttcatc aaaagacctc agcacaagta tattacatga      7140
atcactatcg atatgtctca caggaagatc tagatagtga ggatgagaat gagaactccc      7200
actagtgtgt gaggttctca aagaggggta ttaggagaca agccatttct cctactgtcc      7260
cctgtatcca agaaaagga ggaagtaaaa actgaaaaat aacagactga tcagtgccac       7320
tggccaggcc tgtaggttaa agattaaccc caccctaact gcttgtgcta tctatagatc      7380
acagataatg gtatggagaa atacttgcct tgctcaccac ccccacctag tcatgtacca      7440
catgcttgct caatatatcg tgacccttc acgtgaaccc cttagagttg taagcgggaa       7500
ctcttttttt ggggagttca gttcttgaga cacaagtctg ccaacactcc tggccaaata     7560
aagcctcttc cttctttaac ccggtgtctg agggcatttg tctgtggctc gtcctgctac      7620
a                                                                      7621
```

<210> SEQ ID NO 67
<211> LENGTH: 1295
<212> TYPE: DNA
<213> ORGANISM: Homo sapiens

<400> SEQUENCE: 67

```
gtggggaat aaaagagaga tcagattgtt actgtgtcta tgtagaaaag gaagatataa         60
gaaaccccat tttgatctgt actaagaaaa attgttctgc tttgagatgc tgttaatctg      120
taaccttagc cccaaccctg tgctcacaga aacatgtgct gtgttgaatc aagatttaat      180
ggatctcggg ctgtgcagga tgtgctttgt ttaaaaagtt cttgcaggca atatgctttg      240
tgaaaggcat cgccattctc cattcttgat taaccaggga cacaaatgca ctgcagaaag      300
ctgcagggac ctctgcccaa gaaagcctgg gtattgtcca ggtttccccc aatggagaca      360
gcctgagata tggccttatg ggaagggaaa gaccttacag gtccctcagc ccgacaaggg      420
cctgtgctga ggaggattag cgaaagaaa aggcctcttt gcagttgaga taagaggaag      480
gcatctgtct cctgctcctc cctgggaatg gaatgtctcg gtgtaaaacc cgattgtaca      540
ttctatttac tgagatagga gaaaccgcc ctatggctgg aggtgagaca tgctggcagc      600
aatactgctc tttactgcac tgagatgttt gtgtaaagtc aaacataaac ctggcctaca      660
tgcacatcca ggcagagcac atttccttaa acttatttat gacacagggt cctttgctca      720
```

```
cgtgttttcc tgctgaccct ctcctcacca tcaccctata gtcctgctac attcccctca    780
ccaagatagt agagatagtg atcaataaat actgagagag gctgggcgcg gtggctcacg    840
cctgtaatcc cagcaatttg ggaggccgag gcaggcagat cacgaggtca ggagattgag    900
accatcctgg ttaacacggt gaaacccgt ctctactaaa aatagaaaaa attagccggg     960
cccggtggtg ggcacctgta gttccagcta cttgggaggc tgaggcagga gaatggcatg   1020
aacccgggag gcggaggttt cagtgagccg aaaccatgcc actgcactcc acctgcgtga   1080
cagagcaaaa ctctgtctca ataaataaa taaataataa atactgaggg aactcagagg    1140
tcgatgccgg tgcaggtcct cacttgctga gcgctgctcc cccggaccca cttttctccc   1200
tctatacttt gtccctgtgt cttatttctt ttctcagtct cttatctcca ccttctgagg   1260
aataccacac ggtgtggagg ggcaggcccc cttca                              1295

<210> SEQ ID NO 68
<211> LENGTH: 467
<212> TYPE: DNA
<213> ORGANISM: Homo sapiens

<400> SEQUENCE: 68
gcaggagttc agtcagggtg gtgggaaaaa atgtagaaag atgcaaacct tggaaggcca     60
aaaggtttta catcagtttc ggaacaggat ttggctgaaa gcagccagat tcttttatac    120
ggtgcctgaa agcttaggtt agataacggg atgttaagaa actgatctag ataagttact    180
tagctcggaa cctggccttt aatcattcgt aggactgctc tctcctggga ggggaaccat    240
gttaattatc cacaagtgtg ttgactcaaa gcctttgcca ttatatctat actgaataaa    300
tgaccacagc aacagctagt cgggaccgcg gctgctaact ctttacagca ccctcctcag    360
tgtctgtggg tggcccagcc ccctagctca ctctttcact ggatacctgt gtttgagtgc    420
atttgttcat ctgtcgctgg gtcagggtct gcgggtcaga cctggca                  467

<210> SEQ ID NO 69
<211> LENGTH: 879
<212> TYPE: DNA
<213> ORGANISM: Homo sapiens

<400> SEQUENCE: 69
aggcacccct acggaggaaa tctcaactgc acaaccccta ctgtgcccca attcagcagg     60
aagcagttag agcggtggtc aaacctcccc aatagcactt gggttttcct gttgagaggg    120
ggtactgaga gacaggacta gttggatttc ctaggctggc taagaatccc taagcctagc    180
tgggaaattg accacgtcca cctttaaaca cggggcttgc aatttagctc acacccgacc    240
aatcaggtag taaagagagc tcactaaaat gctaattagg gaaaaacagg aggtaaagaa    300
gtagccaatc atctatcgcc tgagagcaca acaggaggga caatgatcag gatataaacc    360
caggcattca agccagcggt ggctaccctc tttgggtccc ctcccttgt atggaagctc    420 tgttttcact ctattaaatc ttgcaattgc acactttct ggtacgtgtg tgtcacagct    480
caagctgagc tttcgctcac cgtccaccac tgctgtctgc cgctgtcaca gacccacagc    540
tgacttccat ccctctggat ccagcgaggc gcccattgct gctcctgatc gggctaaagg    600
cttgcccttg ttcctgcagg gctaagtgcc caggttcgtc ctaatctagc taaacactag    660
tcactgggtt ccacgattct cttccatgac ccacagcttc taatagagct ataacactcg    720
ccgcttggcc caagattcca ttccttggaa tccatgaggc caagaacccc aggtcagaga    780
```

| | |
|---|---:|
| acacaagact tgccaccatc tcggaagtgg cccgtcacca tcttggaagc gacctgccac | 840 |
| catcttggga acttggggag caaggacccc cagtaacat | 879 |

<210> SEQ ID NO 70
<211> LENGTH: 5707
<212> TYPE: DNA
<213> ORGANISM: Homo sapiens

<400> SEQUENCE: 70

| | |
|---|---:|
| gtcaggcctc tgagcccaag ccaagccatc acatcccctg tgacttgcac gtatacgccc | 60 |
| agatggcctg aagtaactga agaatcacaa aagaagtgaa tatgccctgc cccaccttaa | 120 |
| ctgatgacat tccaccacaa aagtgtaaat agccggtcct tgccttaagt gacgacatta | 180 |
| ccttgtgaaa gtccttttcc tggctcatcc tggctcagaa agcaccccca ctgagcacct | 240 |
| tgcgaccccc actcctgccc gccagagaac aaaaccccctt tgactgtaat tttcctttac | 300 |
| cttcccaaaa cctataaaac agtgccaccc ttatctccct tcgctgactc tctctttgga | 360 |
| ctcagcccgc ctgcacccag gtgaaataaa cagccatgtt gctcacacaa agcctgtttg | 420 |
| gtggtctctt cacgccgacg cacatgaaat ttgatgccgt gacttggatc tggggacctc | 480 |
| ccttgggaga tcaatcccct gtactcctgt tctttgctcc gtgagaaaga tccacctatg | 540 |
| gcctcaggtc tcagactga ccagcccaag gaacatctca tcaatttaa atcaggtaag | 600 |
| cggcctcttc ttactctctt ctccagcctc tctcactgtc cctcaaccac tttctccttt | 660 |
| ccactcttca atctctccct tctcttaatt tcaattcctt tcattttctg ggagagacaa | 720 |
| aggagacacg ttttatccgt ggacccaaaa ctccggtgcc ggtcacggac tgggaaggca | 780 |
| gccttccctt ggtgtttaat cattgcaggg acacctctct gattatacac ccacgtttca | 840 |
| cgggtgtcag accacgcagg gacgcctgcc ttggtccttc acctttagcg gcaagtcccg | 900 |
| ctttttctgag ggaggggcaa gtaccctca acccttctc tttcacccctt agcggcaagt | 960 |
| cccgcttttc taggggggcaa gaatgtccaa taccttattt ccgcacccca acctagtatc | 1020 |
| tccatgcccc aatcctttat ttccatgccc cgaccccta tttccgtgcc ccgacccctt | 1080 |
| atttctgcac cccatccctt atttccgtgc ccgaactct tatatctgca ccccaacccc | 1140 |
| ttttctcact tttctgaaag gtaagaatcc ctgaacccct tccctccgtt tctctactct | 1200 |
| ctcttttctc gaggcttgct tcctccacta taggcaaact tccaccctcc attcctcctt | 1260 |
| ctactccctt ggcctgtgtt ctcaaaaact taaaacctct tcaactcaca cctgacctaa | 1320 |
| aacctaaatg ccttattttc ttctgcaatg ccgcttgacc ccaatacaaa ctcaacagta | 1380 |
| gttccaaata gccagaaaat ggaactttga atttctccat cctgcaagat ctaaataatt | 1440 |
| cttgtcataa aataggcaaa tgatctgagg tgcctgacgt ccaggcattc ttttacacat | 1500 |
| cagtcccttc ctagtctctg tgcccagtgc aactcatccc aaatcttctt tccctcccac | 1560 |
| ctgtcccctc agtcccaatc caagcgtcg ctgagtcttt ctaatcttcc ttttctacag | 1620 |
| acctatctga cctctcccct cctcgccagc ccgagctagg tcccaattct tcctcagcct | 1680 |
| ccgctcctcc acctataat cttttatcg cctcccctcc tcacacctgg tcgggcttac | 1740 |
| agtttcgttc tgtgactagc cctccccac ctgcccagca atttactctt aaaaaggtgg | 1800 |
| ctggagccaa aggcatagtc aaggttaatg ctccttttc tttatcccaa atcagaaccg | 1860 |
| tttaggctct ttttcatcaa atataaaaat ccagcccagt tcatggatcg tttggcagca | 1920 |
| accctgagac actttacagc cctagaccct aaaaggtcaa aaggctgtct tattctcaat | 1980 |
| atacatttta ttatccaatc tgctccccac attaaataaa actccaaaaa ttaaattccg | 2040 |

```
gccctcaaac cccacaacag gatttaacta acctcgcctt caaggtgtac aataatagaa    2100
aaaagttgca attccttgtc cccactgtga gacaaacccc agccgcatct ccagcacaca    2160
agaacttcca aacgcctgaa ccgcagcggc caggtgttcc tccagaacct cctcccccag    2220
gagcttgcta caagtgccag aaacgtggcc accaggccaa ggaatgcctg cagcccagga    2280
ttcctcctaa gccacgtccc atctgtgccg acccccactg gaaatcggac tgtccaactc    2340
acctggcagc cactcccaga gcccctggaa ctctggccca aggctctctg actgcttccc    2400
agatcttctt ggcttagcgg ctgaagactg acgctgcctg attgcctcgg aagcccccta    2460
gaccatcacg gatgcccagc ttcaggtaac tctcacagtg gaaggtaagc ccgtcccctt    2520
cttaatcaat acggaggcta cccactccac attaccttct tttcaagggc cttttccct     2580
tgcctccaca gctgttgtcg gtattgatgg ccaggcttct aaacctctta aaactcccca    2640
actctggggc caacttagac aatactcttt taagcactcc ttttagtta tccccacctg     2700
cccagttccc ttattaggct gagacacttt aactaaattg tctgcttccc tgactattcc    2760
tggactacag ctgcatctca ttgctgccct tcttcccaat ccaaagcctc cttttgcatcc   2820
tcctcttgta tccccaaaac ttaacccgca agtataaaat acctctactc cctccttggt    2880
gactgatcat gcaccccta tcatctcatt aaaacctaat caccccttacg ccactcaacc    2940
ccaatatccc atcccgcagc acgctttaaa aagattaaag cctgttatca ctcgcctgct    3000
acagcacggc cttttaaagc ctataaactc tccttacaat tcccccattt tacctgtcct    3060
aaaaccagac aagccttaca agttagttga ggatctgcgc cttattaacc aaattgtttt    3120
gcctatccac ccagtggtgc caaacccata tattctccta tcctcaatac ctgcctctat    3180
aacccattat tctgttctgg atctcaaaca tgctttcttt actattcctt tgcacccta    3240
atcccagcct ctcttcactt tcacttagac tgaccctgac acccatcaag ctcagcaaaa    3300
tacctaggct gtactgctgc aaagcttcac agacagcccc cattacttca atcaagccca    3360
aatttcttcc tcatctgtta cctatctcgg cataattctc ataaaaacac acgtgctctc    3420
cctgctgatc gtgtccgact aatctctcaa accccagcac cttctacaaa acaacaactc    3480
ctttccttcc taggcatggt tagtgcggtc agaattctta cacaagagcc aggaccacac    3540
cctgtagcct ttctgtccaa acaacttgac ctactgtttt agcctagccc tcatgtctgc    3600
gtgcagtggc tgccgctgca ttaatacttt tagaggccct caaaatcaca aactatgctc    3660
aactcactct ctacagttct cataacttcc aaaatctatt ttcttcctca tacctgatgc    3720
atatactttc tgctccccgg ctccttcagc tgtactcact ctttgttgag tctccctcaa    3780
ttccattgtt cctggcccag acttcaatcc agcctccac attattcctg ataccacacc     3840
tgacacccag gactgtatct ctccgatcca cctgacattc accccatttc ccaaatttc     3900
cttctttcgt gttcctcact ctgatcacac ttgatttatt gatggcggtt ccaccaggcc    3960
taatcgccac acaccagcaa aggcaggtta tgctatagta caagccacta gcccacctct    4020
tagaacctct catttccttt ccatcgtgga aatctatcct caaggaaata acttctcagt    4080
gttccatctg ctattctact actactcaag gattattcag gccccctccc ttccctacac    4140
atcaagctcg aggatttgcc cccacccagg actggcaaat tagctttact caacatgtcc    4200
tgagtcagat aactaaaata cctcttagtc taggtagata atttcactgg ataggtagag    4260
gcctttccca cagggtctga gaaggccacc tcagtcattt cttcctttct gtcagacata    4320
attcctcagt ttagccttcc cacctcaaca cactcttata acagaccagc ctttattagt    4380
```

| | | | | |
|---|---|---|---|---|
| caaatcagcc | aagcagtttt | tcaggctgtt | agtattcagt | gaaaccttta tatcccttac | 4440 |
| ggtcctccat | cttcaagaaa | agtagaatgg | actaaagatc | ttttaaaaac acacctcacc | 4500 |
| aagctcagcc | accaacttaa | aaaggactgg | acaatacttt | aaccactttc ccttctcaga | 4560 |
| attcaggcct | gtcctcggaa | tgctacaggg | tactgcccat | ttgagctcct gtatagacgc | 4620 |
| tccttttat | taggccccag | tctcattcca | gacaccagac | caacttagac tgtgcccaa | 4680 |
| aaaacttgtc | atccctatta | tcttctgtct | agtcatactc | ctattcaccg ttctcaacta | 4740 |
| ctcatacatg | ccctgctctt | gtttacactg | ccggtttaca | gtttctccaa gccatcacag | 4800 |
| ctgatatctc | ctcgtgctat | ccccaaactg | ccactcttaa | ctcttgaagt aaatacataa | 4860 |
| tctttgctgg | caggactatg | ctgaatctcc | ttaggcacta | tctaatcaga tatcctgagt | 4920 |
| tgtcccaatt | cttagaactt | ttatacctgt | ttttctcctt | ctgttattcc atttagtttc | 4980 |
| tcaattcatc | caaaccata | tccaggccat | aaccaataat | tctacacaac aaatgtttct | 5040 |
| tctaacaacc | ccacaatatc | accccttacc | acaagacctc | ccttcagctt aatctctccc | 5100 |
| actctaggtt | cccacgctgc | ccctaatccc | gcttgaagca | gccctgagaa acatcaccca | 5160 |
| ttctctctcc | atatcacccc | ccaaaaattt | tcactgcccc | aacacttcaa cactatttg | 5220 |
| ttttattttt | cttattaata | taagaaggca | ggaatgtcag | gcctctgagc ccaagccaag | 5280 |
| ccattgcatc | ccctgtgact | tgcacatata | agcccagatg | gcctgaagta actgaagaat | 5340 |
| cacaaaagaa | gtgaatatgc | cctgccccac | cttaactgat | gacattccac cacaaaagaa | 5400 |
| gtgtaaatgg | ccggtccttg | ccttaagtga | tgacattacc | ttgtgaaagt cctttcctg | 5460 |
| gctcatcctg | gctcaaaaaa | cacccccact | gagcaccttg | gaccccac tcctgcccgc | 5520 |
| caaagaacaa | acccctttg | actgtaattt | tcctttacct | acccaaatcc tataaaacag | 5580 |
| ccccacccct | atctcccttc | gctgactctc | tttttggact | cagcctgcct gcacccaggt | 5640 |
| gaaataaaca | gccatgttgc | tcacacaaag | cctgtttggt | ggtctcttca catgcacgag | 5700 |
| catgaaa | | | | | 5707 |

<210> SEQ ID NO 71
<211> LENGTH: 5338
<212> TYPE: DNA
<213> ORGANISM: Homo sapiens

<400> SEQUENCE: 71

| | | | | |
|---|---|---|---|---|
| tgggtcagac | acaaagtaaa | cccactccac | taggaactat | gttaaaaaat tttaagtagg | 60 |
| gatttaaggg | agactatgga | gttactatga | caccaggaaa | acttagaact ttgtgtaaga | 120 |
| tagactggcc | agtatttgag | gtgggttggc | catcagaaga | agcctggata gggcccttgt | 180 |
| ttcaaaggta | tgtcataaga | taacctgtaa | gccaggcac | ccagaccagt tcccatgcat | 240 |
| agacacttgg | ttacagctgg | ttttagaacc | ccccaccgtg | gttaagagga cagggagcca | 300 |
| cagtgttagt | ggtgaaagga | cagatagtta | aggaaggatc | ccgctccacc tgccaaggga | 360 |
| agtcggcccc | taaagttctg | tccaatccaa | tatcaggaga | cttatggcag gaaatggcac | 420 |
| cagcgatgcc | cccgcttac | tgagaagaga | gactccccac | ttctgagccc acagcacctg | 480 |
| tgcctccaca | ggacacacac | accactagac | cacccagagt | agacaagaga ggatgtgaag | 540 |
| ctgtgggaga | aaccctccc | ctggtggctc | atttatggcc | taagactgga atacaaatgc | 600 |
| ccctgaggga | gcagcgatat | actggggtag | acgaggatgg | gcatatggta gaaaggagtg | 660 |
| cctttgtgta | tcaacccttc | acctctgctg | atctcctcaa | ctggaagaac aataccccat | 720 |
| cttatagtga | aaagcctcaa | gcattagttg | atttgctcca | aactattatc cagattcata | 780 |

```
accctacttg ggctgatggc caccagctgc tcatgtacct ctttaacaca gatgaaaagc       840
gaagggtgct ccaggcagca actaagtggc tagaggaaca tgctctggcc agttaccaaa       900
acccccagga gtatgtgaga gtccaattac caggaacaga cccccagtgg gacccaaatg       960
aagggccaga catggagaga ctaaaacagt atagagaggc cctcctggaa gggttaaaaa      1020
agggagctca gaaggccaca gatgttaaca aagtctctga ggtcattcaa ggaaaagaag      1080
agagtccagc acaattttac aagggactat gtgaggccta tcgtatgtat actccctttg      1140
atcccaatag ccctgaaaat cagcgcatga ttaacatggc tttagttagt caaagcacca      1200
aagatattag aagaaagctt cagaaacagg ctgggtttgt gagtatgaat acttcacagt      1260
tattaaaaat agccagtcag atgtttgtga gtagagatgt ggcaggccgt agagagagcc      1320
gcaaagaaag caagtgccaa gcccggcaaa acacctatct gctagctgca gctattagag      1380
gagttccccc gaagggccga ggaagggggg accctgggaa aaacactcag tctgaccaac      1440
catgcctgca gcataaccag tgtgcatact gtaaagaaac agcgcattgg aaagacaagt      1500
gcccctagtt aaaagagaaa caaaatggct ctgagccaga ggtttcaggc aaggatgaag      1560
gggccttgtt taatctagca gaaggggttac tggactgagg gggaccgggc tcaggtgccc      1620
ccaatgagcc catggtcaag atgacagtca ggagcaagga cattgagttt cctgtcaata      1680
cttatcctga acattcagta gtaaccaccc cagtcacccc cttatcccaaa aagactattg      1740 atataatcaa agccacagga gtcttgaaaa aacaagcttt ctacttgccc cggacttgta      1800
ctgtagggag acatgaagtg attcaccagt tcttgtacat gcctgactgc cccttgccct      1860
tgctgggaag ggacttgctt agcaagctga gggccaccat ctcttttaca aagcacagct      1920
ctttaccgct aaagttacct ggaatgggag tcattatggc ccttacagtc ccctgggagg      1980
aagaatggac ttttcttaac tgagccaggc caagagatag gaccagctttt ggctaaacag      2040 tggctaaggg tgtgggcaga agataatcct ctggggctag cagtaaacga agcccccgta      2100
accagagaag ctcttgaagg tatccagatc catctccagt gcctgaaggc ctttggaatt      2160 atagcccccct gtcagtctgc ctggaacaca gccctgctgc ctgttcccaa tccaggaacc      2220
aaggtttaca gaccagtata ggacttgcgc ttggttaacc aagctacagt gactttgcac      2280
ccaatggtac ctaaccccgta catgttctta gggttactgc cagctgagga cagctgcttc      2340
acctcctgga cttgaaggac actttctttta gcaccagact agctcctgag agccagaaac      2400
tgtttgcttt ccagtgggaa gatccaggct taggtgtcac cactcagtac acttggaccc      2460
ggcgtcccca agggttcaga aactccctca ctatcttcag ggaggccctg gctcaagacc      2520
tgcgaaagtt tcccgccaga gacctaggct gtgtgttgct ccagtatgtc aacgacctcc      2580
tgctgggaca ccccacagca attgggtgcg ccaaaggaac agacgccctg ctctgacacc      2640
tggaggactg tgagtataag gtgtccaaga agaaagctca gatctgcaga cagcaggtac      2700
gctacctagg atttacaatc cgacagggggg aacgcagcct aggatcagaa agaaagcagg      2760
tcatttgcaa cctaccagag cctaagacca gaaggcaggt gagagaattc ttaggagctg      2820
ttcttagggt tctgcaggtt atggatccca aattttgcag tactggccaa acctctgtac      2880
caagttacaa agagggggtga catggaacct ttcgaatggg ggtcccaaca gcaacaggat      2940
tttcatgagt taaaagaaaa cttcatgtca gccccagccc tgggtctgcc tgacctgaca      3000
aagccattta cactatatgt gtcagagaga gaaaaaatgg cagttagggt tttgaccaag      3060
actgtggggc cctggttgag gccggtggct acctctctaa acaactagac agggtttcca      3120
```

```
aaggttggcc cccgggtttg agggccttag cagcaactgc cctgctagca caagaagcag    3180
ataaactaac ccttgggcaa aacctgaaca taaaggggcc ccccatgcta tggtgacttt    3240
aatgaatacc aaaggacatc attggctaac gaatgctaga ctaaccaagt accaaagctt    3300
gctctgtgaa atccccgca taaccattga aatttgtaaa accctgaacc ccgccacctt    3360
gctcccggta tcagagagcc ctgtcgagcc taactgtgta gaggtgttag acccagttta    3420
ctctagcaga cttgacctcc gggaccaacc ttgggcatca gtggactggg agctgtgcat    3480
ggacaggagc agctttgtca acccacaagg agagaggtgt gcgggatatg cagtggtaac    3540
cgtggacact gtaattgagg ccaaatcatt gcaccaaggt acctcagccc agaaagctga    3600
gctcattgct ttaatttggg ccttagaact cagtgaaggt aaggctgtaa acatttacac    3660
tgactccagg tatgcctttt taaccctcca agtgcatgga gcattatata agaaaaggg     3720 cctgttgaac tctggggtaa aggactaaaa tatcagcaag aaatcttgca attattagaa    3780
aaagtatgga accccaaaa ggtggcagtc atgcactgcg gagtccacca gcgagcttcc     3840
acctcagttg ccttggacaa ctcccaagct gactcagagg ctcgaaaagc agcatctgcc    3900
ccctaccagg catcagtcac agccccctg ctccctcaag cacctgacct tgtacctact     3960
tattttaaag aagaaaaag gactttctac aggcagaggg aggacaggtg atggaagaag     4020
gatggatcca gttaccagat aggaaagtag ctttgccaca gctgctggga gccgcagtcg    4080
tactgactgt gcatgaaacc acccatctag gtcaggggtc acttgaaaag ttgttaggcc    4140
agtatttcta catctcgcat ttgtcagccc ttgccaaaat actggtgcag tggtgtgtaa    4200
cctgccgaca gcacaatgcg aggcagggtc cagctgttct gctcagcata caagtttatg    4260
gagcagctcc ctttgaagat ctccaggtgg acttaacata aatgcccaag tgtggagata    4320
acaagtattt actagttctc atgtatacct actctgggtg agtggaggct tatcaaacac    4380
gaactgagaa agctcgtgaa gtaacccgtg cacttcttcg agatcgtatt cctagatttg    4440
gactgctctt acgaattggc tcagataatg ggttggcatt tgtggctgac ttggtacaga    4500
agacagcaaa ggtattaggg atcacatgga aactgcatgc tgcctcctga cctcaaagtt    4560
caggaaaggt ggagcaaatg aatcagacta tcaagaatag cttagggaaa gtgtgtcagg    4620
aaacaagatt aaaatagata caggctctcc tgatggtatt gtttaaaata agatgtaccc    4680
cttctaaaag aacaggatat tccccttata aatatttgta ccatagaccc cctcccatac    4740
tatggggact cccaggcact ccacaagagc taggtgaaat tgagttaaaa tgacagctat    4800
aggccatagg aaaaattgct caaacaattt cagcctgggt aaatgagagg tgccccatta    4860
gcttattcta cccagttcac cctttctctc caggtgatca agtgtggatc aaggattgga    4920
atgtagtccc cttgtgacca cggtggaaag accccagacc gtcatcttga ccaccccac     4980 agctgtaaag gttgaaggaa tccaagcctg gatccaccac agccatgtga aacctgcagc    5040
ctctgagacc tggaaggtga gaccaagccc agacaacccc tgcaaagtga ctctgagaag    5100
gacgacaagc cctgctgcag tcacacccag aagctgactc atctatgcac agccaaagca    5160
tgaggaaact catcgtggga cttattctcc ttaaaatttg gacttatgta ataaggactt    5220
ccactgattt tccccacatg gaggactgtt cccaatgtat tcatcaggtc actgagtagg    5280
gcaacaagtt aaaacagttt ctgttttata gttattattg ttgcgggaca atcaaaga     5338
```

<210> SEQ ID NO 72
<211> LENGTH: 809
<212> TYPE: DNA
<213> ORGANISM: Homo sapiens

<400> SEQUENCE: 72

```
gcacttggtt tctcaagtca ctcacttggt cctcttccaa ggtgtacttt ccttctttcc      60
tttccttcct ttccttactg ttctaaagct ttttaacaaa cttgcactcc tgctctgaaa     120
cctgcctcag tctctccctc cttctgcctt atgcccctca ttcgaattct cctgaggagg     180
caagaactga agttgtggca gacccatacg gaatcgggt  aacttgggta tctgccaccg     240
gcaacatatt tggcgcacac gatttggata cattccctag tggccattaa gctccaggta     300
atcctcgatg aagaatactg tcctttcaat attcaagaat caccctctta caggggacct     360
ctagactgcc catcagtggg acacgacaga ggcgaaatcc tgccctgtc  tcccttgggc     420
ctggccggat atcgctttca caactcatg  gagccaactc agcaatgaca gctagcaaga     480
ggccaagacc catagaacca ccactgcccc tctgtcagca ggaagcagtt acagaagact     540
gaccttcgtc catttaaccc caaagatttg gggtcttgga ctcttggggg gggaaatgtt     600
acagtgggta gctagtcagg tatgagcagg gcagtagggg gctccacccc acatgcacac     660
caggagtgtt aggcgaccat caggtgatgg tcaggcagtt aactgtttct ctaaagtaat     720
aactggttgc agccggagct agggaaaggc aggctaatag atataaaaca cctgaaactc     780
atcagcagct tctcaataag atctcagga                                      809
```

<210> SEQ ID NO 73
<211> LENGTH: 51
<212> TYPE: DNA
<213> ORGANISM: Homo sapiens

<400> SEQUENCE: 73

```
agctacaccc actatgccca ctgtcagcag gaagaagtta gggcagtcgt c              51
```

<210> SEQ ID NO 74
<211> LENGTH: 5971
<212> TYPE: DNA
<213> ORGANISM: Homo sapiens

<400> SEQUENCE: 74

```
gtcaggcctc tgagcccaag ccaagccatc gcatcccctg tcacttgcac gtacacaccc      60
agatggcctg aagtaactga agaatcacaa aagaagtgaa tatgccctgc ctcacctcaa     120
ctgatgacat tccaccacaa aagaagtgaa atggcctgt  tcctgcctta actgatgaca     180
ttgtcttgtg aaattccttt tcctggctca tcctggctca aaaacctccc ccactgagca     240
ccttgcaacc cctacgcctg ctcgccagag aacaaaaccc ctttgactgt aattttcctt     300
tacctaccca aatattataa aacggcccca ccctatctc  cctttgctga ctctcttttc     360
ggactcagcc cgcaggcacc caggtgatta aaagctgtat tgctcacaca aagcctgttt     420
ggtggtctct tcacacggac gcgcatgaaa tttggtgccg tgactcagat cgggggacct     480
cccttgggag atcaatcccc tgtcctcctg ttctttgctc cgtgaaaaag atccacctac     540
gacctcaggt cctcagaccc accagcccaa ggaacatctc accaatttta aatcgagtaa     600
gcggcctctt cttactctct tcttcaacct ctctcactat ccctcaacca ctttctcctt     660
tccactcttc aatctctccc ttctttcaat ttcaattcct ttcattttct ggtagagaca     720
aaggagacat gttttatccg tggacccaaa accccggcgc cggtcacaga ctgggaaggc     780
agccttccct tggtgtttaa taattgcaga tacgcctctc tgattattca cccacgtttc     840
agaggtgtca gatcacgcag ggacgcctgc cttggtcctt caccctttagc ggcaagtccc     900
```

```
acttttctgg ggggggcaag tacccccaacc ccttctctct gtgtctctac cccgtctcca    960
cctttctggg gggcaagaaa cccctaaccc ttctccttca ctcttagcag caagtcccgc   1020
ttttctagag gaggggcaag tacccccaacc ccttctctcc atgtctctac ctcttctccg   1080
cctttctggg gggcaagaaa ctcccaaccc cttctccttc atccttagcg gcaagtcctg   1140
cttttctggg ggaggggcaa gtacccccaac cttgtatctc tgcgccccga tcccttatgt   1200
ccatgccccg acctcttata tctctgtgct ccgatccctt atttccacgc cccaacctgt   1260
tatatctctg cgccctgatc ccttatttcc atgccccgac cttgtatctc tgcgccccga   1320
ccccttttccc acttttctgg agggtaagaa cccctgaacc ccttccctcc tgtctctatc   1380
ttttctctgg gcttgcttcc ttcactatgg gcaaccttcc accctccatt cctccttctt   1440
ctcccttagc ctgtgttctc aaaaacttaa aacctcttca actcacatct gacctaaaac   1500
ctaaatgcct tactttcttc tgcaatgcca cttgacccca atacaaactc aacagtggta   1560
ccaaatagcc agaaaatggc actttcaatt tttccatcct acaagatata aataattctt   1620
gtcgtaaaat aggcaaacgg tctgaggtgc ctgacgtcca ggcattcttt tacacatcag   1680
tcccttccta gtctctgttc ccaatgcaac tcgtcccaaa tcttccttct ttccctcccg   1740
cctgtcccct cagtcccaac cccaagcatc actgagtctc caatcttcct tttctacaga   1800
tctatctgac ctctcccctc ctcgccaggc cgagctaagt cccaattctt cctcagcccc   1860
ctcttctcca ccctataatc cttttatcac ctcccctcct gacacccggt ctggcttaca   1920
gtttcattcc gtaactagcc ctctgccacc tgcctagcaa tttactctta aaaaggtggc   1980
tggagctaaa gacatagtca aggttaatgc tccttttttct ttatcccaaa tcagatagcg   2040
tttaggctct ttttcatcaa atataaaaat ccagcccagt tcatgactcg tttggcagca   2100
accctgagac tctttacagc cctagaccct aaaacatcaa aaggctgtct tattctcaaa   2160
atacatttta ttacccaatc tgctcccaac attaaataaa actccaaaaa ttaaattctg   2220
gccctcaaac cccacaacgg gattaattaa cctcgccttc aaggtgtaca ataatagaaa   2280
aaagttgcaa ttccttgcct ccactgtgag acaaaccca gccacaactc cagcacacaa   2340
gaacttccaa atgcctgaac cgcagcggcc aggcgttcct ccagaacctc ctctgccagg   2400
agcttgctac aagtgccaga aatctggcca ccaggccaag gaatgcctgc agcccaggat   2460
tcctcctaag tcacgtccca tctgtgcagg accccactgg aaatcggact gtccaactca   2520
cctggcagcc actcccagag ccccctggaac tctggcccaa ggctctctga ctgcttccca   2580
gatcttcttg gcttagcggc tgaagactga cactgcctga tcacctcgga agccccctag   2640
accatcacgg actccgagct tcgggtaacc ttcacagtgg aaggtaagtc cgtcccttc    2700
ttaatgaata cggaggctac ccactccaca ttacctcctt ttcaagggcc tgtttccctt   2760
gcctccataa ctgttgtggg tattgacggc caggtttcta aacctcttaa aactccccaa   2820
ctctggtgcc accttagaca atactctttt aagcactcct ttttagttat ccccacctgc   2880
ccagttccct tattaggcca agacacttta actaaattat ctgcttccct gactattcct   2940
gggctacagc cacatctcat tgccaccttt tcccccactt caaagcctcc ttcacatcct   3000
cctcttgtat cccccacct taacccacaa gtataggata cttctactcc cttcttggtg   3060
accgatcatg caacccttac catctcatta aaatctaatc accccttaccc cactcaacgc   3120
cagtatccca tcccacagca cgctttaaaa agattaaagc ctgttatcac tcgcctgcta   3180
cagcatggcc ttttaaagcc tataaactct ccttacaatt cccccatttt acctgtccta   3240
aaaccagaca agccttacaa gttagttcag gatctgtgcc ttatcaacca aattgttttg   3300
```

```
cctatccacc ccatggtgct gaacccatat actctcctat cctcaatacc tccctctaca   3360
acccattatt ctgttctaga tctcaaacac gctttcttta ctattccttt gcacccttca   3420
tcccagcctc tcttcgcttt cacttggact gaccctgaca cccatcacgc tcagcaaatt   3480
acctgggctg tactgccgca aggcttaaca gacatcccccc attacttcag tcaagcccaa   3540
atttcttcct catctgttac ctgtctcggc gtaattctta gaaaaacaca tgtgctctct   3600
ctgccgatcg tgtctgactg atctctcaaa ccccaacacc ttctacatcc taggcatggt   3660
tagatacttt cgactttaga tacctggttt tgccatccta acaaaaccat tatataaact   3720
cacaaaaaga aacctagctg accccataga tcctaaatcc tttccccact ccttttttccg   3780
ttccttgaag acagctttag agactgcccc aacccgagcg ctccctgact catcccaacc   3840
cttttcatta cacagagctg aagtgcaggg ctgtgcagtc ggaattctta cacaaggacc   3900
gggatcgcgt cctgtagcct ttttgtccaa acaacttgac cttactgttt taggctggcc   3960
atcatgtctc cgtgcagtgg ctgctgccac cccaatactt tcagaggccc ttaaaatcac   4020
aaactatgct caactcactc tctacagctc tcataatttc caaaatctat tttcttcctc   4080
acacctgatg cctatacttt ctgctcccca gctccttcat ctctctgatc cacctgacgt   4140
tcaccccatt tccccacatt tccttctccc ctgtttctca ccctgatcac acttagttta   4200
ttgatggcag ttccaccagg cgtaatcgcc acacaccagc aaaggcaggc tatgctatag   4260
tacaagccac tagcccgcct cttagaacct ctcatttcct ttccattgtg gaaatctatc   4320
ctcgaggaaa taacttctca gtattccatc tgctatgcta ctactcctca gggattattc   4380
aggccccctc tcttccctac acatcaagtt cagggatttg ccccgccca ggactggcaa   4440
attagcttta ctcaacatgc cccgagtcag gaaactaaaa tacctcttat tctaagtaga   4500
cactttcact gaataagtaa aggcctttcc tacagggtct gagaaggcca ccgtagtcat   4560
ttcctccctt ctgtcagaca taattcctta gtttagcctt cccacctcta tacagtctga   4620
taacagacca gccttttatta gtcaaatcag ccaagtagtt tttcaggctc ttagtattca   4680
gtgaaacctt tacatcccct acagtcctct gtcttcagga aagtagaac agactaaagg   4740
tcttttaaaa acacacctca ccaagctcag ccaccaactt aaaaaggact ggacaatact   4800
tttaccactt tcccttctca gaagtcagac ctgtcctcag aatgctacag ggtacagccc   4860
atttgagctc ctgtatagac gctccttttt attaggcccc agtctcattc cagacaccag   4920
accaacttag actgtgcccc aaaaaaactt gtcatcccta ctatcttctg tctagtcata   4980
ctcctattca ccattctcag ctactcatac atgcccgtct cttgtttaca ctgccggttt   5040
acactgtttc tccaagccat cacagctgat atctcctggt gctatcccca aactgccact   5100
cttaactctt gaagtaaata aataatcttt gctggcagga ctatgctgaa tctccttagg   5160
cactctctaa tcagatgtcc tgggtcctcc caattcttag acctttata cctgttttttc   5220
tccttctctt attccattta gtttttcaat tcatacaaaa ccatatccag gccatcacca   5280
atcattctat acaacaaatg tttcttctaa caaccccaca atatcacccc ttaccacaaa   5340
atcttccttc agcttaatct ctcccactct aggttcccaa gccacccaa tcctgctcga   5400
agcagccctg agaaacatcg cccattctct ctctccatac caccccccaa aaattttcgc   5460
caccccaaca cttcaacact attttgtttt atttttcttta ttaatataag aaggcaggaa   5520
tgtcaggcct ctgagcccaa gccaagccat cgcatcccct gtgacttgca catattcgcc   5580
cagatggcct gaagtaactg aagaatcaca aaagaagtga atatgccctg cccgccctta   5640
```

| | |
|---|---|
| actgatgaca ttccaccaca aaagaagtga aaatggcctg ttcctgcctt aactgatgac | 5700 |
| attgtcttgt gaaattcctt ttcctggctc atcctggctc aaaaacctcc cccactgagc | 5760 |
| accttgcaac ccccactcct gcccgccaga gaacaaaccc cctttgactg tcattttcct | 5820 |
| ttacctaccc aaatcttata aaacggcccc acccctatct ccctttgctg actctctttt | 5880 |
| cagacttagc ccgcctgcac ccaggtgatt aaaagctgta ttgctcacac aaagcctgtt | 5940 |
| tggtggtctc ttcacacgga cgcgcatgaa a | 5971 |

<210> SEQ ID NO 75
<211> LENGTH: 2611
<212> TYPE: DNA
<213> ORGANISM: Homo sapiens

<400> SEQUENCE: 75

| | |
|---|---|
| tctgggaggt gtacccaaga gctcattgag aacgggccat gataacgatg gcggttttgt | 60 |
| ggaatagaaa aggggaaat gtggggaaaa gaaagagaga tcaccctcc ccctccccct | 120 |
| ccctctctcc atggtctccc tctccctctc tttccacggt ctccctctga tgccgagccg | 180 |
| aagctggact gtactgctgc catctcggct cactgcaacc tccctgcctg attctcctgc | 240 |
| ctcagcctgc ggagtgcctg cgattgcagg cgcgcgccgc cacgcctgac tggttttcgt | 300 |
| attttttttgg tggagacggg gtttcgctgt gttggccggg ctggtctcca gctcctaacc | 360 |
| gccagtgatc cgccagcctc ggcctcccgc ggtgccggga ttgcagacgg agtctggttc | 420 |
| actcagtgct caatggtgcc caggctggag tgcagtggcg tgatctcggc tcgctacaac | 480 |
| ctccacctcc cagccgcctg ccttggcctc ccaaagtgct gagagtgcag cctctgccag | 540 |
| gccgacaccc cgtctgggaa ttgaggagcg tctctgcctg gccgccatc gtctgggacg | 600 |
| tgaggagccc ctctgcctgg ctgcccagtc tggaaagtga ggagtgtctc tgcccggccg | 660 |
| ccatcccatc taggaagtga ggagcgcctc ttcccggccg ccatcccatc taggaagtga | 720 |
| ggagcgtctc tgcccggcca cccatcgtct gagatgtggg gagcgcctct gccccgccac | 780 |
| ctcatctggg atgtgaggag cacctctgcc cggccgcgac ccgtctgggg aggtgaggag | 840 |
| cgtcactgcc tagccgcccc gtctgagaag tgaggagacc cccgcctgg caaccgcccc | 900 |
| gtctgagaag tgaggagccc ctccgcccgg cagccacccc gtctgggaag tgaggagcgt | 960 |
| ctccgcccgg cagccacccc gtctggggagg gaggtggggg ggtcagcgcc ccgcccggcc | 1020 |
| agccgccccg tccgagaggg aggtggggag ggtcagcccc ccgcccggcc agccgccccg | 1080 |
| tctgggaggt gaggggcgcc tctgcccagc cgccccctact gggaagtgag gagcccctct | 1140 |
| gcccggccac caccccgtct gggatgtgta cccaacagct cattgagaac gggccatgat | 1200 |
| gacagtggcg gttttgtgga atagaaaggg gggaaggtg gggaaaagat tgagaaatcg | 1260 |
| gatggttgcc gtgtctgtgt agaaagaagt agacatggga gactttttcat tttgttctgt | 1320 |
| actaagaaaa attcttctgc cttgggatcc tgttgatctg tgaccttacc cccaaccctg | 1380 |
| tgctctctga aacatgtgct gtgtccactc agggttaaat ggattaaggg cggtgcaaga | 1440 |
| tgtgcttttgt taaacagatg cttgaaggca gcatgctcgt taagagtcat caccactccc | 1500 |
| taatctcaag tacccaggga cacaaacact gcggaaggcc gcagggtcct ctgcctagga | 1560 |
| aaaccacaga cctttgttca cttgtttatc tgctgacctt ccctccacta ttgtcctatg | 1620 |
| accctgccaa atcctcctct gcgagaaaca cccaagaatg atcaattaaa aaaaaaaat | 1680 |
| aaagctgttt aaacacaaaa aaaaaaaaa aaaagaaag agatcagatt gttactgtgt | 1740 |
| ctgtgtagaa agaactagac ataggagact ccattgtgtt ctgtactaag aaaaattctt | 1800 |

```
ctgccttggg atgctgttaa tctataacct taccccaac cccgtgctct ctgaaacatg    1860
tgctgtgtcc actaagggtt aaatggatta agggcggtgc aagatgtgct ttgttaaaca    1920
gatgcttgaa ggcagcatgc tcgttaagag tcatcaccac tccctaatct caagtaccca    1980
gggacacaaa cactgcggaa ggccgcaggg tcctctgcct aggaaaacca cagacctttg    2040
ttcacttgtt tatctgctga ccttccctcc actattgtcc tatgaccctg ccaaatcctc    2100
ctctgcgaga aacacccaag aatgatcaat taaaaaaaaa aaataaagct gtttaaacac    2160
aaaaaaaaaa aaaaaaaaag aaagagatca gattgttact gtgtctgtgt agaaagaact    2220
agacatagga gactccattg tgttctgtac taagaaaaat tcttctgcct tgggatgctg    2280
ttaatctata accttacccc caacccgtg ctctctgaaa catgtgctgt gtccactaag    2340
ggttaaatgg attaagggcg gtgcaagatg tgctttgtta aacagatgct tgaaggcagc    2400
atgctcgtta agagtcatca ccactcccta atctcaagta cccagggaca caaacactgc    2460
ggaaggcggc ggcggggcgc tctgcctagg aaaaccagag agctttgttc acatgtttat    2520
ctgctgacct tccctccact attgtcctat gaccctgcca aatccccctc tctgagaaac    2580
agccaagaat gatcaataaa tactaagaaa a                                   2611
```